US012447015B2

(12) United States Patent
Girard et al.

(10) Patent No.: US 12,447,015 B2
(45) Date of Patent: Oct. 21, 2025

(54) PROSTHETIC HEART VALVE AND TRANSCATHETER DELIVERED ENDOPROSTHESIS COMPRISING A PROSTHETIC HEART VALVE AND A STENT

(71) Applicant: JenaValve Technology, Inc., Irvine, CA (US)

(72) Inventors: Michael J. Girard, Lino Lakes, MN (US); Randy Lane, Iangley (CA); Arnulf Mayer, Markt Schwaben (DE)

(73) Assignee: JenaValve Technology, Inc., Irvine, CA (US)

( * ) Notice: Subject to any disclaimer, the term of this patent is extended or adjusted under 35 U.S.C. 154(b) by 33 days.

(21) Appl. No.: 18/175,319

(22) Filed: Feb. 27, 2023

(65) Prior Publication Data

US 2023/0200982 A1 Jun. 29, 2023

Related U.S. Application Data

(63) Continuation of application No. 16/794,423, filed on Feb. 19, 2020, now Pat. No. 11,589,981, which is a (Continued)

(30) Foreign Application Priority Data

May 25, 2010 (EP) .................................... 10163831

(51) Int. Cl.
*A61F 2/24* (2006.01)

(52) U.S. Cl.
CPC .... *A61F 2/2418* (2013.01); *A61F 2220/0025* (2013.01); *A61F 2220/0075* (2013.01); *A61F 2240/001* (2013.01)

(58) Field of Classification Search
CPC .... A61F 2/2412; A61F 2/2418; A61F 2/2409; A61F 2220/0025; A61F 2220/0075;
(Continued)

(56) References Cited

U.S. PATENT DOCUMENTS

| | | |
|---|---|---|
| 15,192 A | 6/1856 | Peale |
| 388,776 A | 8/1888 | Hall |

(Continued)

FOREIGN PATENT DOCUMENTS

| | | |
|---|---|---|
| AU | 757647 B2 | 2/2003 |
| AU | 776895 B2 | 9/2004 |

(Continued)

OTHER PUBLICATIONS

US 6,331,185 B1, 12/2001, Gambale et al. (withdrawn)

(Continued)

*Primary Examiner* — Suba Ganesan
(74) *Attorney, Agent, or Firm* — Greenberg Traurig, LLP; Christopher C. Bolten; Robert D. Ward

(57) ABSTRACT

The invention relates to a prosthetic heart valve (100) for an endoprosthesis (1) used in the treatment of a stenotic cardiac valve and/or a cardiac valve insufficiency. The prosthetic heart valve (100) comprises of a plurality of leaflets (102), which consist of a natural and/or synthetic material and have a first opened position for opening the heart chamber and a second closed position for closing the heart chamber, the leaflets (102) being able to switch between their first and second position in response to the blood flow through the heart. In addition, the prosthetic heart valve (100) comprises a leaflet support portion (103), consisting of biological and/or synthetic material for mounting of the prosthetic heart valve (100) to a stent (10), and a bendable transition area (104) which forms a junction between the leaflets (102) and the leaflet support portion (103), the transition area (104) progressing essentially in a U-shaped manner similar to a cusp shape of a natural aortic or pulmonary heart valve for reducing tissue stresses during opening and closing motion of the leaflets (102). The invention further relates to
(Continued)

Figure 1:
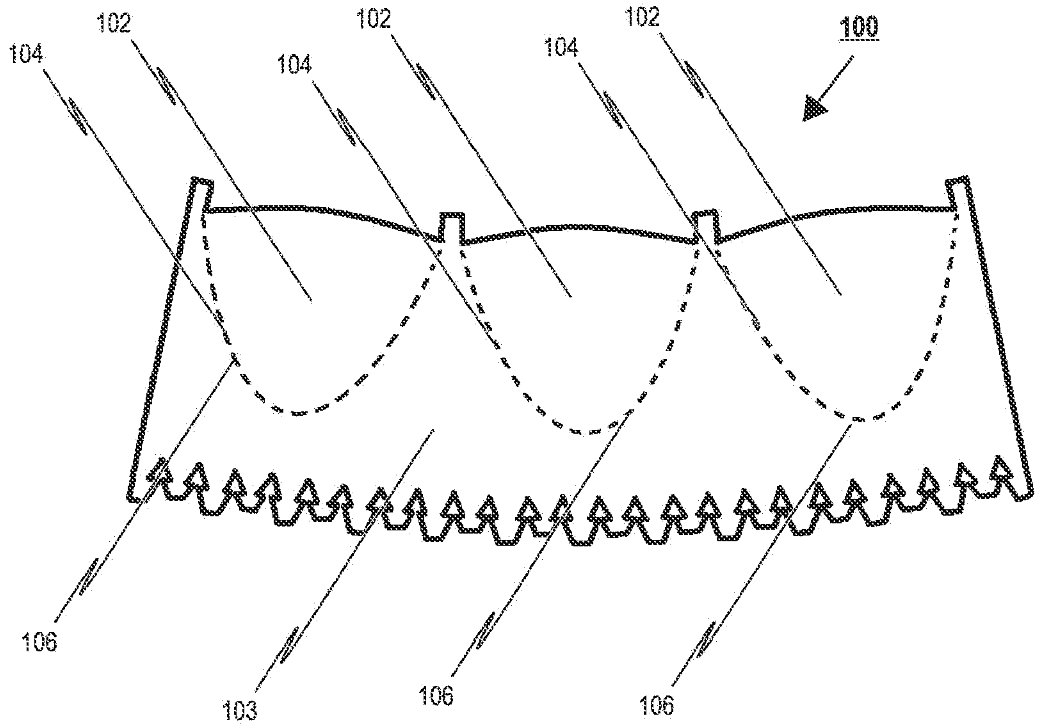

an endoprosthesis (1) comprising a prosthetic heart valve (100) and a stent (10).

20 Claims, 28 Drawing Sheets

Related U.S. Application Data continuation of application No. 15/658,955, filed on Jul. 25, 2017, now Pat. No. 10,603,164, which is a continuation of application No. 13/114,582, filed on May 24, 2011, now Pat. No. 9,744,031.

(60) Provisional application No. 61/348,036, filed on May 25, 2010.

(58) Field of Classification Search
CPC ........ A61F 2240/001; A61F 2230/0056; A61F 2230/0065
See application file for complete search history.

(56) References Cited

U.S. PATENT DOCUMENTS

| | | | |
|---|---|---|---|
| 944,214 | A | 12/1909 | Rydquist |
| 2,121,182 | A | 6/1938 | Benjamin |
| 2,669,896 | A | 2/1954 | Clough |
| 2,682,057 | A | 6/1954 | Lord |
| 2,701,559 | A | 2/1955 | Cooper |
| 2,832,078 | A | 4/1958 | Williams |
| 3,029,819 | A | 4/1962 | Edward et al. |
| 3,099,016 | A | 7/1963 | Lowell et al. |
| 3,113,586 | A | 12/1963 | Edmark, Jr. et al. |
| 3,130,418 | A | 4/1964 | Head et al. |
| 3,143,742 | A | 8/1964 | Cromie |
| 3,210,836 | A | 10/1965 | Johanson et al. |
| 3,221,006 | A | 11/1965 | Moore et al. |
| 3,334,629 | A | 8/1967 | Cohn |
| 3,365,728 | A | 1/1968 | Lowell et al. |
| 3,367,364 | A | 2/1968 | Cruz, Jr. et al. |
| 3,409,013 | A | 11/1968 | Henry et al. |
| 3,445,916 | A | 5/1969 | Schulte et al. |
| 3,540,431 | A | 11/1970 | Mobin-Uddin et al. |
| 3,548,417 | A | 12/1970 | Kischer et al. |
| 3,570,014 | A | 3/1971 | Hancock et al. |
| 3,574,865 | A | 4/1971 | Hamaker |
| 3,587,115 | A | 6/1971 | Shiley et al. |
| 3,592,184 | A | 7/1971 | Watkins et al. |
| 3,628,535 | A | 12/1971 | Ostrowsky et al. |
| 3,642,004 | A | 2/1972 | Osthagen et al. |
| 3,657,744 | A | 4/1972 | Ersek |
| 3,671,979 | A | 6/1972 | Moulopoulos |
| 3,714,671 | A | 2/1973 | Edwards et al. |
| 3,725,961 | A | 4/1973 | Magovern et al. |
| 3,755,823 | A | 9/1973 | Hancock |
| 3,795,246 | A | 3/1974 | Sturgeon |
| 3,839,741 | A | 10/1974 | Haller |
| 3,868,956 | A | 3/1975 | Alfidi et al. |
| 3,874,388 | A | 4/1975 | King et al. |
| 3,983,581 | A | 10/1976 | Angell et al. |
| 3,997,923 | A | 12/1976 | Possis |
| 4,035,849 | A | 7/1977 | Angell et al. |
| 4,056,854 | A | 11/1977 | Boretos et al. |
| 4,078,268 | A | 3/1978 | Possis |
| 4,084,268 | A | 4/1978 | Ionescu et al. |
| 4,106,126 | A | 8/1978 | Traenkle |
| 4,106,129 | A | 8/1978 | Carpentier et al. |
| 4,118,806 | A | 10/1978 | Porier et al. |
| 4,164,046 | A | 8/1979 | Cooley |
| 4,182,446 | A | 1/1980 | Penny |
| 4,191,218 | A | 3/1980 | Clark et al. |
| 4,214,587 | A | 7/1980 | Sakura, Jr. |
| 4,215,871 | A | 8/1980 | Hirsch et al. |
| 4,222,126 | A | 9/1980 | Boretos et al. |
| 4,233,690 | A | 11/1980 | Akins |
| 4,261,342 | A | 4/1981 | Aranguren Duo |
| 4,263,680 | A | 4/1981 | Reul et al. |
| 4,265,694 | A | 5/1981 | Boretos et al. |
| 4,291,420 | A | 9/1981 | Reul |
| 4,297,749 | A | 11/1981 | Davis et al. |
| 4,319,831 | A | 3/1982 | Matsui et al. |
| RE30,912 | E | 4/1982 | Hancock |
| 4,323,358 | A | 4/1982 | Lentz et al. |
| 4,326,306 | A | 4/1982 | Poler |
| 4,339,831 | A | 7/1982 | Johnson |
| 4,343,048 | A | 8/1982 | Ross et al. |
| 4,345,340 | A | 8/1982 | Rosen |
| 4,350,492 | A | 9/1982 | Wright et al. |
| 4,373,216 | A | 2/1983 | Klawitter |
| 4,388,735 | A | 6/1983 | Ionescu et al. |
| 4,406,022 | A | 9/1983 | Roy |
| 4,423,809 | A | 1/1984 | Mazzocco |
| 4,425,908 | A | 1/1984 | Simon |
| 4,441,215 | A | 4/1984 | Kaster |
| 4,441,216 | A | 4/1984 | Ionescu et al. |
| 4,470,157 | A | 9/1984 | Love |
| 4,484,579 | A | 11/1984 | Meno et al. |
| 4,485,816 | A | 12/1984 | Krumme |
| 4,491,986 | A | 1/1985 | Gabbay |
| 4,501,030 | A | 2/1985 | Lane |
| 4,502,488 | A | 3/1985 | Degironimo et al. |
| 4,531,943 | A | 7/1985 | Van Tassel et al. |
| 4,535,483 | A | 8/1985 | Klawitter et al. |
| 4,546,499 | A | 10/1985 | Possis et al. |
| 4,562,597 | A | 1/1986 | Possis et al. |
| 4,574,803 | A | 3/1986 | Storz |
| 4,580,568 | A | 4/1986 | Gianturco |
| 4,592,340 | A | 6/1986 | Boyles |
| 4,602,911 | A | 7/1986 | Ahmadi et al. |
| 4,605,407 | A | 8/1986 | Black et al. |
| 4,610,688 | A | 9/1986 | Silvestrini et al. |
| 4,612,011 | A | 9/1986 | Kautzky |
| 4,617,932 | A | 10/1986 | Kornberg |
| 4,619,246 | A | 10/1986 | Molgaard-Nielsen et al. |
| 4,643,732 | A | 2/1987 | Pietsch et al. |
| 4,647,283 | A | 3/1987 | Carpentier et al. |
| 4,648,881 | A | 3/1987 | Carpentier et al. |
| 4,655,218 | A | 4/1987 | Kulik et al. |
| 4,655,771 | A | 4/1987 | Wallsten |
| 4,662,885 | A | 5/1987 | DiPisa, Jr. |
| 4,665,906 | A | 5/1987 | Jervis |
| 4,665,918 | A | 5/1987 | Garza et al. |
| 4,680,031 | A | 7/1987 | Alonso |
| 4,681,908 | A | 7/1987 | Broderick et al. |
| 4,687,483 | A | 8/1987 | Fisher et al. |
| 4,692,164 | A | 9/1987 | Dzemeshkevich et al. |
| 4,705,516 | A | 11/1987 | Barone et al. |
| 4,710,192 | A | 12/1987 | Liotta et al. |
| 4,733,665 | A | 3/1988 | Palmaz |
| 4,755,181 | A | 7/1988 | Igoe |
| 4,759,758 | A | 7/1988 | Gabbay |
| 4,769,029 | A | 9/1988 | Patel |
| 4,777,951 | A | 10/1988 | Cribier et al. |
| 4,787,899 | A | 11/1988 | Lazarus |
| 4,787,901 | A | 11/1988 | Baykut |
| 4,796,629 | A | 1/1989 | Grayzel |
| 4,797,901 | A | 1/1989 | Goerne et al. |
| 4,806,595 | A | 2/1989 | Noishiki et al. |
| 4,819,751 | A | 4/1989 | Shimada et al. |
| 4,829,990 | A | 5/1989 | Thuroff et al. |
| 4,834,755 | A | 5/1989 | Silvestrini et al. |
| 4,846,830 | A | 7/1989 | Knoch et al. |
| 4,851,001 | A | 7/1989 | Taheri |
| 4,856,516 | A | 8/1989 | Hillstead |
| 4,865,600 | A | 9/1989 | Carpentier et al. |
| 4,872,874 | A | 10/1989 | Taheri |
| 4,873,978 | A | 10/1989 | Ginsburg |
| 4,878,495 | A | 11/1989 | Grayzel |
| 4,878,906 | A | 11/1989 | Lindemann et al. |
| 4,883,458 | A | 11/1989 | Shiber |
| 4,885,005 | A | 12/1989 | Nashef et al. |
| 4,909,252 | A | 3/1990 | Goldberger |
| 4,917,102 | A | 4/1990 | Miller et al. |
| 4,922,905 | A | 5/1990 | Strecker |

(56) References Cited

U.S. PATENT DOCUMENTS 4,927,426 A 5/1990 Dretler
4,950,227 A 8/1990 Savin et al.
4,953,553 A 9/1990 Tremulis
4,954,126 A 9/1990 Wallsten
4,966,604 A 10/1990 Reiss
4,969,890 A 11/1990 Sugita et al.
4,979,939 A 12/1990 Shiber
4,986,830 A 1/1991 Owens et al.
4,994,077 A 2/1991 Dobben
5,002,556 A 3/1991 Ishida et al.
5,002,559 A 3/1991 Tower
5,002,566 A 3/1991 Carpentier et al.
5,007,896 A 4/1991 Shiber
5,026,366 A 6/1991 Leckrone
5,026,377 A 6/1991 Burton et al.
5,032,128 A 7/1991 Alonso
5,035,706 A 7/1991 Giantureo et al.
5,037,434 A 8/1991 Lane
5,047,041 A 9/1991 Samuels
5,053,008 A 10/1991 Bajaj
5,059,177 A 10/1991 Towne et al.
5,061,273 A 10/1991 Yock
5,061,277 A 10/1991 Carpentier et al.
5,064,435 A 11/1991 Porter
5,078,720 A 1/1992 Burton et al.
5,080,668 A 1/1992 Bolz et al.
5,085,635 A 2/1992 Cragg
5,089,015 A 2/1992 Ross
5,094,661 A 3/1992 Levy et al.
5,104,399 A 4/1992 Lazarus
5,104,407 A 4/1992 Lam et al.
5,108,425 A 4/1992 Hwang
5,122,154 A 6/1992 Rhodes
5,132,473 A 7/1992 Furutaka et al.
5,141,494 A 8/1992 Danforth et al.
5,143,987 A 9/1992 Hansel et al.
5,147,388 A 9/1992 Yamazaki
5,152,771 A 10/1992 Sabbaghian et al.
5,159,937 A 11/1992 Tremulis
5,161,547 A 11/1992 Tower
5,163,953 A 11/1992 Vince
5,163,955 A 11/1992 Love et al.
5,167,628 A 12/1992 Boyles
5,178,632 A 1/1993 Hanson
5,192,301 A 3/1993 Kamiya et al.
5,193,546 A 3/1993 Shaknovich
5,197,979 A 3/1993 Quintero et al.
5,201,757 A 4/1993 Heyn et al.
5,207,695 A 5/1993 Trout, III
5,209,741 A 5/1993 Spaeth
5,211,183 A 5/1993 Wilson
5,215,541 A 6/1993 Nashef et al.
5,217,481 A 6/1993 Barbara
5,217,483 A 6/1993 Tower
5,232,445 A 8/1993 Bonzel
5,234,447 A 8/1993 Kaster et al.
5,234,456 A 8/1993 Silvestrini
5,238,004 A 8/1993 Sahatjian et al.
5,258,008 A 11/1993 Wilk
5,258,023 A 11/1993 Reger
5,258,042 A 11/1993 Mehta
5,272,909 A 12/1993 Nguyen et al.
5,275,580 A 1/1994 Yamazaki
5,279,612 A 1/1994 Eberhardt
5,282,847 A 2/1994 Trescony et al.
5,287,861 A 2/1994 Wilk
5,295,958 A 3/1994 Shturman
5,327,774 A 7/1994 Nguyen et al.
5,330,486 A 7/1994 Wilk
5,330,500 A 7/1994 Song
5,332,402 A 7/1994 Teitelbaum
5,336,258 A 8/1994 Quintero et al.
5,342,348 A 8/1994 Kaplan
5,344,426 A 9/1994 Lau et al.
5,344,427 A 9/1994 Cottenceau et al.
5,344,442 A 9/1994 Deac
5,350,398 A 9/1994 Pavcnik et al.
5,350,399 A 9/1994 Erlebacher et al.
5,352,240 A 10/1994 Ross
5,354,330 A 10/1994 Hanson et al.
5,360,444 A 11/1994 Kusuhara
5,368,608 A 11/1994 Levy et al.
5,370,685 A 12/1994 Stevens
5,380,054 A 1/1995 Galvis
5,387,235 A 2/1995 Chuter
5,389,096 A 2/1995 Aita et al.
5,389,106 A 2/1995 Tower
5,397,351 A 3/1995 Pavcnik et al.
5,397,355 A 3/1995 Marin et al.
5,409,019 A 4/1995 Wilk
5,411,552 A 5/1995 Andersen et al.
5,415,633 A 5/1995 Lazarus et al.
5,425,739 A 6/1995 Jessen
5,425,762 A 6/1995 Muller
5,429,144 A 7/1995 Wilk
5,431,676 A 7/1995 Dubrul et al.
5,433,723 A 7/1995 Lindenberg et al.
5,443,446 A 8/1995 Shturman
5,443,449 A 8/1995 Buelna
5,443,477 A 8/1995 Marin et al.
5,443,495 A 8/1995 Buscemi et al.
5,443,499 A 8/1995 Schmitt
5,449,384 A 9/1995 Johnson
5,456,712 A 10/1995 Maginot
5,456,713 A 10/1995 Chuter
5,464,449 A 11/1995 Ryan et al.
5,469,868 A 11/1995 Reger
5,470,320 A 11/1995 Tiefenbrun et al.
5,476,506 A 12/1995 Lunn
5,476,508 A 12/1995 Amstrup
5,476,510 A 12/1995 Eberhardt et al.
5,480,423 A 1/1996 Ravenscroft et al.
5,480,424 A 1/1996 Cox
5,486,193 A 1/1996 Bourne et al.
5,487,760 A 1/1996 Villafana
5,489,294 A 2/1996 McVenes et al.
5,489,297 A 2/1996 Duran
5,489,298 A 2/1996 Love et al.
5,496,346 A 3/1996 Horzewski et al.
5,499,995 A 3/1996 Teirstein
5,500,014 A 3/1996 Quijano et al.
5,500,015 A 3/1996 Deac
5,507,767 A 4/1996 Maeda et al.
5,509,930 A 4/1996 Love
5,522,881 A 6/1996 Lentz
5,527,337 A 6/1996 Stack et al.
5,530,949 A 6/1996 Koda et al.
5,534,007 A 7/1996 St. Germain et al.
5,540,712 A 7/1996 Kleshinski et al.
5,545,133 A 8/1996 Burns et al.
5,545,209 A 8/1996 Roberts et al.
5,545,211 A 8/1996 An et al.
5,545,214 A 8/1996 Stevens
5,549,665 A 8/1996 Vesely et al.
5,549,666 A 8/1996 Hata et al.
5,554,119 A 9/1996 Harrison et al.
5,554,185 A 9/1996 Block et al.
5,569,274 A 10/1996 Rapacki et al.
5,571,167 A 11/1996 Maginot
5,571,174 A 11/1996 Love et al.
5,571,175 A 11/1996 Vanney et al.
5,571,215 A 11/1996 Sterman et al.
5,573,520 A 11/1996 Schwartz et al.
5,575,818 A 11/1996 Pinchuk
5,580,922 A 12/1996 Park et al.
5,591,185 A 1/1997 Kilmer et al.
5,591,195 A 1/1997 Taheri et al.
5,593,434 A 1/1997 Williams
5,595,571 A 1/1997 Jaffe et al.
5,596,471 A 1/1997 Hanlin
5,607,464 A 3/1997 Trescony et al.
5,607,465 A 3/1997 Camilli
5,609,626 A 3/1997 Quijano et al.
5,613,982 A 3/1997 Goldstein

(56) References Cited

U.S. PATENT DOCUMENTS 5,618,299 A 4/1997 Khosravi et al.
5,626,553 A 5/1997 Frassica et al.
5,628,784 A 5/1997 Strecker
5,632,778 A 5/1997 Goldstein
5,634,942 A 6/1997 Chevillon et al.
5,643,278 A 7/1997 Wijay
5,645,559 A 7/1997 Hachtman et al.
5,653,684 A 8/1997 Laptewicz et al.
5,653,745 A 8/1997 Trescony et al.
5,653,749 A 8/1997 Love et al.
5,655,548 A 8/1997 Nelson et al.
5,662,124 A 9/1997 Wilk
5,662,671 A 9/1997 Barbut et al.
5,662,703 A 9/1997 Yurek et al.
5,665,115 A 9/1997 Cragg
5,667,523 A 9/1997 Bynon et al.
5,674,277 A 10/1997 Freitag
5,674,298 A 10/1997 Levy et al.
5,679,112 A 10/1997 Levy et al.
5,681,345 A 10/1997 Euteneuer
5,682,906 A 11/1997 Sterman et al.
5,683,451 A 11/1997 Lenker et al.
5,690,644 A 11/1997 Yurek et al.
5,693,083 A 12/1997 Baker et al.
5,693,088 A 12/1997 Lazarus
5,693,310 A 12/1997 Gries et al.
5,695,498 A 12/1997 Tower
5,697,972 A 12/1997 Kim et al.
5,700,269 A 12/1997 Pinchuk et al.
5,702,368 A 12/1997 Stevens et al.
5,709,713 A 1/1998 Evans et al.
5,713,917 A 2/1998 Leonhardt et al.
5,713,950 A 2/1998 Cox
5,713,951 A 2/1998 Garrison et al.
5,713,953 A 2/1998 Vallana et al.
5,716,370 A 2/1998 Williamson, IV et al.
5,716,417 A 2/1998 Girard et al.
5,718,725 A 2/1998 Sterman et al.
5,720,391 A 2/1998 Dohm et al.
5,720,776 A 2/1998 Chuter et al.
5,725,549 A 3/1998 Lam
5,725,550 A 3/1998 Nadal
5,728,068 A 3/1998 Leone et al.
5,728,151 A 3/1998 Garrison et al.
5,733,267 A 3/1998 Del Toro
5,733,325 A 3/1998 Robinson et al.
5,735,842 A 4/1998 Krueger et al.
5,746,476 A 5/1998 Novak et al.
5,746,709 A 5/1998 Rom et al.
5,746,765 A 5/1998 Kleshinski et al.
5,746,775 A 5/1998 Levy et al.
5,749,890 A 5/1998 Shaknovich
5,749,921 A 5/1998 Lenker et al.
5,755,682 A 5/1998 Knudson et al.
5,755,777 A 5/1998 Chuter
5,755,783 A 5/1998 Stobie et al.
5,756,476 A 5/1998 Epstein et al.
5,758,663 A 6/1998 Wilk et al.
5,766,151 A 6/1998 Valley et al.
5,769,780 A 6/1998 Hata et al.
5,769,812 A 6/1998 Stevens et al.
5,769,882 A 6/1998 Fogarty et al.
5,769,887 A 6/1998 Brown et al.
5,772,609 A 6/1998 Nguyen et al.
5,776,188 A 7/1998 Shepherd et al.
5,782,809 A 7/1998 Umeno et al.
5,782,904 A 7/1998 White et al.
5,795,331 A 8/1998 Cragg et al.
5,797,946 A 8/1998 Chin
5,797,960 A 8/1998 Stevens et al.
5,799,661 A 9/1998 Boyd et al.
5,800,456 A 9/1998 Maeda et al.
5,800,508 A 9/1998 Goicoechea et al.
5,800,531 A 9/1998 Cosgrove et al.
5,807,327 A 9/1998 Green et al.
5,807,384 A 9/1998 Mueller
5,807,405 A 9/1998 Vanney et al.
5,810,836 A 9/1998 Hussein et al.
5,814,016 A 9/1998 Valley et al.
5,817,113 A 10/1998 Gifford, III et al.
5,817,126 A 10/1998 Imran
5,823,956 A 10/1998 Roth et al.
5,824,037 A 10/1998 Fogarty et al.
5,824,038 A 10/1998 Wall
5,824,041 A 10/1998 Lenker et al.
5,824,043 A 10/1998 Cottone, Jr.
5,824,053 A 10/1998 Khosravi et al.
5,824,055 A 10/1998 Spiridigliozzi et al.
5,824,056 A 10/1998 Rosenberg
5,824,061 A 10/1998 Quijano et al.
5,824,063 A 10/1998 Cox
5,824,064 A 10/1998 Taheri
5,824,071 A 10/1998 Nelson et al.
5,824,080 A 10/1998 Lamuraglia
5,829,447 A 11/1998 Stevens et al.
5,830,222 A 11/1998 Makower
5,836,869 A 11/1998 Kudo et al.
5,840,081 A 11/1998 Andersen et al.
5,841,382 A 11/1998 Walden et al.
5,843,158 A 12/1998 Lenker et al.
5,843,161 A 12/1998 Solovay
5,843,181 A 12/1998 Jaffe et al.
5,851,232 A 12/1998 Lois
5,853,419 A 12/1998 Imran
5,853,420 A 12/1998 Chevillon et al.
5,855,210 A 1/1999 Sterman et al.
5,855,597 A 1/1999 Jayaraman
5,855,600 A 1/1999 Alt
5,855,601 A 1/1999 Bessler et al.
5,855,602 A 1/1999 Angell
5,860,966 A 1/1999 Tower
5,860,996 A 1/1999 Urban et al.
5,861,024 A 1/1999 Rashidi
5,861,028 A 1/1999 Angell
5,865,723 A 2/1999 Love
5,868,783 A 2/1999 Tower
5,873,812 A 2/1999 Ciana et al.
5,873,906 A 2/1999 Lau et al.
5,876,373 A 3/1999 Giba et al.
5,876,419 A 3/1999 Carpenter et al.
5,876,434 A 3/1999 Flomenblit et al.
5,876,448 A 3/1999 Thompson et al.
5,878,751 A 3/1999 Hussein et al.
5,880,242 A 3/1999 Hu et al.
5,885,228 A 3/1999 Rosenman et al.
5,885,238 A 3/1999 Stevens et al.
5,885,259 A 3/1999 Berg
5,888,201 A 3/1999 Stinson et al.
5,891,160 A 4/1999 Williamson, IV et al.
5,891,191 A 4/1999 Stinson
5,895,399 A 4/1999 Barbut et al.
5,895,420 A 4/1999 Mirsch, II et al.
5,899,936 A 5/1999 Goldstein
5,906,619 A 5/1999 Olson et al.
5,907,893 A 6/1999 Zadno-Azizi et al.
5,908,028 A 6/1999 Wilk
5,908,029 A 6/1999 Knudson et al.
5,908,451 A 6/1999 Yeo
5,908,452 A 6/1999 Bokros et al.
5,910,144 A 6/1999 Hayashi
5,910,154 A 6/1999 Tsugita et al.
5,911,734 A 6/1999 Tsugita et al.
5,911,752 A 6/1999 Dustrude et al.
5,913,842 A 6/1999 Boyd et al.
5,916,193 A 6/1999 Stevens et al.
5,922,022 A 7/1999 Nash et al.
5,924,424 A 7/1999 Stevens et al.
5,925,012 A 7/1999 Murphy-Chutorian et al.
5,925,063 A 7/1999 Khosravi
5,928,281 A 7/1999 Huynh et al.
5,931,848 A 8/1999 Saadat
5,935,119 A 8/1999 Guy et al.
5,935,161 A 8/1999 Robinson et al.
5,935,163 A 8/1999 Gabbay

(56) References Cited

U.S. PATENT DOCUMENTS 5,938,632 A 8/1999 Ellis
5,938,697 A 8/1999 Killion et al.
5,941,908 A 8/1999 Goldsteen et al.
5,944,019 A 8/1999 Knudson et al.
5,944,738 A 8/1999 Amplatz et al.
5,948,017 A 9/1999 Taheri
5,954,764 A 9/1999 Parodi
5,954,766 A 9/1999 Zadno-Azizi et al.
5,957,949 A 9/1999 Leonhardt et al.
5,961,549 A 10/1999 Nguyen et al.
5,964,405 A 10/1999 Benary et al.
5,964,798 A 10/1999 Imran
5,968,064 A 10/1999 Selmon et al.
5,968,068 A 10/1999 Dehdashtian et al.
5,968,070 A 10/1999 Bley et al.
5,971,993 A 10/1999 Hussein et al.
5,975,949 A 11/1999 Holliday et al.
5,976,153 A 11/1999 Fischell et al.
5,976,155 A 11/1999 Foreman et al.
5,976,174 A 11/1999 Ruiz
5,976,178 A 11/1999 Goldsteen et al.
5,976,192 A 11/1999 McIntyre et al.
5,976,650 A 11/1999 Campbell et al.
5,979,455 A 11/1999 Maginot
5,980,455 A 11/1999 Daniel et al.
5,980,533 A 11/1999 Holman
5,980,548 A 11/1999 Evans et al.
5,984,956 A 11/1999 Tweden et al.
5,984,957 A 11/1999 Laptewicz, Jr. et al.
5,984,959 A 11/1999 Robertson et al.
5,984,964 A 11/1999 Roberts et al.
5,987,344 A 11/1999 West
5,989,276 A 11/1999 Houser et al.
5,989,287 A 11/1999 Yang et al.
5,993,469 A 11/1999 McKenzie et al.
5,993,481 A 11/1999 Marcade et al.
5,997,525 A 12/1999 March et al.
5,997,557 A 12/1999 Barbut et al.
5,997,563 A 12/1999 Kretzers
5,997,573 A 12/1999 Quijano et al.
5,999,678 A 12/1999 Murphy-Chutorian et al.
6,001,123 A 12/1999 Lau
6,001,126 A 12/1999 Nguyen-Thien-Nhon
6,004,261 A 12/1999 Sinofsky et al.
6,004,347 A 12/1999 McNamara et al.
6,004,348 A 12/1999 Banas et al.
6,007,543 A 12/1999 Ellis et al.
6,010,449 A 1/2000 Selmon et al.
6,010,522 A 1/2000 Barbut et al.
6,010,530 A 1/2000 Goicoechea
6,010,531 A 1/2000 Donlon et al.
6,012,457 A 1/2000 Lesh
6,013,854 A 1/2000 Moriuchi
6,015,431 A 1/2000 Thornton et al.
6,019,777 A 2/2000 Mackenzie
6,019,778 A 2/2000 Wilson et al.
6,022,370 A 2/2000 Tower
6,026,814 A 2/2000 LaFontaine et al.
6,027,476 A 2/2000 Sterman et al.
6,027,520 A 2/2000 Tsugita et al.
6,027,525 A 2/2000 Suh et al.
6,029,671 A 2/2000 Stevens et al.
6,029,672 A 2/2000 Vanney et al.
6,033,582 A 3/2000 Lee et al.
6,035,856 A 3/2000 LaFontaine et al.
6,036,677 A 3/2000 Javier, Jr. et al.
6,036,697 A 3/2000 DiCaprio
6,042,554 A 3/2000 Rosenman et al.
6,042,581 A 3/2000 Ryan et al.
6,042,589 A 3/2000 Marianne
6,042,598 A 3/2000 Tsugita et al.
6,042,607 A 3/2000 Williamson, IV et al.
6,045,565 A 4/2000 Ellis et al.
6,051,014 A 4/2000 Jang
6,051,104 A 4/2000 Oriaran et al.
6,053,924 A 4/2000 Hussein
6,053,942 A 4/2000 Eno et al.
6,056,743 A 5/2000 Ellis et al.
6,059,809 A 5/2000 Amor et al.
6,059,827 A 5/2000 Fenton, Jr.
6,066,160 A 5/2000 Colvin et al.
6,067,988 A 5/2000 Mueller
6,068,638 A 5/2000 Makower
6,071,292 A 6/2000 Makower et al.
6,074,416 A 6/2000 Berg et al.
6,074,417 A 6/2000 Peredo
6,074,418 A 6/2000 Buchanan et al.
6,076,529 A 6/2000 Vanney et al.
6,076,742 A 6/2000 Benary
6,077,297 A 6/2000 Robinson et al.
6,079,414 A 6/2000 Roth
6,080,163 A 6/2000 Hussein et al.
6,080,170 A 6/2000 Nash et al.
6,083,257 A 7/2000 Taylor et al.
6,091,042 A 7/2000 Benary
6,092,526 A 7/2000 LaFontaine et al.
6,092,529 A 7/2000 Cox
6,093,166 A 7/2000 Knudson et al.
6,093,177 A 7/2000 Javier, Jr. et al.
6,093,185 A 7/2000 Ellis et al.
6,093,203 A 7/2000 Uflacker
6,093,530 A 7/2000 McIlroy et al.
6,096,074 A 8/2000 Pedros
6,102,941 A 8/2000 Tweden et al.
6,102,944 A 8/2000 Huynh et al.
6,106,550 A 8/2000 Magovern et al.
6,110,191 A 8/2000 Dehdashtian et al.
6,110,198 A 8/2000 Fogarty et al.
6,110,201 A 8/2000 Quijano et al.
6,113,612 A 9/2000 Swanson et al.
6,113,630 A 9/2000 Vanney et al.
6,113,823 A 9/2000 Eno
6,117,169 A 9/2000 Moe
6,120,520 A 9/2000 Saadat et al.
6,120,534 A 9/2000 Ruiz
6,123,682 A 9/2000 Knudson et al.
6,123,723 A 9/2000 Konya et al.
6,125,852 A 10/2000 Stevens et al.
6,126,649 A 10/2000 Vantassel et al.
6,126,654 A 10/2000 Giba et al.
6,126,685 A 10/2000 Lenker et al.
6,126,686 A 10/2000 Badylak et al.
6,132,451 A 10/2000 Payne et al.
6,132,473 A 10/2000 Williams et al.
6,132,986 A 10/2000 Pathak et al.
6,139,510 A 10/2000 Palermo
6,139,541 A 10/2000 Vanney et al.
6,142,987 A 11/2000 Tsugita
6,143,021 A 11/2000 Staehle
6,143,987 A 11/2000 Makita
6,146,366 A 11/2000 Schachar
6,146,415 A 11/2000 Fitz
6,146,417 A 11/2000 Ischinger
6,152,937 A 11/2000 Peterson et al.
6,152,956 A 11/2000 Pierce
6,155,264 A 12/2000 Ressemann et al.
6,156,031 A 12/2000 Aita et al.
6,156,055 A 12/2000 Ravenscroft
6,156,531 A 12/2000 Pathak et al.
6,157,852 A 12/2000 Selmon et al.
6,159,225 A 12/2000 Makower
6,159,239 A 12/2000 Greenhalgh
6,162,208 A 12/2000 Hipps
6,162,245 A 12/2000 Jayaraman
6,165,185 A 12/2000 Shennib et al.
6,165,188 A 12/2000 Saadat et al.
6,165,200 A 12/2000 Tsugita et al.
6,165,209 A 12/2000 Patterson et al.
6,167,605 B1 1/2001 Morales
6,168,579 B1 1/2001 Tsugita
6,168,614 B1 1/2001 Andersen et al.
6,168,616 B1 1/2001 Brown, III
6,171,251 B1 1/2001 Mueller et al.
6,171,327 B1 1/2001 Daniel et al.

(56) References Cited

U.S. PATENT DOCUMENTS

| | | | |
|---|---|---|---|
| 6,171,335 | B1 | 1/2001 | Wheatley et al. |
| 6,177,514 | B1 | 1/2001 | Pathak et al. |
| 6,179,859 | B1 | 1/2001 | Bates et al. |
| 6,182,664 | B1 | 2/2001 | Cosgrove |
| 6,182,668 | B1 | 2/2001 | Tweden et al. |
| 6,183,481 | B1 | 2/2001 | Lee et al. |
| 6,186,972 | B1 | 2/2001 | Nelson et al. |
| 6,187,016 | B1 | 2/2001 | Hedges et al. |
| 6,190,353 | B1 | 2/2001 | Makower et al. |
| 6,190,393 | B1 | 2/2001 | Bevier et al. |
| 6,190,405 | B1 | 2/2001 | Culombo et al. |
| 6,193,726 | B1 | 2/2001 | Vanney |
| 6,193,734 | B1 | 2/2001 | Bolduc et al. |
| 6,196,230 | B1 | 3/2001 | Hall et al. |
| 6,197,050 | B1 | 3/2001 | Eno et al. |
| 6,197,053 | B1 | 3/2001 | Cosgrove et al. |
| 6,197,296 | B1 | 3/2001 | Davies et al. |
| 6,197,324 | B1 | 3/2001 | Crittenden |
| 6,200,311 | B1 | 3/2001 | Danek et al. |
| 6,200,336 | B1 | 3/2001 | Pavcnik et al. |
| 6,203,550 | B1 | 3/2001 | Olson |
| 6,203,556 | B1 | 3/2001 | Evans et al. |
| 6,206,888 | B1 | 3/2001 | Bicek et al. |
| 6,206,911 | B1 | 3/2001 | Milo |
| 6,210,408 | B1 | 4/2001 | Chandrasekaran et al. |
| 6,210,957 | B1 | 4/2001 | Carpentier et al. |
| 6,213,126 | B1 | 4/2001 | LaFontaine et al. |
| 6,214,036 | B1 | 4/2001 | Letendre et al. |
| 6,214,041 | B1 | 4/2001 | Tweden et al. |
| 6,214,054 | B1 | 4/2001 | Cunanan et al. |
| 6,214,055 | B1 | 4/2001 | Simionescu et al. |
| 6,217,527 | B1 | 4/2001 | Selmon et al. |
| 6,217,549 | B1 | 4/2001 | Selmon et al. |
| 6,217,575 | B1 | 4/2001 | DeVore et al. |
| 6,217,609 | B1 | 4/2001 | Haverkost |
| 6,218,662 | B1 | 4/2001 | Tchakarov et al. |
| 6,221,006 | B1 | 4/2001 | Dubrul et al. |
| 6,221,049 | B1 | 4/2001 | Selmon et al. |
| 6,221,091 | B1 | 4/2001 | Khosravi |
| 6,221,096 | B1 | 4/2001 | Aiba et al. |
| 6,221,100 | B1 | 4/2001 | Strecker |
| 6,223,752 | B1 | 5/2001 | Vanney et al. |
| 6,224,584 | B1 | 5/2001 | March et al. |
| 6,231,544 | B1 | 5/2001 | Tsugita et al. |
| 6,231,546 | B1 | 5/2001 | Milo et al. |
| 6,231,551 | B1 | 5/2001 | Barbut |
| 6,231,587 | B1 | 5/2001 | Makower |
| 6,231,602 | B1 | 5/2001 | Carpentier et al. |
| 6,235,000 | B1 | 5/2001 | Milo et al. |
| 6,237,607 | B1 | 5/2001 | Vanney et al. |
| 6,238,406 | B1 | 5/2001 | Ellis et al. |
| 6,241,667 | B1 | 6/2001 | Vetter et al. |
| 6,241,738 | B1 | 6/2001 | Dereume |
| 6,241,741 | B1 | 6/2001 | Duhaylongsod et al. |
| 6,241,757 | B1 | 6/2001 | An et al. |
| 6,245,102 | B1 | 6/2001 | Jayaraman |
| 6,245,103 | B1 | 6/2001 | Stinson |
| 6,245,105 | B1 | 6/2001 | Nguyen et al. |
| 6,248,112 | B1 | 6/2001 | Gambale et al. |
| 6,248,116 | B1 | 6/2001 | Chevillon et al. |
| 6,250,305 | B1 | 6/2001 | Tweden |
| 6,251,079 | B1 | 6/2001 | Gambale et al. |
| 6,251,104 | B1 | 6/2001 | Kesten et al. |
| 6,251,116 | B1 | 6/2001 | Shennib et al. |
| 6,251,135 | B1 | 6/2001 | Stinson et al. |
| 6,251,418 | B1 | 6/2001 | Ahern et al. |
| 6,253,768 | B1 | 7/2001 | Wilk |
| 6,253,769 | B1 | 7/2001 | LaFontaine et al. |
| 6,254,564 | B1 | 7/2001 | Wilk et al. |
| 6,254,635 | B1 | 7/2001 | Schroeder et al. |
| 6,254,636 | B1 | 7/2001 | Peredo |
| 6,257,634 | B1 | 7/2001 | Wei |
| 6,258,052 | B1 | 7/2001 | Milo |
| 6,258,087 | B1 | 7/2001 | Edwards et al. |
| 6,258,114 | B1 | 7/2001 | Konya et al. |
| 6,258,115 | B1 | 7/2001 | Dubrul |
| 6,258,119 | B1 | 7/2001 | Hussein et al. |
| 6,258,120 | B1 | 7/2001 | McKenzie et al. |
| 6,258,129 | B1 | 7/2001 | Dybdal et al. |
| 6,258,150 | B1 | 7/2001 | Mackellar |
| 6,261,304 | B1 | 7/2001 | Hall et al. |
| 6,267,783 | B1 | 7/2001 | Letendre et al. |
| 6,269,819 | B1 | 8/2001 | Oz et al. |
| 6,270,513 | B1 | 8/2001 | Tsugita et al. |
| 6,270,521 | B1 | 8/2001 | Fischell et al. |
| 6,270,526 | B1 | 8/2001 | Cox |
| 6,273,876 | B1 | 8/2001 | Klima et al. |
| 6,273,895 | B1 | 8/2001 | Pinchuk et al. |
| 6,276,661 | B1 | 8/2001 | Laird |
| 6,277,555 | B1 | 8/2001 | Duran et al. |
| 6,283,127 | B1 | 9/2001 | Sterman et al. |
| 6,283,951 | B1 | 9/2001 | Flaherty et al. |
| 6,283,983 | B1 | 9/2001 | Makower et al. |
| 6,283,995 | B1 | 9/2001 | Moe et al. |
| 6,285,903 | B1 | 9/2001 | Rosenthal et al. |
| 6,287,317 | B1 | 9/2001 | Makower et al. |
| 6,287,334 | B1 | 9/2001 | Moll et al. |
| 6,287,338 | B1 | 9/2001 | Sarnowski et al. |
| 6,287,339 | B1 | 9/2001 | Vazquez et al. |
| 6,290,709 | B1 | 9/2001 | Ellis et al. |
| 6,290,728 | B1 | 9/2001 | Phelps et al. |
| 6,296,662 | B1 | 10/2001 | Caffey |
| 6,299,637 | B1 | 10/2001 | Shaolian et al. |
| 6,302,875 | B1 | 10/2001 | Makower et al. |
| 6,302,892 | B1 | 10/2001 | Wilk |
| 6,302,906 | B1 | 10/2001 | Goicoechea et al. |
| 6,306,164 | B1 | 10/2001 | Kujawski |
| 6,309,382 | B1 | 10/2001 | Garrison et al. |
| 6,309,417 | B1 | 10/2001 | Spence et al. |
| 6,311,693 | B1 | 11/2001 | Sterman et al. |
| 6,312,465 | B1 | 11/2001 | Griffin et al. |
| 6,319,281 | B1 | 11/2001 | Patel |
| 6,322,548 | B1 | 11/2001 | Payne et al. |
| 6,322,593 | B1 | 11/2001 | Pathak et al. |
| 6,325,067 | B1 | 12/2001 | Sterman et al. |
| 6,327,772 | B1 | 12/2001 | Zadno-Azizi et al. |
| 6,330,884 | B1 | 12/2001 | Kim |
| 6,331,189 | B1 | 12/2001 | Wolinsky et al. |
| 6,334,873 | B1 | 1/2002 | Lane et al. |
| 6,336,934 | B1 | 1/2002 | Gilson et al. |
| 6,336,937 | B1 | 1/2002 | Vonesh et al. |
| 6,338,735 | B1 | 1/2002 | Stevens |
| 6,338,740 | B1 | 1/2002 | Carpentier |
| 6,342,070 | B1 | 1/2002 | Nguyen-Thien-Nhon |
| 6,344,044 | B1 | 2/2002 | Fulkerson et al. |
| 6,346,074 | B1 | 2/2002 | Roth |
| 6,346,116 | B1 | 2/2002 | Brooks et al. |
| 6,348,063 | B1 | 2/2002 | Yassour et al. |
| 6,350,248 | B1 | 2/2002 | Knudson et al. |
| 6,350,277 | B1 | 2/2002 | Kocur |
| 6,350,278 | B1 | 2/2002 | Lenker et al. |
| 6,352,547 | B1 | 3/2002 | Brown et al. |
| 6,352,554 | B2 | 3/2002 | De Paulis |
| 6,352,708 | B1 | 3/2002 | Duran et al. |
| 6,357,104 | B1 | 3/2002 | Myers |
| 6,358,277 | B1 | 3/2002 | Duran |
| 6,361,519 | B1 | 3/2002 | Knudson et al. |
| 6,361,545 | B1 | 3/2002 | Macoviak et al. |
| 6,363,938 | B2 | 4/2002 | Saadat et al. |
| 6,363,939 | B1 | 4/2002 | Wilk |
| 6,364,895 | B1 | 4/2002 | Greenhalgh |
| 6,368,338 | B1 | 4/2002 | Konya et al. |
| 6,371,970 | B1 | 4/2002 | Khosravi et al. |
| 6,371,983 | B1 | 4/2002 | Lane |
| 6,375,615 | B1 | 4/2002 | Flaherty et al. |
| 6,378,221 | B1 | 4/2002 | Ekholm, Jr. et al. |
| 6,379,319 | B1 | 4/2002 | Garibotto et al. |
| 6,379,365 | B1 | 4/2002 | Diaz |
| 6,379,372 | B1 | 4/2002 | Dehdashtian et al. |
| 6,379,383 | B1 | 4/2002 | Palmaz et al. |
| 6,379,740 | B1 | 4/2002 | Rinaldi et al. |
| 6,380,457 | B1 | 4/2002 | Yurek et al. |
| 6,383,193 | B1 | 5/2002 | Cathcart et al. |
| 6,387,119 | B2 | 5/2002 | Wolf et al. |

(56) References Cited

U.S. PATENT DOCUMENTS 6,387,122 B1 5/2002 Cragg
6,390,098 B1 5/2002 LaFontaine et al.
6,391,051 B2 5/2002 Sullivan, III et al.
6,391,538 B1 5/2002 Vyavahare et al.
6,395,208 B1 5/2002 Herweck et al.
6,398,807 B1 6/2002 Chouinard et al.
6,401,720 B1 6/2002 Stevens et al.
6,402,736 B1 6/2002 Brown et al.
6,402,740 B1 6/2002 Ellis et al.
6,406,488 B1 6/2002 Tweden et al.
6,406,491 B1 6/2002 Vanney
6,406,493 B1 6/2002 Tu et al.
6,409,697 B2 6/2002 Eno et al.
6,409,750 B1 6/2002 Hyodoh et al.
6,409,751 B1 6/2002 Hall et al.
6,409,755 B1 6/2002 Vrba
6,409,759 B1 6/2002 Peredo
6,413,275 B1 7/2002 Nguyen et al.
6,416,490 B1 7/2002 Ellis et al.
6,416,510 B1 7/2002 Altman et al.
6,423,089 B1 7/2002 Gingras et al.
6,425,916 B1 7/2002 Garrison et al.
6,432,119 B1 8/2002 Saadat
6,432,126 B1 8/2002 Gambale et al.
6,432,127 B1 8/2002 Kim et al.
6,432,132 B1 8/2002 Cottone et al.
6,440,164 B1 8/2002 DiMatteo et al.
6,443,158 B1 9/2002 LaFontaine et al.
6,447,522 B2 9/2002 Gambale et al.
6,447,539 B1 9/2002 Nelson et al.
6,451,025 B1 9/2002 Jervis
6,451,054 B1 9/2002 Stevens
6,454,760 B2 9/2002 Vanney
6,454,794 B1 9/2002 Knudson et al.
6,454,799 B1 9/2002 Schreck
6,458,092 B1 10/2002 Gambale et al.
6,458,140 B2 10/2002 Akin et al.
6,458,153 B1 10/2002 Bailey et al.
6,458,323 B1 10/2002 Boekstegers
6,461,382 B1 10/2002 Cao
6,464,709 B2 10/2002 Shennib et al.
6,468,303 B1 10/2002 Amplatz et al.
6,468,660 B2 10/2002 Ogle et al.
6,471,723 B1 10/2002 Ashworth et al.
6,475,169 B2 11/2002 Ferrera
6,475,226 B1 11/2002 Belef et al.
6,475,239 B1 11/2002 Campbell et al.
6,475,244 B2 11/2002 Herweck et al.
6,478,819 B2 11/2002 Moe
6,479,079 B1 11/2002 Pathak et al.
6,482,220 B1 11/2002 Mueller
6,482,228 B1 11/2002 Norred
6,485,501 B1 11/2002 Green
6,485,502 B2 11/2002 Don Michael et al.
6,485,513 B1 11/2002 Fan
6,485,524 B2 11/2002 Strecker
6,487,581 B1 11/2002 Spence et al.
6,488,704 B1 12/2002 Connelly et al.
6,491,689 B1 12/2002 Ellis et al.
6,491,707 B2 12/2002 Makower et al.
6,494,211 B1 12/2002 Boyd et al.
6,494,897 B2 12/2002 Sterman et al.
6,494,909 B2 12/2002 Greenhalgh
6,503,272 B2 1/2003 Duerig et al.
6,508,496 B1 1/2003 Huang
6,508,803 B1 1/2003 Horikawa et al.
6,508,825 B1 1/2003 Selmon et al.
6,508,833 B2 1/2003 Pavcnik et al.
6,509,145 B1 1/2003 Torrianni
6,511,458 B2 1/2003 Milo et al.
6,511,491 B2 1/2003 Grudem et al.
6,514,217 B1 2/2003 Selmon et al.
6,514,271 B2 2/2003 Evans et al.
6,517,527 B2 2/2003 Gambale et al.
6,517,558 B2 2/2003 Gittings et al.
6,517,573 B1 2/2003 Pollock et al.
6,521,179 B1 2/2003 Girardot et al.
6,524,323 B1 2/2003 Nash et al.
6,524,335 B1 2/2003 Hartley et al.
6,527,800 B1 3/2003 McGuckin, Jr. et al.
6,530,949 B2 3/2003 Konya et al.
6,530,952 B2 3/2003 Vesely
6,533,807 B2 3/2003 Wolinsky et al.
6,537,297 B2 3/2003 Tsugita et al.
6,537,310 B1 3/2003 Palmaz et al.
6,540,768 B1 4/2003 Diaz et al.
6,540,782 B1 4/2003 Snyders
6,544,230 B1 4/2003 Flaherty et al.
6,547,827 B2 4/2003 Carpentier et al.
6,551,303 B1 4/2003 Van Tassel et al.
6,558,318 B1 5/2003 Daniel et al.
6,558,417 B2 5/2003 Peredo
6,558,418 B2 5/2003 Carpentier et al.
6,558,429 B2 5/2003 Taylor
6,559,132 B1 5/2003 Holmer
6,561,998 B1 5/2003 Roth et al.
6,562,031 B2 5/2003 Chandrasekaran et al.
6,562,058 B2 5/2003 Seguin et al.
6,562,063 B1 5/2003 Euteneuer et al.
6,562,069 B2 5/2003 Cai et al.
6,564,805 B2 5/2003 Garrison et al.
6,565,528 B1 5/2003 Mueller
6,565,594 B1 5/2003 Herweck et al.
6,569,145 B1 5/2003 Shmulewitz et al.
6,569,147 B1 5/2003 Evans et al.
6,569,196 B1 5/2003 Vesely
6,572,642 B2 6/2003 Rinaldi et al.
6,572,643 B1 6/2003 Gharibadeh
6,572,652 B2 6/2003 Shaknovich
6,575,168 B2 6/2003 LaFontaine et al.
6,579,311 B1 6/2003 Makower
6,582,444 B2 6/2003 Wilk
6,582,460 B1 6/2003 Cryer
6,582,462 B1 6/2003 Andersen et al.
6,585,756 B1 7/2003 Strecker
6,585,758 B1 7/2003 Chouinard et al.
6,585,766 B1 7/2003 Huynh et al.
6,589,279 B1 7/2003 Anderson et al.
6,592,546 B1 7/2003 Barbut et al.
6,592,614 B2 7/2003 Lenker et al.
6,599,304 B1 7/2003 Selmon et al.
6,600,803 B2 7/2003 Bruder et al.
6,605,053 B1 8/2003 Kamm et al.
6,605,112 B1 8/2003 Moll et al.
6,605,113 B2 8/2003 Wilk
6,608,040 B1 8/2003 Lin et al.
6,610,077 B1 8/2003 Hancock et al.
6,610,085 B1 8/2003 Lazarus
6,610,100 B2 8/2003 Phelps et al.
6,613,069 B2 9/2003 Boyd et al.
6,613,077 B2 9/2003 Gilligan et al.
6,613,079 B1 9/2003 Wolinsky et al.
6,613,081 B2 9/2003 Kim et al.
6,613,086 B1 9/2003 Moe et al.
6,616,675 B1 9/2003 Evard et al.
6,616,682 B2 9/2003 Joergensen et al.
6,622,604 B1 9/2003 Chouinard et al.
6,623,491 B2 9/2003 Thompson
6,623,518 B2 9/2003 Thompson et al.
6,623,521 B2 9/2003 Steinke et al.
6,626,938 B1 9/2003 Butaric et al.
6,626,939 B1 9/2003 Burnside et al.
6,632,241 B1 10/2003 Hancock et al.
6,632,243 B1 10/2003 Zadno-Azizi et al.
6,632,470 B2 10/2003 Morra et al.
6,635,068 B1 10/2003 Dubrul et al.
6,635,079 B2 10/2003 Unsworth et al.
6,635,080 B1 10/2003 Lauterjung et al.
6,635,085 B1 10/2003 Caffey et al.
6,638,237 B1 10/2003 Guiles et al.
6,638,247 B1 10/2003 Selmon et al.
6,638,293 B1 10/2003 Makower et al.
6,641,610 B2 11/2003 Wolf et al.
6,651,670 B2 11/2003 Rapacki et al.

(56) References Cited

U.S. PATENT DOCUMENTS 6,651,672 B2 11/2003 Roth
6,652,540 B1 11/2003 Cole et al.
6,652,546 B1 11/2003 Nash et al.
6,652,555 B1 11/2003 Vantassel et al.
6,652,571 B1 11/2003 White et al.
6,652,578 B2 11/2003 Bailey et al.
6,655,386 B1 12/2003 Makower et al.
6,656,213 B2 12/2003 Solem
6,660,003 B1 12/2003 DeVore et al.
6,660,024 B1 12/2003 Flaherty et al.
6,663,588 B2 12/2003 DuBois et al.
6,663,663 B2 12/2003 Kim et al.
6,663,667 B2 12/2003 Dehdashtian et al.
6,666,863 B2 12/2003 Wentzel et al.
6,669,709 B1 12/2003 Cohn et al.
6,669,724 B2 12/2003 Park et al.
6,673,089 B1 1/2004 Yassour et al.
6,673,101 B1 1/2004 Fitzgerald et al.
6,673,106 B2 1/2004 Mitelberg et al.
6,673,109 B2 1/2004 Cox
6,676,668 B2 1/2004 Mercereau et al.
6,676,692 B2 1/2004 Rabkin et al.
6,676,693 B1 1/2004 Belding et al.
6,676,698 B2 1/2004 McGuckin, Jr. et al.
6,679,268 B2 1/2004 Stevens et al.
6,682,543 B2 1/2004 Barbut et al.
6,682,558 B2 1/2004 Tu et al.
6,682,559 B2 1/2004 Myers et al.
6,685,648 B2 2/2004 Flaherty et al.
6,685,739 B2 2/2004 DiMatteo et al.
6,689,144 B2 2/2004 Gerberding
6,689,164 B1 2/2004 Seguin
6,692,512 B2 2/2004 Jang
6,692,513 B2 2/2004 Streeter et al.
6,694,983 B2 2/2004 Wolf et al.
6,695,864 B2 2/2004 Macoviak et al.
6,695,865 B2 2/2004 Boyle et al.
6,695,875 B2 2/2004 Stelter et al.
6,695,878 B2 2/2004 McGuckin, Jr. et al.
6,699,274 B2 3/2004 Stinson
6,701,932 B2 3/2004 Knudson et al.
6,702,851 B1 3/2004 Chinn et al.
6,709,425 B2 3/2004 Gambale et al.
6,709,444 B1 3/2004 Makower
6,712,842 B1 3/2004 Gifford, III et al.
6,712,843 B2 3/2004 Elliott
6,714,841 B1 3/2004 Wright et al.
6,714,842 B1 3/2004 Ito
6,719,770 B2 4/2004 Laufer et al.
6,719,787 B2 4/2004 Cox
6,719,788 B2 4/2004 Cox
6,719,789 B2 4/2004 Cox
6,723,116 B2 4/2004 Taheri
6,723,122 B2 4/2004 Yang et al.
6,726,677 B1 4/2004 Flaherty et al.
6,729,356 B1 5/2004 Baker et al.
6,730,118 B2 5/2004 Spenser et al.
6,730,121 B2 5/2004 Ortiz et al.
6,730,377 B2 5/2004 Wang
6,733,513 B2 5/2004 Boyle et al.
6,733,525 B2 5/2004 Yang et al.
6,736,827 B1 5/2004 McAndrew et al.
6,736,839 B2 5/2004 Cummings
6,736,845 B2 5/2004 Marquez et al.
6,736,846 B2 5/2004 Cox
6,743,252 B1 6/2004 Bates et al.
6,746,464 B1 6/2004 Makower
6,752,828 B2 6/2004 Thornton
6,755,854 B2 6/2004 Gillick et al.
6,755,855 B2 6/2004 Yurek et al.
6,758,855 B2 7/2004 Fulton, III et al.
6,764,503 B1 7/2004 Ishimaru
6,764,509 B2 7/2004 Chinn et al.
6,767,345 B2 7/2004 St. Germain et al.
6,767,362 B2 7/2004 Schreck
6,769,434 B2 8/2004 Liddicoat et al.
6,773,454 B2 8/2004 Wholey et al.
6,773,455 B2 8/2004 Allen et al.
6,773,456 B1 8/2004 Gordon et al.
6,774,278 B1 8/2004 Ragheb et al.
6,776,791 B1 8/2004 Stallings et al.
6,786,925 B1 9/2004 Schoon et al.
6,786,929 B2 9/2004 Gambale et al.
6,790,229 B1 9/2004 Berreklouw
6,790,230 B2 9/2004 Beyersdorf et al.
6,790,237 B2 9/2004 Stinson
6,792,979 B2 9/2004 Konya et al.
6,797,000 B2 9/2004 Simpson et al.
6,797,002 B2 9/2004 Spence et al.
6,802,319 B2 10/2004 Stevens et al.
6,802,858 B2 10/2004 Gambale et al.
6,805,711 B2 10/2004 Quijano et al.
6,808,498 B2 10/2004 Laroya et al.
6,808,504 B2 10/2004 Schorgl et al.
6,808,529 B2 10/2004 Fulkerson
6,814,746 B2 11/2004 Thompson et al.
6,814,754 B2 11/2004 Greenhalgh
6,820,676 B2 11/2004 Palmaz et al.
6,821,211 B2 11/2004 Otten et al.
6,821,297 B2 11/2004 Snyders
6,824,041 B2 11/2004 Grieder et al.
6,824,970 B2 11/2004 Vyavahare et al.
6,830,568 B1 12/2004 Kesten et al.
6,830,575 B2 12/2004 Stenzel et al.
6,830,584 B1 12/2004 Seguin
6,830,585 B1 12/2004 Artof et al.
6,830,586 B2 12/2004 Quijano et al.
6,837,901 B2 1/2005 Rabkin et al.
6,837,902 B2 1/2005 Nguyen et al.
6,840,957 B2 1/2005 DiMatteo et al.
6,843,802 B1 1/2005 Villalobos et al.
6,846,325 B2 1/2005 Liddicoat
6,849,084 B2 2/2005 Rabkin et al.
6,849,085 B2 2/2005 Marton
6,854,467 B2 2/2005 Boekstegers
6,860,898 B2 3/2005 Stack et al.
6,861,211 B2 3/2005 Levy et al.
6,863,668 B2 3/2005 Gillespie et al.
6,863,684 B2 3/2005 Kim et al.
6,863,688 B2 3/2005 Ralph et al.
6,866,650 B2 3/2005 Stevens et al.
6,866,669 B2 3/2005 Buzzard et al.
6,872,223 B2 3/2005 Roberts et al.
6,872,226 B2 3/2005 Cali et al.
6,875,231 B2 4/2005 Anduiza et al.
6,881,199 B2 4/2005 Wilk et al.
6,881,220 B2 4/2005 Edwin et al.
6,883,522 B2 4/2005 Spence et al.
6,887,266 B2 5/2005 Williams et al.
6,890,330 B2 5/2005 Streeter et al.
6,890,340 B2 5/2005 Duane
6,893,459 B1 5/2005 Macoviak
6,893,460 B2 5/2005 Spenser et al.
6,896,690 B1 5/2005 Lambrecht et al.
6,899,704 B2 5/2005 Sterman et al.
6,905,743 B1 6/2005 Chen et al.
6,908,481 B2 6/2005 Cribier
6,911,036 B2 6/2005 Douk et al.
6,911,040 B2 6/2005 Johnson et al.
6,911,043 B2 6/2005 Myers et al.
6,913,021 B2 7/2005 Knudson et al.
6,913,600 B2 7/2005 Valley et al.
6,916,304 B2 7/2005 Eno et al.
6,920,674 B2 7/2005 Thornton
6,920,732 B2 7/2005 Mårtensson
6,926,690 B2 8/2005 Renati
6,926,732 B2 8/2005 Derus et al.
6,929,009 B2 8/2005 Makower et al.
6,929,011 B2 8/2005 Knudson et al.
6,929,653 B2 8/2005 Strecter
6,936,058 B2 8/2005 Forde et al.
6,936,066 B2 8/2005 Palmaz et al.
6,936,067 B2 8/2005 Buchanan
6,939,352 B2 9/2005 Buzzard et al.

(56) References Cited

U.S. PATENT DOCUMENTS 6,939,359 B2 9/2005 Tu et al.
6,939,365 B1 9/2005 Fogarty et al.
6,939,370 B2 9/2005 Hartley et al.
6,942,682 B2 9/2005 Vrba et al.
6,945,949 B2 9/2005 Wilk
6,945,997 B2 9/2005 Huynh et al.
6,949,080 B2 9/2005 Wolf et al.
6,949,118 B2 9/2005 Kohler et al.
6,951,571 B1 10/2005 Srivastava
6,953,332 B1 10/2005 Kurk et al.
6,953,481 B2 10/2005 Phelps et al.
6,955,175 B2 10/2005 Stevens et al.
6,955,681 B2 10/2005 Evans et al.
6,964,652 B2 11/2005 Guiles et al.
6,964,673 B2 11/2005 Tsugita et al.
6,964,676 B1 11/2005 Gerberding et al.
6,969,395 B2 11/2005 Eskuri
6,972,025 B2 12/2005 Wasdyke
6,972,029 B2 12/2005 Mayrhofer et al.
6,974,464 B2 12/2005 Quijano et al.
6,974,474 B2 12/2005 Pavcnik et al.
6,974,476 B2 12/2005 McGuckin, Jr. et al.
6,976,990 B2 12/2005 Mowry
6,979,350 B2 12/2005 Moll et al.
6,984,242 B2 1/2006 Campbell et al.
6,984,244 B2 1/2006 Perez et al.
6,986,742 B2 1/2006 Hart et al.
6,986,784 B1 1/2006 Weiser et al.
6,988,949 B2 1/2006 Wang
6,989,027 B2 1/2006 Allen et al.
6,989,028 B2 1/2006 Lashinski et al.
6,991,649 B2 1/2006 Sievers
7,001,425 B2 2/2006 McCullagh et al.
7,004,176 B2 2/2006 Lau
7,008,397 B2 3/2006 Tweden et al.
7,011,095 B2 3/2006 Wolf et al.
7,011,681 B2 3/2006 Vesely
7,014,655 B2 3/2006 Barbarash et al.
7,018,401 B1 3/2006 Hyodoh et al.
7,018,406 B2 3/2006 Seguin et al.
7,018,408 B2 3/2006 Bailey et al.
7,022,134 B1 4/2006 Quijano et al.
7,025,773 B2 4/2006 Gittings et al.
7,025,780 B2 4/2006 Gabbay
7,025,791 B2 4/2006 Levine et al.
7,028,692 B2 4/2006 Sterman et al.
7,037,331 B2 5/2006 Mitelberg et al.
7,037,333 B2 5/2006 Myers et al.
7,041,128 B2 5/2006 McGuckin, Jr. et al.
7,041,132 B2 5/2006 Quijano et al.
7,044,966 B2 5/2006 Svanidze et al.
7,048,014 B2 5/2006 Hyodoh et al.
7,048,757 B2 5/2006 Shaknovich
7,050,276 B2 5/2006 Nishiyama
7,074,236 B2 7/2006 Rabkin et al.
7,078,163 B2 7/2006 Torrianni
7,081,132 B2 7/2006 Cook et al.
7,097,658 B2 8/2006 Oktay
7,097,659 B2 8/2006 Woolfson et al.
7,101,396 B2 9/2006 Artof et al.
7,105,016 B2 9/2006 Shiu et al.
7,108,715 B2 9/2006 Lawrence-Brown et al.
7,115,141 B2 10/2006 Menz et al.
7,118,585 B2 10/2006 Addis
7,122,020 B2 10/2006 Mogul
7,125,418 B2 10/2006 Duran et al.
7,128,759 B2 10/2006 Osborne et al.
7,137,184 B2 11/2006 Schreck
7,141,063 B2 11/2006 White et al.
7,141,064 B2 11/2006 Scott et al.
7,143,312 B1 11/2006 Wang et al.
7,147,662 B1 12/2006 Pollock et al.
7,147,663 B1 12/2006 Berg et al.
7,153,324 B2 12/2006 Case et al.
7,160,319 B2 1/2007 Chouinard et al.
7,163,556 B2 1/2007 Xie et al.
7,166,097 B2 1/2007 Barbut
7,175,652 B2 2/2007 Cook et al.
7,175,653 B2 2/2007 Gaber
7,175,654 B2 2/2007 Bonsignore et al.
7,175,656 B2 2/2007 Khairkhahan
7,179,290 B2 2/2007 Cao
7,186,265 B2 3/2007 Sharkawy et al.
7,189,258 B2 3/2007 Johnson et al.
7,189,259 B2 3/2007 Simionescu et al.
7,191,018 B2 3/2007 Gielen et al.
7,191,406 B1 3/2007 Barber et al.
7,195,641 B2 3/2007 Palmaz et al.
7,198,646 B2 4/2007 Figulla et al.
7,201,761 B2 4/2007 Woolfson et al.
7,201,772 B2 4/2007 Schwammenthal et al.
7,214,344 B2 5/2007 Carpentier et al.
7,217,287 B2 5/2007 Wilson et al.
7,235,092 B2 6/2007 Banas et al.
7,235,093 B2 6/2007 Gregorich
7,238,200 B2 7/2007 Lee et al.
7,241,257 B1 7/2007 Ainsworth et al.
7,252,682 B2 8/2007 Seguin
7,258,696 B2 8/2007 Rabkin et al.
7,258,891 B2 8/2007 Pacetti et al.
7,261,732 B2 8/2007 Justino
7,264,632 B2 9/2007 Wright et al.
7,267,686 B2 9/2007 DiMatteo et al.
7,276,078 B2 10/2007 Spenser et al.
7,276,084 B2 10/2007 Yang et al.
7,285,130 B2 10/2007 Austin
7,297,150 B2 11/2007 Cartledge et al.
7,300,457 B2 11/2007 Palmaz
7,300,463 B2 11/2007 Liddicoat
7,311,730 B2 12/2007 Gabbay
7,314,449 B2 1/2008 Pfeiffer et al.
7,314,485 B2 1/2008 Mathis
7,314,880 B2 1/2008 Chang et al.
7,316,706 B2 1/2008 Bloom et al.
7,316,712 B2 1/2008 Peredo
7,317,005 B2 1/2008 Hoekstra et al.
7,317,942 B2 1/2008 Brown
7,317,950 B2 1/2008 Lee
7,318,278 B2 1/2008 Zhang et al.
7,318,998 B2 1/2008 Goldstein et al.
7,319,096 B2 1/2008 Malm et al.
7,320,692 B1 1/2008 Bender et al.
7,320,704 B2 1/2008 Lashinski et al.
7,320,705 B2 1/2008 Quintessenza
7,320,706 B2 1/2008 Al-Najjar
7,322,932 B2 1/2008 Xie et al.
7,323,006 B2 1/2008 Andreas et al.
7,323,066 B1 1/2008 Budron
7,326,174 B2 2/2008 Cox et al.
7,326,219 B2 2/2008 Mowry et al.
7,326,236 B2 2/2008 Andreas et al.
7,327,862 B2 2/2008 Murphy et al.
7,329,278 B2 2/2008 Seguin et al.
7,329,279 B2 2/2008 Haug et al.
7,329,280 B2 2/2008 Bolling et al.
7,329,777 B2 2/2008 Harter et al.
7,331,991 B2 2/2008 Kheradvar et al.
7,331,993 B2 2/2008 White
7,333,643 B2 2/2008 Murphy et al.
7,335,158 B2 2/2008 Taylor
7,335,213 B1 2/2008 Hyde et al.
7,335,218 B2 2/2008 Wilson et al.
7,335,490 B2 2/2008 Van Gilst et al.
7,338,484 B2 3/2008 Schoon et al.
7,338,520 B2 3/2008 Bailey et al.
7,361,189 B2 4/2008 Case et al.
7,361,190 B2 4/2008 Shaoulian et al.
7,364,588 B2 4/2008 Mathis et al.
7,371,258 B2 5/2008 Woo et al.
7,374,560 B2 5/2008 Ressemann et al.
7,374,571 B2 5/2008 Pease et al.
7,377,895 B2 5/2008 Spence et al.
7,377,938 B2 5/2008 Sarac et al.
7,377,940 B2 5/2008 Ryan et al.

(56) References Cited

U.S. PATENT DOCUMENTS 7,381,210 B2 6/2008 Zarbatany et al.
7,381,216 B2 6/2008 Buzzard et al.
7,381,218 B2 6/2008 Schreck
7,381,219 B2 6/2008 Salahieh et al.
7,381,220 B2 6/2008 Macoviak et al.
7,384,411 B1 6/2008 Condado
7,387,640 B2 6/2008 Cummings
7,389,874 B2 6/2008 Quest et al.
7,390,325 B2 6/2008 Wang et al.
7,393,358 B2 7/2008 Malewicz
7,393,360 B2 7/2008 Spenser et al.
7,396,364 B2 7/2008 Moaddeb et al.
7,399,315 B2 7/2008 Iobbi
7,402,171 B2 7/2008 Osborne et al.
7,404,792 B2 7/2008 Spence et al.
7,404,793 B2 7/2008 Lau et al.
7,405,259 B2 7/2008 Frye et al.
7,410,499 B2 8/2008 Bicer
7,412,274 B2 8/2008 Mejia
7,412,290 B2 8/2008 Janke et al.
7,415,861 B2 8/2008 Sokel
7,416,530 B2 8/2008 Turner et al.
7,422,603 B2 9/2008 Lane
7,422,606 B2 9/2008 Ung-Chhun et al.
7,423,032 B2 9/2008 Ozaki et al.
7,426,413 B2 9/2008 Balczewski et al.
7,427,279 B2 9/2008 Frazier et al.
7,427,287 B2 9/2008 Turovskiy et al.
7,427,291 B2 9/2008 Liddicoat et al.
7,429,269 B2 9/2008 Schwammenthal et al.
7,430,448 B1 9/2008 Zimmer et al.
7,430,484 B2 9/2008 Ohara
7,431,691 B1 10/2008 Wilk
7,431,733 B2 10/2008 Knight
7,435,059 B2 10/2008 Smith et al.
7,435,257 B2 10/2008 Lashinski et al.
7,442,204 B2 10/2008 Schwammenthal et al.
RE40,570 E 11/2008 Carpentier et al.
7,445,630 B2 11/2008 Lashinski et al.
7,445,631 B2 11/2008 Salahieh et al.
7,445,632 B2 11/2008 McGuckin, Jr. et al.
7,452,371 B2 11/2008 Pavcnik et al.
7,455,689 B2 11/2008 Johnson
7,462,156 B2 12/2008 Mitrev
7,462,184 B2 12/2008 Worley et al.
7,462,191 B2 12/2008 Spenser et al.
7,468,050 B1 12/2008 Kantrowitz
7,470,282 B2 12/2008 Shelso
7,470,284 B2 12/2008 Lambrecht et al.
7,470,285 B2 12/2008 Nugent et al.
7,473,271 B2 1/2009 Gunderson
7,473,275 B2 1/2009 Marquez
7,473,417 B2 1/2009 Zeltinger et al.
7,476,196 B2 1/2009 Spence et al.
7,476,199 B2 1/2009 Spence et al.
7,476,200 B2 1/2009 Tal
7,476,244 B2 1/2009 Buzzard et al.
7,481,838 B2 1/2009 Carpentier et al.
7,485,088 B2 2/2009 Murphy et al.
7,485,143 B2 2/2009 Webler et al.
7,488,346 B2 2/2009 Navia
7,491,232 B2 2/2009 Bolduc et al.
7,493,869 B1 2/2009 Foster et al.
7,497,824 B2 3/2009 Taylor
7,500,949 B2 3/2009 Gottlieb et al.
7,500,989 B2 3/2009 Solem et al.
7,503,929 B2 3/2009 Johnson et al.
7,503,930 B2 3/2009 Sharkawy et al.
7,507,199 B2 3/2009 Wang et al.
7,510,572 B2 3/2009 Gabbay
7,510,574 B2 3/2009 Lê et al.
7,510,575 B2 3/2009 Spenser et al.
7,510,577 B2 3/2009 Moaddeb et al.
7,513,863 B2 4/2009 Bolling et al.
7,513,909 B2 4/2009 Lane et al.
7,522,950 B2 4/2009 Fuimaono et al.
7,524,330 B2 4/2009 Berreklouw
7,530,253 B2 5/2009 Spenser et al.
7,530,995 B2 5/2009 Quijano et al.
7,534,261 B2 5/2009 Friedman
7,544,206 B2 6/2009 Cohn
7,547,322 B2 6/2009 Sarac et al.
7,553,324 B2 6/2009 Andreas et al.
7,556,386 B2 7/2009 Smith
7,556,646 B2 7/2009 Yang et al.
7,569,071 B2 8/2009 Haverkost et al.
7,578,828 B2 8/2009 Gittings et al.
7,585,321 B2 9/2009 Cribier
7,591,848 B2 9/2009 Allen
7,594,974 B2 9/2009 Cali et al.
7,601,159 B2 10/2009 Ewers et al.
7,601,195 B2 10/2009 Ichikawa
7,608,099 B2 10/2009 Johnson et al.
7,611,534 B2 11/2009 Kapadia et al.
7,618,446 B2 11/2009 Andersen et al.
7,622,276 B2 11/2009 Cunanan et al.
7,625,403 B2 12/2009 Krivoruchko
7,628,802 B2 12/2009 White et al.
7,628,803 B2 12/2009 Pavcnik et al.
7,632,296 B2 12/2009 Malewicz
7,632,298 B2 12/2009 Hijlkema et al.
7,635,386 B1 12/2009 Gammie
7,641,687 B2 1/2010 Chinn et al.
7,651,519 B2 1/2010 Dittman
7,655,034 B2 2/2010 Mitchell et al.
7,674,282 B2 3/2010 Wu et al.
7,682,390 B2 3/2010 Seguin
7,704,222 B2 4/2010 Wilk et al.
7,704,277 B2 4/2010 Zakay et al.
7,712,606 B2 5/2010 Salahieh et al.
7,715,903 B2 5/2010 Hartley et al.
7,717,955 B2 5/2010 Lane et al.
7,722,638 B2 5/2010 Deyette, Jr. et al.
7,722,662 B2 5/2010 Steinke et al.
7,722,666 B2 5/2010 Lafontaine
7,722,671 B1 5/2010 Carlyle et al.
7,731,742 B2 6/2010 Schlick et al.
7,735,493 B2 6/2010 Van Der Burg et al.
7,736,327 B2 6/2010 Wilk et al.
7,736,388 B2 6/2010 Goldfarb et al.
7,743,481 B2 6/2010 Lafont et al.
7,748,389 B2 7/2010 Salahieh et al.
7,758,625 B2 7/2010 Wu et al.
7,763,065 B2 7/2010 Schmid et al.
7,771,463 B2 8/2010 Ton et al.
7,771,467 B2 8/2010 Svensson
7,776,083 B2 8/2010 Vesely
7,780,725 B2 8/2010 Haug et al.
7,780,726 B2 8/2010 Seguin
7,785,360 B2 8/2010 Freitag
7,794,487 B2 9/2010 Majercak et al.
7,799,046 B2 9/2010 White et al.
7,799,065 B2 9/2010 Pappas
7,803,185 B2 9/2010 Gabbay
7,806,919 B2 10/2010 Bloom et al.
7,823,267 B2 11/2010 Bolduc
7,824,442 B2 11/2010 Salahieh et al.
7,824,443 B2 11/2010 Salahieh et al.
7,833,262 B2 11/2010 McGuckin, Jr. et al.
7,837,727 B2 11/2010 Goetz et al.
7,846,203 B2 12/2010 Cribier
7,846,204 B2 12/2010 Letac et al.
7,854,758 B2 12/2010 Taheri
7,857,845 B2 12/2010 Stacchino et al.
7,862,602 B2 1/2011 Licata et al.
7,867,274 B2 1/2011 Hill et al.
7,887,583 B2 2/2011 Macoviak
7,892,276 B2 2/2011 Stocker et al.
7,892,292 B2 2/2011 Stack et al.
7,896,913 B2 3/2011 Damm et al.
7,896,915 B2 3/2011 Guyenot et al.
7,914,569 B2 3/2011 Nguyen et al.
7,914,574 B2 3/2011 Schmid et al.
7,914,575 B2 3/2011 Guyenot et al.

(56) References Cited

U.S. PATENT DOCUMENTS

| | | | |
|---|---|---|---|
| 7,918,880 | B2 | 4/2011 | Austin |
| 7,927,363 | B2 | 4/2011 | Perouse |
| 7,938,851 | B2 | 5/2011 | Olson et al. |
| 7,947,071 | B2 | 5/2011 | Schmid et al. |
| 7,947,075 | B2 | 5/2011 | Goetz et al. |
| 7,951,189 | B2 | 5/2011 | Haverkost et al. |
| 7,959,666 | B2 | 6/2011 | Salahieh et al. |
| 7,959,672 | B2 | 6/2011 | Salahieh et al. |
| 7,967,853 | B2 | 6/2011 | Eidenschink et al. |
| 7,972,359 | B2 | 7/2011 | Kreidler |
| 7,972,376 | B1 | 7/2011 | Dove et al. |
| 7,972,378 | B2 | 7/2011 | Tabor et al. |
| 7,988,724 | B2 | 8/2011 | Salahieh et al. |
| 7,993,386 | B2 | 8/2011 | Elliott |
| 8,002,824 | B2 | 8/2011 | Jenson et al. |
| 8,002,825 | B2 | 8/2011 | Letac et al. |
| 8,012,198 | B2 | 9/2011 | Hill et al. |
| 8,021,421 | B2 | 9/2011 | Fogarty et al. |
| RE42,818 | E | 10/2011 | Cali et al. |
| RE42,857 | E | 10/2011 | Cali et al. |
| 8,038,704 | B2 | 10/2011 | Sherburne |
| 8,038,709 | B2 | 10/2011 | Palasis et al. |
| 8,043,450 | B2 | 10/2011 | Cali et al. |
| 8,048,153 | B2 | 11/2011 | Salahieh et al. |
| 8,052,715 | B2 | 11/2011 | Quinn et al. |
| 8,052,749 | B2 | 11/2011 | Salahieh et al. |
| 8,052,750 | B2 | 11/2011 | Tuval et al. |
| 8,057,540 | B2 | 11/2011 | Letac et al. |
| 8,062,355 | B2 | 11/2011 | Figulla et al. |
| 8,062,536 | B2 | 11/2011 | Liu et al. |
| 8,062,537 | B2 | 11/2011 | Tuominen et al. |
| 8,062,749 | B2 | 11/2011 | Shelestak et al. |
| 8,070,799 | B2 | 12/2011 | Righini et al. |
| 8,075,641 | B2 | 12/2011 | Aravanis et al. |
| 8,083,788 | B2 | 12/2011 | Acosta et al. |
| 8,092,518 | B2 | 1/2012 | Schreck |
| 8,092,520 | B2 | 1/2012 | Quadri |
| 8,092,521 | B2 | 1/2012 | Figulla et al. |
| 8,128,676 | B2 | 3/2012 | Cummings |
| 8,128,681 | B2 | 3/2012 | Shoemaker et al. |
| 8,133,217 | B2 | 3/2012 | Stokes et al. |
| 8,133,270 | B2 | 3/2012 | Kheradvar et al. |
| 8,136,659 | B2 | 3/2012 | Salahieh et al. |
| 8,137,394 | B2 | 3/2012 | Stocker et al. |
| 8,137,398 | B2 | 3/2012 | Tuval et al. |
| 8,147,534 | B2 | 4/2012 | Berez et al. |
| 8,157,853 | B2 | 4/2012 | Laske et al. |
| 8,167,894 | B2 | 5/2012 | Miles et al. |
| 8,172,896 | B2 | 5/2012 | McNamara et al. |
| 8,182,528 | B2 | 5/2012 | Salahieh et al. |
| 8,192,351 | B2 | 6/2012 | Fishler et al. |
| 8,206,437 | B2 | 6/2012 | Bonhoeffer et al. |
| 8,211,107 | B2 | 7/2012 | Parks et al. |
| 8,216,174 | B2 | 7/2012 | Wilk et al. |
| 8,216,301 | B2 | 7/2012 | Bonhoeffer et al. |
| 8,221,493 | B2 | 7/2012 | Boyle et al. |
| 8,226,707 | B2 | 7/2012 | White |
| 8,226,710 | B2 | 7/2012 | Nguyen et al. |
| 8,231,670 | B2 | 7/2012 | Salahieh et al. |
| 8,236,049 | B2 | 8/2012 | Rowe et al. |
| 8,236,241 | B2 | 8/2012 | Carpentier et al. |
| 8,246,675 | B2 | 8/2012 | Zegdi |
| 8,246,678 | B2 | 8/2012 | Salahieh et al. |
| 8,252,051 | B2 | 8/2012 | Chau et al. |
| 8,252,052 | B2 | 8/2012 | Salahieh et al. |
| 8,277,500 | B2 | 10/2012 | Schmid et al. |
| 8,287,584 | B2 | 10/2012 | Salahieh et al. |
| 8,303,653 | B2 | 11/2012 | Bonhoeffer et al. |
| 8,308,798 | B2 | 11/2012 | Pintor et al. |
| 8,317,858 | B2 | 11/2012 | Straubinger et al. |
| 8,323,335 | B2 | 12/2012 | Rowe et al. |
| 8,328,868 | B2 | 12/2012 | Paul et al. |
| 8,343,136 | B2 | 1/2013 | Howat et al. |
| 8,343,213 | B2 | 1/2013 | Salahieh et al. |
| 8,348,995 | B2 | 1/2013 | Tuval et al. |
| 8,348,996 | B2 | 1/2013 | Tuval et al. |
| 8,348,999 | B2 | 1/2013 | Kheradvar et al. |
| 8,357,387 | B2 | 1/2013 | Dove et al. |
| 8,366,767 | B2 | 2/2013 | Zhang |
| 8,372,134 | B2 | 2/2013 | Schlick et al. |
| 8,376,865 | B2 | 2/2013 | Forster et al. |
| 8,377,117 | B2 | 2/2013 | Keidar et al. |
| 8,382,822 | B2 | 2/2013 | Pavcnik et al. |
| 8,398,704 | B2 | 3/2013 | Straubinger et al. |
| 8,398,708 | B2 | 3/2013 | Meiri et al. |
| 8,403,983 | B2 | 3/2013 | Quadri et al. |
| 8,414,641 | B2 | 4/2013 | Stocker et al. |
| 8,414,643 | B2 | 4/2013 | Tuval et al. |
| 8,414,644 | B2 | 4/2013 | Quadri et al. |
| 8,414,645 | B2 | 4/2013 | Dwork et al. |
| 8,439,961 | B2 | 5/2013 | Jagger et al. |
| 8,445,278 | B2 | 5/2013 | Everaerts et al. |
| 8,460,365 | B2 | 6/2013 | Haverkost et al. |
| 8,465,540 | B2 | 6/2013 | Straubinger et al. |
| 8,468,667 | B2 | 6/2013 | Straubinger et al. |
| 8,470,023 | B2 | 6/2013 | Eidenschink et al. |
| 8,491,650 | B2 | 7/2013 | Wiemeyer et al. |
| 8,512,394 | B2 | 8/2013 | Schmid et al. |
| 8,512,399 | B2 | 8/2013 | Lafontaine |
| 8,512,400 | B2 | 8/2013 | Tran et al. |
| 8,512,401 | B2 | 8/2013 | Murray, III et al. |
| 8,523,936 | B2 | 9/2013 | Schmid et al. |
| 8,535,368 | B2 | 9/2013 | Headley, Jr. et al. |
| 8,540,762 | B2 | 9/2013 | Schmid et al. |
| 8,545,547 | B2 | 10/2013 | Schmid et al. |
| 8,545,552 | B2 | 10/2013 | Garrison et al. |
| 8,551,160 | B2 | 10/2013 | Figulla et al. |
| 8,556,880 | B2 | 10/2013 | Freyman et al. |
| 8,556,966 | B2 | 10/2013 | Jenson |
| 8,568,475 | B2 | 10/2013 | Nguyen et al. |
| 8,579,962 | B2 | 11/2013 | Salahieh et al. |
| 8,579,965 | B2 | 11/2013 | Bonhoeffer et al. |
| 8,585,756 | B2 | 11/2013 | Bonhoeffer et al. |
| 8,585,759 | B2 | 11/2013 | Bumbalough |
| 8,591,570 | B2 | 11/2013 | Revuelta et al. |
| 8,597,226 | B2 | 12/2013 | Wilk et al. |
| 8,603,159 | B2 | 12/2013 | Seguin et al. |
| 8,603,160 | B2 | 12/2013 | Salahieh et al. |
| 8,617,235 | B2 | 12/2013 | Schmid et al. |
| 8,617,236 | B2 | 12/2013 | Paul et al. |
| 8,623,074 | B2 | 1/2014 | Ryan |
| 8,623,075 | B2 | 1/2014 | Murray, III et al. |
| 8,623,076 | B2 | 1/2014 | Salahieh et al. |
| 8,623,078 | B2 | 1/2014 | Salahieh et al. |
| 8,628,562 | B2 | 1/2014 | Cummings |
| 8,628,571 | B1 | 1/2014 | Hacohen et al. |
| 8,647,381 | B2 | 2/2014 | Essinger et al. |
| 8,668,733 | B2 | 3/2014 | Haug et al. |
| 8,672,997 | B2 | 3/2014 | Drasler et al. |
| 8,679,174 | B2 | 3/2014 | Ottma et al. |
| 8,685,077 | B2 | 4/2014 | Laske et al. |
| 8,696,743 | B2 | 4/2014 | Holecek et al. |
| 8,721,713 | B2 | 5/2014 | Tower et al. |
| 8,721,717 | B2 | 5/2014 | Shoemaker et al. |
| 8,734,508 | B2 | 5/2014 | Hastings et al. |
| 8,758,430 | B2 | 6/2014 | Ferrari et al. |
| 8,764,818 | B2 | 7/2014 | Gregg |
| 8,778,020 | B2 | 7/2014 | Gregg et al. |
| 8,790,395 | B2 | 7/2014 | Straubinger et al. |
| 8,795,305 | B2 | 8/2014 | Martin et al. |
| 8,795,356 | B2 | 8/2014 | Quadri et al. |
| 8,808,356 | B2 | 8/2014 | Braido et al. |
| 8,808,364 | B2 | 8/2014 | Palasis et al. |
| 8,828,078 | B2 | 9/2014 | Salahieh et al. |
| 8,828,079 | B2 | 9/2014 | Thielen et al. |
| 8,840,662 | B2 | 9/2014 | Salahieh et al. |
| 8,840,663 | B2 | 9/2014 | Salahieh et al. |
| 8,845,721 | B2 | 9/2014 | Braido et al. |
| 8,851,286 | B2 | 10/2014 | Chang et al. |
| 8,852,272 | B2 | 10/2014 | Gross et al. |
| 8,858,620 | B2 | 10/2014 | Salahieh et al. |
| 8,894,703 | B2 | 11/2014 | Salahieh et al. |
| 8,932,349 | B2 | 1/2015 | Jenson et al. |
| 8,940,014 | B2 | 1/2015 | Gamarra et al. |

(56) References Cited

U.S. PATENT DOCUMENTS 8,951,243 B2 2/2015 Crisostomo et al.
8,951,299 B2 2/2015 Paul et al.
8,956,383 B2 2/2015 Aklog et al.
8,992,608 B2 3/2015 Haug et al.
8,998,976 B2 4/2015 Gregg et al.
9,005,273 B2 4/2015 Salahieh et al.
9,011,521 B2 4/2015 Haug et al.
9,023,099 B2 5/2015 Duffy et al.
9,028,542 B2 5/2015 Hill et al.
9,039,756 B2 5/2015 White
9,044,318 B2 6/2015 Straubinger et al.
9,131,926 B2 9/2015 Crisostomo et al.
9,149,358 B2 10/2015 Tabor et al.
9,168,130 B2 10/2015 Straubinger et al.
9,168,131 B2 10/2015 Yohanan et al.
9,168,136 B2 10/2015 Yang et al.
9,180,005 B1 11/2015 Lashinski et al.
9,186,482 B2 11/2015 Dorn
9,211,266 B2 12/2015 Iwazawa et al.
9,216,082 B2 12/2015 Von Segesser et al.
9,248,037 B2 2/2016 Roeder et al.
9,265,608 B2 2/2016 Miller et al.
9,277,991 B2 3/2016 Salahieh et al.
9,277,993 B2 3/2016 Gamarra et al.
9,301,840 B2 4/2016 Nguyen et al.
9,301,843 B2 4/2016 Richardson et al.
9,308,085 B2 4/2016 Salahieh et al.
9,320,599 B2 4/2016 Salahieh et al.
9,326,853 B2 5/2016 Olson et al.
9,358,106 B2 6/2016 Salahieh et al.
9,358,110 B2 6/2016 Paul et al.
9,370,419 B2 6/2016 Hill et al.
9,370,421 B2 6/2016 Crisostomo et al.
9,387,076 B2 7/2016 Paul et al.
9,393,094 B2 7/2016 Salahieh et al.
9,393,113 B2 7/2016 Salahieh et al.
9,393,114 B2 7/2016 Sutton et al.
9,393,115 B2 7/2016 Tabor et al.
9,415,567 B2 8/2016 Sogard et al.
9,421,083 B2 8/2016 Eidenschink et al.
9,439,759 B2 9/2016 Straubinger et al.
9,463,084 B2 10/2016 Stinson
9,474,598 B2 10/2016 Gregg et al.
9,474,609 B2 10/2016 Haverkost et al.
9,492,276 B2 11/2016 Lee et al.
9,510,945 B2 12/2016 Sutton et al.
9,526,609 B2 12/2016 Salahieh et al.
9,532,872 B2 1/2017 Salahieh et al.
9,539,091 B2 1/2017 Yang et al.
9,554,924 B2 1/2017 Schlick et al.
9,597,432 B2 3/2017 Nakamura
9,649,212 B2 5/2017 Fargahi
9,717,593 B2 8/2017 Alkhatib et al.
D800,908 S 10/2017 Hariton et al.
9,775,709 B2 10/2017 Miller et al.
9,788,945 B2 10/2017 Ottma et al.
9,861,476 B2 1/2018 Salahieh et al.
9,867,694 B2 1/2018 Girard et al.
9,867,699 B2 1/2018 Straubinger et al.
9,872,768 B2 1/2018 Paul et al.
9,889,002 B2 2/2018 Bonhoeffer et al.
9,901,445 B2 2/2018 Backus et al.
9,949,824 B2 4/2018 Bonhoeffer et al.
9,956,075 B2 5/2018 Salahieh et al.
9,968,761 B2 5/2018 Brecker
9,987,133 B2 6/2018 Straubinger et al.
10,092,324 B2 10/2018 Gillespie et al.
10,143,552 B2 12/2018 Wallace et al.
10,154,901 B2 12/2018 Straubinger et al.
10,321,987 B2 6/2019 Wang et al.
10,363,134 B2 7/2019 Figulla et al.
10,543,084 B2 1/2020 Guyenot et al.
10,575,947 B2 3/2020 Straubinger et al.
10,638,918 B2 5/2020 Atarot et al.
10,702,382 B2 7/2020 Straubinger et al.
10,709,555 B2 7/2020 Schreck et al.
11,266,497 B2 3/2022 Cao et al.
12,121,461 B2 10/2024 Schreck et al.
12,171,658 B2 12/2024 Chu et al.
12,232,957 B2 2/2025 Straubinger et al.
2001/0000041 A1 3/2001 Selmon et al.
2001/0001314 A1 5/2001 Davison et al.
2001/0002445 A1 5/2001 Vesely
2001/0004683 A1 6/2001 Gambale et al.
2001/0004690 A1 6/2001 Gambale et al.
2001/0004699 A1 6/2001 Gittings et al.
2001/0007956 A1 7/2001 Letac et al.
2001/0008969 A1 7/2001 Evans et al.
2001/0010017 A1 7/2001 Letac et al.
2001/0011187 A1 8/2001 Pavcnik et al.
2001/0011189 A1 8/2001 Drasler et al.
2001/0012948 A1 8/2001 Vanney
2001/0014813 A1 8/2001 Saadat et al.
2001/0016700 A1 8/2001 Eno et al.
2001/0018596 A1 8/2001 Selmon et al.
2001/0020172 A1 9/2001 Selmon et al.
2001/0021872 A1 9/2001 Bailey et al.
2001/0025196 A1 9/2001 Chinn et al.
2001/0025643 A1 10/2001 Foley
2001/0027287 A1 10/2001 Shmulewitz et al.
2001/0027338 A1 10/2001 Greenberg
2001/0027339 A1 10/2001 Boatman et al.
2001/0029385 A1 10/2001 Shennib et al.
2001/0032013 A1 10/2001 Marton
2001/0034547 A1 10/2001 Hall et al.
2001/0037117 A1 11/2001 Gambale et al.
2001/0037141 A1 11/2001 Yee et al.
2001/0037149 A1 11/2001 Wilk
2001/0039426 A1 11/2001 Makower et al.
2001/0039445 A1 11/2001 Hall et al.
2001/0039450 A1 11/2001 Pavcnik et al.
2001/0041902 A1 11/2001 Lepulu et al.
2001/0041928 A1 11/2001 Pavcnik et al.
2001/0041930 A1 11/2001 Globerman et al.
2001/0044631 A1 11/2001 Akin et al.
2001/0044634 A1 11/2001 Don Michael et al.
2001/0044647 A1 11/2001 Pinchuk et al.
2001/0044652 A1 11/2001 Moore
2001/0044656 A1 11/2001 Williamson, IV et al.
2001/0047165 A1 11/2001 Makower et al.
2001/0049523 A1 12/2001 DeVore et al.
2001/0051822 A1 12/2001 Stack et al.
2001/0053930 A1 12/2001 Kugler et al.
2001/0053932 A1 12/2001 Phelps et al.
2002/0002349 A1 1/2002 Flaherty et al.
2002/0002396 A1 1/2002 Fulkerson
2002/0002401 A1 1/2002 McGuckin, Jr. et al.
2002/0004662 A1 1/2002 Wilk
2002/0004663 A1 1/2002 Gittings et al.
2002/0007138 A1 1/2002 Wilk et al.
2002/0010489 A1 1/2002 Grayzel et al.
2002/0010508 A1 1/2002 Chobotov
2002/0026233 A1 2/2002 Shaknovich
2002/0029014 A1 3/2002 Jayaraman
2002/0029079 A1 3/2002 Kim et al.
2002/0029981 A1 3/2002 Nigam
2002/0032476 A1 3/2002 Gambale et al.
2002/0032478 A1 3/2002 Boekstegers et al.
2002/0032480 A1 3/2002 Spence et al.
2002/0032481 A1 3/2002 Gabbay
2002/0035390 A1 3/2002 Schaldach et al.
2002/0035396 A1 3/2002 Heath
2002/0042650 A1 4/2002 Vardi et al.
2002/0042651 A1 4/2002 Liddicoat et al.
2002/0045846 A1 4/2002 Kaplon et al.
2002/0045928 A1 4/2002 Boekstegers
2002/0045929 A1 4/2002 Diaz
2002/0049486 A1 4/2002 Knudson et al.
2002/0052651 A1 5/2002 Myers et al.
2002/0055767 A1 5/2002 Forde et al.
2002/0055769 A1 5/2002 Wang
2002/0055772 A1 5/2002 McGuckin, Jr. et al.
2002/0055774 A1 5/2002 Liddicoat
2002/0055775 A1 5/2002 Carpentier et al.

(56) References Cited

U.S. PATENT DOCUMENTS

| | | | |
|---|---|---|---|
| 2002/0058897 | A1 | 5/2002 | Renati |
| 2002/0058987 | A1 | 5/2002 | Butaric et al. |
| 2002/0058993 | A1 | 5/2002 | Landau et al. |
| 2002/0058995 | A1 | 5/2002 | Stevens |
| 2002/0062146 | A1 | 5/2002 | Makower et al. |
| 2002/0065478 | A1 | 5/2002 | Knudson et al. |
| 2002/0065485 | A1 | 5/2002 | DuBois et al. |
| 2002/0072699 | A1 | 6/2002 | Knudson et al. |
| 2002/0072789 | A1 | 6/2002 | Hackett et al. |
| 2002/0077566 | A1 | 6/2002 | Laroya et al. |
| 2002/0077654 | A1 | 6/2002 | Javier, Jr. et al. |
| 2002/0077696 | A1 | 6/2002 | Zadno-Azizi et al. |
| 2002/0082584 | A1 | 6/2002 | Rosenman et al. |
| 2002/0082585 | A1 | 6/2002 | Carroll et al. |
| 2002/0082609 | A1 | 6/2002 | Green |
| 2002/0092535 | A1 | 7/2002 | Wilk |
| 2002/0092536 | A1 | 7/2002 | LaFontaine et al. |
| 2002/0095111 | A1 | 7/2002 | Tweden et al. |
| 2002/0095173 | A1 | 7/2002 | Mazzocchi et al. |
| 2002/0095206 | A1 | 7/2002 | Addonizio et al. |
| 2002/0095209 | A1 | 7/2002 | Zadno-Azizi et al. |
| 2002/0099405 | A1 | 7/2002 | Yurek et al. |
| 2002/0099439 | A1 | 7/2002 | Schwartz et al. |
| 2002/0100484 | A1 | 8/2002 | Hall et al. |
| 2002/0103533 | A1 | 8/2002 | Langberg et al. |
| 2002/0107565 | A1 | 8/2002 | Greenhalgh |
| 2002/0111627 | A1 | 8/2002 | Vincent-Prestigiacomo |
| 2002/0111665 | A1 | 8/2002 | Lauterjung |
| 2002/0111668 | A1 | 8/2002 | Smith |
| 2002/0111672 | A1 | 8/2002 | Kim et al. |
| 2002/0111674 | A1 | 8/2002 | Chouinard et al. |
| 2002/0117789 | A1 | 8/2002 | Childers et al. |
| 2002/0120322 | A1 | 8/2002 | Thompson et al. |
| 2002/0120323 | A1 | 8/2002 | Thompson et al. |
| 2002/0120328 | A1 | 8/2002 | Pathak et al. |
| 2002/0123698 | A1 | 9/2002 | Garibotto et al. |
| 2002/0123786 | A1 | 9/2002 | Gittings et al. |
| 2002/0123790 | A1 | 9/2002 | White et al. |
| 2002/0123802 | A1 | 9/2002 | Snyders |
| 2002/0128552 | A1 | 9/2002 | Nowlin et al. |
| 2002/0133183 | A1 | 9/2002 | Lentz et al. |
| 2002/0133226 | A1 | 9/2002 | Marquez et al. |
| 2002/0138087 | A1 | 9/2002 | Shennib et al. |
| 2002/0138138 | A1 | 9/2002 | Yang |
| 2002/0143285 | A1 | 10/2002 | Eno et al. |
| 2002/0143289 | A1 | 10/2002 | Ellis et al. |
| 2002/0143387 | A1 | 10/2002 | Soetikno et al. |
| 2002/0144696 | A1 | 10/2002 | Sharkawy et al. |
| 2002/0151913 | A1 | 10/2002 | Berg et al. |
| 2002/0151970 | A1 | 10/2002 | Garrison et al. |
| 2002/0156522 | A1 | 10/2002 | Ivancev et al. |
| 2002/0161377 | A1 | 10/2002 | Rabkin |
| 2002/0161383 | A1 | 10/2002 | Akin et al. |
| 2002/0161390 | A1 | 10/2002 | Mouw |
| 2002/0161392 | A1 | 10/2002 | Dubrul |
| 2002/0161394 | A1 | 10/2002 | Macoviak et al. |
| 2002/0161424 | A1 | 10/2002 | Rapacki et al. |
| 2002/0161426 | A1 | 10/2002 | Iancea |
| 2002/0165479 | A1 | 11/2002 | Wilk |
| 2002/0165576 | A1 | 11/2002 | Boyle et al. |
| 2002/0165606 | A1 | 11/2002 | Wolf et al. |
| 2002/0173842 | A1 | 11/2002 | Buchanan |
| 2002/0177766 | A1 | 11/2002 | Mogul |
| 2002/0177772 | A1 | 11/2002 | Altman et al. |
| 2002/0177840 | A1 | 11/2002 | Farnholtz |
| 2002/0177894 | A1 | 11/2002 | Acosta et al. |
| 2002/0179098 | A1 | 12/2002 | Makower et al. |
| 2002/0183716 | A1 | 12/2002 | Herweck et al. |
| 2002/0183781 | A1 | 12/2002 | Casey et al. |
| 2002/0186558 | A1 | 12/2002 | Plank et al. |
| 2002/0188341 | A1 | 12/2002 | Elliott |
| 2002/0188344 | A1 | 12/2002 | Bolea et al. |
| 2002/0193782 | A1 | 12/2002 | Ellis et al. |
| 2002/0193871 | A1 | 12/2002 | Beyersdorf et al. |
| 2002/0198594 | A1 | 12/2002 | Schreck |
| 2003/0004541 | A1 | 1/2003 | Linder et al. |
| 2003/0004560 | A1 | 1/2003 | Chobotov et al. |
| 2003/0009189 | A1 | 1/2003 | Gilson et al. |
| 2003/0014104 | A1 | 1/2003 | Cribier |
| 2003/0018377 | A1 | 1/2003 | Berg et al. |
| 2003/0018379 | A1 | 1/2003 | Knudson et al. |
| 2003/0023300 | A1 | 1/2003 | Bailey et al. |
| 2003/0023303 | A1 | 1/2003 | Palmaz et al. |
| 2003/0027332 | A1 | 2/2003 | Lafrance et al. |
| 2003/0028213 | A1 | 2/2003 | Thill et al. |
| 2003/0028247 | A1 | 2/2003 | Cali |
| 2003/0033001 | A1 | 2/2003 | Igaki |
| 2003/0036791 | A1 | 2/2003 | Philipp et al. |
| 2003/0036795 | A1 | 2/2003 | Andersen et al. |
| 2003/0040736 | A1 | 2/2003 | Stevens et al. |
| 2003/0040771 | A1 | 2/2003 | Hyodoh et al. |
| 2003/0040772 | A1 | 2/2003 | Hyodoh et al. |
| 2003/0040791 | A1 | 2/2003 | Oktay |
| 2003/0040792 | A1 | 2/2003 | Gabbay |
| 2003/0042186 | A1 | 3/2003 | Boyle |
| 2003/0044315 | A1 | 3/2003 | Boekstegers |
| 2003/0045828 | A1 | 3/2003 | Wilk |
| 2003/0050694 | A1 | 3/2003 | Yang et al. |
| 2003/0055371 | A1 | 3/2003 | Wolf et al. |
| 2003/0055495 | A1 | 3/2003 | Pease et al. |
| 2003/0057156 | A1 | 3/2003 | Peterson et al. |
| 2003/0060844 | A1 | 3/2003 | Borillo et al. |
| 2003/0065386 | A1 | 4/2003 | Weadock |
| 2003/0069492 | A1 | 4/2003 | Abrams et al. |
| 2003/0069646 | A1 | 4/2003 | Stinson |
| 2003/0070944 | A1 | 4/2003 | Nigam |
| 2003/0073973 | A1 | 4/2003 | Evans et al. |
| 2003/0074058 | A1 | 4/2003 | Sherry |
| 2003/0078561 | A1 | 4/2003 | Gambale et al. |
| 2003/0078652 | A1 | 4/2003 | Sutherland |
| 2003/0083730 | A1 | 5/2003 | Stinson |
| 2003/0093145 | A1 | 5/2003 | Lawrence-Brown et al. |
| 2003/0100918 | A1 | 5/2003 | Duane |
| 2003/0100919 | A1 | 5/2003 | Hopkins et al. |
| 2003/0100920 | A1 | 5/2003 | Akin et al. |
| 2003/0105514 | A1 | 6/2003 | Phelps et al. |
| 2003/0109924 | A1 | 6/2003 | Cribier |
| 2003/0109930 | A1 | 6/2003 | Bluni et al. |
| 2003/0114912 | A1 | 6/2003 | Sequin et al. |
| 2003/0114913 | A1 | 6/2003 | Spenser et al. |
| 2003/0120195 | A1 | 6/2003 | Milo et al. |
| 2003/0125795 | A1 | 7/2003 | Pavcnik et al. |
| 2003/0130726 | A1 | 7/2003 | Thorpe et al. |
| 2003/0130727 | A1 | 7/2003 | Drasler et al. |
| 2003/0130729 | A1 | 7/2003 | Paniagua et al. |
| 2003/0130746 | A1 | 7/2003 | Ashworth et al. |
| 2003/0135257 | A1 | 7/2003 | Taheri |
| 2003/0139796 | A1 | 7/2003 | Sequin et al. |
| 2003/0139798 | A1 | 7/2003 | Brown et al. |
| 2003/0139803 | A1 | 7/2003 | Sequin et al. |
| 2003/0139804 | A1 | 7/2003 | Hankh et al. |
| 2003/0144657 | A1 | 7/2003 | Bowe et al. |
| 2003/0144732 | A1 | 7/2003 | Cosgrove et al. |
| 2003/0149474 | A1 | 8/2003 | Becker |
| 2003/0149475 | A1 | 8/2003 | Hyodoh et al. |
| 2003/0149476 | A1 | 8/2003 | Damm et al. |
| 2003/0149477 | A1 | 8/2003 | Gabbay |
| 2003/0149478 | A1 | 8/2003 | Figulla et al. |
| 2003/0153971 | A1 | 8/2003 | Chandrasekaran |
| 2003/0153974 | A1 | 8/2003 | Spenser et al. |
| 2003/0158573 | A1 | 8/2003 | Gittings et al. |
| 2003/0158595 | A1 | 8/2003 | Randall et al. |
| 2003/0163193 | A1 | 8/2003 | Widenhouse |
| 2003/0163198 | A1 | 8/2003 | Morra et al. |
| 2003/0165352 | A1 | 9/2003 | Ibrahim et al. |
| 2003/0171803 | A1 | 9/2003 | Shimon |
| 2003/0171805 | A1 | 9/2003 | Berg et al. |
| 2003/0176884 | A1 | 9/2003 | Berrada et al. |
| 2003/0181850 | A1 | 9/2003 | Diamond et al. |
| 2003/0181938 | A1 | 9/2003 | Roth et al. |
| 2003/0181942 | A1 | 9/2003 | Sutton et al. |
| 2003/0187495 | A1 | 10/2003 | Cully et al. |
| 2003/0191449 | A1 | 10/2003 | Nash et al. |
| 2003/0191516 | A1 | 10/2003 | Weldon et al. |

(56) References Cited

U.S. PATENT DOCUMENTS

2003/0191519 A1 10/2003 Lombardi et al.
2003/0191526 A1 10/2003 Van Tassel et al.
2003/0195457 A1 10/2003 LaFontaine et al.
2003/0195458 A1 10/2003 Phelps et al.
2003/0195609 A1 10/2003 Berenstein et al.
2003/0195620 A1 10/2003 Huynh et al.
2003/0198722 A1 10/2003 Johnston, Jr. et al.
2003/0199759 A1 10/2003 Richard
2003/0199913 A1 10/2003 Dubrul et al.
2003/0199963 A1 10/2003 Tower et al.
2003/0199971 A1 10/2003 Tower et al.
2003/0199972 A1 10/2003 Zadno-Azizi et al.
2003/0204160 A1 10/2003 Kamm et al.
2003/0204249 A1 10/2003 Letort
2003/0208224 A1 11/2003 Broome
2003/0212410 A1 11/2003 Stenzel et al.
2003/0212413 A1 11/2003 Wilk
2003/0212429 A1 11/2003 Keegan et al.
2003/0212452 A1 11/2003 Zadno-Azizi et al.
2003/0212454 A1 11/2003 Scott et al.
2003/0216678 A1 11/2003 March et al.
2003/0216679 A1 11/2003 Wolf et al.
2003/0216774 A1 11/2003 Larson
2003/0220661 A1 11/2003 Mowry et al.
2003/0220667 A1 11/2003 Van Der Burg et al.
2003/0225445 A1 12/2003 Derus et al.
2003/0229366 A1 12/2003 Reggie et al.
2003/0229390 A1 12/2003 Ashton et al.
2003/0233117 A1 12/2003 Adams et al.
2003/0236542 A1 12/2003 Makower
2003/0236567 A1 12/2003 Elliot
2003/0236568 A1 12/2003 Hojeibane et al.
2003/0236570 A1 12/2003 Cook et al.
2004/0004926 A1 1/2004 Maeda
2004/0006298 A1 1/2004 Wilk
2004/0006380 A1 1/2004 Buck et al.
2004/0015225 A1 1/2004 Kim et al.
2004/0015228 A1 1/2004 Lombardi et al.
2004/0018651 A1 1/2004 Nadeau
2004/0019348 A1 1/2004 Stevens et al.
2004/0019374 A1 1/2004 Hojeibane et al.
2004/0026389 A1 2/2004 Kessler et al.
2004/0033364 A1 2/2004 Spiridigliozzi et al.
2004/0034411 A1 2/2004 Quijano et al.
2004/0037946 A1 2/2004 Morra et al.
2004/0039343 A1 2/2004 Eppstein et al.
2004/0039436 A1 2/2004 Spenser et al.
2004/0044350 A1 3/2004 Martin et al.
2004/0044361 A1 3/2004 Frazier et al.
2004/0044392 A1 3/2004 Von Oepen
2004/0044400 A1 3/2004 Cheng et al.
2004/0044402 A1 3/2004 Jung et al.
2004/0049204 A1 3/2004 Harari et al.
2004/0049207 A1 3/2004 Goldfarb et al.
2004/0049224 A1 3/2004 Buehlmann et al.
2004/0049226 A1 3/2004 Keegan et al.
2004/0049262 A1 3/2004 Obermiller et al.
2004/0049266 A1 3/2004 Anduiza et al.
2004/0058097 A1 3/2004 Weder
2004/0059280 A1 3/2004 Makower et al.
2004/0059407 A1 3/2004 Escamilla et al.
2004/0059409 A1 3/2004 Stenzel
2004/0059429 A1 3/2004 Amin et al.
2004/0073157 A1 4/2004 Knudson et al.
2004/0073198 A1 4/2004 Gilson et al.
2004/0073238 A1 4/2004 Makower
2004/0073289 A1 4/2004 Hartley
2004/0077987 A1 4/2004 Rapacki et al.
2004/0077988 A1 4/2004 Tweden et al.
2004/0077990 A1 4/2004 Knudson et al.
2004/0078950 A1 4/2004 Schreck
2004/0082904 A1 4/2004 Houde et al.
2004/0082967 A1 4/2004 Broome et al.
2004/0082989 A1 4/2004 Cook et al.
2004/0087982 A1 5/2004 Eskuri
2004/0088042 A1 5/2004 Kim et al.
2004/0088045 A1 5/2004 Cox
2004/0092858 A1 5/2004 Wilson et al.
2004/0092989 A1 5/2004 Wilson et al.
2004/0093005 A1 5/2004 Durcan
2004/0093016 A1 5/2004 Root et al.
2004/0093060 A1 5/2004 Seguin et al.
2004/0093063 A1 5/2004 Wright et al.
2004/0093070 A1 5/2004 Hojeibane et al.
2004/0093075 A1 5/2004 Kuehne
2004/0097788 A1 5/2004 Mourlas et al.
2004/0098022 A1 5/2004 Barone
2004/0098098 A1 5/2004 McGuckin, Jr. et al.
2004/0098099 A1 5/2004 McCullagh et al.
2004/0098112 A1 5/2004 DiMatteo et al.
2004/0102855 A1 5/2004 Shank
2004/0106931 A1 6/2004 Guiles et al.
2004/0106976 A1 6/2004 Bailey et al.
2004/0106990 A1 6/2004 Spence et al.
2004/0107004 A1 6/2004 Levine et al.
2004/0111096 A1 6/2004 Tu et al.
2004/0113306 A1 6/2004 Rapacki et al.
2004/0116951 A1 6/2004 Rosengart
2004/0116999 A1 6/2004 Ledergerber
2004/0117004 A1 6/2004 Osborne et al.
2004/0117009 A1 6/2004 Cali et al.
2004/0118415 A1 6/2004 Hall et al.
2004/0122318 A1 6/2004 Flaherty et al.
2004/0122347 A1 6/2004 Knudson et al.
2004/0122468 A1 6/2004 Yodfat et al.
2004/0122514 A1 6/2004 Fogarty et al.
2004/0122516 A1 6/2004 Fogarty et al.
2004/0127847 A1 7/2004 DuBois et al.
2004/0127912 A1 7/2004 Rabkin et al.
2004/0127936 A1 7/2004 Salahieh et al.
2004/0127979 A1 7/2004 Wilson et al.
2004/0127982 A1 7/2004 Machold et al.
2004/0133154 A1 7/2004 Flaherty et al.
2004/0133225 A1 7/2004 Makower
2004/0133274 A1 7/2004 Webler et al.
2004/0138694 A1 7/2004 Tran et al.
2004/0138742 A1 7/2004 Myers et al.
2004/0138743 A1 7/2004 Myers et al.
2004/0138745 A1 7/2004 Macoviak et al.
2004/0147868 A1 7/2004 Bardsley et al.
2004/0147869 A1 7/2004 Wolf et al.
2004/0148018 A1 7/2004 Carpentier et al.
2004/0148021 A1 7/2004 Cartledge et al.
2004/0153094 A1 8/2004 Dunfee et al.
2004/0153145 A1 8/2004 Simionescu et al.
2004/0153146 A1 8/2004 Lashinski et al.
2004/0158143 A1 8/2004 Flaherty et al.
2004/0158277 A1 8/2004 Lowe et al.
2004/0163094 A1 8/2004 Matsui et al.
2004/0167444 A1 8/2004 Laroya et al.
2004/0167565 A1 8/2004 Beulke et al.
2004/0167573 A1 8/2004 Williamson, IV et al.
2004/0167620 A1 8/2004 Ortiz et al.
2004/0168691 A1 9/2004 Sharkawy et al.
2004/0176791 A1 9/2004 Lim et al.
2004/0181140 A1 9/2004 Falwell et al.
2004/0186378 A1 9/2004 Gesswein
2004/0186507 A1 9/2004 Hall et al.
2004/0186557 A1 9/2004 Gambale et al.
2004/0186558 A1 9/2004 Pavcnik et al.
2004/0186563 A1 9/2004 Lobbi
2004/0186565 A1 9/2004 Schreck
2004/0186587 A1 9/2004 Ahern
2004/0193180 A1 9/2004 Buzzard et al.
2004/0193244 A1 9/2004 Hartley et al.
2004/0193252 A1 9/2004 Perez et al.
2004/0193261 A1 9/2004 Berreklouw
2004/0197695 A1 10/2004 Aono
2004/0199245 A1 10/2004 Lauterjung
2004/0204683 A1 10/2004 McGuckin, Jr. et al.
2004/0204755 A1 10/2004 Robin
2004/0206363 A1 10/2004 McCarthy et al.
2004/0210104 A1 10/2004 Lau et al.
2004/0210190 A1 10/2004 Kohler et al.

(56) References Cited

U.S. PATENT DOCUMENTS

| | | | |
|---|---|---|---|
| 2004/0210240 | A1 | 10/2004 | Saint |
| 2004/0210301 | A1 | 10/2004 | Obermiller |
| 2004/0210304 | A1 | 10/2004 | Seguin et al. |
| 2004/0210306 | A1 | 10/2004 | Quijano et al. |
| 2004/0210307 | A1 | 10/2004 | Khairkhahan |
| 2004/0215317 | A1 | 10/2004 | Cummings |
| 2004/0215331 | A1 | 10/2004 | Chew et al. |
| 2004/0215333 | A1 | 10/2004 | Duran et al. |
| 2004/0215339 | A1 | 10/2004 | Drasler et al. |
| 2004/0219180 | A1 | 11/2004 | Gambale et al. |
| 2004/0220598 | A1 | 11/2004 | Bolduc et al. |
| 2004/0220655 | A1 | 11/2004 | Swanson et al. |
| 2004/0225321 | A1 | 11/2004 | Krolik et al. |
| 2004/0225353 | A1 | 11/2004 | McGuckin, Jr. et al. |
| 2004/0225354 | A1 | 11/2004 | Allen et al. |
| 2004/0225355 | A1 | 11/2004 | Stevens |
| 2004/0236411 | A1 | 11/2004 | Sarac et al. |
| 2004/0236418 | A1 | 11/2004 | Stevens |
| 2004/0243143 | A1 | 12/2004 | Corcoran et al. |
| 2004/0243221 | A1 | 12/2004 | Fawzi et al. |
| 2004/0249343 | A1 | 12/2004 | Cioanta |
| 2004/0254594 | A1 | 12/2004 | Alfaro |
| 2004/0254636 | A1 | 12/2004 | Flagle et al. |
| 2004/0260389 | A1 | 12/2004 | Case et al. |
| 2004/0260390 | A1 | 12/2004 | Sarac et al. |
| 2004/0260393 | A1 | 12/2004 | Rahdert et al. |
| 2004/0260394 | A1 | 12/2004 | Douk et al. |
| 2004/0267357 | A1 | 12/2004 | Allen et al. |
| 2005/0000858 | A1 | 1/2005 | Roovers |
| 2005/0004505 | A1 | 1/2005 | Phelps et al. |
| 2005/0004558 | A1 | 1/2005 | Gambale et al. |
| 2005/0004648 | A1 | 1/2005 | Boekstegers |
| 2005/0008589 | A1 | 1/2005 | Legrand et al. |
| 2005/0009000 | A1 | 1/2005 | Wilhelm et al. |
| 2005/0010246 | A1 | 1/2005 | Streeter et al. |
| 2005/0010285 | A1 | 1/2005 | Lambrecht et al. |
| 2005/0010287 | A1 | 1/2005 | Macoviak et al. |
| 2005/0015112 | A1 | 1/2005 | Cohn et al. |
| 2005/0021136 | A1 | 1/2005 | Xie et al. |
| 2005/0025857 | A1 | 2/2005 | Schoenherr et al. |
| 2005/0027305 | A1 | 2/2005 | Shiu et al. |
| 2005/0027348 | A1 | 2/2005 | Case et al. |
| 2005/0033220 | A1 | 2/2005 | Wilk et al. |
| 2005/0033398 | A1 | 2/2005 | Seguin |
| 2005/0033402 | A1 | 2/2005 | Cully et al. |
| 2005/0038495 | A1 | 2/2005 | Greenan |
| 2005/0038509 | A1 | 2/2005 | Ashe |
| 2005/0043585 | A1 | 2/2005 | Datta et al. |
| 2005/0043711 | A1 | 2/2005 | Corcoran et al. |
| 2005/0043757 | A1 | 2/2005 | Arad et al. |
| 2005/0043759 | A1 | 2/2005 | Chanduszko |
| 2005/0043760 | A1 | 2/2005 | Fogarty et al. |
| 2005/0043781 | A1 | 2/2005 | Foley |
| 2005/0043790 | A1 | 2/2005 | Seguin |
| 2005/0049674 | A1 | 3/2005 | Berra et al. |
| 2005/0049692 | A1 | 3/2005 | Numamoto et al. |
| 2005/0049696 | A1 | 3/2005 | Siess et al. |
| 2005/0055088 | A1 | 3/2005 | Liddicoat et al. |
| 2005/0060016 | A1 | 3/2005 | Wu et al. |
| 2005/0060018 | A1 | 3/2005 | Dittman |
| 2005/0060029 | A1 | 3/2005 | Le et al. |
| 2005/0060030 | A1 | 3/2005 | Lashinski et al. |
| 2005/0065594 | A1 | 3/2005 | DiMatteo et al. |
| 2005/0070794 | A1 | 3/2005 | Deal et al. |
| 2005/0070957 | A1 | 3/2005 | Das |
| 2005/0075584 | A1 | 4/2005 | Cali |
| 2005/0075662 | A1 | 4/2005 | Pedersen et al. |
| 2005/0075712 | A1 | 4/2005 | Biancucci et al. |
| 2005/0075717 | A1 | 4/2005 | Nguyen et al. |
| 2005/0075719 | A1 | 4/2005 | Bergheim |
| 2005/0075720 | A1 | 4/2005 | Nguyen et al. |
| 2005/0075724 | A1 | 4/2005 | Svanidze et al. |
| 2005/0075725 | A1 | 4/2005 | Rowe |
| 2005/0075726 | A1 | 4/2005 | Svanidze et al. |
| 2005/0075727 | A1 | 4/2005 | Wheatley |
| 2005/0075730 | A1 | 4/2005 | Myers et al. |
| 2005/0075731 | A1 | 4/2005 | Artof et al. |
| 2005/0075776 | A1 | 4/2005 | Cho |
| 2005/0084595 | A1 | 4/2005 | Shukla et al. |
| 2005/0085841 | A1 | 4/2005 | Eversull et al. |
| 2005/0085842 | A1 | 4/2005 | Eversull et al. |
| 2005/0085843 | A1 | 4/2005 | Opolski et al. |
| 2005/0085890 | A1 | 4/2005 | Rasmussen et al. |
| 2005/0085900 | A1 | 4/2005 | Case et al. |
| 2005/0090846 | A1 | 4/2005 | Pedersen et al. |
| 2005/0090890 | A1 | 4/2005 | Wu et al. |
| 2005/0096568 | A1 | 5/2005 | Kato |
| 2005/0096692 | A1 | 5/2005 | Linder et al. |
| 2005/0096724 | A1 | 5/2005 | Stenzel et al. |
| 2005/0096726 | A1 | 5/2005 | Sequin et al. |
| 2005/0096734 | A1 | 5/2005 | Majercak et al. |
| 2005/0096735 | A1 | 5/2005 | Hojeibane et al. |
| 2005/0096736 | A1 | 5/2005 | Osse et al. |
| 2005/0096738 | A1 | 5/2005 | Cali et al. |
| 2005/0096768 | A1 | 5/2005 | Huang et al. |
| 2005/0098547 | A1 | 5/2005 | Cali et al. |
| 2005/0100580 | A1 | 5/2005 | Osborne et al. |
| 2005/0101903 | A1 | 5/2005 | Kohler et al. |
| 2005/0101904 | A1 | 5/2005 | Wilk |
| 2005/0101968 | A1 | 5/2005 | Dadourian |
| 2005/0102020 | A1 | 5/2005 | Grayzel et al. |
| 2005/0107822 | A1 | 5/2005 | Wasdyke |
| 2005/0107871 | A1 | 5/2005 | Realyvasquez et al. |
| 2005/0113902 | A1 | 5/2005 | Geiser et al. |
| 2005/0113904 | A1 | 5/2005 | Shank et al. |
| 2005/0113910 | A1 | 5/2005 | Paniagua et al. |
| 2005/0119688 | A1 | 6/2005 | Bergheim |
| 2005/0119728 | A1 | 6/2005 | Sarac |
| 2005/0119736 | A1 | 6/2005 | Zilla et al. |
| 2005/0125075 | A1 | 6/2005 | Meade et al. |
| 2005/0131438 | A1 | 6/2005 | Cohn |
| 2005/0137499 | A1 | 6/2005 | Sheets et al. |
| 2005/0137609 | A1 | 6/2005 | Guiraudon |
| 2005/0137681 | A1 | 6/2005 | Shoemaker et al. |
| 2005/0137682 | A1 | 6/2005 | Justino |
| 2005/0137683 | A1 | 6/2005 | Hezi-Yamit et al. |
| 2005/0137686 | A1 | 6/2005 | Salahieh et al. |
| 2005/0137687 | A1 | 6/2005 | Salahieh et al. |
| 2005/0137688 | A1 | 6/2005 | Salahieh et al. |
| 2005/0137689 | A1 | 6/2005 | Salahieh et al. |
| 2005/0137690 | A1 | 6/2005 | Salahieh et al. |
| 2005/0137691 | A1 | 6/2005 | Salahieh et al. |
| 2005/0137692 | A1 | 6/2005 | Haug et al. |
| 2005/0137693 | A1 | 6/2005 | Haug et al. |
| 2005/0137694 | A1 | 6/2005 | Haug et al. |
| 2005/0137695 | A1 | 6/2005 | Salahieh et al. |
| 2005/0137696 | A1 | 6/2005 | Salahieh et al. |
| 2005/0137697 | A1 | 6/2005 | Salahieh et al. |
| 2005/0137698 | A1 | 6/2005 | Salahieh et al. |
| 2005/0137699 | A1 | 6/2005 | Salahieh et al. |
| 2005/0137701 | A1 | 6/2005 | Salahieh et al. |
| 2005/0137702 | A1 | 6/2005 | Haug et al. |
| 2005/0138689 | A1 | 6/2005 | Aukerman |
| 2005/0143804 | A1 | 6/2005 | Haverkost |
| 2005/0143807 | A1 | 6/2005 | Pavcnik et al. |
| 2005/0143809 | A1 | 6/2005 | Salahieh et al. |
| 2005/0148997 | A1 | 7/2005 | Valley et al. |
| 2005/0149159 | A1 | 7/2005 | Andreas et al. |
| 2005/0149166 | A1 | 7/2005 | Schaeffer et al. |
| 2005/0149181 | A1 | 7/2005 | Eberhardt |
| 2005/0150775 | A1 | 7/2005 | Zhang et al. |
| 2005/0159726 | A1 | 7/2005 | Evans et al. |
| 2005/0165352 | A1 | 7/2005 | Henry et al. |
| 2005/0165477 | A1 | 7/2005 | Anduiza et al. |
| 2005/0165479 | A1 | 7/2005 | Drews et al. |
| 2005/0171597 | A1 | 8/2005 | Boatman et al. |
| 2005/0171598 | A1 | 8/2005 | Schaeffer |
| 2005/0177227 | A1 | 8/2005 | Heim et al. |
| 2005/0182483 | A1 | 8/2005 | Osborne et al. |
| 2005/0182486 | A1 | 8/2005 | Gabbay |
| 2005/0186349 | A1 | 8/2005 | Loper et al. |
| 2005/0187616 | A1 | 8/2005 | Realyvasquez |
| 2005/0192527 | A1 | 9/2005 | Gharib et al. |
| 2005/0192665 | A1 | 9/2005 | Spenser et al. |

(56) References Cited

U.S. PATENT DOCUMENTS

2005/0197694 A1 9/2005 Pai et al.
2005/0197695 A1 9/2005 Stacchino et al.
2005/0203549 A1 9/2005 Realyvasquez
2005/0203605 A1 9/2005 Dolan
2005/0203614 A1 9/2005 Forster et al.
2005/0203615 A1 9/2005 Forster et al.
2005/0203616 A1 9/2005 Cribier
2005/0203617 A1 9/2005 Forster et al.
2005/0203618 A1 9/2005 Sharkawy et al.
2005/0203818 A9 9/2005 Rotman et al.
2005/0209580 A1 9/2005 Freyman
2005/0214342 A1 9/2005 Tweden et al.
2005/0222664 A1 10/2005 Parker
2005/0222668 A1 10/2005 Schaeffer et al.
2005/0222674 A1 10/2005 Paine
2005/0228334 A1 10/2005 Knudson et al.
2005/0228472 A1 10/2005 Case et al.
2005/0228495 A1 10/2005 Macoviak
2005/0228496 A1 10/2005 Mensah et al.
2005/0234546 A1 10/2005 Nugent et al.
2005/0240200 A1 10/2005 Bergheim
2005/0240262 A1 10/2005 White
2005/0240263 A1 10/2005 Fogarty et al.
2005/0251243 A1 11/2005 Seppala et al.
2005/0251250 A1 11/2005 Verhoeven et al.
2005/0251251 A1 11/2005 Cribier
2005/0251252 A1 11/2005 Stobie
2005/0256532 A1 11/2005 Nayak et al.
2005/0261759 A1 11/2005 Lambrecht et al.
2005/0267523 A1 12/2005 Devellian et al.
2005/0267560 A1 12/2005 Bates
2005/0267567 A1 12/2005 Shalev
2005/0267573 A9 12/2005 Macoviak et al.
2005/0283231 A1 12/2005 Haug et al.
2005/0283962 A1 12/2005 Boudjemline
2005/0288627 A1 12/2005 Mogul
2005/0288685 A1 12/2005 Gulles et al.
2005/0288706 A1 12/2005 Widomski et al.
2006/0004439 A1 1/2006 Spenser et al.
2006/0004442 A1 1/2006 Spenser et al.
2006/0004469 A1 1/2006 Sokel
2006/0009841 A1 1/2006 McGuckin, Jr. et al.
2006/0009842 A1 1/2006 Huynh et al.
2006/0015168 A1 1/2006 Gunderson
2006/0025855 A1 2/2006 Lashinski et al.
2006/0025857 A1 2/2006 Bergheim et al.
2006/0028766 A1 2/2006 Khizroev
2006/0041218 A1 2/2006 Phelps et al.
2006/0047338 A1 3/2006 Jenson et al.
2006/0047343 A1 3/2006 Oviatt et al.
2006/0052736 A1 3/2006 Tweden et al.
2006/0052867 A1 3/2006 Revuelta et al.
2006/0058775 A1 3/2006 Stevens et al.
2006/0058864 A1 3/2006 Schaeffer et al.
2006/0058871 A1 3/2006 Zakay et al.
2006/0058872 A1 3/2006 Salahieh et al.
2006/0064151 A1 3/2006 Guterman et al.
2006/0069424 A1 3/2006 Acosta et al.
2006/0074477 A1 4/2006 Berthiaume et al.
2006/0074484 A1 4/2006 Huber
2006/0074485 A1 4/2006 Realyvasquez
2006/0077447 A1 4/2006 Sojian et al.
2006/0085060 A1 4/2006 Campbell
2006/0089711 A1 4/2006 Dolan
2006/0100685 A1 5/2006 Seguin et al.
2006/0111770 A1 5/2006 Pavcnik et al.
2006/0116757 A1 6/2006 Lashinski et al.
2006/0122692 A1 6/2006 Gilad et al.
2006/0135961 A1 6/2006 Rosenman et al.
2006/0135964 A1 6/2006 Vesely
2006/0136034 A1 6/2006 Modesitt et al.
2006/0142846 A1 6/2006 Pavcnik et al.
2006/0142848 A1 6/2006 Gabbay
2006/0149360 A1 7/2006 Schwammenthal et al.
2006/0155312 A1 7/2006 Levine et al.
2006/0155363 A1 7/2006 LaDuca et al.
2006/0155366 A1 7/2006 LaDuca et al.
2006/0161248 A1 7/2006 Case et al.
2006/0161249 A1 7/2006 Realyvasquez et al.
2006/0161265 A1 7/2006 Levine et al.
2006/0167474 A1 7/2006 Bloom et al.
2006/0167543 A1 7/2006 Bailey et al.
2006/0173524 A1 8/2006 Salahieh et al.
2006/0178740 A1 8/2006 Stacchino et al.
2006/0190070 A1 8/2006 Dieck et al.
2006/0193885 A1 8/2006 Leonard Neethling et al.
2006/0195134 A1 8/2006 Crittenden
2006/0195183 A1 8/2006 Navia et al.
2006/0195186 A1 8/2006 Drews et al.
2006/0206192 A1 9/2006 Tower et al.
2006/0206202 A1 9/2006 Bonhoeffer et al.
2006/0210597 A1 9/2006 Hiles
2006/0212110 A1 9/2006 Osborne et al.
2006/0212111 A1 9/2006 Case et al.
2006/0217802 A1 9/2006 Ruiz et al.
2006/0224183 A1 10/2006 Freudenthal
2006/0229561 A1 10/2006 Huszar
2006/0229700 A1 10/2006 Acosta et al.
2006/0229718 A1 10/2006 Marquez
2006/0229719 A1 10/2006 Marquez et al.
2006/0241745 A1 10/2006 Solem
2006/0246584 A1 11/2006 Covelli
2006/0247570 A1 11/2006 Pokorney
2006/0247763 A1 11/2006 Slater
2006/0253191 A1 11/2006 Salahieh et al.
2006/0259134 A1 11/2006 Schwammenthal et al.
2006/0259135 A1 11/2006 Navia et al.
2006/0259136 A1 11/2006 Nguyen et al.
2006/0259137 A1 11/2006 Artof et al.
2006/0265043 A1 11/2006 Mandrusov et al.
2006/0265056 A1 11/2006 Nguyen et al.
2006/0270958 A1 11/2006 George
2006/0271149 A1 11/2006 Berez et al.
2006/0271161 A1 11/2006 Meyer et al.
2006/0271166 A1 11/2006 Thill et al.
2006/0271175 A1 11/2006 Woolfson et al.
2006/0276873 A1 12/2006 Sato
2006/0276874 A1 12/2006 Wilson et al.
2006/0276882 A1 12/2006 Case et al.
2006/0276887 A1 12/2006 Brady et al.
2006/0282161 A1 12/2006 Huynh et al.
2006/0287668 A1 12/2006 Fawzi et al.
2006/0287717 A1 12/2006 Rowe et al.
2006/0287719 A1 12/2006 Rowe et al.
2006/0290027 A1 12/2006 O'Connor et al.
2006/0293745 A1 12/2006 Carpentier et al.
2007/0005129 A1 1/2007 Damm et al.
2007/0005131 A1 1/2007 Taylor
2007/0005132 A1 1/2007 Simionescu et al.
2007/0010876 A1 1/2007 Salahieh et al.
2007/0010877 A1 1/2007 Salahieh et al.
2007/0010878 A1 1/2007 Rafiee et al.
2007/0010887 A1 1/2007 Williams et al.
2007/0016286 A1 1/2007 Herrmann et al.
2007/0016288 A1 1/2007 Gurskis et al.
2007/0020248 A1 1/2007 Everaerts et al.
2007/0021826 A1 1/2007 Case et al.
2007/0027518 A1 2/2007 Case et al.
2007/0027520 A1 2/2007 Sherburne
2007/0027533 A1 2/2007 Douk
2007/0027535 A1 2/2007 Purdy, Jr. et al.
2007/0032856 A1 2/2007 Limon
2007/0032879 A1 2/2007 Levine et al.
2007/0038291 A1 2/2007 Case et al.
2007/0038295 A1 2/2007 Case et al.
2007/0043420 A1 2/2007 Lostetter
2007/0043424 A1 2/2007 Pryor
2007/0043431 A1 2/2007 Melsheimer
2007/0043435 A1 2/2007 Seguin et al.
2007/0050014 A1 3/2007 Johnson
2007/0051377 A1 3/2007 Douk et al.
2007/0055340 A1 3/2007 Pryor
2007/0056346 A1 3/2007 Spenser et al.
2007/0060998 A1 3/2007 Butterwick et al.

(56) References Cited

U.S. PATENT DOCUMENTS

| | | | |
|---|---|---|---|
| 2007/0061002 | A1 | 3/2007 | Paul, Jr. et al. |
| 2007/0061008 | A1 | 3/2007 | Salahieh et al. |
| 2007/0073389 | A1 | 3/2007 | Bolduc et al. |
| 2007/0073392 | A1 | 3/2007 | Heyninck-Jantz et al. |
| 2007/0078504 | A1 | 4/2007 | Mialhe |
| 2007/0078509 | A1 | 4/2007 | Lotfy |
| 2007/0078510 | A1 | 4/2007 | Ryan |
| 2007/0088431 | A1 | 4/2007 | Bourang et al. |
| 2007/0093869 | A1 | 4/2007 | Bloom et al. |
| 2007/0093887 | A1 | 4/2007 | Case et al. |
| 2007/0100427 | A1 | 5/2007 | Perouse |
| 2007/0100435 | A1 | 5/2007 | Case et al. |
| 2007/0100439 | A1 | 5/2007 | Cangialosi et al. |
| 2007/0100440 | A1 | 5/2007 | Figulla et al. |
| 2007/0100449 | A1 | 5/2007 | O'Neil et al. |
| 2007/0112355 | A1 | 5/2007 | Salahieh et al. |
| 2007/0112358 | A1 | 5/2007 | Abbott et al. |
| 2007/0112415 | A1 | 5/2007 | Bartlett |
| 2007/0112422 | A1 | 5/2007 | Dehdashtian |
| 2007/0118214 | A1 | 5/2007 | Salahieh et al. |
| 2007/0123700 | A1 | 5/2007 | Ueda et al. |
| 2007/0123979 | A1 | 5/2007 | Perier et al. |
| 2007/0135889 | A1 | 6/2007 | Moore et al. |
| 2007/0142906 | A1 | 6/2007 | Figulla et al. |
| 2007/0142907 | A1 | 6/2007 | Moaddeb et al. |
| 2007/0155010 | A1 | 7/2007 | Farnsworth et al. |
| 2007/0156233 | A1 | 7/2007 | Kapadia et al. |
| 2007/0162102 | A1 | 7/2007 | Ryan et al. |
| 2007/0162103 | A1 | 7/2007 | Case et al. |
| 2007/0162107 | A1 | 7/2007 | Haug et al. |
| 2007/0162113 | A1 | 7/2007 | Sharkawy et al. |
| 2007/0173918 | A1 | 7/2007 | Dreher et al. |
| 2007/0173932 | A1 | 7/2007 | Cali et al. |
| 2007/0179592 | A1 | 8/2007 | Schaeffer |
| 2007/0179600 | A1 | 8/2007 | Vardi |
| 2007/0185513 | A1 | 8/2007 | Woolfson et al. |
| 2007/0185565 | A1 | 8/2007 | Schwammenthal et al. |
| 2007/0185571 | A1 | 8/2007 | Kapadia et al. |
| 2007/0198078 | A1 | 8/2007 | Berra et al. |
| 2007/0198097 | A1 | 8/2007 | Zegdi |
| 2007/0203391 | A1 | 8/2007 | Bloom et al. |
| 2007/0203503 | A1 | 8/2007 | Salahieh et al. |
| 2007/0203560 | A1 | 8/2007 | Forster et al. |
| 2007/0203576 | A1 | 8/2007 | Lee et al. |
| 2007/0208550 | A1 | 9/2007 | Cao et al. |
| 2007/0213813 | A1 | 9/2007 | Von Segesser et al. |
| 2007/0225681 | A1 | 9/2007 | House |
| 2007/0225802 | A1 | 9/2007 | Forsell |
| 2007/0232898 | A1 | 10/2007 | Huynh et al. |
| 2007/0233222 | A1 | 10/2007 | Roeder et al. |
| 2007/0233228 | A1 | 10/2007 | Eberhardt et al. |
| 2007/0233237 | A1 | 10/2007 | Krivoruchko |
| 2007/0233238 | A1 | 10/2007 | Huynh et al. |
| 2007/0238979 | A1 | 10/2007 | Huynh et al. |
| 2007/0239254 | A1 | 10/2007 | Chia et al. |
| 2007/0239265 | A1 | 10/2007 | Birdsall |
| 2007/0239266 | A1 | 10/2007 | Birdsall |
| 2007/0239269 | A1 | 10/2007 | Dolan et al. |
| 2007/0239271 | A1 | 10/2007 | Nguyen |
| 2007/0239273 | A1 | 10/2007 | Allen |
| 2007/0244543 | A1 | 10/2007 | Mitchell |
| 2007/0244544 | A1 | 10/2007 | Birdsall et al. |
| 2007/0244545 | A1 | 10/2007 | Birdsall et al. |
| 2007/0244546 | A1 | 10/2007 | Francis |
| 2007/0244551 | A1 | 10/2007 | Stobie |
| 2007/0244552 | A1 | 10/2007 | Salahieh et al. |
| 2007/0244553 | A1 | 10/2007 | Rafiee et al. |
| 2007/0244554 | A1 | 10/2007 | Rafiee et al. |
| 2007/0244555 | A1 | 10/2007 | Rafiee et al. |
| 2007/0244556 | A1 | 10/2007 | Rafiee et al. |
| 2007/0244557 | A1 | 10/2007 | Rafiee et al. |
| 2007/0250151 | A1 | 10/2007 | Pereira |
| 2007/0250160 | A1 | 10/2007 | Rafiee |
| 2007/0255386 | A1 | 11/2007 | Tenne |
| 2007/0255390 | A1 | 11/2007 | Ducke et al. |
| 2007/0255394 | A1 | 11/2007 | Ryan |
| 2007/0255396 | A1 | 11/2007 | Douk et al. |
| 2007/0260301 | A1 | 11/2007 | Chuter et al. |
| 2007/0260327 | A1 | 11/2007 | Case et al. |
| 2007/0265701 | A1 | 11/2007 | Gurskis et al. |
| 2007/0270751 | A1 | 11/2007 | Stangenes et al. |
| 2007/0270943 | A1 | 11/2007 | Solem et al. |
| 2007/0273813 | A1 | 11/2007 | Yoshida et al. |
| 2007/0282436 | A1 | 12/2007 | Pinchuk |
| 2007/0287717 | A1 | 12/2007 | Fanning et al. |
| 2007/0288000 | A1 | 12/2007 | Bonan |
| 2007/0288087 | A1 | 12/2007 | Fearnot et al. |
| 2007/0288089 | A1 | 12/2007 | Gurskis et al. |
| 2008/0004688 | A1 | 1/2008 | Spenser et al. |
| 2008/0004696 | A1 | 1/2008 | Vesely |
| 2008/0009934 | A1 | 1/2008 | Schneider et al. |
| 2008/0009940 | A1 | 1/2008 | Cribier |
| 2008/0015671 | A1 | 1/2008 | Bonhoeffer |
| 2008/0021546 | A1 | 1/2008 | Patz et al. |
| 2008/0021552 | A1 | 1/2008 | Gabbay |
| 2008/0022504 | A1 | 1/2008 | Melsheimer |
| 2008/0033534 | A1 | 2/2008 | Cook et al. |
| 2008/0033541 | A1 | 2/2008 | Gelbart et al. |
| 2008/0039925 | A1 | 2/2008 | Ishimaru et al. |
| 2008/0039934 | A1 | 2/2008 | Styrc |
| 2008/0045921 | A1 | 2/2008 | Anderson et al. |
| 2008/0048656 | A1 | 2/2008 | Tan et al. |
| 2008/0065001 | A1 | 3/2008 | DiNucci et al. |
| 2008/0065011 | A1 | 3/2008 | Marchand et al. |
| 2008/0065206 | A1 | 3/2008 | Liddicoat |
| 2008/0071361 | A1 | 3/2008 | Tuval et al. |
| 2008/0071362 | A1 | 3/2008 | Tuval et al. |
| 2008/0071363 | A1 | 3/2008 | Tuval et al. |
| 2008/0071366 | A1 | 3/2008 | Tuval et al. |
| 2008/0071368 | A1 | 3/2008 | Tuval et al. |
| 2008/0071369 | A1 | 3/2008 | Tuval et al. |
| 2008/0077227 | A1 | 3/2008 | Ouellette et al. |
| 2008/0077234 | A1 | 3/2008 | Styrc |
| 2008/0077236 | A1 | 3/2008 | Letac et al. |
| 2008/0082165 | A1 | 4/2008 | Wilson et al. |
| 2008/0082166 | A1 | 4/2008 | Styrc et al. |
| 2008/0086205 | A1 | 4/2008 | Gordy et al. |
| 2008/0097586 | A1 | 4/2008 | Pavcnik et al. |
| 2008/0102439 | A1 | 5/2008 | Tian et al. |
| 2008/0109070 | A1 | 5/2008 | Wagner et al. |
| 2008/0125859 | A1 | 5/2008 | Salahieh et al. |
| 2008/0127707 | A1 | 6/2008 | Kokish et al. |
| 2008/0133002 | A1 | 6/2008 | Gelbart et al. |
| 2008/0133003 | A1 | 6/2008 | Seguin et al. |
| 2008/0140188 | A1 | 6/2008 | Rahdert et al. |
| 2008/0140189 | A1 | 6/2008 | Nguyen et al. |
| 2008/0147105 | A1 | 6/2008 | Wilson et al. |
| 2008/0147180 | A1 | 6/2008 | Ghione et al. |
| 2008/0147181 | A1 | 6/2008 | Ghione et al. |
| 2008/0147182 | A1 | 6/2008 | Righini et al. |
| 2008/0154355 | A1 | 6/2008 | Benichou et al. |
| 2008/0154356 | A1 | 6/2008 | Obermiller et al. |
| 2008/0161909 | A1 | 7/2008 | Kheradvar et al. |
| 2008/0161910 | A1 | 7/2008 | Revuelta et al. |
| 2008/0161911 | A1 | 7/2008 | Revuelta et al. |
| 2008/0172119 | A1 | 7/2008 | Yamasaki et al. |
| 2008/0177381 | A1 | 7/2008 | Navia et al. |
| 2008/0183273 | A1 | 7/2008 | Mesana et al. |
| 2008/0188928 | A1 | 8/2008 | Salahieh et al. |
| 2008/0195193 | A1 | 8/2008 | Purdy et al. |
| 2008/0195199 | A1 | 8/2008 | Kheradvar et al. |
| 2008/0200977 | A1 | 8/2008 | Paul et al. |
| 2008/0208209 | A1 | 8/2008 | Fischer et al. |
| 2008/0208327 | A1 | 8/2008 | Rowe |
| 2008/0208328 | A1 | 8/2008 | Antocci et al. |
| 2008/0208332 | A1 | 8/2008 | Lamphere et al. |
| 2008/0215143 | A1 | 9/2008 | Seguin |
| 2008/0215144 | A1 | 9/2008 | Ryan et al. |
| 2008/0221672 | A1 | 9/2008 | Lamphere et al. |
| 2008/0221703 | A1 | 9/2008 | Que et al. |
| 2008/0228254 | A1 | 9/2008 | Ryan |
| 2008/0228263 | A1 | 9/2008 | Ryan |
| 2008/0234443 | A1 | 9/2008 | Kiss et al. |
| 2008/0234797 | A1 | 9/2008 | Styrc |

(56) References Cited

U.S. PATENT DOCUMENTS

| | | | |
|---|---|---|---|
| 2008/0234814 | A1 | 9/2008 | Salahieh et al. |
| 2008/0243246 | A1 | 10/2008 | Ryan et al. |
| 2008/0255651 | A1 | 10/2008 | Dwork |
| 2008/0255660 | A1 | 10/2008 | Guyenot et al. |
| 2008/0255661 | A1 | 10/2008 | Straubinger et al. |
| 2008/0262590 | A1 | 10/2008 | Murray |
| 2008/0262592 | A1 | 10/2008 | Jordan et al. |
| 2008/0262593 | A1 | 10/2008 | Ryan et al. |
| 2008/0262602 | A1 | 10/2008 | Wilk et al. |
| 2008/0264102 | A1 | 10/2008 | Berra |
| 2008/0269878 | A1 | 10/2008 | Iobbi |
| 2008/0275549 | A1 | 11/2008 | Rowe |
| 2008/0275550 | A1 | 11/2008 | Kheradvar et al. |
| 2008/0288054 | A1 | 11/2008 | Pulnev et al. |
| 2009/0005863 | A1 | 1/2009 | Goetz et al. |
| 2009/0012356 | A1 | 1/2009 | Dann et al. |
| 2009/0012600 | A1 | 1/2009 | Styrc et al. |
| 2009/0030512 | A1 | 1/2009 | Thielen et al. |
| 2009/0048656 | A1 | 2/2009 | Wen |
| 2009/0054968 | A1 | 2/2009 | Bonhoeffer et al. |
| 2009/0054969 | A1 | 2/2009 | Salahieh et al. |
| 2009/0054976 | A1 | 2/2009 | Tuval et al. |
| 2009/0062908 | A1 | 3/2009 | Bonhoeffer et al. |
| 2009/0069886 | A1 | 3/2009 | Suri et al. |
| 2009/0069887 | A1 | 3/2009 | Righini et al. |
| 2009/0069889 | A1 | 3/2009 | Suri et al. |
| 2009/0069890 | A1 | 3/2009 | Suri et al. |
| 2009/0076598 | A1 | 3/2009 | Salahieh et al. |
| 2009/0082844 | A1 | 3/2009 | Zacharias et al. |
| 2009/0082858 | A1 | 3/2009 | Nugent et al. |
| 2009/0085900 | A1 | 4/2009 | Weiner |
| 2009/0093876 | A1 | 4/2009 | Nitzan et al. |
| 2009/0093877 | A1 | 4/2009 | Keidar et al. |
| 2009/0099640 | A1 | 4/2009 | Weng |
| 2009/0099641 | A1 | 4/2009 | Wu et al. |
| 2009/0099643 | A1 | 4/2009 | Hyodoh et al. |
| 2009/0099653 | A1 | 4/2009 | Suri et al. |
| 2009/0112309 | A1 | 4/2009 | Jaramillo et al. |
| 2009/0138079 | A1 | 5/2009 | Tuval et al. |
| 2009/0157175 | A1 | 6/2009 | Benichou |
| 2009/0163951 | A1 | 6/2009 | Simmons et al. |
| 2009/0164004 | A1 | 6/2009 | Cohn |
| 2009/0164006 | A1 | 6/2009 | Seguin et al. |
| 2009/0171432 | A1 | 7/2009 | Von Segesser et al. |
| 2009/0171447 | A1 | 7/2009 | Von Segesser et al. |
| 2009/0171456 | A1 | 7/2009 | Kveen et al. |
| 2009/0182405 | A1 | 7/2009 | Arnault De La Menardiere et al. |
| 2009/0192585 | A1 | 7/2009 | Bloom et al. |
| 2009/0192586 | A1 | 7/2009 | Tabor et al. |
| 2009/0192591 | A1 | 7/2009 | Ryan et al. |
| 2009/0192601 | A1 | 7/2009 | Rafiee et al. |
| 2009/0198316 | A1 | 8/2009 | Laske et al. |
| 2009/0198323 | A1 | 8/2009 | Johnson et al. |
| 2009/0210052 | A1 | 8/2009 | Forster et al. |
| 2009/0216310 | A1 | 8/2009 | Straubinger et al. |
| 2009/0216312 | A1* | 8/2009 | Straubinger .......... A61F 2/2418 623/1.36 |
| 2009/0216313 | A1 | 8/2009 | Straubinger et al. |
| 2009/0222076 | A1 | 9/2009 | Figulla et al. |
| 2009/0222082 | A1 | 9/2009 | Lock et al. |
| 2009/0234407 | A1 | 9/2009 | Hastings et al. |
| 2009/0234443 | A1 | 9/2009 | Ottma et al. |
| 2009/0240264 | A1 | 9/2009 | Tuval et al. |
| 2009/0240320 | A1 | 9/2009 | Tuval et al. |
| 2009/0248143 | A1 | 10/2009 | Laham |
| 2009/0259306 | A1 | 10/2009 | Rowe |
| 2009/0264759 | A1 | 10/2009 | Byrd |
| 2009/0264997 | A1 | 10/2009 | Salahieh et al. |
| 2009/0276040 | A1 | 11/2009 | Rowe et al. |
| 2009/0281619 | A1 | 11/2009 | Le et al. |
| 2009/0287290 | A1 | 11/2009 | Macaulay et al. |
| 2009/0287296 | A1 | 11/2009 | Manasse |
| 2009/0287299 | A1 | 11/2009 | Tabor et al. |
| 2009/0299462 | A1 | 12/2009 | Fawzi et al. |
| 2009/0319037 | A1 | 12/2009 | Rowe et al. |
| 2010/0004739 | A1 | 1/2010 | Vesely |
| 2010/0004740 | A1 | 1/2010 | Seguin et al. |
| 2010/0011564 | A1 | 1/2010 | Millwee et al. |
| 2010/0022948 | A1 | 1/2010 | Wilson et al. |
| 2010/0030328 | A1 | 2/2010 | Seguin et al. |
| 2010/0036479 | A1 | 2/2010 | Hill et al. |
| 2010/0036485 | A1 | 2/2010 | Seguin |
| 2010/0049313 | A1 | 2/2010 | Alon et al. |
| 2010/0057051 | A1 | 3/2010 | Howat et al. |
| 2010/0057185 | A1 | 3/2010 | Melsheimer et al. |
| 2010/0069852 | A1 | 3/2010 | Kelley |
| 2010/0069916 | A1 | 3/2010 | Cully et al. |
| 2010/0070027 | A1 | 3/2010 | Bonhoeffer et al. |
| 2010/0082089 | A1 | 4/2010 | Quadri et al. |
| 2010/0082094 | A1 | 4/2010 | Quadri et al. |
| 2010/0087913 | A1 | 4/2010 | Rabkin et al. |
| 2010/0094399 | A1 | 4/2010 | Dorn et al. |
| 2010/0094411 | A1 | 4/2010 | Tuval et al. |
| 2010/0100167 | A1 | 4/2010 | Bortlein et al. |
| 2010/0121434 | A1 | 5/2010 | Paul et al. |
| 2010/0131054 | A1 | 5/2010 | Tuval et al. |
| 2010/0131057 | A1 | 5/2010 | Subramanian et al. |
| 2010/0137979 | A1 | 6/2010 | Tuval et al. |
| 2010/0145439 | A1 | 6/2010 | Seguin et al. |
| 2010/0152840 | A1 | 6/2010 | Seguin et al. |
| 2010/0160725 | A1 | 6/2010 | Kiser et al. |
| 2010/0161045 | A1 | 6/2010 | Righini |
| 2010/0168839 | A1 | 7/2010 | Braido et al. |
| 2010/0174362 | A1 | 7/2010 | Straubinger et al. |
| 2010/0185275 | A1 | 7/2010 | Richter et al. |
| 2010/0185277 | A1 | 7/2010 | Braido et al. |
| 2010/0191320 | A1* | 7/2010 | Straubinger .......... A61F 2/2418 623/1.26 |
| 2010/0191326 | A1 | 7/2010 | Alkhatib |
| 2010/0198346 | A1 | 8/2010 | Keogh et al. |
| 2010/0210991 | A1 | 8/2010 | Wilk et al. |
| 2010/0219092 | A1 | 9/2010 | Salahieh et al. |
| 2010/0234932 | A1 | 9/2010 | Arbefeuille et al. |
| 2010/0234940 | A1 | 9/2010 | Dolan |
| 2010/0239917 | A1 | 9/2010 | Lee et al. |
| 2010/0249908 | A1 | 9/2010 | Chau et al. |
| 2010/0249915 | A1 | 9/2010 | Zhang |
| 2010/0249916 | A1 | 9/2010 | Zhang |
| 2010/0249917 | A1 | 9/2010 | Zhang |
| 2010/0249918 | A1 | 9/2010 | Zhang |
| 2010/0256723 | A1 | 10/2010 | Murray |
| 2010/0262231 | A1 | 10/2010 | Tuval et al. |
| 2010/0268332 | A1 | 10/2010 | Tuval et al. |
| 2010/0280459 | A1 | 11/2010 | Werner |
| 2010/0280495 | A1 | 11/2010 | Paul et al. |
| 2010/0286768 | A1 | 11/2010 | Alkhatib |
| 2010/0292779 | A1 | 11/2010 | Straubinger et al. |
| 2010/0292780 | A1 | 11/2010 | Straubinger et al. |
| 2010/0292785 | A1 | 11/2010 | Seguin et al. |
| 2010/0298931 | A1 | 11/2010 | Quadri et al. |
| 2011/0004297 | A1 | 1/2011 | Sogard et al. |
| 2011/0015616 | A1 | 1/2011 | Straubinger et al. |
| 2011/0022157 | A1 | 1/2011 | Essinger et al. |
| 2011/0029066 | A1 | 2/2011 | Gilad et al. |
| 2011/0034852 | A1 | 2/2011 | Hausler et al. |
| 2011/0040366 | A1 | 2/2011 | Goetz et al. |
| 2011/0040374 | A1 | 2/2011 | Goetz et al. |
| 2011/0071613 | A1 | 3/2011 | Wood et al. |
| 2011/0093007 | A1 | 4/2011 | Abbott et al. |
| 2011/0098805 | A1 | 4/2011 | Dwork et al. |
| 2011/0106244 | A1 | 5/2011 | Ferrari et al. |
| 2011/0118545 | A1 | 5/2011 | Williams et al. |
| 2011/0137397 | A1 | 6/2011 | Chau et al. |
| 2011/0166637 | A1 | 7/2011 | Irwin et al. |
| 2011/0190862 | A1 | 8/2011 | Bashiri et al. |
| 2011/0190874 | A1 | 8/2011 | Celermajer et al. |
| 2011/0208290 | A1 | 8/2011 | Straubinger et al. |
| 2011/0208297 | A1 | 8/2011 | Tuval et al. |
| 2011/0224780 | A1 | 9/2011 | Tabor et al. |
| 2011/0238159 | A1 | 9/2011 | Guyenot et al. |
| 2011/0238167 | A1 | 9/2011 | Dove et al. |
| 2011/0257729 | A1 | 10/2011 | Spenser et al. |
| 2011/0257733 | A1 | 10/2011 | Dwork |
| 2011/0257735 | A1 | 10/2011 | Salahieh et al. |

(56) References Cited

U.S. PATENT DOCUMENTS

| | | | |
|---|---|---|---|
| 2011/0264191 | A1 | 10/2011 | Rothstein |
| 2011/0264196 | A1 | 10/2011 | Savage et al. |
| 2011/0264203 | A1 | 10/2011 | Dwork et al. |
| 2011/0276121 | A1 | 11/2011 | Levine |
| 2011/0276129 | A1 | 11/2011 | Salahieh et al. |
| 2011/0288626 | A1 | 11/2011 | Straubinger et al. |
| 2011/0288634 | A1 | 11/2011 | Tuval et al. |
| 2011/0295363 | A1 | 12/2011 | Girard et al. |
| 2011/0319989 | A1 | 12/2011 | Lane et al. |
| 2012/0016469 | A1 | 1/2012 | Salahieh et al. |
| 2012/0016471 | A1 | 1/2012 | Salahieh et al. |
| 2012/0022633 | A1 | 1/2012 | Olson et al. |
| 2012/0022642 | A1 | 1/2012 | Haug et al. |
| 2012/0029627 | A1 | 2/2012 | Salahieh et al. |
| 2012/0035719 | A1 | 2/2012 | Forster et al. |
| 2012/0035720 | A1 | 2/2012 | Cali et al. |
| 2012/0041547 | A1 | 2/2012 | Duffy et al. |
| 2012/0041549 | A1 | 2/2012 | Salahieh et al. |
| 2012/0041550 | A1 | 2/2012 | Salahieh et al. |
| 2012/0046740 | A1 | 2/2012 | Paul et al. |
| 2012/0053683 | A1 | 3/2012 | Salahieh et al. |
| 2012/0059447 | A1 | 3/2012 | Zilla et al. |
| 2012/0065464 | A1 | 3/2012 | Ellis et al. |
| 2012/0078347 | A1 | 3/2012 | Braido et al. |
| 2012/0078357 | A1 | 3/2012 | Conklin |
| 2012/0078360 | A1 | 3/2012 | Rafiee |
| 2012/0089224 | A1 | 4/2012 | Haug et al. |
| 2012/0100182 | A1 | 4/2012 | Mooney et al. |
| 2012/0101571 | A1 | 4/2012 | Thambar et al. |
| 2012/0101572 | A1 | 4/2012 | Kovalsky et al. |
| 2012/0116496 | A1 | 5/2012 | Chuter et al. |
| 2012/0123515 | A1 | 5/2012 | Hosford et al. |
| 2012/0123529 | A1 | 5/2012 | Levi et al. |
| 2012/0130468 | A1 | 5/2012 | Khosravi et al. |
| 2012/0132547 | A1 | 5/2012 | Salahieh et al. |
| 2012/0136430 | A1 | 5/2012 | Sochman et al. |
| 2012/0143084 | A1 | 6/2012 | Shoham |
| 2012/0165957 | A1 | 6/2012 | Everland et al. |
| 2012/0172982 | A1 | 7/2012 | Stacchino et al. |
| 2012/0179244 | A1 | 7/2012 | Schankereli et al. |
| 2012/0185030 | A1 | 7/2012 | Igaki et al. |
| 2012/0197379 | A1 | 8/2012 | Laske et al. |
| 2012/0209374 | A1 | 8/2012 | Bonhoeffer et al. |
| 2012/0209376 | A1 | 8/2012 | Hauser et al. |
| 2012/0221100 | A1 | 8/2012 | Huber |
| 2012/0226341 | A1 | 9/2012 | Schreck et al. |
| 2012/0283715 | A1 | 11/2012 | Mihalik et al. |
| 2012/0283823 | A1 | 11/2012 | Bonhoeffer et al. |
| 2012/0303113 | A1 | 11/2012 | Benichou et al. |
| 2012/0303116 | A1 | 11/2012 | Gorman, III et al. |
| 2012/0305441 | A1 | 12/2012 | Murray et al. |
| 2012/0310332 | A1 | 12/2012 | Murray et al. |
| 2012/0316637 | A1 | 12/2012 | Holm et al. |
| 2012/0330408 | A1 | 12/2012 | Hillukka et al. |
| 2012/0330409 | A1 | 12/2012 | Haug et al. |
| 2013/0013057 | A1 | 1/2013 | Salahieh et al. |
| 2013/0018457 | A1 | 1/2013 | Gregg et al. |
| 2013/0030519 | A1 | 1/2013 | Tran et al. |
| 2013/0030520 | A1 | 1/2013 | Lee et al. |
| 2013/0046373 | A1 | 2/2013 | Cartledge et al. |
| 2013/0053949 | A1 | 2/2013 | Pintor et al. |
| 2013/0066342 | A1 | 3/2013 | Dell et al. |
| 2013/0066419 | A1 | 3/2013 | Gregg |
| 2013/0071441 | A1 | 3/2013 | Iwazawa et al. |
| 2013/0073037 | A1 | 3/2013 | Gregg et al. |
| 2013/0079867 | A1 | 3/2013 | Hoffman et al. |
| 2013/0079869 | A1 | 3/2013 | Straubinger et al. |
| 2013/0089655 | A1 | 4/2013 | Gregg |
| 2013/0090728 | A1 | 4/2013 | Solem |
| 2013/0090729 | A1 | 4/2013 | Gregg et al. |
| 2013/0096664 | A1 | 4/2013 | Goetz et al. |
| 2013/0116778 | A1 | 5/2013 | Gregg et al. |
| 2013/0118949 | A1 | 5/2013 | Chang et al. |
| 2013/0123757 | A1 | 5/2013 | Crisostomo et al. |
| 2013/0123795 | A1 | 5/2013 | Gamarra et al. |
| 2013/0123796 | A1 | 5/2013 | Sutton et al. |
| 2013/0123898 | A1 | 5/2013 | Tung et al. |
| 2013/0138207 | A1 | 5/2013 | Quadri et al. |
| 2013/0144203 | A1 | 6/2013 | Wilk et al. |
| 2013/0144276 | A1 | 6/2013 | Crisostomo et al. |
| 2013/0158653 | A1 | 6/2013 | Gamarra et al. |
| 2013/0158655 | A1 | 6/2013 | Sutton et al. |
| 2013/0158656 | A1 | 6/2013 | Sutton et al. |
| 2013/0166017 | A1 | 6/2013 | Cartledge et al. |
| 2013/0178930 | A1 | 7/2013 | Straubinger et al. |
| 2013/0184813 | A1 | 7/2013 | Quadri et al. |
| 2013/0190865 | A1 | 7/2013 | Anderson |
| 2013/0204359 | A1 | 8/2013 | Thubrikar et al. |
| 2013/0231735 | A1 | 9/2013 | Deem et al. |
| 2013/0245752 | A1 | 9/2013 | Goetz et al. |
| 2013/0253342 | A1 | 9/2013 | Griswold et al. |
| 2013/0253635 | A1 | 9/2013 | Straubinger et al. |
| 2013/0253640 | A1 | 9/2013 | Meiri et al. |
| 2013/0268067 | A1 | 10/2013 | Forster et al. |
| 2013/0274865 | A1 | 10/2013 | Haverkost et al. |
| 2013/0274870 | A1 | 10/2013 | Lombardi et al. |
| 2013/0289698 | A1 | 10/2013 | Wang et al. |
| 2013/0296999 | A1 | 11/2013 | Burriesci et al. |
| 2013/0304199 | A1 | 11/2013 | Sutton et al. |
| 2013/0310917 | A1 | 11/2013 | Richter et al. |
| 2013/0310923 | A1 | 11/2013 | Kheradvar et al. |
| 2013/0310928 | A1 | 11/2013 | Morriss et al. |
| 2013/0325101 | A1 | 12/2013 | Goetz et al. |
| 2013/0338595 | A1 | 12/2013 | Voss |
| 2013/0338755 | A1 | 12/2013 | Goetz et al. |
| 2013/0345799 | A1 | 12/2013 | Lafontaine |
| 2014/0012368 | A1 | 1/2014 | Sugimoto et al. |
| 2014/0012370 | A1 | 1/2014 | Bonhoeffer et al. |
| 2014/0018911 | A1 | 1/2014 | Zhou et al. |
| 2014/0052239 | A1 | 2/2014 | Kong et al. |
| 2014/0058501 | A1 | 2/2014 | Bonhoeffer et al. |
| 2014/0083190 | A1 | 3/2014 | Kaack et al. |
| 2014/0088680 | A1 | 3/2014 | Costello et al. |
| 2014/0094904 | A1 | 4/2014 | Salahieh et al. |
| 2014/0114390 | A1 | 4/2014 | Tobis et al. |
| 2014/0114405 | A1 | 4/2014 | Paul et al. |
| 2014/0114406 | A1 | 4/2014 | Salahieh et al. |
| 2014/0114407 | A1 | 4/2014 | Rajamannan |
| 2014/0121763 | A1 | 5/2014 | Duffy et al. |
| 2014/0121766 | A1 | 5/2014 | Salahieh et al. |
| 2014/0128969 | A1 | 5/2014 | Hill et al. |
| 2014/0135912 | A1 | 5/2014 | Salahieh et al. |
| 2014/0207229 | A1 | 7/2014 | Shoemaker et al. |
| 2014/0222039 | A1 | 8/2014 | Khosrovaninejad |
| 2014/0222142 | A1 | 8/2014 | Kovalsky et al. |
| 2014/0236287 | A1 | 8/2014 | Clague et al. |
| 2014/0243962 | A1 | 8/2014 | Wilson et al. |
| 2014/0243963 | A1 | 8/2014 | Sheps et al. |
| 2014/0243967 | A1 | 8/2014 | Salahieh et al. |
| 2014/0249621 | A1 | 9/2014 | Eidenschink |
| 2014/0249622 | A1 | 9/2014 | Carmi et al. |
| 2014/0257473 | A1 | 9/2014 | Rajamannan |
| 2014/0277414 | A1 | 9/2014 | Kheradvar |
| 2014/0296962 | A1 | 10/2014 | Cartledge et al. |
| 2014/0309732 | A1 | 10/2014 | Solem |
| 2014/0316518 | A1 | 10/2014 | Kheradvar et al. |
| 2014/0330371 | A1 | 11/2014 | Gloss et al. |
| 2014/0343669 | A1 | 11/2014 | Lane et al. |
| 2014/0379068 | A1 | 12/2014 | Thielen et al. |
| 2015/0012085 | A1 | 1/2015 | Salahieh et al. |
| 2015/0032056 | A1 | 1/2015 | Okamura et al. |
| 2015/0073540 | A1 | 3/2015 | Salahieh et al. |
| 2015/0073541 | A1 | 3/2015 | Salahieh et al. |
| 2015/0088252 | A1 | 3/2015 | Jenson et al. |
| 2015/0094804 | A1 | 4/2015 | Bonhoeffer et al. |
| 2015/0105857 | A1 | 4/2015 | Bonhoeffer et al. |
| 2015/0127092 | A1 | 5/2015 | Straubinger et al. |
| 2015/0127094 | A1 | 5/2015 | Salahieh et al. |
| 2015/0142102 | A1 | 5/2015 | Lafontaine et al. |
| 2015/0209142 | A1 | 7/2015 | Paul et al. |
| 2015/0209146 | A1 | 7/2015 | Hill et al. |
| 2015/0223933 | A1 | 8/2015 | Haug et al. |
| 2015/0238315 | A1 | 8/2015 | Rabito et al. |
| 2015/0245909 | A1 | 9/2015 | Salahieh et al. |

(56) References Cited

U.S. PATENT DOCUMENTS

| | | | |
|---|---|---|---|
| 2015/0272731 | A1 | 10/2015 | Racchini et al. |
| 2015/0320557 | A1 | 11/2015 | Sutton et al. |
| 2015/0335423 | A1 | 11/2015 | Gregg et al. |
| 2015/0352252 | A1 | 12/2015 | Nakamura et al. |
| 2015/0359997 | A1 | 12/2015 | Crisostomo et al. |
| 2016/0022418 | A1 | 1/2016 | Salahieh et al. |
| 2016/0045306 | A1 | 2/2016 | Agrawal et al. |
| 2016/0045307 | A1 | 2/2016 | Yohanan et al. |
| 2016/0051362 | A1 | 2/2016 | Cooper et al. |
| 2016/0067040 | A1 | 3/2016 | Agrawal et al. |
| 2016/0120645 | A1 | 5/2016 | Alon |
| 2016/0135951 | A1 | 5/2016 | Salahieh et al. |
| 2016/0143731 | A1 | 5/2016 | Backus et al. |
| 2016/0158003 | A1 | 6/2016 | Wallace et al. |
| 2016/0166384 | A1 | 6/2016 | Olson et al. |
| 2016/0199184 | A1 | 7/2016 | Ma et al. |
| 2016/0206423 | A1 | 7/2016 | O'Connor et al. |
| 2016/0213467 | A1 | 7/2016 | Backus et al. |
| 2016/0220256 | A1 | 8/2016 | Khosrovaninejad |
| 2016/0220359 | A1 | 8/2016 | Backus et al. |
| 2016/0220360 | A1 | 8/2016 | Lin et al. |
| 2016/0220365 | A1 | 8/2016 | Backus et al. |
| 2016/0250024 | A1 | 9/2016 | Hill et al. |
| 2016/0256271 | A1 | 9/2016 | Backus et al. |
| 2016/0262878 | A1 | 9/2016 | Backus et al. |
| 2016/0346107 | A1 | 12/2016 | Matthison-Hansen et al. |
| 2016/0354203 | A1 | 12/2016 | Tuval et al. |
| 2016/0374793 | A1 | 12/2016 | Lafontaine et al. |
| 2016/0376063 | A1 | 12/2016 | Salahieh et al. |
| 2017/0000609 | A1 | 1/2017 | Gross et al. |
| 2017/0007400 | A1 | 1/2017 | Sogard et al. |
| 2017/0027654 | A1 | 2/2017 | Frimer et al. |
| 2017/0027693 | A1 | 2/2017 | Paul et al. |
| 2017/0049563 | A1 | 2/2017 | Straubinger et al. |
| 2017/0049568 | A1 | 2/2017 | Straubinger et al. |
| 2017/0056172 | A1 | 3/2017 | Salahieh et al. |
| 2017/0065410 | A1 | 3/2017 | Straubinger et al. |
| 2017/0087343 | A1 | 3/2017 | Assaf et al. |
| 2017/0095595 | A1 | 4/2017 | Nakamura |
| 2017/0189177 | A1 | 7/2017 | Schweich, Jr. et al. |
| 2017/0212723 | A1 | 7/2017 | Atarot et al. |
| 2017/0265849 | A1 | 9/2017 | Assaf et al. |
| 2017/0333230 | A1 | 11/2017 | Folan et al. |
| 2017/0348013 | A1 | 12/2017 | Mottola et al. |
| 2018/0325604 | A1 | 11/2018 | Atarot et al. |
| 2018/0368976 | A1 | 12/2018 | Bonhoeffer et al. |
| 2019/0328522 | A1 | 10/2019 | Straubinger et al. |
| 2020/0054449 | A1 | 2/2020 | Min et al. |
| 2021/0038313 | A1 | 2/2021 | Sholev et al. |
| 2021/0322153 | A1 | 10/2021 | Tuval et al. |
| 2022/0192765 | A1 | 6/2022 | Brasset et al. |
| 2022/0304803 | A1 | 9/2022 | Guyenot et al. |

FOREIGN PATENT DOCUMENTS

| | | | | |
|---|---|---|---|---|
| AU | 777443 | B2 | 10/2004 | |
| AU | 778831 | B2 | 12/2004 | |
| AU | 2004231189 | A1 | 12/2004 | |
| AU | 2004242527 | A1 | 1/2005 | |
| AU | 2001281277 | B2 | 9/2005 | |
| AU | 2006308187 | A1 | 5/2007 | |
| AU | 2006310681 | A1 | 5/2007 | |
| AU | 2006328896 | A1 | 6/2007 | |
| AU | 2002329324 | B2 | 7/2007 | |
| AU | 2007294199 | A1 | 3/2008 | |
| AU | 2009200985 | A1 | 4/2009 | |
| AU | 2008305600 | A1 * | 4/2010 | ........... A61F 2/2403 |
| AU | 2006328896 | B2 | 8/2013 | |
| CA | 2378589 | A1 | 2/2001 | |
| CA | 2381192 | A1 | 2/2001 | |
| CA | 2385662 | A1 | 3/2001 | |
| CA | 2407987 | A1 | 11/2001 | |
| CA | 2418958 | A1 | 2/2002 | |
| CA | 2435962 | A1 | 8/2002 | |
| CA | 2457755 | A1 | 2/2003 | |
| CA | 2436258 | A1 | 1/2005 | |
| CA | 2848485 | A1 | 1/2005 | |
| CA | 2848490 | A1 | 1/2005 | |
| CA | 2595233 | A1 | 7/2006 | |
| CA | 2627409 | A1 | 5/2007 | |
| CA | 2627555 | A1 | 5/2007 | |
| CA | 2634358 | A1 | 6/2007 | |
| CA | 2657839 | A1 | 3/2008 | |
| CA | 2659690 | A1 | 3/2008 | |
| CN | 1338951 | A | 3/2002 | |
| CN | 1342443 | A | 4/2002 | |
| CN | 1745727 | A | 3/2006 | |
| CN | 2762776 | Y | 3/2006 | |
| CN | 1897892 | A | 1/2007 | |
| CN | 2933337 | Y | 8/2007 | |
| CN | 101011298 | A | 8/2007 | |
| CN | 101431963 | A | 5/2009 | |
| CN | 101605509 | A | 12/2009 | |
| CN | 101623217 | A | 1/2010 | |
| CN | 101700199 | A | 5/2010 | |
| CN | 101720211 | A | 6/2010 | |
| CN | 102271626 | A | 12/2011 | |
| CN | 102413793 | A | 4/2012 | |
| CN | 103118630 | A | 5/2013 | |
| DE | 2815756 | A1 | 10/1979 | |
| DE | 3640745 | A1 | 6/1987 | |
| DE | 3920657 | A1 | 1/1991 | |
| DE | 4316971 | A1 | 11/1994 | |
| DE | 19532846 | A1 | 3/1997 | |
| DE | 19546692 | A1 | 6/1997 | |
| DE | 19633901 | A1 | 2/1998 | |
| DE | 20003874 | U1 | 5/2000 | |
| DE | 19857887 | A1 | 7/2000 | |
| DE | 19907646 | A1 | 8/2000 | |
| DE | 10010073 | A1 | 9/2001 | |
| DE | 10010074 | A1 | 10/2001 | |
| DE | 10034105 | C1 | 4/2002 | |
| DE | 10049812 | A1 | 4/2002 | |
| DE | 10049813 | C1 | 4/2002 | |
| DE | 10049814 | A1 | 4/2002 | |
| DE | 10049815 | A1 | 4/2002 | |
| DE | 10048814 | A1 | 5/2002 | |
| DE | 10121210 | A1 | 11/2002 | |
| DE | 19546692 | C2 | 11/2002 | |
| DE | 10301026 | A1 | 2/2004 | |
| DE | 10049812 | B4 | 6/2004 | |
| DE | 10302447 | A1 | 7/2004 | |
| DE | 10335948 | B3 | 2/2005 | |
| DE | 10010074 | B4 | 4/2005 | |
| DE | 19857887 | B4 | 5/2005 | |
| DE | 10049815 | B4 | 10/2005 | |
| DE | 10010073 | B4 | 12/2005 | |
| DE | 102005003632 | A1 | 8/2006 | |
| DE | 102005051849 | A1 | 5/2007 | |
| DE | 102005052628 | A1 | 5/2007 | |
| DE | 202007005491 | U1 | 6/2007 | |
| DE | 20221871 | U1 | 9/2008 | |
| DE | 69937568 | T2 | 9/2008 | |
| DK | 1112042 | T3 | 2/2008 | |
| DK | 200800058 | U1 | 6/2008 | |
| DK | 200800058 | U3 | 7/2008 | |
| DK | 1259195 | T3 | 2/2009 | |
| DK | 1281375 | T3 | 5/2012 | |
| EP | 0084395 | A1 | 7/1983 | |
| EP | 0103546 | A1 | 3/1984 | |
| EP | 0254701 | A1 | 1/1988 | |
| EP | 0103546 | B1 | 5/1988 | |
| EP | 0144167 | B1 | 11/1989 | |
| EP | 0402036 | A1 | 12/1990 | |
| EP | 0402176 | A2 | 12/1990 | |
| EP | 0411118 | A1 | 2/1991 | |
| EP | 0458877 | A1 | 12/1991 | |
| EP | 0515324 | A1 | 11/1992 | |
| EP | 0547135 | A1 | 6/1993 | |
| EP | 0579523 | A1 | 1/1994 | |
| EP | 0402176 | B1 | 4/1994 | |
| EP | 0592410 | A1 | 4/1994 | |
| EP | 0597967 | A1 | 5/1994 | |
| EP | 0597967 | A4 | 12/1994 | |

(56) References Cited

FOREIGN PATENT DOCUMENTS

| | | | |
|---|---|---|---|
| EP | 0458877 | B1 | 5/1995 |
| EP | 0657147 | A2 | 6/1995 |
| EP | 0592410 | B1 | 10/1995 |
| EP | 0696447 | A2 | 2/1996 |
| EP | 0402036 | B1 | 4/1996 |
| EP | 0729364 | A1 | 9/1996 |
| EP | 0732088 | A2 | 9/1996 |
| EP | 0756498 | A1 | 2/1997 |
| EP | 0409929 | B1 | 4/1997 |
| EP | 0778775 | A1 | 6/1997 |
| EP | 0786970 | A1 | 8/1997 |
| EP | 0792624 | A1 | 9/1997 |
| EP | 0797957 | A1 | 10/1997 |
| EP | 0797958 | A1 | 10/1997 |
| EP | 0799604 | A1 | 10/1997 |
| EP | 0801928 | A1 | 10/1997 |
| EP | 0815798 | A2 | 1/1998 |
| EP | 0826346 | A1 | 3/1998 |
| EP | 0829239 | A1 | 3/1998 |
| EP | 0836834 | A2 | 4/1998 |
| EP | 0850607 | A1 | 7/1998 |
| EP | 0853921 | A2 | 7/1998 |
| EP | 0858779 | A1 | 8/1998 |
| EP | 0871414 | A1 | 10/1998 |
| EP | 0876796 | A2 | 11/1998 |
| EP | 0876803 | A2 | 11/1998 |
| EP | 0778775 | B1 | 1/1999 |
| EP | 0888142 | A1 | 1/1999 |
| EP | 0888750 | A1 | 1/1999 |
| EP | 0895752 | A1 | 2/1999 |
| EP | 0896813 | A2 | 2/1999 |
| EP | 0903122 | A2 | 3/1999 |
| EP | 0876796 | A3 | 5/1999 |
| EP | 0928615 | A1 | 7/1999 |
| EP | 0657147 | B1 | 8/1999 |
| EP | 0934728 | A2 | 8/1999 |
| EP | 0938877 | A2 | 9/1999 |
| EP | 0943302 | A2 | 9/1999 |
| EP | 0597967 | B1 | 12/1999 |
| EP | 0696447 | B1 | 1/2000 |
| EP | 0971649 | A1 | 1/2000 |
| EP | 0986348 | A1 | 3/2000 |
| EP | 1000590 | A1 | 5/2000 |
| EP | 1011523 | A1 | 6/2000 |
| EP | 1020166 | A1 | 7/2000 |
| EP | 1027870 | A1 | 8/2000 |
| EP | 1041942 | A1 | 10/2000 |
| EP | 1041943 | A1 | 10/2000 |
| EP | 1051204 | A2 | 11/2000 |
| EP | 1057459 | A1 | 12/2000 |
| EP | 1057460 | A1 | 12/2000 |
| EP | 1078610 | A2 | 2/2001 |
| EP | 1088529 | A2 | 4/2001 |
| EP | 1089676 | A2 | 4/2001 |
| EP | 1093771 | A2 | 4/2001 |
| EP | 1097676 | A1 | 5/2001 |
| EP | 1112042 | A1 | 7/2001 |
| EP | 1112097 | A1 | 7/2001 |
| EP | 1117446 | A1 | 7/2001 |
| EP | 1158937 | A1 | 12/2001 |
| EP | 0547135 | B1 | 1/2002 |
| EP | 0729364 | B1 | 1/2002 |
| EP | 1164976 | A1 | 1/2002 |
| EP | 1166721 | A2 | 1/2002 |
| EP | 1171061 | A1 | 1/2002 |
| EP | 1206179 | A1 | 5/2002 |
| EP | 0756498 | B1 | 7/2002 |
| EP | 1233731 | A1 | 8/2002 |
| EP | 0986348 | B1 | 9/2002 |
| EP | 1235537 | A1 | 9/2002 |
| EP | 1248655 | A1 | 10/2002 |
| EP | 1251804 | A1 | 10/2002 |
| EP | 1251805 | A2 | 10/2002 |
| EP | 1255510 | A1 | 11/2002 |
| EP | 1257305 | A1 | 11/2002 |
| EP | 1259193 | A1 | 11/2002 |
| EP | 1259195 | A1 | 11/2002 |
| EP | 0959815 | B1 | 12/2002 |
| EP | 0971649 | B1 | 12/2002 |
| EP | 1262201 | A1 | 12/2002 |
| EP | 1264582 | A2 | 12/2002 |
| EP | 1281357 | A2 | 2/2003 |
| EP | 1281375 | A2 | 2/2003 |
| EP | 0888142 | B1 | 5/2003 |
| EP | 1112097 | B1 | 6/2003 |
| EP | 1330213 | A1 | 7/2003 |
| EP | 0937439 | B1 | 9/2003 |
| EP | 1017868 | B1 | 9/2003 |
| EP | 1340473 | A2 | 9/2003 |
| EP | 1347785 | A1 | 10/2003 |
| EP | 1354569 | A1 | 10/2003 |
| EP | 1356793 | A2 | 10/2003 |
| EP | 1281375 | A3 | 12/2003 |
| EP | 1340473 | A3 | 2/2004 |
| EP | 1041943 | B1 | 3/2004 |
| EP | 1356793 | A3 | 3/2004 |
| EP | 1395208 | A1 | 3/2004 |
| EP | 1401359 | A2 | 3/2004 |
| EP | 0871414 | B1 | 4/2004 |
| EP | 1406561 | A2 | 4/2004 |
| EP | 1408882 | A1 | 4/2004 |
| EP | 1042045 | B1 | 5/2004 |
| EP | 1414295 | A2 | 5/2004 |
| EP | 0819013 | B1 | 6/2004 |
| EP | 1430853 | A2 | 6/2004 |
| EP | 1347785 | B1 | 7/2004 |
| EP | 1435878 | A1 | 7/2004 |
| EP | 1435879 | A1 | 7/2004 |
| EP | 1439800 | A2 | 7/2004 |
| EP | 1441672 | A1 | 8/2004 |
| EP | 0954248 | B1 | 9/2004 |
| EP | 1452153 | A1 | 9/2004 |
| EP | 0987998 | B1 | 10/2004 |
| EP | 1206179 | B1 | 10/2004 |
| EP | 1469797 | A1 | 10/2004 |
| EP | 1087727 | B1 | 11/2004 |
| EP | 1115452 | B1 | 11/2004 |
| EP | 1117446 | B1 | 11/2004 |
| EP | 1472996 | A1 | 11/2004 |
| EP | 1477202 | A2 | 11/2004 |
| EP | 1107710 | B1 | 12/2004 |
| EP | 1233731 | B1 | 12/2004 |
| EP | 1484081 | A1 | 12/2004 |
| EP | 1494616 | A2 | 1/2005 |
| EP | 1499366 | A1 | 1/2005 |
| EP | 1143879 | B1 | 3/2005 |
| EP | 1516599 | A2 | 3/2005 |
| EP | 1518518 | A2 | 3/2005 |
| EP | 1229864 | B1 | 4/2005 |
| EP | 1253875 | B1 | 4/2005 |
| EP | 1519697 | A1 | 4/2005 |
| EP | 1521414 | A1 | 4/2005 |
| EP | 1522278 | A2 | 4/2005 |
| EP | 1088529 | B1 | 6/2005 |
| EP | 1093771 | B1 | 6/2005 |
| EP | 1251803 | B1 | 6/2005 |
| EP | 1430853 | A3 | 6/2005 |
| EP | 1539047 | A2 | 6/2005 |
| EP | 1547533 | A2 | 6/2005 |
| EP | 1059894 | B1 | 7/2005 |
| EP | 1551274 | A2 | 7/2005 |
| EP | 1551336 | A1 | 7/2005 |
| EP | 1000590 | B1 | 8/2005 |
| EP | 1027013 | B1 | 8/2005 |
| EP | 1078610 | B1 | 8/2005 |
| EP | 1560542 | A1 | 8/2005 |
| EP | 1562515 | A1 | 8/2005 |
| EP | 1570809 | A1 | 9/2005 |
| EP | 1576937 | A2 | 9/2005 |
| EP | 0943302 | B1 | 10/2005 |
| EP | 1267753 | B1 | 10/2005 |
| EP | 1582178 | A2 | 10/2005 |
| EP | 1582179 | A2 | 10/2005 |
| EP | 1011523 | B1 | 11/2005 |

(56) References Cited

FOREIGN PATENT DOCUMENTS

| | | | |
|---|---|---|---|
| EP | 1067869 | B1 | 11/2005 |
| EP | 1469797 | B1 | 11/2005 |
| EP | 1589902 | A1 | 11/2005 |
| EP | 1598031 | A2 | 11/2005 |
| EP | 1600110 | A1 | 11/2005 |
| EP | 1600121 | A1 | 11/2005 |
| EP | 0786970 | B1 | 12/2005 |
| EP | 1156757 | B1 | 12/2005 |
| EP | 1603493 | A2 | 12/2005 |
| EP | 1605871 | | 12/2005 |
| EP | 1021141 | B1 | 1/2006 |
| EP | 1614400 | A2 | 1/2006 |
| EP | 1616531 | A2 | 1/2006 |
| EP | 1616536 | A2 | 1/2006 |
| EP | 1041942 | B1 | 6/2006 |
| EP | 1441672 | A4 | 6/2006 |
| EP | 1663070 | A2 | 6/2006 |
| EP | 1667614 | A1 | 6/2006 |
| EP | 1494616 | A4 | 7/2006 |
| EP | 1690515 | A1 | 8/2006 |
| EP | 1702247 | A2 | 9/2006 |
| EP | 1051204 | B1 | 12/2006 |
| EP | 1734902 | A1 | 12/2006 |
| EP | 1395208 | B1 | 1/2007 |
| EP | 1251805 | B1 | 3/2007 |
| EP | 1255510 | B1 | 4/2007 |
| EP | 1499366 | B1 | 7/2007 |
| EP | 1600121 | B1 | 7/2007 |
| EP | 1835948 | A1 | 9/2007 |
| EP | 1112042 | B1 | 11/2007 |
| EP | 1251797 | B1 | 11/2007 |
| EP | 1616531 | B1 | 12/2007 |
| EP | 1863545 | A2 | 12/2007 |
| EP | 1878407 | A1 | 1/2008 |
| EP | 1886649 | A2 | 2/2008 |
| EP | 1406561 | A4 | 3/2008 |
| EP | 1893132 | A2 | 3/2008 |
| EP | 1900343 | A2 | 3/2008 |
| EP | 1901681 | A1 | 3/2008 |
| EP | 1435878 | B1 | 4/2008 |
| EP | 1886649 | A3 | 4/2008 |
| EP | 1251804 | B1 | 7/2008 |
| EP | 1968491 | A2 | 9/2008 |
| EP | 1259195 | B1 | 10/2008 |
| EP | 1980220 | A1 | 10/2008 |
| EP | 1994913 | A2 | 11/2008 |
| EP | 1994913 | A3 | 12/2008 |
| EP | 2000115 | A2 | 12/2008 |
| EP | 1560542 | A4 | 1/2009 |
| EP | 1408882 | B1 | 2/2009 |
| EP | 1255510 | B3 | 3/2009 |
| EP | 1330213 | B1 | 3/2009 |
| EP | 2033593 | A1 | 3/2009 |
| EP | 2047824 | A1 | 4/2009 |
| EP | 2059192 | A1 | 5/2009 |
| EP | 2074964 | A1 | 7/2009 |
| EP | 1401359 | B1 | 8/2009 |
| EP | 1968491 | B1 | 7/2010 |
| EP | 1259193 | B1 | 11/2010 |
| EP | 2257242 | | 12/2010 |
| EP | 2266503 | A2 | 12/2010 |
| EP | 2266504 | A2 | 12/2010 |
| EP | 1893132 | B1 | 3/2011 |
| EP | 2266503 | A3 | 4/2011 |
| EP | 2266504 | A3 | 4/2011 |
| EP | 2059192 | B1 | 7/2011 |
| EP | 1441672 | B1 | 9/2011 |
| EP | 2364669 | A2 | 9/2011 |
| EP | 2366363 | A1 | 9/2011 |
| EP | 2387977 | A1 | 11/2011 |
| EP | 1603493 | B1 | 12/2011 |
| EP | 1281375 | B1 | 2/2012 |
| EP | 2364669 | A3 | 3/2012 |
| EP | 2047824 | B1 | 5/2012 |
| EP | 2474287 | A1 | 7/2012 |
| EP | 2340075 | B1 | 3/2013 |
| EP | 2387977 | B1 | 11/2013 |
| EP | 1551274 | B1 | 12/2014 |
| EP | 2874812 | A1 | 5/2015 |
| EP | 2749254 | B1 | 6/2015 |
| EP | 1702247 | B1 | 8/2015 |
| EP | 2926766 | A1 | 10/2015 |
| EP | 1519697 | B1 | 11/2015 |
| EP | 1863545 | B1 | 11/2015 |
| EP | 1835948 | B1 | 2/2016 |
| EP | 1734902 | B1 | 6/2016 |
| EP | 3028668 | A1 | 6/2016 |
| EP | 1539047 | B1 | 11/2016 |
| EP | 1667614 | B1 | 12/2016 |
| EP | 3181096 | A1 | 6/2017 |
| EP | 2659861 | B1 | 3/2019 |
| EP | 1667614 | B2 | 4/2020 |
| EP | 3270825 | B1 | 4/2020 |
| EP | 3730094 | A1 | 10/2020 |
| EP | 3730094 | B1 | 4/2024 |
| ES | 2293734 | T3 | 3/2008 |
| ES | 2313954 | T3 | 3/2009 |
| ES | 2353733 | T3 | 3/2011 |
| ES | 2381337 | T3 | 5/2012 |
| ES | 2421438 | T3 | 9/2013 |
| FI | 8311 | U1 | 5/2009 |
| FR | 2432305 | A1 | 2/1980 |
| FR | 2788217 | A1 | 7/2000 |
| FR | 2815844 | A1 | 5/2002 |
| FR | 2826863 | A1 | 1/2003 |
| FR | 2828263 | A1 | 2/2003 |
| FR | 2874812 | A1 | 3/2006 |
| FR | 2828263 | B1 | 5/2007 |
| GB | 2018950 | A | 10/1979 |
| GB | 2056023 | A | 3/1981 |
| GB | 2316322 | A | 2/1998 |
| GB | 2316322 | B | 10/1998 |
| GB | 2398214 | A | 8/2004 |
| GB | 2398245 | A | 8/2004 |
| GB | 2398245 | B | 3/2007 |
| GB | 2433700 | A | 7/2007 |
| GB | 2433700 | B | 12/2007 |
| GB | 2440809 | A | 2/2008 |
| GB | 2440809 | B | 8/2011 |
| HK | 1053600 | A1 | 7/2012 |
| JP | S5286296 | A | 7/1977 |
| JP | S54137896 | A | 9/1979 |
| JP | S62227352 | A | 10/1987 |
| JP | S6449571 | A | 2/1989 |
| JP | H0447576 | B2 | 8/1992 |
| JP | H04505866 | A | 10/1992 |
| JP | H06505187 | A | 6/1994 |
| JP | H06343703 | A | 12/1994 |
| JP | H07504091 | A | 5/1995 |
| JP | H07505803 | A | 6/1995 |
| JP | H07265339 | A | 10/1995 |
| JP | H0833715 | A | 2/1996 |
| JP | H1049571 | A | 2/1998 |
| JP | H10507673 | A | 7/1998 |
| JP | H11503056 | A | 3/1999 |
| JP | 2001000460 | A | 1/2001 |
| JP | 2001504016 | A | 3/2001 |
| JP | 2001526574 | A | 12/2001 |
| JP | 2002525168 | A | 8/2002 |
| JP | 2002525169 | A | 8/2002 |
| JP | 2002536115 | A | 10/2002 |
| JP | 2003515386 | A | 5/2003 |
| JP | 2003518984 | A | 6/2003 |
| JP | 2003523262 | A | 8/2003 |
| JP | 2003524504 | A | 8/2003 |
| JP | 2004504111 | A | 2/2004 |
| JP | 2004130068 | A | 4/2004 |
| JP | 2004514467 | A | 5/2004 |
| JP | 2004255186 | A | 9/2004 |
| JP | 2004267750 | A | 9/2004 |
| JP | 2004283461 | A | 10/2004 |
| JP | 2005505343 | A | 2/2005 |
| JP | 2005103321 | A | 4/2005 |
| JP | 2005118585 | A | 5/2005 |

(56) References Cited

FOREIGN PATENT DOCUMENTS

| | | | |
|---|---|---|---|
| JP | 2007521125 | A | 8/2007 |
| JP | 2007296375 | A | 11/2007 |
| JP | 2007298375 | A | 11/2007 |
| JP | 2007534381 | A | 11/2007 |
| JP | 2007536003 | A | 12/2007 |
| JP | 2008506497 | A | 3/2008 |
| JP | 2008514345 | A | 5/2008 |
| JP | 2008535572 | A | 9/2008 |
| JP | 2008539985 | A | 11/2008 |
| JP | 2008541865 | A | 11/2008 |
| JP | 2009034529 | A | 2/2009 |
| JP | 2009061293 | A | 3/2009 |
| JP | 2009509635 | A | 3/2009 |
| JP | 4246433 | B2 | 4/2009 |
| JP | 2009520535 | A | 5/2009 |
| JP | 2009131397 | A | 6/2009 |
| JP | 4295460 | B2 | 7/2009 |
| JP | 2009528905 | A | 8/2009 |
| JP | 2009534157 | A | 9/2009 |
| JP | 2010525896 | A | 7/2010 |
| JP | 2010526609 | A | 8/2010 |
| JP | 4636794 | B2 | 2/2011 |
| JP | 2011509805 | A | 3/2011 |
| JP | 4739223 | B2 | 8/2011 |
| JP | 2012500665 | A | 1/2012 |
| JP | 4904362 | B2 | 3/2012 |
| JP | 4912395 | B2 | 4/2012 |
| JP | 2012518446 | A | 8/2012 |
| JP | 2013520260 | A | 6/2013 |
| JP | 2013521884 | A | 6/2013 |
| JP | 2013526388 | A | 6/2013 |
| JP | 5341455 | B2 | 11/2013 |
| JP | 2013540495 | A | 11/2013 |
| JP | 6144009 | B2 | 6/2017 |
| JP | 6449571 | B2 | 1/2019 |
| PT | 1112042 | E | 1/2008 |
| PT | 1259195 | E | 12/2008 |
| PT | 1259193 | E | 1/2011 |
| PT | 1281375 | E | 3/2012 |
| PT | 1994913 | E | 8/2013 |
| RU | 2149037 | C1 | 5/2000 |
| SE | 7901667 | L | 10/1979 |
| SU | 1271508 | A1 | 11/1986 |
| SU | 1371700 | A1 | 2/1988 |
| WO | WO-8402266 | A1 | 6/1984 |
| WO | WO-9009102 | A1 | 8/1990 |
| WO | WO-9014804 | A1 | 12/1990 |
| WO | WO-9117720 | A1 | 11/1991 |
| WO | WO-9203990 | A1 | 3/1992 |
| WO | WO-9212690 | A1 | 8/1992 |
| WO | WO-9214419 | A1 | 9/1992 |
| WO | WO-9217118 | A1 | 10/1992 |
| WO | WO-9301768 | A1 | 2/1993 |
| WO | WO-9315693 | A1 | 8/1993 |
| WO | WO-9320757 | A2 | 10/1993 |
| WO | WO-9504556 | A2 | 2/1995 |
| WO | WO-9504556 | A3 | 4/1995 |
| WO | WO-9511055 | A1 | 4/1995 |
| WO | WO-9524873 | A1 | 9/1995 |
| WO | WO-9528183 | A1 | 10/1995 |
| WO | WO-9528899 | A1 | 11/1995 |
| WO | WO-9529640 | A1 | 11/1995 |
| WO | WO-9529713 | A1 | 11/1995 |
| WO | WO-9613227 | A1 | 5/1996 |
| WO | WO-9614032 | A1 | 5/1996 |
| WO | WO-9624306 | A1 | 8/1996 |
| WO | WO-9630072 | A1 | 10/1996 |
| WO | WO-9632972 | A1 | 10/1996 |
| WO | WO-9635469 | A1 | 11/1996 |
| WO | WO-9639962 | A1 | 12/1996 |
| WO | WO-9639964 | A1 | 12/1996 |
| WO | WO-9639965 | A1 | 12/1996 |
| WO | WO-9640012 | A1 | 12/1996 |
| WO | WO-9713463 | A1 | 4/1997 |
| WO | WO-9713471 | A1 | 4/1997 |
| WO | WO-9724082 | A1 | 7/1997 |
| WO | WO-9727893 | A1 | 8/1997 |
| WO | WO-9727897 | A1 | 8/1997 |
| WO | WO-9727898 | A1 | 8/1997 |
| WO | WO-9728839 | A1 | 8/1997 |
| WO | WO-9732551 | A1 | 9/1997 |
| WO | WO-9732615 | A1 | 9/1997 |
| WO | WO-9743961 | A1 | 11/1997 |
| WO | WO-9748350 | A1 | 12/1997 |
| WO | WO-9803118 | A1 | 1/1998 |
| WO | WO-9806356 | A1 | 2/1998 |
| WO | WO-9808456 | A1 | 3/1998 |
| WO | WO-9810714 | A1 | 3/1998 |
| WO | WO-9811846 | A1 | 3/1998 |
| WO | WO-9814137 | A1 | 4/1998 |
| WO | WO-9816161 | A1 | 4/1998 |
| WO | WO-9819633 | A1 | 5/1998 |
| WO | WO-9824373 | A1 | 6/1998 |
| WO | WO-9825533 | A1 | 6/1998 |
| WO | WO-9825549 | A1 | 6/1998 |
| WO | WO-9829057 | A1 | 7/1998 |
| WO | WO-9836790 | A1 | 8/1998 |
| WO | WO-9838916 | A1 | 9/1998 |
| WO | WO-9838925 | A1 | 9/1998 |
| WO | WO-9838939 | A1 | 9/1998 |
| WO | WO-9838941 | A1 | 9/1998 |
| WO | WO-9839038 | A1 | 9/1998 |
| WO | WO-9843556 | A1 | 10/1998 |
| WO | WO-9844869 | A1 | 10/1998 |
| WO | WO-9846115 | A2 | 10/1998 |
| WO | WO-9846119 | A1 | 10/1998 |
| WO | WO-9846165 | A1 | 10/1998 |
| WO | WO-9849964 | A1 | 11/1998 |
| WO | WO-9850103 | A1 | 11/1998 |
| WO | WO-9853759 | A2 | 12/1998 |
| WO | WO-9853761 | A1 | 12/1998 |
| WO | WO-9855027 | A2 | 12/1998 |
| WO | WO-9855047 | A1 | 12/1998 |
| WO | WO-9857590 | A1 | 12/1998 |
| WO | WO-9857591 | A1 | 12/1998 |
| WO | WO-9857592 | A1 | 12/1998 |
| WO | WO-9857599 | A2 | 12/1998 |
| WO | WO-9907296 | A1 | 2/1999 |
| WO | WO-9908624 | A1 | 2/1999 |
| WO | WO-9915112 | A1 | 4/1999 |
| WO | WO-9915220 | A1 | 4/1999 |
| WO | WO-9917671 | A1 | 4/1999 |
| WO | WO-9917683 | A1 | 4/1999 |
| WO | WO-9921490 | A1 | 5/1999 |
| WO | WO-9921510 | A1 | 5/1999 |
| WO | WO-9922655 | A1 | 5/1999 |
| WO | WO-9922656 | A1 | 5/1999 |
| WO | WO-9922658 | A1 | 5/1999 |
| WO | WO-9925273 | A1 | 5/1999 |
| WO | WO-9927985 | A1 | 6/1999 |
| WO | WO-9933414 | A1 | 7/1999 |
| WO | WO-9935977 | A1 | 7/1999 |
| WO | WO-9935979 | A1 | 7/1999 |
| WO | WO-9935980 | A1 | 7/1999 |
| WO | WO-9936000 | A1 | 7/1999 |
| WO | WO-9936001 | A1 | 7/1999 |
| WO | WO-9937337 | A2 | 7/1999 |
| WO | WO-9938459 | A2 | 8/1999 |
| WO | WO-9940853 | A1 | 8/1999 |
| WO | WO-9940868 | A1 | 8/1999 |
| WO | WO-9940963 | A1 | 8/1999 |
| WO | WO-9940964 | A1 | 8/1999 |
| WO | WO-9942058 | A1 | 8/1999 |
| WO | WO-9944524 | A2 | 9/1999 |
| WO | WO-9944540 | A2 | 9/1999 |
| WO | WO-9944542 | A2 | 9/1999 |
| WO | WO-9947071 | A1 | 9/1999 |
| WO | WO-9947075 | A1 | 9/1999 |
| WO | WO-9948545 | A1 | 9/1999 |
| WO | WO-9948549 | A2 | 9/1999 |
| WO | WO-9949793 | A1 | 10/1999 |
| WO | WO-9949910 | A2 | 10/1999 |
| WO | WO-9951162 | A1 | 10/1999 |
| WO | WO-9951165 | A1 | 10/1999 |

(56) References Cited

FOREIGN PATENT DOCUMENTS

| | | | |
|---|---|---|---|
| WO | WO-9953863 | A1 | 10/1999 |
| WO | WO-9953987 | A1 | 10/1999 |
| WO | WO-9955406 | A1 | 11/1999 |
| WO | WO-9960941 | A1 | 12/1999 |
| WO | WO-9962430 | A1 | 12/1999 |
| WO | WO-9966863 | A2 | 12/1999 |
| WO | WO-0002503 | A1 | 1/2000 |
| WO | WO-0009059 | A2 | 2/2000 |
| WO | WO-0009195 | A1 | 2/2000 |
| WO | WO-0010623 | A1 | 3/2000 |
| WO | WO-0012029 | A1 | 3/2000 |
| WO | WO-0013722 | A1 | 3/2000 |
| WO | WO-0015146 | A1 | 3/2000 |
| WO | WO-0015147 | A1 | 3/2000 |
| WO | WO-0015148 | A1 | 3/2000 |
| WO | WO-0015149 | A1 | 3/2000 |
| WO | WO-0015275 | A2 | 3/2000 |
| WO | WO-0016848 | A1 | 3/2000 |
| WO | WO-0018302 | A2 | 4/2000 |
| WO | WO-0018323 | A2 | 4/2000 |
| WO | WO-0018325 | A1 | 4/2000 |
| WO | WO-0018326 | A1 | 4/2000 |
| WO | WO-0018330 | A1 | 4/2000 |
| WO | WO-0018331 | A2 | 4/2000 |
| WO | WO-0018333 | A1 | 4/2000 |
| WO | WO-0018445 | A1 | 4/2000 |
| WO | WO-0018462 | A2 | 4/2000 |
| WO | WO-0021436 | A1 | 4/2000 |
| WO | WO-0021461 | A2 | 4/2000 |
| WO | WO-0021463 | A1 | 4/2000 |
| WO | WO-0021464 | A1 | 4/2000 |
| WO | WO-0024449 | A1 | 5/2000 |
| WO | WO-0025702 | A1 | 5/2000 |
| WO | WO-0028922 | A1 | 5/2000 |
| WO | WO-0028924 | A2 | 5/2000 |
| WO | WO-0033725 | A2 | 6/2000 |
| WO | WO-0035376 | A1 | 6/2000 |
| WO | WO-0036997 | A1 | 6/2000 |
| WO | WO-0041632 | A1 | 7/2000 |
| WO | WO-0041633 | A1 | 7/2000 |
| WO | WO-0041652 | A1 | 7/2000 |
| WO | WO-0043051 | A1 | 7/2000 |
| WO | WO-0044211 | A1 | 7/2000 |
| WO | WO-0044308 | A2 | 8/2000 |
| WO | WO-0044311 | A2 | 8/2000 |
| WO | WO-0044313 | A1 | 8/2000 |
| WO | WO-0044331 | A1 | 8/2000 |
| WO | WO-0045711 | A1 | 8/2000 |
| WO | WO-0045874 | A1 | 8/2000 |
| WO | WO-0045886 | A2 | 8/2000 |
| WO | WO-0047136 | A1 | 8/2000 |
| WO | WO-0047139 | A1 | 8/2000 |
| WO | WO-0048531 | A1 | 8/2000 |
| WO | WO-0049952 | A1 | 8/2000 |
| WO | WO-0049954 | A2 | 8/2000 |
| WO | WO-0049956 | A1 | 8/2000 |
| WO | WO-0049970 | A1 | 8/2000 |
| WO | WO-0053122 | A1 | 9/2000 |
| WO | WO-0053125 | A1 | 9/2000 |
| WO | WO-0054660 | A1 | 9/2000 |
| WO | WO-0054661 | A1 | 9/2000 |
| WO | WO-0056224 | A1 | 9/2000 |
| WO | WO-0056225 | A1 | 9/2000 |
| WO | WO-0056387 | A1 | 9/2000 |
| WO | WO-0060995 | A2 | 10/2000 |
| WO | WO-0062714 | A1 | 10/2000 |
| WO | WO-0066007 | A1 | 11/2000 |
| WO | WO-0066009 | A1 | 11/2000 |
| WO | WO-0066035 | A1 | 11/2000 |
| WO | WO-0067661 | A2 | 11/2000 |
| WO | WO-0069345 | A1 | 11/2000 |
| WO | WO-0069367 | A1 | 11/2000 |
| WO | WO-0069504 | A1 | 11/2000 |
| WO | WO-0071195 | A1 | 11/2000 |
| WO | WO-0078226 | A1 | 12/2000 |
| WO | WO-0105331 | A1 | 1/2001 |
| WO | WO-0106959 | A1 | 2/2001 |
| WO | WO-0108566 | A1 | 2/2001 |
| WO | WO-0108596 | A1 | 2/2001 |
| WO | WO-0108602 | A2 | 2/2001 |
| WO | WO-0110209 | A1 | 2/2001 |
| WO | WO-0110320 | A1 | 2/2001 |
| WO | WO-0110340 | A1 | 2/2001 |
| WO | WO-0110341 | A2 | 2/2001 |
| WO | WO-0110343 | A1 | 2/2001 |
| WO | WO-0110347 | A1 | 2/2001 |
| WO | WO-0110348 | A1 | 2/2001 |
| WO | WO-0110349 | A1 | 2/2001 |
| WO | WO-0110350 | A1 | 2/2001 |
| WO | WO-0117440 | A1 | 3/2001 |
| WO | WO-0117456 | A1 | 3/2001 |
| WO | WO-0135864 | A1 | 5/2001 |
| WO | WO-0135870 | A1 | 5/2001 |
| WO | WO-0136870 | A1 | 5/2001 |
| WO | WO-0139700 | A1 | 6/2001 |
| WO | WO-0141679 | A1 | 6/2001 |
| WO | WO-0149185 | A1 | 7/2001 |
| WO | WO-0149187 | A1 | 7/2001 |
| WO | WO-0149213 | A2 | 7/2001 |
| WO | WO-0151104 | A1 | 7/2001 |
| WO | WO-0154625 | A1 | 8/2001 |
| WO | WO-0158503 | A1 | 8/2001 |
| WO | WO-0162189 | A1 | 8/2001 |
| WO | WO-0047139 | A9 | 9/2001 |
| WO | WO-0164137 | A1 | 9/2001 |
| WO | WO-0176510 | A2 | 10/2001 |
| WO | WO-0182837 | A2 | 11/2001 |
| WO | WO-0197715 | A1 | 12/2001 |
| WO | WO-0211647 | A2 | 2/2002 |
| WO | WO-0219926 | A1 | 3/2002 |
| WO | WO-0222054 | A1 | 3/2002 |
| WO | WO-0224118 | A1 | 3/2002 |
| WO | WO-0236048 | A1 | 5/2002 |
| WO | WO-0241789 | A2 | 5/2002 |
| WO | WO-0243620 | A1 | 6/2002 |
| WO | WO-0247575 | A2 | 6/2002 |
| WO | WO-0249540 | A2 | 6/2002 |
| WO | WO-02051489 | A2 | 7/2002 |
| WO | WO-02056798 | A2 | 7/2002 |
| WO | WO-02056955 | A1 | 7/2002 |
| WO | WO-02058745 | A1 | 8/2002 |
| WO | WO-02060509 | A1 | 8/2002 |
| WO | WO-02067782 | A2 | 9/2002 |
| WO | WO-02069842 | A2 | 9/2002 |
| WO | WO-02076349 | A1 | 10/2002 |
| WO | WO-02100297 | A2 | 12/2002 |
| WO | WO-02100301 | A1 | 12/2002 |
| WO | WO-02102286 | A1 | 12/2002 |
| WO | WO-03003943 | A2 | 1/2003 |
| WO | WO-03003949 | A2 | 1/2003 |
| WO | WO-03007795 | A2 | 1/2003 |
| WO | WO-03009785 | A1 | 2/2003 |
| WO | WO-03011195 | A2 | 2/2003 |
| WO | WO-03013239 | A2 | 2/2003 |
| WO | WO-03015851 | A1 | 2/2003 |
| WO | WO-03022183 | A1 | 3/2003 |
| WO | WO-03028592 | A1 | 4/2003 |
| WO | WO-03030776 | A2 | 4/2003 |
| WO | WO-03032869 | A1 | 4/2003 |
| WO | WO-03032870 | A1 | 4/2003 |
| WO | WO-03037222 | A2 | 5/2003 |
| WO | WO-03037227 | A2 | 5/2003 |
| WO | WO-03047460 | A2 | 6/2003 |
| WO | WO-03047468 | A1 | 6/2003 |
| WO | WO-03047648 | A2 | 6/2003 |
| WO | WO-03051231 | A2 | 6/2003 |
| WO | WO-03063729 | A2 | 8/2003 |
| WO | WO-03079928 | A2 | 10/2003 |
| WO | WO-03079932 | A2 | 10/2003 |
| WO | WO-03079933 | A1 | 10/2003 |
| WO | WO-03088873 | A1 | 10/2003 |
| WO | WO-03015851 | B1 | 11/2003 |
| WO | WO-03063729 | A3 | 11/2003 |
| WO | WO-03092554 | A1 | 11/2003 |

(56) References Cited

FOREIGN PATENT DOCUMENTS

| | | | |
|---|---|---|---|
| WO | WO-03094793 | A1 | 11/2003 |
| WO | WO-03094797 | A1 | 11/2003 |
| WO | WO-03096932 | A1 | 11/2003 |
| WO | WO-03096935 | A1 | 11/2003 |
| WO | WO-03101195 | A1 | 12/2003 |
| WO | WO-03103949 | A1 | 12/2003 |
| WO | WO-03003949 | A3 | 1/2004 |
| WO | WO-2004004597 | A2 | 1/2004 |
| WO | WO-2004006803 | A1 | 1/2004 |
| WO | WO-2004006804 | A1 | 1/2004 |
| WO | WO-2004014256 | A1 | 2/2004 |
| WO | WO-2004016200 | A1 | 2/2004 |
| WO | WO-2004016201 | A2 | 2/2004 |
| WO | WO-2004019811 | A2 | 3/2004 |
| WO | WO-2004019817 | A1 | 3/2004 |
| WO | WO-2004019825 | A1 | 3/2004 |
| WO | WO-2004021922 | A2 | 3/2004 |
| WO | WO-2004023980 | A2 | 3/2004 |
| WO | WO-2004019811 | A9 | 4/2004 |
| WO | WO-2004026117 | A2 | 4/2004 |
| WO | WO-2004026173 | A2 | 4/2004 |
| WO | WO-2004028399 | A2 | 4/2004 |
| WO | WO-2004030515 | A2 | 4/2004 |
| WO | WO-2004041126 | A1 | 5/2004 |
| WO | WO-2004043293 | A2 | 5/2004 |
| WO | WO-2004043301 | A1 | 5/2004 |
| WO | WO-2004047681 | A1 | 6/2004 |
| WO | WO-2004058106 | A2 | 7/2004 |
| WO | WO-2004062980 | A1 | 7/2004 |
| WO | WO-2004058106 | A3 | 8/2004 |
| WO | WO-2004064671 | A2 | 8/2004 |
| WO | WO-2004066876 | A1 | 8/2004 |
| WO | WO-2004071352 | A1 | 8/2004 |
| WO | WO-2004082527 | A2 | 9/2004 |
| WO | WO-2004082528 | A2 | 9/2004 |
| WO | WO-2004082536 | A1 | 9/2004 |
| WO | WO-2004089250 | A1 | 10/2004 |
| WO | WO-2004089253 | A1 | 10/2004 |
| WO | WO-2004093728 | A2 | 11/2004 |
| WO | WO-2004096100 | A1 | 11/2004 |
| WO | WO-2004103162 | A2 | 12/2004 |
| WO | WO-2004105651 | A1 | 12/2004 |
| WO | WO-2005002466 | A2 | 1/2005 |
| WO | WO-2005004753 | A1 | 1/2005 |
| WO | WO-2005007343 | A1 | 1/2005 |
| WO | WO-2005009285 | A2 | 2/2005 |
| WO | WO-2005011534 | A1 | 2/2005 |
| WO | WO-2005011535 | A2 | 2/2005 |
| WO | WO-2005021063 | A2 | 3/2005 |
| WO | WO-2005023155 | A1 | 3/2005 |
| WO | WO-2005027790 | A1 | 3/2005 |
| WO | WO-2005027797 | A1 | 3/2005 |
| WO | WO-2005032622 | A2 | 4/2005 |
| WO | WO-2005034812 | A1 | 4/2005 |
| WO | WO-2005010215 | A3 | 5/2005 |
| WO | WO-2005046528 | A1 | 5/2005 |
| WO | WO-2005046529 | A1 | 5/2005 |
| WO | WO-2005048883 | A1 | 6/2005 |
| WO | WO-2005062980 | A2 | 7/2005 |
| WO | WO-2005063980 | A1 | 7/2005 |
| WO | WO-2005065585 | A1 | 7/2005 |
| WO | WO-2005065594 | A1 | 7/2005 |
| WO | WO-2005070343 | A1 | 8/2005 |
| WO | WO-2005072654 | A1 | 8/2005 |
| WO | WO-2005076890 | A2 | 8/2005 |
| WO | WO-2005084595 | A1 | 9/2005 |
| WO | WO-2005087140 | A1 | 9/2005 |
| WO | WO-2005096993 | A1 | 10/2005 |
| WO | WO-2005102015 | A2 | 11/2005 |
| WO | WO-2005110240 | A1 | 11/2005 |
| WO | WO-2005112779 | A1 | 12/2005 |
| WO | WO-2006005015 | A2 | 1/2006 |
| WO | WO-2006005082 | A2 | 1/2006 |
| WO | WO-2006009690 | A1 | 1/2006 |
| WO | WO-2006026371 | A1 | 3/2006 |
| WO | WO-2006027499 | A2 | 3/2006 |
| WO | WO-2005062980 | A3 | 5/2006 |
| WO | WO-2006058163 | A2 | 6/2006 |
| WO | WO-2006065949 | A2 | 6/2006 |
| WO | WO-2006066327 | A1 | 6/2006 |
| WO | WO-2006068944 | A2 | 6/2006 |
| WO | WO-2006070372 | A2 | 7/2006 |
| WO | WO-2006076890 | A1 | 7/2006 |
| WO | WO-2006083763 | A1 | 8/2006 |
| WO | WO-2006086135 | A2 | 8/2006 |
| WO | WO-2006086736 | A2 | 8/2006 |
| WO | WO-2006089517 | A1 | 8/2006 |
| WO | WO-2006093795 | A1 | 9/2006 |
| WO | WO-2006102063 | A2 | 9/2006 |
| WO | WO-2006108090 | A2 | 10/2006 |
| WO | WO-2006118766 | A1 | 11/2006 |
| WO | WO-2006124649 | A2 | 11/2006 |
| WO | WO-2006127756 | A2 | 11/2006 |
| WO | WO-2006127765 | A1 | 11/2006 |
| WO | WO-2006129441 | A1 | 12/2006 |
| WO | WO-2006132948 | A1 | 12/2006 |
| WO | WO-2006133959 | A1 | 12/2006 |
| WO | WO-2006138173 | A2 | 12/2006 |
| WO | WO-2006138391 | A2 | 12/2006 |
| WO | WO-2007009117 | A1 | 1/2007 |
| WO | WO-2007009609 | A1 | 1/2007 |
| WO | WO-2007013999 | A2 | 2/2007 |
| WO | WO-2007033093 | A2 | 3/2007 |
| WO | WO-2007035471 | A2 | 3/2007 |
| WO | WO-2005102015 | A3 | 4/2007 |
| WO | WO-2006138391 | A9 | 4/2007 |
| WO | WO-2007044285 | A2 | 4/2007 |
| WO | WO-2007047488 | A2 | 4/2007 |
| WO | WO-2007047945 | A2 | 4/2007 |
| WO | WO-2007048529 | A1 | 5/2007 |
| WO | WO-2007051620 | A1 | 5/2007 |
| WO | WO-2007053243 | A2 | 5/2007 |
| WO | WO-2007058847 | A2 | 5/2007 |
| WO | WO-2007059252 | A1 | 5/2007 |
| WO | WO-2006086736 | A3 | 6/2007 |
| WO | WO-2007071436 | A2 | 6/2007 |
| WO | WO-2007092354 | A2 | 8/2007 |
| WO | WO-2007097983 | A2 | 8/2007 |
| WO | WO-2007098232 | A2 | 8/2007 |
| WO | WO-2007053243 | A3 | 9/2007 |
| WO | WO-2007120543 | A1 | 10/2007 |
| WO | WO-2007071436 | A3 | 11/2007 |
| WO | WO-2007123658 | A1 | 11/2007 |
| WO | WO-2007123956 | A2 | 11/2007 |
| WO | WO-2007127351 | A1 | 11/2007 |
| WO | WO-2007127352 | A1 | 11/2007 |
| WO | WO-2007033093 | A3 | 1/2008 |
| WO | WO-2007071436 | B1 | 1/2008 |
| WO | WO-2008028569 | A1 | 3/2008 |
| WO | WO-2008031103 | A2 | 3/2008 |
| WO | WO-2008035337 | A2 | 3/2008 |
| WO | WO-2008040555 | A2 | 4/2008 |
| WO | WO-2008045949 | A2 | 4/2008 |
| WO | WO-2008047354 | A2 | 4/2008 |
| WO | WO-2008051554 | A2 | 5/2008 |
| WO | WO-2008070442 | A1 | 6/2008 |
| WO | WO-2008070797 | A2 | 6/2008 |
| WO | WO-2008079962 | A1 | 7/2008 |
| WO | WO-2008098191 | A2 | 8/2008 |
| WO | WO-2008100599 | A1 | 8/2008 |
| WO | WO-2008101083 | A2 | 8/2008 |
| WO | WO-2008118481 | A2 | 10/2008 |
| WO | WO-2008125153 | A1 | 10/2008 |
| WO | WO-2008137603 | A2 | 11/2008 |
| WO | WO-2008138584 | A1 | 11/2008 |
| WO | WO-2008150529 | A1 | 12/2008 |
| WO | WO-2009002548 | A1 | 12/2008 |
| WO | WO-2009024859 | A2 | 2/2009 |
| WO | WO-2009029199 | A1 | 3/2009 |
| WO | WO-2009042196 | A2 | 4/2009 |
| WO | WO-2009045334 | A1 | 4/2009 |
| WO | WO-2009045338 | A1 | 4/2009 |
| WO | WO-2009053497 | A1 | 4/2009 |
| WO | WO-2009054397 | A1 | 4/2009 |

(56) References Cited

FOREIGN PATENT DOCUMENTS

| | | |
|---|---|---|
| WO | WO-2007044285 A3 | 5/2009 |
| WO | WO-2009061389 A2 | 5/2009 |
| WO | WO-2009085206 A2 | 7/2009 |
| WO | WO-2009091509 A1 | 7/2009 |
| WO | WO-2009094188 A2 | 7/2009 |
| WO | WO-2009094501 A1 | 7/2009 |
| WO | WO-2009100198 A2 | 8/2009 |
| WO | WO-2009106545 A1 | 9/2009 |
| WO | WO-2009108615 A1 | 9/2009 |
| WO | WO-2009111241 A2 | 9/2009 |
| WO | WO-2009137712 A1 | 11/2009 |
| WO | WO-2009149462 A2 | 12/2009 |
| WO | WO-2009155561 A2 | 12/2009 |
| WO | WO-2010022138 A2 | 2/2010 |
| WO | WO-2010042950 A2 | 4/2010 |
| WO | WO-2010043950 A2 | 4/2010 |
| WO | WO-2010044851 A1 | 4/2010 |
| WO | WO-2010045238 A2 | 4/2010 |
| WO | WO-2010045297 A2 | 4/2010 |
| WO | WO-2010049160 A1 | 5/2010 |
| WO | WO-2010083558 A1 | 7/2010 |
| WO | WO-2010086460 A1 | 8/2010 |
| WO | WO-2010098857 A1 | 9/2010 |
| WO | WO-2010104638 A2 | 9/2010 |
| WO | WO-2010045238 A3 | 10/2010 |
| WO | WO-2010141626 A2 | 12/2010 |
| WO | WO-2011008812 A2 | 1/2011 |
| WO | WO-2011008853 A2 | 1/2011 |
| WO | WO-2011035327 A1 | 3/2011 |
| WO | WO-2011051043 A1 | 5/2011 |
| WO | WO-2011057087 A1 | 5/2011 |
| WO | WO-2011060386 A2 | 5/2011 |
| WO | WO-2011102968 A1 | 8/2011 |
| WO | WO-2011102970 A1 | 8/2011 |
| WO | WO-2011104269 A1 | 9/2011 |
| WO | WO-2011120050 A1 | 9/2011 |
| WO | WO-2011126749 A1 | 10/2011 |
| WO | WO-2011133368 A1 | 10/2011 |
| WO | WO-2011144351 A2 | 11/2011 |
| WO | WO-2011147849 A1 | 12/2011 |
| WO | WO-2012002228 A1 | 1/2012 |
| WO | WO-2012023980 A1 | 2/2012 |
| WO | WO-2012036742 A2 | 3/2012 |
| WO | WO-2012038550 A1 | 3/2012 |
| WO | WO-2012039748 A2 | 3/2012 |
| WO | WO-2012082952 A2 | 6/2012 |
| WO | WO-2012106491 A1 | 8/2012 |
| WO | WO-2012116368 A2 | 8/2012 |
| WO | WO-2012142189 A1 | 10/2012 |
| WO | WO-2012145546 A1 | 10/2012 |
| WO | WO-2012162228 A1 | 11/2012 |
| WO | WO-2013009975 A1 | 1/2013 |
| WO | WO-2013028387 A2 | 2/2013 |
| WO | WO-2013033791 A1 | 3/2013 |
| WO | WO-2013074671 A1 | 5/2013 |
| WO | WO-2013096545 A1 | 6/2013 |
| WO | WO-2013134214 A1 | 9/2013 |
| WO | WO-2014056644 A1 | 4/2014 |
| WO | WO-2014072439 A1 | 5/2014 |
| WO | WO-2014072439 A9 | 7/2014 |
| WO | WO-2015028209 A1 | 3/2015 |
| WO | WO-2015063118 A1 | 5/2015 |
| WO | WO-2016093877 A1 | 6/2016 |
| WO | WO-2016126511 A2 | 8/2016 |
| WO | WO-2016150806 A1 | 9/2016 |
| WO | WO-2016177562 A1 | 11/2016 |
| WO | WO-2021242607 A1 | 12/2021 |
| WO | WO-2023156879 A1 | 8/2023 |

OTHER PUBLICATIONS

US 8,062,356 B2, 11/2011, Salahieh et al. (withdrawn)
US 8,062,357 B2, 11/2011, Salahieh et al. (withdrawn)
US 8,075,614 B2, 12/2011, Salahieh et al. (withdrawn)
US 8,133,271 B2, 03/2012, Salahieh et al. (withdrawn)
US 8,211,170 B2, 07/2012, Paul et al. (withdrawn)
Akins C.W., et al., "Risk of Reoperative Valve Replacement for Failed Mitral and Aortic Bioprostheses," The Annals of Thoracic Surgery, 65:545-1552 (Jan. 1998). Retrieved from the Internet: URL: http://ats.ctsnetjournals.org/cgi/contenUfull/65/6/1545 (Jan. 1998).
Allen et al., "What are the characteristics of the ideal endovascular graft for abdominal aortic aneurysm exclusion?", J. Endovasc. Surg., vol. 4(2), May 1997, pp. 195-202.
Anabtawi I.N., et al., "Experimental evaluation of myocardial tunnelization as a method of myocardial revascularization," Journal of Thoracic and Cardiovascular Surgery, 58(5):638-646 (Nov. 1969).
Andersen H.R., et al., "Transluminal Implantation of Artificial Heart Valves. Description of a New Expandable Aortic Valve and Initial Results with Implantation by Catheter Technique in Closed Chest Pigs," European Heart Journal, May 1992, vol. 13, pp. 704-708.
"Aortenklappenbioprothese erfolgreich in der Entwicklung," May 16, 2003, 1 page (with English Translation).
Archie J.P., et al., "Intramyocardial Pressure: Effect of Preload on Transmural Distribution of Systolic Coronary Blood Flow," The American Journal of Cardiology, 35(6):904-911 (Jun. 1975).
Baba H., et al., "Hemodynamic effects of venous valves in aorta-coronary bypass grafts," The Journal of Thoracic and Cardiovascular Surgery, 71(5):774-778 (May 1976).
Babaliaros V., et al., "State of the Art Percutaneous Intervention for the Treatment of Valvular Heart Disease: A Review of the Current Technologies and Ongoing Research in the Field of Percutaneous Valve Replacement and Repair," Cardiology, 2007, vol. 107, pp. 87-96.
Bailey S.R., "Percutaneous Expandable Prosthetic Valves," Textbook of Interventional Cardiology, Second Edition, W.B. Saunders Company, 1994, vol. 2, pp. 1268-1276.
Block P.C., et al., "Percutaneous Approaches to Valvular Heart Disease," Current Cardiology Reports, Mar. 2005, vol. 7(2), pp. 108-113.
Blum et al., "Endoluminal Stent—Grafts for Intrarenal Abdominal Aortic Aneurysms." New Engl. J. Med., 336:13-20 (Jan. 1997).
Bonhoeffer et al., "Percutaneous Mitral Valve Dilatation with the Multi-Track System," Catheterization and Cardiovascular Interventions—Official Journal of the Society for Cardiac Angiograhy & Interventions, United States (Oct. 1999), pp. 178-183.
Bonhoeffer P., et al., "Percutaneous Insertion of the Pulmonary Valve," Journal of the American College of Cardiology, May 15, 2002, vol. 39, pp. 1664-1669.
Bonhoeffer P., et al., "Percutaneous Replacement of Pulmonary Valve in a Right-Ventricle to Pulmonary-Artery Prosthetic Conduit with Valve Dysfunction," Lancet, Oct. 2000, vol. 356, pp. 1403-1405.
Bonhoeffer P., et al., "Technique and Results of Percutaneous Mitral Valvuloplasty With the Multi-Track System," Journal of Interventional Cardiology, 13(4):263-268 (Aug. 2000).
Bonhoeffer P., et al., "Transcatheter Implantation of a Bovine Valve in Pulmonary Position: A Lamb Study," Circulation, Aug. 15, 2000, vol. 102, pp. 813-816.
Boudjemline et al., "Percutaneous Implantation of a Biological Valve in Aortic Position: Preliminary Results in a Sheep Study, " European Heart Journal, vol. 22, p. 630, Abstract Only (Sep. 2001).
Boudjemline Y., et al., "Images in Cardiovascular Medicine: Percutaneous Aortic Valve Replacement in Animals," Circulation, United States, Mar. 16, 2004, vol. 109, p. e161.
Boudjemline Y., et al., "Is Percutaneous Implantation of a Bovine Venous Valve in the Inferior Vena Cava a Reliable Technique to Treat Chronic Venous Insufficiency Syndrome?," Medical Science Monitor, Poland, Mar. 2004, vol. 10(3), pp. BR61-BR66.
Boudjemline Y., et al., "Off-Pump Replacement of the Pulmonary Valve in Large Right Ventricular Outflow Tracts: A Hybrid Approach," Journal of Thoracic and Cardiovascular Surgery, United States, Apr. 2005, vol. 129(4), pp. 831-837.
Boudjemline Y., et al., "Percutaneous Aortic Valve Replacement: Will We Get There?," Heart, British Cardiac Society, England, Dec. 2001, vol. 86, pp. 705-706.

(56) References Cited

OTHER PUBLICATIONS

Boudjemline Y., et al., "Percutaneous Implantation of a Biological Valve in the Aorta to Treat Aortic Valve Insufficiency—A Sheep Study," Medical Science Monitor, Apr. 12, 2002, vol. 8(4), pp. BR113-BR116.
Boudjemline Y., et al., "Percutaneous Implantation of a Valve in the Descending Aorta in Lambs," European Heart Journal, Jul. 2002, vol. 23, pp. 1045-1049.
Boudjemline Y., et al., "Percutaneous Pulmonary Valve Replacement in a Large Right Ventricular Outflow Tract: An Experimental Study," Journal of the American College of Cardiology, Mar. 17, 2004, vol. 43(6), pp. 1082-1087.
Boudjemline Y., et al., "Percutaneous Valve Insertion: A New Approach?," Journal of Thoracic and Cardiovascular Surgery, United States, Mar. 2003, vol. 125(3), pp. 741-742.
Boudjemline Y., et al., "Stent Implantation Combined with a Valve Replacement to Treat Degenerated Right Ventricle to Pulmonary Artery Prosthetic Conduits," European Heart Journal, Sep. 2001, vol. 22, p. 355.
Boudjemline Y., et al., "Steps Toward Percutaneous Aortic Valve Replacement," Circulation, Feb. 12, 2002, vol. 105, pp. 775-778.
Boudjemline Y., et al., "The Percutaneous Implantable Heart Valve," Progress in Pediatric Cardiology, Ireland, 2001, vol. 14, pp. 89-93.
Boudjemline Y., et al., "Transcatheter Reconstruction of the Right Heart," Cardiology in the Young, England, 2003, vol. 13, pp. 308-311.
Bruce C.J., et al., "Right-sided Valve Disease Deserves Little More Respect," Circulation, 119(2):2726-2734 (May 2009).
Coats L., et al., "The Potential Impact of Percutaneous Pulmonary Valve Stent Implantation on Right Ventricular Outflow Tract Re-Intervention," European Journal of Cardio-Thoracic Surgery, England, Apr. 2005, vol. 27, pp. 536-543.
Commeau P et al., "Percutaneous Balloon Dilatation of calcific aortic Valve Stenosis: Anatomical and Haemodynamic Evaluation," British Heart Journal, 59:227-238 (Feb. 1988).
Cribier A., et al., "Percutaneous Transcatheter Implantation of an Aortic Valve Prosthesis for Calcific Aortic Stenosis: First Human Case Description," Circulation, 2002, vol. 106, pp. 3006-3008.
Cribier et al., "Early Experience with Percutaneous Transcatheter Implantation of Heart Valve Prosthesis for the Treatment of End-Stage Inoperable Patients with Calcific Aortic Stenosis", J. of Am. Coll. of Cardio, Feb. 18, 2004, 43(4), pp. 698-703.
Cribier et al., "Percutaneous Transluminal Valvuloplasty of Acquired Aortic Stenosis in Elderly Patients: An Alternative to Valve Replacement?", The Lancet, Jan. 11, 1986, pp. 63-67.
Cunanan et al., "Tissue Characterization and Calcification Potential of Commercial Bioprosthetic Heart Valves." Ann. Thorac. Surg., May 15, 2001, pp. S417-421.
Cunliffe et al., "Glutaraldehyde Inactivation of Exotic Animal Viruses in Swine Heart Tissue," Applied and Environmental Microbiology, Greenport, New York, vol. 37, No. 5, May 1979, pp. 1044-1046.
Dake et al., "Transluminal Placement of Endovascular Stent-Grafts for the Treatment of Descending Thoracic Aortic Aneurysms." New Engl. J. of Med., 331(26):1729-34 (Dec. 1994).
Dalby et al., "Non-Surgical Aortic Valve Replacement" Br. J. Cardiol., 10(6):450-452 (Nov. 2003).
Davidson M.J., et al., "Percutaneous Therapies for Valvular Heart Disease," Cardiovascular Pathology, Jan. 2006, vol. 15, pp. 123-129.
Dewey et al., "Transapical aortic valve implantation: An Animal Feasibility Study", The annals of thoracic surgery, 82:110-116 (Feb. 2006).
Dhasmana et al., "Factors Associated With Periprosthetic Leakage Following Primary Mitral Valve Replacement: With Special Consideration of Suture Technique." Annals of Thorac. Surg., (Feb. 1983), 35(2), pp. 170-178.
Dotter, "Transluminally-Placed Coilspring Endarterial Tube Grafts," Investigative Radiology, pp. 329-332 (Oct. 1969).
Emery et al., "Replacement of the Aortic Valve in Patients Under 50 Years of Age: Long-Term Follow-Up of the St. Jude Medical Prosthesis." Ann. Thorac. Surg., 75:1815-1819 (Jun. 2003).
European Search Report dated Aug. 10, 2011 for EP Application No. 06824992.9.
European Search Report for EP Patent Appl. Serial No. 12179049.7 (1257), dated Oct. 30, 2012, 4 pages.
European Search Report for EP Patent Appl. Serial No. 12179075.2 (1257), dated Oct. 29, 2012, 3 pages.
European Search Report for EP Patent Appl. Serial No. 12179141.2 (1257), dated Nov. 2, 2012, 3 pages.
European Search Report for EP Patent Appl. Serial No. 12179146.1 (1257), dated Nov. 7, 2012, 8 pages.
European Search Report for EP Patent Appl. Serial No. 12179330.1 (1257), dated Nov. 22, 2012, 3 pages.
European Search Report for EP Patent Appl. Serial No. 12179338.4 (1257), dated Nov. 2, 2012, 3 pages.
European Search Report for EP Patent Appl. Serial No. 12179339.2 (1257), dated Oct. 29, 2012, 4 pages.
European Search Report for EP Patent Appl. Serial No. 12179914.2 (1257), dated Nov. 7, 2012, 6 pages.
European Search Report for EP Patent Appl. Serial No. 13150337.7 (1257), dated Jul. 9, 2013, 3 pages.
European Search Report for EP Patent Appl. Serial No. 13183134.9 (1651), dated Nov. 19, 2013, 3 pages.
European Search Report for EP Patent Appl. Serial No. 14159630.4 (1651), dated May 22, 2014, 3 pages.
European Search Report for EP Patent Appl. Serial No. 14161991.6 (1651), dated Jun. 3, 2014, 3 pages.
European Search Report for EP Patent Appl. Serial No. 15167832.3 (1651), dated Jul. 23, 2015, 3 pages.
European Search Report for EP Patent Appl. Serial No. 15167847.1 (1651), dated Jul. 23, 2015, 3 pages.
European Search Report for EP Patent Appl. Serial No. 17196833.2, dated Mar. 6, 2018, 4 pages.
European Search Report for EP Patent Appl. Serial No. 18164490.7, dated Sep. 17, 2018 5 pages.
European Search Report from EP Patent Office for EP Application No. 15177718.2, dated Jan. 18, 2016, 4 pages.
European Search Report from EP Patent Office for EP Application No. 15177731.5, dated Apr. 14, 2016, 4 pages.
European Search Report from EP Patent Office for EP Application No. 16151726.3, dated Feb. 25, 2016, 4 pages.
Extended European Search Report dated Apr. 11, 2008 in EP Patent Appl. Serial No. 081630410, 5 pages.
Extended EP Search Report dated Sep. 24, 2020 in EP Patent Appl. Serial No. 20165841.6 (JVT-0280).
Extended European Search Report for Application No. 10183946.2.4-2320 dated Feb. 14, 2012, 7 pages.
Extended European Search Report dated Aug. 9, 2018 in EP Patent Appl. Serial No. 18158901.1 (1113).
Extended European Search Report dated Jun. 12, 2018 in EP Patent Appl. Serial No. 17209326.2 (1113).
Extended European Search Report dated May 16, 2012 in EP Patent Appl. Serial No. 11178135.7 (1257).
Extended European Search Report for Application No. 11178076.3-1257 dated Feb. 29, 2012, 5 pages.
Extended European Search Report from EP Patent Office for EP Application No. 17162616.1, dated Jul. 27, 2017, 7 pages.
Extended European Search Report dated Apr. 9, 2014 in EP Patent Appl. Serial No. 14164683.6.
Extended European Search Report dated May 9, 2013 in EP Patent Appl. Serial No. 130178309.4,4 pages.
Extended European Search Report dated Aug. 19, 2011 in EP Patent Appl. Serial No. 07827132.7.
Extended European Search Report dated Feb. 27, 2017 in EP Patent Appl. Serial No. 16186773,6 pages.
Extended European Search Report dated Sep. 29, 2014 in EP Patent Appl. No. 14164680, 5 pages.
Extended European Search Report for Application No. 07116242.4-2310 dated Mar. 31, 2008, 10 pages.
Extended European Search Report for Application No. 09154935.2, dated May 29, 2009, 7 pages.

(56) References Cited

OTHER PUBLICATIONS

Extended European Search Report for Application No. 10012198.7 dated Mar. 23, 2011, 7 pages.
Extended European Search Report for Application No. 10168525.3-1257 dated Feb. 3, 2011, 13 pages.
Extended European Search Report for Application No. 11153142.2-1257 dated Aug. 3, 2011, 10 pages.
Extended European Search Report for Application No. 11165093.3-1257 dated Aug. 30, 2011, 6 pages.
Extended European Search Report for Application No. 11178073.0-1257 dated Oct. 14, 2011, 5 pages.
Extended European Search Report for Application No. 11178145.6-1257 dated Feb. 29, 2012, 5 pages.
Extended European Search Report for Application No. 13188858.8-1651 dated Jan. 13, 2014, 6 pages.
Extended European Search Report for Application No. 19195062 dated Jan. 2, 2020, 7 pages.
Extended European Search Report for EP Patent Appl. Serial No. 06827630.2 dated Jun. 7, 2010, 5 pages.
Extended European Search Report for EP Patent Appl. Serial No. 07110318.8, dated May 29, 2008, 10 pages.
Extended European Search Report for EP Patent Appl. Serial No. 10163478.0, dated Mar. 22, 2011, 9 pages.
Extended European Search Report for EP Patent Appl. Serial No. 10184842.2, dated Mar. 23, 2011, 7 pages.
Extended European Search Report for EP Patent Appl. Serial No. 11162971.3, dated Jun. 30, 2011, 5 pages.
Extended European Search Report for EP Patent Appl. Serial No. 13163918.9, dated Jul. 24, 2013, 8 pages.
Extended European Search Report for EP Patent Appl. Serial No. 14179639.1, dated Mar. 9, 2015, 7 pages.
Extended European Search Report for EP Patent Appl. Serial No. 16201320.5, dated May 19, 2017, 6 pages.
Extended European Search Report for EP Patent Appl. Serial No. 18200191.7, dated May 6, 2019, 8 pages.
Ferrari, "Entwicklung eines Verfahrens zum transvaskularen Aortenklappenersatz," Habilitationsschrift, Medizinische Fakultat der Friedrich-Schiller-Universitat Jena, Sep. 2003, pp. 1-159. (With English Translation).
Ferrari, "Entwicklung eines Verfahrens zum transvaskulären Aortenklappenersatz," Habilitationsschrift, Medizinische Fakultät der Friedrich-Schiller-Universität Jena, Sep. 2003, pp. 49-52. (With English Translation).
Ferrari M.W., "Transarterial Aortic Valve Replacement with a Self Expanding Stent in Pigs," Heart, vol. 90, No. 11, doi:10.1136/hrt.2003.028951, ISSN 1355-6037, XP055137208, Nov. 2004, pp. 1326-1331.
Filsoufi F., et al., "Long-term Outcomes of Tricuspid Valve Replacement in the Current Era," Ann. Thorac. Surg., 8(3):845-850 (Sep. 2005).
Fluency Vascular Stent Graft Instructions for Use, May 2014, 20 pages.
Greeenberg, "Abdominal Aortic Endografting: Fixation and Sealing." J. Am. Coll. Surg., 194(1):S79-S87 (Jan. 2002).
Grossi A.E. et al., "Impact of Minimally Invasive Valvular Heart Surgery: A Case-Control Study", Ann. Thorac. Surg., 71:807-810 (Mar. 2001).
Gummert J.F. et al., Cardiac Surgery in Germany During 2006: A Report on Behalf of the German Society for Thoracic and Cardiovascular Surgery, Thorac. Cardiov. Surg., vol. 55, (Sep. 2007), pp. 343-350.
Gummert J.F. et al., "Cardiac Surgery in Germany During 2007: A Report on Behalf of the German Society for Thoracic and Cardiovascular Surgery," Thorac. Cardiov. Surg., vol. 56, (Sep. 2008), pp. 328-336.
Hanzel G.S., et al., "Complications of Percutaneous Aortic Valve Replacement: Experience with the Cribier-Edwards TM Percutaneous Heart Valve," EuroIntervention Supplements, 2006, vol. 1(A), pp. A3-A8.
Heinrich R.S., et al., "Experimental analysis of fluid mechanical energy losses in aortic valve stenosis: importance of pressure recovery", Ann Biomed Eng., Nov.-Dec. 1996, vol. 24(6), pp. 685-694.
Hijazi Z.M., "Transcatheter Valve Replacement: A New Era of Percutaneous Cardiac Intervention Begins", J. of Am. College of Cardio., Nov. 6, 2004, vol. 43, No. 6, pp. 1088-1089.
Hourihan M., et al., "Transcatheter Umbrella Closure of Valvular and Paravalvular Leaks", JACC, Boston, Massachusetts, 20(6):1371-1377 (Nov. 1992).
Huber C.H., et al., "Direct Access Valve Replacement (DAVR)—are we entering a new era in cardiac surgery?" European Journal of Cardio-thoracic Surgery, vol. 29, Jan. 19, 2006, pp. 380-385.
Huber C.H., et al., "Direct-Access Valve Replacement: A Novel Approach for Off-Pump Valve Implantation Using Valved Stents," Journal of the American College of Cardiology, Jul. 19, 2005, vol. 46(2), pp. 366-370.
Huber C.H., et al., "Do Valved Stents Compromise Coronary Flow?," European Journal of Cardio-thoracic Surgery, Jan. 23, 2004, vol. 25, pp. 754-759.
Ing F., "Stents: What's Available to the Pediatric Interventional Cardiologist?" Catheterization and Cardiovascular Interventions, 57:374-386 (Jun. 2002).
International Search Report dated Dec. 29, 2003 in Intl PCT Patent Appl. U.S. Appl. No. PCT/DE2003/002669.
International Search Report and Written Opinion for PCT Application No. PCT/EP2009/052230 dated Jun. 29, 2009, 12 pages.
International Search Report and Written Opinion for PCT Application No. PCT/EP2010/052429 dated Jun. 14, 2010, 12 pages.
International Search Report and Written Opinion for PCT Application No. PCT/EP2011/002524 dated Apr. 23, 2012, 15 pages.
International Search Report and Written Opinion for PCT Application No. PCT/EP2011/052674 dated Jul. 5, 2011, 12 pages.
International Search Report for PCT Application No. PCT/US1999/020736 dated Jan. 28, 2000, 3 pages.
International Search Report and Written Opinion for PCT Application No. PCT/EP2009/050762 dated Jun. 23, 2009, 12 pages.
International Search Report & Written Opinion dated Feb. 20, 2024 in Int'l PCT Patent Appl. Serial No. PCT/IB2023/037029 (0464-P040-PCT).
International Search Report & Written Opinion mailed Jul. 18, 2016 for PCT Patent Appl No. PCT/EP2016/059839, 10 pages.
International Search Report & Written Report Opinion dated Apr. 17, 2024 in Int'l PCT Patent Appl. Serial No. PCT/US2023/080979 (P041-PCT) (411001).
International Search Report and Written Opinion for Appl. No. PCT/EP2016/055783, mailed on May 30, 2016, 15 pages.
International Search Report and Written Opinion for Application No. PCT/EP2013/057431 dated Jul. 26, 2013, 9 pages.
International Search Report and Written Opinion for Application No. PCT/IB2018/050438 mailed Apr. 12, 2018, 11 pages.
International Search Report and Written Opinion for International Application No. PCT/EP2010/063306, dated Nov. 17, 2010, 9 pages.
International Search Report and Written Opinion for PCT Application No. PCT/EP2006/010519 dated Mar. 1, 2007, 13 pages.
International Search Report and Written Opinion for PCT Application No. PCT/US06/36286 dated Jul. 9, 2007, 4 pages.
International Search Report and Written Opinion for PCT Application No. PCT/US2004/041513 dated Jun. 10, 2005, 4 pages.
International Search Report and Written Opinion for PCT Application No. PCT/US2004/043607 dated Mar. 20, 2006, 4 pages.
International Search Report and Written Opinion for PCT Application No. PCT/US2005/020947 dated Oct. 6, 2005, 5 pages.
International Search Report and Written Opinion for PCT Application No. PCT/US2006/038352 dated May 19, 2008, 4 pages.
International Search Report and Written Opinion for PCT Application No. PCT/US2006/043484 dated Jun. 25, 2008, 4 pages.
International Search Report and Written Opinion for PCT Application No. PCT/US2007/003992 dated Jan. 10, 2008, 5 pages.
International Search Report and Written Opinion for PCT Application No. PCT/US2007/02970 dated Oct. 19, 2007, 7 pages.

(56) References Cited

OTHER PUBLICATIONS

International Search Report and Written Opinion for PCT Application No. PCT/US2009/060531 dated May 13, 2010, 6 pages.
International Search Report and Written Opinion for PCT/DE2006/000056 dated Jun. 7, 2006, 11 pages.
International Search Report and Written Opinion for PCT/EP2007/061117 dated May 20, 2008, 16 pages.
International Search Report and Written Opinion for PCT/EP2008/003803 dated Aug. 20, 2008, 10 pages.
International Search Report and Written Opinion for PCT/EP2009/055958 dated Oct. 21, 2009, 8 pages.
International Search Report and Written Opinion for PCT/EP2010/056558 dated Oct. 7, 2010, 14 pages.
International Search Report and Written Opinion for PCT/EP2012/067617 dated Dec. 19, 2012, 10 pages.
International Search Report and Written Opinion for PCT/IL2007/001149 dated May 1, 2008, 4 pages.
International Search Report and Written Opinion for PCT/US2011/027730 dated May 25, 2011, 9 pages.
International Search Report and Written Opinion of the International Search Authority for International Application No. PCT/EP2008/064558, date of completion of report is Mar. 18, 2009, 14 pages.
International Search Report dated Jan. 28, 2008 in Int'l PCT Application Serial No. PCT/EP2007/007413, 4 pages.
International Search Report dated Jul. 7, 2015 in Int'l PCT Application Serial No. PCT/EP2014/065817, 6 pages.
International Search Report dated Nov. 3, 2011 in Int'l PCT Application Serial No. PCT/EP2011/058506, 4 pages.
International Search Report dated Dec. 18, 2012 in Int'l PCT Patent Application Serial No. PCT/EP2012/067714, 3 pages.
International Search Report for Application No. PCT/DE2001/000837, dated Aug. 7, 2001, 4 pages.
International Search Report for Application No. PCT/EP2006/012455, mailed Sep. 27, 2007, 5 pages.
International Search Report for Application No. PCT/EP2010/057798, dated Sep. 12, 2010, 6 pages.
International Search Report for Application No. PCT/EP2011/066677, dated Feb. 17, 2012, 7 pages.
International Search Report for Application No. PCT/EP2012/067617 mailed Dec. 19, 2012, 3 pages.
International Search Report for Application No. PCT/EP2013/073318, dated Apr. 17, 2014, 5 pages.
International Search Report for Application No. PCT/EP2016/055783, mailed on May 30, 2016, 5 pages.
International Search Report for Application No. PCT/EP2016/058532, dated Jul. 11, 2016, 4 pages.
International Search Report for Application No. PCT/IB2008/002180, dated Apr. 15, 2009, 7 pages.
International Search Report for Application No. PCT/IB2018/050438 mailed Apr. 12, 2018, 3 pages.
International Search Report for PCT/DE2001/000836 dated Jun. 13, 2001, 6 pages.
International Search Report for PCT/EP2006/010023 dated Mar. 30, 2007, 6 pages.
International Search Report for PCT/IB2017/052718, dated Sep. 5, 2017, 4 pages.
Invitation to Pay Additional Fees & Partial Search Report dated Feb. 28, 2024 in Int'l PCT Patent Appl. Serial No. PCT/US2023/080979 (P41-PCT).
Kato et al., "Traumatic Thoracic Aortic Aneurysm: Treatment with Endovascular Stent-Grafts." Radiol., 205:657-662 (Dec. 1997).
Khambadkone S., et al., "Nonsurgical Pulmonary Valve Replacement: Why, When, and How?," Catheterization and Cardiovascular Interventions, United States, Jul. 2004, vol. 62, pp. 401-408.
Khambadkone S., et al., "Percutaneous Implantation of Pulmonary Valves," Expert Review of Cardiovascular Therapy (England), Nov. 2003, vol. 1(4), pp. 541-548.
Khambadkone S., et al., "Percutaneous Pulmonary Valve Implantation: Early and Medium Term Results," Circulation, Oct. 28, 2003, vol. 108(17), p. IV-375.
Klein A.L., et al., "Age-related Prevalence of Valvular Regurgitation in Normal Subjects: A Comprehensive Color Flow Examination of 118 Volunteers," Journal of the American Society of Echocardiography, vol. 3, No. 1, (Jan. 1990), pp. 54-63.
Knudsen et al., "Catheter-implanted prosthetic heart valves", Intl J. of Art. Organs, 16(5): 253-262, May 1993.
Kort et al., "Minimally Invasive Aortic Valve Replacement: Echocardiographic and Clinical Results." Am. Heart J., Sep. 2001, vol. 142(3), pp. 476-481.
Kuzela L., et al., "Experimental evaluation of direct transventricular revascularization," Journal of Thoracic and Cardiovascular Surgery, 57(6):770-773 (Jun. 1969).
Laborde et al., "Percutaneous Implantation of the Corevalve Aortic Valve Prosthesis for Patients Presenting High Risk for Surgical Valve Replacement," EuroIntervention, 1(4):472-474 (Feb. 2006).
Lawrence et al., "Percutaneous Endovascular Graft: Experimental Evaluation", Radiology, May 1987, vol. 163(2), pp. 357-360.
Levi et al., "Future of Interventional Cardiology in Pediactrics." Current Opinion in Cardiol., 18:79-90 (Mar. 2003).
Levy, "Mycobacterium chelonei Infection of Porcine Heart Valves." The New England Journal of Medicine, Washington DC, 297(12), Sep. 22, 1977, pp. 667-668.
Lichtenstein et al., "Transapical Transcatheter Aortic Valve Implantation in Humans: Initial Clinical Experience", circulation, American Heart Association vol. 114, Jul. 31, 2006, pp. 591-596.
Lichtenstein, S.V., "Closed heart surgery: Back to the future" The Journal of Thoracic and Cardiovascular Surgery, vol. 131(5), May 2006, pp. 941-943.
Liu et al., "Effect of Fiber Orientation on the Stress Distribution within a Leaflet of a Polymer Composite Heart Valve in be Closed Position", Journal of Biomechanics, 4:1099-1106 (Jan. 2007).
Lonescu et al., "Prevalence and Clinical Significance of Incidental Paraprosthetic Valvar Regurgitation: A prospective study using transesophageal echocardiography." Heart, 89:1316-21 (Oct. 2003).
Love S.C et al., The Autogenous Tissue Heart Valve: Current Status, Journal of Cardiac Surgery, , Mar. 1991, vol. 6(4), pp. 499-507.
Lutter G., et al., "Percutaneous Aortic Valve Replacement: An Experimental Study. I. Studies on Implantation," Journal of Thoracic and Cardiovascular Surgery, Apr. 2002, vol. 123(4), pp. 768-776.
Lutter G., et al., "Percutaneous Valve Replacement: Current State and Future Prospects," Annals of Thoracic Surgery, Netherlands, Dec. 2004, vol. 78, pp. 2199-2206.
Ma L., et al., "Double-Crowned Valved Stents for Off-Pump Mitral Valve Replacement," European Journal of Cardio-Thoracic Surgery, Jun. 13, 2005, vol. 28(2), pp. 194-199.
Mack, M.J., "Minimally invasive cardiac surgery", Surg Endosc, 20:S488-S492 (Mar. 2006).
Magovern et al., "Twenty-five-Year Review of the Magovern-Cromie Sutureless Aortic Valve", Ann. Thorac. Surg., 48:S33-S334 (Jan. 1989).
Maraj et al., Evaluation of Hemolysis in Patients with Prosthetic Heart Valves, Clin. Cardiol. 21:387-392 (Jun. 1998).
Marcus RH et al., "Assessment of small-diameter aortic mechanical prostheses: physiological relevance of the Doppler gradient, utility of flow augmentation, and limitations of orifice area estimation," Circulation, 98(9):866-872 (Sep. 1998).
McKay G. R. et al., "The Mansfield Scientific Aortic Valvuloplasty Registry: Overview of Acute Hemodynamic Results and Procedural Complications." J. Am. Coll. Cardiol., 17(2):485-491 (Feb. 1991).
Mills N.L., et al., "Valvulotomy of valves in the saphenous vein graft before coronary artery bypass," The Journal of Thoracic and Cardiovascular Surgery, 71(6):878-879 (Jun. 1976).
Mirich et al., "Percutaneously Placed Endovascular Grafts for Aortic Aneurysms: Feasibility Study", Radiology, 170:1033-1037 (Mar. 1989).
Moazami N et al. "Transluminal Aortic Valve Placement: a Fesibility Study with a Newly Designed Collapsible Aortic Valve", ASAIO Journal, vol. 42, No. 2, Mar.-Apr. 1996.

(56) References Cited

OTHER PUBLICATIONS

Moulopoulos et al., "Catheter-Mounted Aortic Valves," Annals of Thoracic Surg., vol. 11, No. 5, May 1971, pp. 423-430.
Munro I., et al., "The possibility of myocardial revascularization by creation of a left ventriculocoronary artery fistula," The Journal of Thoracic and Cardiovascular Surgery, 58(1):25-32 (Jul. 1969).
Nath J., et al., Impact of Tricuspid Regurgitation on Long-term Survival, Journal of the American College of Cardiology, 43(3):405-406 (Feb. 2004).
Nietlispach F., et al., "Current Balloon-Expandable Transcatheter Heart Valve and Delivery Systems", Catheterization and Cardiovascular Interventions, 75:295-300 (Sep. 2009).
Palacios I.F., "Percutaneous Valve Replacement and Repair: Fiction or Reality?," Journal of American College of Cardiology, Oct. 2004, vol. 44(8), pp. 1662-1663.
Palmaz J.C., et al., "Expandable Intrahepatic Portacaval Shunt Stents: Early Experience in the Dog," American Journal of Roentgenology, 145 (4):821-825 (Oct. 1985).
Palmaz J.C., et al., "Expandable Intrahepatic Portacaval Shunt Stents in Dogs with Chronic Portal Hypertension," American Journal of Roentgenology, 147(6):1251-1254 (Dec. 1986).
Paniagua et al., "Percutaneous Heart Valve in the Chronic in Vitro Testing Model." Circulation, Sep. 17, 2002, vol. 106: e51-e52.
Parodi J.C., et al., "Transfemoral Intraluminal Graft Implantation for Abdominal Aortic Aneurysms", Ann. Vasc. Surg., 5(6):491-499 (Nov. 1991).
Partial European Search Report dated Feb. 28, 2012 in EP Patent Appl. Serial No. 11178135.7 (1257).
Partial European Search Report for Application No. 10168525.3-1269 dated Sep. 20, 2010, 5 pages.
Partial European Search Report for Application No. 07116242.4-2310 dated Jan. 14, 2008, 5 pages.
Partial European Search Report for Application No. 11153142.2-1257 dated Apr. 4, 2011, 5 pages.
Partial European Search Report for EP Patent Appl. Serial No. 07110318.8, dated Mar. 10, 2008, 6 pages.
Partial European Search Report for EP Patent Appl. Serial No. 10163478.0, dated Nov. 2, 2010, 6 pages.
Partial International Search Report for International Application No. PCT/EP2014/055044, filed Mar. 13, 2014, 7 pages.
Paul et al., U.S. Appl. No. 12/578,463 entitled "Medical Devices and Delivery Systems for Delivering Medical Devices," filed Oct. 13, 2009, 79 pages.
Pavcnik D., et al., "Aortic and Venous Valve for Percutaneous Insertion," Minimally Invasive Therapy & Allied Technologies, Jan. 2000, vol. 9(3/4), pp. 287-292.
Pavcnik D., et al., "Development and Initial Experimental Evaluation of a Prosthetic Aortic Valve for Transcatheter Placement." Radiology, 183:151-154 (Apr. 1992).
Pavcnik et al., "Percutaneous Bioprosthetic Venous Valve: A Long-term Study in Sheep," Jounal of Vascular Surg., vol. 35, No. 3, Mar. 2002, pp. 598-603.
Pawelec-Wojtalk M., "Closure of left ventricle perforation with the use of muscular VSD occluder," European Journal of Cardia-Thoracic Surgery, 27(4):714-716 (Apr. 2005).
Pelton A.R., et al., "Medical Uses of Nitinol," Materials Science Forum, Jan. 2000, vol. 327-328, pp. 63-70.
Phillips et al., "A Temporary Catheter-Tip Aortic Valve: Hemodynamic Effects on Experimental Acute Aortic Insufficiency", Annals of Thoracic Surg., Feb. 1976, 21(2), pp. 134-136.
Phillips S.J., et al., "Improvement in Forward Coronary Blood Flow by Using a Reversed Saphenous Vein with a Competent Valve," The Annals of Thoracic Surgery, vol. 21 (1), Jan. 1976, pp. 12-15.
Preliminary Search Report (Rapport De Recherche Preliminaire) dated Jul. 8, 2002 in French Patent Application No. 0110444 (2 pages).
Raillat et al., "Treatment of Iliac Artery Stenosis with the Wallstent Endoprosthesis." AJR, Mar. 1990, vol. 154(3), pp. 613-616.
Remadi et al., "Preliminary results of 130 aortic valve replacements with a new mechanical bileaflet prosthesis: The Edwards MIRA valve," Interactive Cardiovasc. and Thorac. Surg., 2:80-83 (Mar. 2003).
Rogers J.H., et al., "The Tricuspid Valve: Current Perspective and Evolving Management of Tricuspid Regurgitation," Circulation, 119(20):2718-2725 (May 2009).
Ruiz C.E., "Transcatheter Aortic Valve Implantation and Mitral Valve Repair: State of the Art," Pediatric Cardiology, Jun. 2005, vol. 26(3), pp. 289-294.
Saliba Z., et al., "Treatment of Obstructions of Prosthetic Conduits by Percutaneous Implantation of Stents," Archives Des Maladies Du Coeur Et Des Vaisseaux, May 1999, pp. 591-596.
Schurink et al., "Stent Attachment Site—related Endoleakage after Stent Graft Treatment: An in vitro study of the effects of graft size, stent type, and atherosclerotic wall changes", J. Vasc. Surg., vol. 30(4), Oct. 1999, pp. 658-667.
Search Report dated Oct. 15, 2003 from the European Patent Office for European Patent Application No. EP 02291953.4, 2 pages.
Search Report from the European Patent Office dated Dec. 11, 2002 for European Patent Application No. EP 02291954.4, 4 pages.
Sochman et al., "Percutaneous Transcatheter Aortic Disc Valve Prosthesis Implantation: A Feasibility Study." Cardiovasc. Intervent. Radiol., Sep. 2000, 23: 384-388.
Stanley et al., "Evaluation of Patient Selection Guidelines for Endoluminal AAA Repair With the Zenith Stent Graft: The Australasian Experience." J. Endovasc. Ther., 8:457-464 (Oct. 2001).
Stassano P., et al., "Mid-term Results of the Valve-on-Valve Technique for Bioprosthetic Failure," European Journal of Cardiothoracic Surgery, Oct. 2000, vol. 18, pp. 453-457.
Stein D.P., et al., "Turbulent blood flow in the ascending aorta of humans with normal and diseased aortic valves", Circulation Research by American Heart Association, 39:58-65 (Jul. 1976).
Steinhoff et al., "Tissue Engineering of Pulmonary Heart Valves on Allogenic Acellular Matrix Conduits." Circulation102 [suppl. III], pp. III-50-III-55 (Nov. 2000).
Supplemental Search Report from EP Patent Office for EP Application No. 04813777.2, dated Aug. 19, 2011.
Supplemental Search Report from EP Patent Office for EP Application No. 04815634.3, dated Aug. 19, 2011.
Supplemental Search Report from EP Patent Office for EP Application No. 05758878.2, dated Oct. 24, 2011.
Supplementary European Search Report dated Jan. 2, 2012 in EP Patent Appl. Serial No. 09820051.2.
Thompson et al., "Endoluminal stent grafting of the thoracic aorta: Initial experience with the Gore Excluder," Journal of Vascular Surgery, Jun. 2002, pp. 1163-1170.
Topol, Eric., Textbook of Interventional Cardiology, 4th Ed; Chapter 24: "Endovascular Options for Peripheral Arterial Occlusive and Aneurysmal Disease," Saunders, pp. 499-503, 949-953 (Dec. 2003).
Triennial Review of the National Nanotechnology Initiative: "A Matter of Size", The National Academies Press, Washington DC, V-13, Retrieved from the Internet: URL: http://www.nap.edu/catalog/11752/a-matter-of-size-triennial-review-of-the-national-nanotechnology, 200 pages (Mar. 2006) (Parts 1-5).
Vahanian et al., "Percutaneous Approaches to Valvular Disease", Circulation, Apr. 6, 2004, 109: 1572-1579.
Van Herwerden et al., "Percutaneous Valve Implantation: Back to the Future?", Euro. Heart J., Sep. 2002, 23(18): 1415-1416.
Walther et al., "Transapical approach for sutureless stent-fixed aortic valve implantation: experimental results", European Journal of Cardio-thoracic Surgery 29, 703-708 (May 2006).
Webb J.G., et al., "Percutaneous Aortic Valve Implantation Retrograde from the Femoral Artery," Circulation, American Heart Association, Feb. 14, 2006, vol. 113, pp. 842-850.
Weerasinghe A., et al., "First Redo Heart Valve Replacement: A 10-Year Analysis," Circulation, 99(5):655-658 (Feb. 1999).
Weyman Ab et al., "Aortic Stenosis: Physics and Physiology—What Do the Numbers Really Mean?", Rev Cardiovasc Med., 6(1):23-32 (Jan. 2005).

(56) References Cited

OTHER PUBLICATIONS

White et al., "Endoleak as a Complication of Endoluminal Grafting of Abdominal Aortic Aneurysms: Classification, Incidence, Diagnosis, and Management," J. Endovasc. Surg., 4:152-168 (May 1997).
Written Opinion dated Mar. 30, 2007 in Int'l PCT Application Serial No. PCT/EP2006/010023, 10 Pages.
Written Opinion dated Sep. 27, 2007 in Int'l Application No. PCT/EP2006/012455, 11 pages.
Written Opinion for Application No. PCT/EP2007/007413, mailed Jan. 28, 2008, 5 pages.
Written Opinion for Application No. PCT/EP2011/058506, mailed Nov. 3, 2011, 5 pages.
Written Opinion for Application No. PCT/EP2014/065817, mailed Jan. 7, 2015, 7 pages.
Written Opinion for PCT/EP2012/067714 dated Dec. 18, 2012, 5 Pages.
Yonga G.O., et al., "Percutaneous Transvenous Mitral Commissurotomy in Juvenile Mitral Stenosis", East African Medical Journal, 80(4):172-174 (Apr. 2003).
Yoshioka et al., "Self-Expanding Endovascular Graft: An Experimental Study in Dogs." AJR 151, Oct. 1988, pp. 673-676.
EPO Communication of a Notice of Opposition in EP Patent No. 3 730 094 dated Jan. 30, 2025 (363002).

* cited by examiner

PROSTHETIC HEART VALVE AND TRANSCATHETER DELIVERED ENDOPROSTHESIS COMPRISING A PROSTHETIC HEART VALVE AND A STENT

This application is a continuation of U.S. application Ser. No. 16/794,423, filed Feb. 19, 2020, now U.S. Pat. No. 11,589,981, which is a continuation of U.S. application Ser. No. 15/658,955, filed on Jul. 25, 2017, now U.S. Pat. No. 10,603,164, which is a continuation of U.S. application Ser. No. 13/114,582, filed on May 24, 2011, now U.S. Pat. No. 9,744,031, which claims priority to U.S. Provisional Application No. 61/348,036 filed on May 25, 2010, and to EP Application No. 10163831.0, filed on May 25, 2010, the entire disclosures of each of which are incorporated herein by reference.

The present disclosure relates to a prosthetic heart valve. Specifically, the present disclosure relates to a prosthetic heart valve for a transcatheter delivered endoprosthesis used in the treatment of a stenotic cardiac valve and/or a cardiac valve insufficiency.

The present disclosure also relates to a transcatheter delivered endoprosthesis that includes a prosthetic heart valve and a stent for positioning and anchoring of the prosthetic heart valve at the implantation site in the heart of a patient. Specifically, the present disclosure also relates to a collapsible and expandable prosthesis incorporating a prosthetic heart valve and a stent that can be delivered to the implant site using a catheter for treatment of a stenosis (narrowing) of a cardiac valve and/or a cardiac valve insufficiency.

The expression "narrowing (stenosis) of a cardiac valve and/or cardiac valve insufficiency" may include a functional defect of one or more cardiac valves, which is either genetic or has developed. A cardiac defect of this type might affect each of the four heart valves, although the aortic and mitral valves are affected much more often than the right-sided part of the heart (pulmonary and tricuspid valves). The functional defect can result in narrowing (stenosis), inability to close (insufficiency) or a combination of the two (combined vitium). This disclosure relates to a prosthetic heart valve as well as a transcatheter delivered endoprosthesis that includes a prosthetic heart valve and an expandable stent capable of being implanted transluminally in a patient's body and enlarged radially after being introduced by transcatheter delivery for treating such a heart valve defect.

The human heart has four valves which control the blood flow circulating through the human body. On the left side of the heart are the mitral valve, located between the left atrium and the left ventricle, and the aortic valve, located between the left ventricle and the aorta. Both of these valves direct the oxygenated blood, coming from the lungs into the aorta for distribution through the body. The tricuspid valve, located between the right atrium and the right ventricle, and the pulmonary valve, located between the right ventricle and the pulmonary artery, however, are situated on the right side of the heart and direct deoxygenated blood, coming from the body, to the lungs.

The native heart valves are passive structures that open and close in response to differential pressures induced by the pumping motions of the heart. They consist of moveable leaflets designed to open and close in response to the said differential pressure. Normally, the mitral valve has two leaflets and the tricuspid valve has at least two, preferably three leaflets. The aortic and pulmonary valves, however, have normally at least two, preferably three leaflets, also often referred to as "cusps" because of their half-moon like appearance. In the present disclosure, the terms "leaflet" and "cusps" have the same meaning.

Heart valve diseases are classified into two major categories, named stenosis and insufficiency. In the case of a stenosis, the native heart valve does not open properly, whereby insufficiency represents the opposite effect showing deficient closing properties. Medical conditions like high blood pressure, inflammatory and infectious processes can lead to such cardiac valve dysfunctions. Either way in most cases the native valves have to be treated by surgery. In this regard, treatment can either include reparation of the diseased heart valve with preservation of the patient's own valve or the valve could be replaced by a mechanical or biological substitutes also referred to as prosthetic heart valves. Particularly for aortic heart valves, however, it is frequently necessary to introduce a heart valve replacement.

In principle, there are two possibilities of treating the diseased heart valve, when inserting a prosthetic heart valve: The first way includes extracting at least major parts of the diseased heart valve. The second alternative way provides leaving the diseased heart valve in place and pressing the diseased leaflets aside to create space for the prosthetic heart valve.

Biological or mechanical prosthetic heart valves are typically surgically sewn into the cardiac valve bed through an opening in the chest after removal of the diseased cardiac valve. This operation necessitates the use of a heart-lung machine to maintain the patient's circulation during the procedure and cardiac arrest is induced during implantation of the prosthesis. This is a risky surgical procedure with associated dangers for the patient, as well as a long post-operative treatment and recovery phase. Such an operation can often not be considered with justifiable risk in the case of polypathic patients.

Minimally-invasive forms of treatment have been developed recently which are characterized by allowing the procedure to be performed under local anesthesia. One approach provides for the use of a catheter system to implant a self-expandable stent to which is connected a collapsible heart valve. Such a self-expandable endoprosthesis can be guided via a catheter system to the implantation site within the heart through an inguinal artery or vein. After reaching the implantation site, the stent with the prosthetic heart valve affixed thereto can then be unfolded.

An increasing number of patients suffer from stenosis (narrowing) of cardiac valve and/or cardiac valve insufficiency. In this regard, the issue concerning the provision of long term durability is involved with developing prosthetic heart valves. Each of the four major heart valves open and close about 100,000 times a day and stability requirements for replacements valves are particularly high.

Moreover, there is the danger that—due to the dynamic fluid pressure from blood flow through the prosthetic heart valve, the leaflet material, or the threads (e.g. sutures) used in fastening the prosthetic heart valve to the stent may tear or break. These component failures over the course of time may result in loss of overall valve function.

On the basis of the problems outlined above and other issues with current transcatheter technologies, certain embodiments of the present disclosure address the issue of providing a prosthetic heart valve, as well as a self-expandable endoprosthesis for treating a narrowed cardiac valve or a cardiac valve insufficiency which realizes optimum long term durability, excellent hemodynamics (e.g. low pressure gradients and minimal regurgitation), minimization of paravalvular leakage, accurate device alignment and positioning, no coronary obstruction, prevention of device migration and avoidance of heart block. In addition, the disclosure provides an improved attachment of a prosthetic heart valve to a corresponding collapsible stent structure, thereby distributing stress loads over a greater surface area and thus reducing the potential for stress concentration points throughout the prosthetic heart valve, resulting in improved durability.

In this regard and as it will be described later in detail, the disclosure provides a prosthetic heart valve for a transcatheter delivered endoprosthesis used in the treatment of a stenosis (narrowing) of a cardiac valve and/or a cardiac valve insufficiency. The prosthetic heart valve comprises at least two leaflets, a skirt portion, and a transition area representing a junction between the leaflets and the skirt portion. Each of the at least two leaflets of the prosthetic heart valve consists of natural tissue or synthetic material and has a first opened position for opening the patient's heart chamber and a second closed position for closing the patient's heart chamber, the at least two leaflets being able to switch between their first and second position in response to the blood flow through the patient's heart. The skirt portion consists of natural tissue or synthetic material and is used for mounting of the prosthetic heart valve to a stent. The transition area, which represents a junction between the at least two leaflets of the prosthetic heart valve and the skirt portion, progresses approximately in a U-shaped manner, similar to a cusp shape of a natural aortic or pulmonary heart valve, thereby reducing stresses within the heart valve material during opening and closing motion of the at least two leaflets.

The expression "natural tissue" as used herein means naturally occurring tissue, i.e. biological tissue obtained from the patient, from another human donor, or from a nonhuman animal. On the other hand, the herein used expression "natural tissue" shall also cover tissue fabricated by tissue engineering in the laboratory, for example, from combinations of engineered extracellular matrices ("scaffolds"), cells, and biologically active molecules.

As it will be described in detail later on, in some embodiments of the present disclosure, the prosthetic heart valve either comprises xenografts homografts or synthetic, nonbiological, non-thrombogenic materials. Homografts are either human donor valves, e.g., heart valves, or replacements made of human tissue, e.g., pericardial tissue. In contrast, xenografts describe valves received from animals, e.g., heart valves, or made of animal tissue, e.g., pericardial tissue, typically porcine or bovine respectively. These natural tissues normally contain tissue proteins (i.e., collagen and elastin) acting as a supportive framework and determining the pliability and firmness of the tissue.

It is conceivable to increase the stability of said natural tissues by applying chemical fixation. That is, the natural tissue may be exposed to one or more chemical fixatives (i.e. tanning agents) that form cross-linkages between the polypeptide chains within the protein structures of the natural tissue material. Examples of these chemical fixative agents include: formalaldehyde, glutaraldehyde, dialdehyde starch, hexamethylene diisocyanate and certain polyepoxy compounds.

So far, a major problem with the implantation of conventional biological prosthetic heart valves is that the natural tissue material can become calcified, resulting in undesirable stiffening or degradation of the prosthetic heart valve.

Even without calcification, high valve stresses can lead to mechanical failure of components of the heart valve. In order to overcome problems with mechanical failure and potential stress induced calcification that limit valve durability, some embodiments of the disclosure describe an improved construction of the prosthetic heart valve, the design of the disclosed prosthetic heart valve is suited for reducing stresses, and reducing the potential for calcification to improve durability of the heart valve.

In addition, the disclosure provides an improved attachment of a prosthetic heart valve to a corresponding collapsible stent structure, thereby distributing stress loads over a greater surface area and thus reducing the potential for stress concentration points throughout the prosthetic heart valve, resulting in improved durability.

In some embodiment of the disclosure, the prosthetic heart valve may be made of one piece of flat pericardial tissue. This pericardial tissue can either be extracted from an animal's heart (xenograft) or a human's heart (homograft). Subsequently, the extracted tissue may be cut by a laser cutting system, a die press, a water jet cutting system or by hand with a variety of cutting instruments in order to form a pattern representing each of the at least two leaflets or in another embodiment individual leaflets. This pattern may also include the skirt portion in some embodiments. The skirt portion represents an area of the prosthetic heart valve that is used for connecting the prosthetic heart valve to a stent, for example, by means of sutures. Current prosthetic heart valves consist of separated leaflets and skirt portions, wherein the separated leaflets and skirt portions are sewn together by the time the biological heart valve is connected to the stent. According to the "one piece" embodiment described herein, however, the leaflets are integrally formed with the leaflet support portion, that is the prosthetic heart valve is made of one piece of flat pericardial tissue.

The pattern of the prosthetic heart valve, which represents each of the at least two and preferably three leaflets and the skirt portion, shall substantially be constructed like a native aortic or pulmonary heart valve. To this end, the pattern is preferably designed so as to form leaflets in the aforementioned cusp manner, having three half-moon shaped leaflets like the aortic or pulmonary heart valve. The leaflets can be designed in various shapes such as the geometry of an ellipse, U-shape or substantially oval. In this regard, preferably each of the three different leaflets is formed in such a manner that all of them have the same extent; however, it is also conceivable to design them in different sizes.

The shaping of the leaflets into said pattern, for minimizing stresses in the closed position of the prosthetic heart valve, can be achieved in several ways. Most importantly, the mechanical properties of the leaflets of the prosthetic heart valve are influenced by the free margin and the shape of the supported edges. To this end, in an advantageous embodiment disclosed herein, the leaflets are formed into a predetermined 3D shape, by means of a cross-linking the flat tissue on a mandrel. Subsequently, potentially occurring excess material is trimmed off by means of a laser, knife, or water jet respectively to form the edges of the 3D shape. Between the leaflets and the skirt portion, the valve pattern shows a transition area progressing in a substantial U-shaped manner, similar to the cusp shape of a natural aortic or pulmonary heart valve.

In another embodiment of the present disclosure, the lower end section of the prosthetic heart valve exhibits a tapered or flared shape. Such a tapered or flared shape may be advantageous regarding the attachment of the prosthetic heart valve to a corresponding stent. As will be explained in more detail hereinafter, a corresponding stent may comprise a tapered or flared lower end section in order to improve the anchoring of the stent at the implantation site. As a consequence, it may be useful to construct the lower end section of the prosthetic heart valve in a tapered or flared shape, so as to prevent paravalvular leakage between the stent and the blood vessel.

According to another embodiment of the present disclosure, the leaflets may have a cuspidal geometry, which is formed in an elliptically, u-shaped or oval manner. Such a cuspdial geometry reduces the potential for stress concentrations and therefore minimizes the potential for areas of wear and calcium deposition. In another embodiment of the present disclosure all three leaflets are shaped to the same extent, absorbing loads equally throughout the cardiac cycle. However, it is conceivable to assemble a device with leaflets of varying designs.

With reference to another embodiment of the present disclosure, the leaflet portion of the prosthetic heart valve is designed to provide redundant coaptation for potential annular distortion. In particular, redundant coaptation means that each of the leaflets covers more than one third of the inner diameter of the respective stent, in the closed position of the valve. The redundant coaptation may reduce stress on the leaflets and provides reliable closure of the heart chamber in the second closed position of the leaflets, even in the case of an annular distortion. That is, the prosthetic heart valve of the present disclosure is capable of preventing regurgitation even if the size of the heart valve annulus has been altered (annular distortion).

In another embodiment of the present disclosure, the prosthetic heart valve comprises a plurality of fastening holes provided along the progression of the bendable transition area. These fastening holes are preferably introduced into the tissue of the prosthetic heart valve before the valve is attached to the corresponding stent. This plurality of fastening holes may reduce the time needed for attachment of the prosthetic heart valve to the retaining arches of the corresponding stent.

According to another aspect of the present disclosure, the prosthetic heart valve is designed for collapsing and delivering in a catheter. To this end, the prosthetic heart valve can be designed in such a way as to fit inside the corresponding stent structure. Furthermore, it is conceivable that the design of the prosthetic heart valve comprises certain folds in order to allow for collapsing to very small diameters.

In another embodiment of the invention, the tissue material of the prosthetic heart valve has a thickness of 160 μm to 300 μm, preferably from 220 μm to 260 μm. However, it should be noted that the thickness may be dependent on the tissue material of the prosthetic heart valve. In general, the thickness of bovine tissue is thicker than the thickness of porcine tissue.

The blood vessels and heart valve orifices of the individual patients can have significantly varying diameter, accordingly, the prosthetic heart valve may have a diameter ranging form 19 mm to 28 mm. Thus, the prosthetic heart valve of the present disclosure is adapted to fit to the individual characteristics of individual patient's heart anatomy.

In another embodiment of the present disclosure, the bendable transition area of the prosthetic heart valve is attached to retaining arches of the stent by means of sutures, having a diameter larger than the diameter of the sutures used for attachment of the prosthetic heart valve to an annular collar of the stent. Due to this, the prosthetic heart valve can be reliably attached to the stent without adding too much bulk to the stent, in order to collapse the endoprosthesis to a small diameter.

The disclosure also provides a transcatheter delivered endoprosthesis having a prosthetic heart valve affixed to a stent. The stent provides retaining arches which are configured once in the expanded state to be in a gradually uniform U-shape. The transition area of the tissue is attached to the retaining arches of the stent in a number of possible embodiments. The purpose of the retaining arches is to control the motion of the leaflets during the opening and closing phases of the valve in a manner which minimizes the stresses associated with the cyclic motion.

In general, current transcatheter prosthetic heart valves consist of separated leaflets and skirt portions, wherein the separated leaflets and skirt portions are sewn together by the time the biological heart valve is connected to the stent. Hence, with the conventional prosthetic heart valves, additional suture lines are necessary, causing stress concentration and reduced flexibility of the heart valve, thus leading to earlier calcification of the prosthetic heart valves.

In order to reduce or minimize stress concentration and to enhance flexibility of the heart valve, in some embodiments as disclosed herein the leaflets are integrally formed with the skirt portion. For example, a single piece of pericardium may be used for forming the prosthetic heart valve. As an alternative, the skirt portion may consist of multiple pieces of tissue, e.g. three pieces of tissue, which are sewn together by the time the biological heart valve is connected to the stent, wherein the leaflets are integrally formed with the tissue material of the pieces which together form the skirt portion. For example, three individual tissue panels may be utilized to construct the valve portion of the prosthetic heart valve. Whether a single piece of pericardium or three panels are used, the tissue structure is sutured to the stent structure to create the desired U-shape of the leaflets. This U-shape helps distribute the load on the leaflets throughout the cardiac cycle, but especially when in the closed position.

By avoiding that the leaflets must be sewn to the skirt portion(s), greater strength and durability of the heart valve assembly may be provided, as the strength and integrity of a uniform piece of tissue is improved from separate pieces of tissue sewn together. Additionally, the advantages of not having a seam include reduced assembly time (less suturing), less overall bulk when collapsing the prosthesis for small catheter delivery and more flexible leaflets at the transition area that could improve leaflet motion and hemodynamics.

The natural tissue material used for the manufacture of prosthetic heart valves typically contains connective tissue proteins (i.e., collagen and elastin) that act as supportive framework of the tissue material. In order to strengthen this compound of tissue proteins, a chemical fixation process may be performed, linking the proteins together. This technique usually involves the exposure of the natural tissue material to one or more chemical fixatives that form the cross-linkages between the polypeptide chains of the collagen molecules. In this regard, it is conceivable to apply different cross-linking techniques for different parts of the prosthetic heart valve tissue. For instance, the leaflets of the prosthetic heart valve could be treated by a different chemical fixative agent than the skirt portion in order to obtain diverse rigidity within the prosthetic heart valve.

In addition, it is conceivable to have leaflets and a skirt which are not integral. In this case, different cross-linking techniques may be applied to the leaflets and the skirt.

Examples of chemical fixative agents conceivably used for cross-linking of the prosthetic heart valve, according to the present disclosure include: aldehydes, (e.g. formaldehyde, glutaraldehyde, dialdehyde starch, para formaldehyde, glyceroaldehyde, glyoxal acetaldehyde, acrolein), diisocyanates (e.g., hexamethylene diisocyanate), carbodlimides, photooxidation, and certain polyepoxy compounds (e.g., Denacol-810, -512).

According to some of the disclosed embodiments, the prosthetic heart valve is mounted to the inner surface of a support stent. This arrangement facilitates protection of the prosthetic heart valve material during collapse and deployment. This is because the prosthetic heart valve is not in contact with the inner wall of the implantation catheter, and thus may not get stuck on the inner surface thereof. On this account, damage to the prosthetic heart valve is avoided. Also, such an endoprosthesis can be collapsed to a smaller diameter compared with a prosthetic heart valve mounted to the outer surface of the stent, hence providing the possibility to use smaller catheters.

On the other hand, it is conceivable to mount the prosthetic heart valve to the outer surface of a support stent. That is, the skirt portion could be in direct contact with the diseased native heart valve and could be attached to the stent by means of sutures. Mounting the prosthetic heart valve to the outer surface of the stent supports the load transfer from the leaflet to the stent. This greatly reduces stresses on the leaflets during closing and consequently improves the durability thereof. Also, it is possible to design the valve to obtain improved hemodynamics in the case of mounting the skirt portion and commissures to the outer surface of the stent. Additionally, the heart valve material which is in direct contact with the diseased native heart valve provides a good interface for sealing against leakage (i.e., paravalvular leakage), tissue in-growth and attachment. The stent designs for this endoprosthesis uniquely accommodate this valve embodiment and advantages, whereas for cage-like transcatheter delivered stent designs this is not possible.

The prosthetic heart valve can be made from pericardial tissue, for example, human pericardial tissue, preferably animal pericardial tissue, whereby bovine or porcine pericardial tissue is preferred. However, it is conceivable to employ kangaroo, ostrich, whale or any other suitable xeno- or homograft tissue of any feasible dimension.

Preferably, porcine tissue thicknesses of 220 to 260 μm after fixation shall be used to manufacture the biological prosthetic heart valves. Of course, this example is not a limitation of the possible kinds of tissues and their dimensions. Rather, it is conceivable to employ kangaroo, ostrich, whale or any other suitable xeno- or homograft tissue of any feasible dimension.

Many aspects of the disclosed prosthetic heart valve embodiments may become clear considering the structure of a corresponding stent to which the prosthetic heart valve may be attached in order to form a transcatheter delivered endoprosthesis used in the treatment of a stenosis (narrowing) of a cardiac valve and/or a cardiac valve insufficiency.

According to an aspect of the disclosure, a stent suitable for implantation with the aforementioned prosthetic heart valve may comprise positioning arches configured to be positioned within the pockets of the patient's native heart valve. Furthermore, the stent may comprise retaining arches. In detail, for each positioning arch one retaining arch may be provided. In the implanted state of the stent, the respective head portions of the positioning arches are positioned within the pockets of the patient's native heart valve such that the positioning arches are located on a first side of a plurality of native heart valve leaflets. On the other hand, in the implanted state of the stent, the retaining arches of the stent are located on a second side of the native heart valve leaflets opposite the first side. In this respect, the positioning arches on the one hand and the retaining arches on the other hand clamp the native heart valve leaflets in a paper-clip manner.

Hence, the positioning arches of the stent are designed to engage in the pockets of the native (diseased) cardiac valve which allows accurate positioning of the stent and a prosthetic heart valve affixed to the stent. Furthermore, in the implanted state, each positioning arch co-operates with a corresponding retaining arch resulting in clipping of the native leaflet between the two arches. In this way, the positioning and retaining arches hold the stent in position and substantially eliminate axial rotation of the stent In a preferred embodiment, the positioning arch may be formed such as to have a substantially convex shape. In this way, the shape of each positioning arch provides an additional clipping force against the native valve leaflet.

The at least one retaining arch of the stent may be connected to a corresponding positioning arch by a connecting web. The retaining arch may extend substantially parallel to the positioning arch, thus having essentially the same shape. The shape of the retaining arch basically represents a U-shape with a small gap at its lower end. This gap is surrounded by a connection portion which originates during the fabrication of the tip of the positioning arches. The connection portion may be similar to a U- or V-shape and links the two sides of a retaining arch.

Along the retaining arches of the stent, a plurality of fastening holes and optionally one or more notches may be provided. Preferably, these fastening holes and notches are longitudinally distributed at given positions along the retaining arches and guide at least one thread or thin wire to fasten the tissue components of the prosthetic heart valve to the stent, thereby enabling a precise positioning of the tissue components on the stent. The means provided for fastening the tissue components of the biological prosthetic heart valve to the retaining arches of the stent (thread or thin wire) is guided by way of the fastening holes and notches to ensure accurate repeatable securement of the bioprosthetic heart valve within the stent structure. This accurate securement of the biological prosthesis substantially reduces the potential for longitudinal displacement of the biological prosthetic heart valve relative to the stent.

According to another embodiment of the present disclosure, the aforementioned plurality of retaining arches are provided with one or more fastening notches which can be used to fix the bendable transition area to the stent. To this end, the retaining arches may be segmented by a plurality of bending edges forming said fastening notches and defining bending points of the retaining arches. The fastening notches simplify the attachment of the bendable transition area of the prosthetic heart valve to the retaining arches.

In another aspect of the stent which is suitable for implantation with a biological prosthetic heart valve as disclosed herein, the retaining arches are cut from the material portion of a small metal tube in an shape that when expanded essentially form the U-shaped structure corresponding to the aforementioned progression of the transition area.

At the lower end of the stent, an annular collar may be provided. The annular collar may serve as a supporting body through which the radial forces, developing due to the self-expansion, are transmitted to the vascular wall. Attached to the annular collar is the skirt portion of the biological prosthetic heart valve. Typically, this attachment is implemented by means of suturing.

The intent of the self expanding annular collar in combination with the attached skirt region of the valve is to provide sufficient radial forces so as to seal and prevent paravalvular leakage. In addition, the collar aids in anchoring the prosthesis in the annulus to prevent migration. This collar may incorporate a flared or tapered structure to further enhance securement.

As mentioned above, a prosthetic heart valve can be attached to a corresponding stent in order to provide a transcatheter delivered endoprosthesis which can be used in the treatment of a stenosis (narrowing) of a cardiac valve and/or a cardiac valve insufficiency.

A prosthetic heart valve made from pericardial tissue material may be attached to the retaining arches and annular collar of the afore-mentioned stent by means of braided multi-filament polyester sutures. These sutures may have any suitable diameter, typically about 0.07 mm.

In order to increase the strength of the connection of biological prosthetic heart valve to the stent, however, it is conceivable to increase the size of the multi-filament sutures, for example, up to 0.2 mm. In this way, it is possible that the fundamental bond between the transition area of the prosthetic heart valve and the retaining arches of the stent exhibits additional stability. On the other hand, the remaining sutures shall be kept as thin as possible to enable collapsing of the endoprosthesis to a small diameter.

A common running stitch pattern may be used to obtain said bonding. According to the disclosure, the stitch pattern is preferably a locking stitch or a blanket stitch respectively. Of course, any other suitable stitch pattern (i.e. overlocking stitch, slipstitch or topstitch) is also possible.

Considering the stress concentration due to direct stitching in the heart valve material, another aspect of the disclosure may provide that the material of the prosthetic heart valve is reinforced to improve its suture retention force. To this end, laser cut suturing holes may be introduced into the prosthetic heart valve tissue with the laser cutting process strengthening the tissue area around the cut hole. Predefined laser cutting holes might also ease the suturing process itself and reduce stresses on the material of the prosthetic heart valve due to the penetration of the needle during stitching.

In another embodiment of the present disclosure, the connection of the prosthetic heart valve material to a stent may be reinforced by means of reinforcement elements. Such reinforcement elements are intended to reduce stress concentrations in the material of the prosthetic heart valve that may occur from direct stitching in the valve material. In particular, the reinforcement elements might reduce stress concentration in the tissue material of the prosthetic heart valve at the connection between the bendable transition area and the retaining arches of the stent. The reinforcement elements may be placed between an inner suture and the prosthetic heart valve material, thus distributing aforementioned stresses, caused by the stitching, over a larger area of the valve material. These reinforcement elements can be used at discrete locations or continuously along the path of the stitching. For example, they can be placed opposite to the retaining arches of the stent on the other side of the prosthetic heart valve material.

Reinforcement elements may be applied in order to avoid direct contact between knots of the sutures and the tissue of the prosthetic heart valve, thereby reducing abrasion of the prosthetic heart valve tissue due to rubbing against said sutures. To reduce direct contact between the heart valve tissue and the stent structure or any other metallic component of the endoprosthesis, reinforcement elements can further be used to prevent the tissue of the prosthetic heart valve from directly contacting the stent structure or any other metallic component respectively.

In this regard, it is also conceivable to locate reinforcement elements along the entire surface of the prosthetic heart valve. Preferably, such reinforcement elements could also be located at or near the upper edge of the leaflets. These upper edges, building the commissures of the endoprosthesis, are exposed to an increased tension, which are more likely to tear during the operation of the prosthetic heart valve.

Moreover, it is also feasible to place said reinforcement elements inside the tissue of the prosthetic heart valve, instead of a mere attachment on the surface of the prosthetic heart valve. In this regard, it may be advantageous to have a layer of tissue or synthetic material of different mechanical properties inside the aforementioned prosthetic heart valve. This alternative embodiment may be especially useful in order to reinforce the leaflets of the prosthetic heart valve in order to increase their ability to yield mechanical stresses occurring during the operation of the endoprosthesis.

Reinforcement elements can be used at discrete locations or continuously along the path of the stitching. For example, they can be placed opposite to the retaining arches of the stent on the other side of the prosthetic heart valve material.

The reinforcement elements may be folded or formed in such a way that round edges are formed. These round edges are designed to reduce or avoid abrasion of the valve material during opening and closing of the prosthetic heart valve.

With regard to a further embodiment of the present disclosure, the reinforcement elements comprise at least one inner cushion, which is mounted to the inner surface of the bendable transition area of the prosthetic heart valve. This inner cushion is arranged essentially opposite the retaining arches and/or to the commissure attachment region of the stent. Opposite in this context means that the inner cushion is mounted on an opposite side of the prosthetic heart valve. The inner cushion is designed to reduce the stress concentrations in the tissue that occur from direct stitching in the tissue. In more detail, the inner cushion prevents the prosthetic heart valve tissue from directly contacting knots of the suture. Due to this, wear of the heart valve tissue is reduced, as said knots do not rub on the surface of the tissue, during opening and closing of the heart valve.

In a further embodiment, the at least one inner cushion may be a pledget made of one or multiple layer materials. The inner cushion may consist of materials, for examples, like polyester velour, PTFE, pericardial tissue or any other material suitable for forming round edges, distributing or buffering stresses in the valve material, due to the sutures. On this account, the material of the inner cushion can be made from flat sheets or fabrics such as knits or woven constructions. It is to be noted that the reinforcement elements can be applied in order to span between stent struts, in particular across a gap, located at the lower end of the retaining arches, to help support the valve material across said gap.

In an alternative implementation, the reinforcement elements may consist of a wire rail placed at the inner surface of the bendable transition area of the prosthetic heart valve, essentially opposite the retaining arch of the stent. The wire rail may be secured in place using a stitch pattern meant to accommodate the wire rail and the valve material to the stent. In comparison to the inner cushion mentioned above, such a wire rail could be easier to attach to the material of the prosthetic heart valve. Furthermore the already rounded shape of the rail does not require the wire rail to be folded in order to obtain rounded edges for prevention of valve material abrasion.

It is preferable that said wire rail is made of Nitinol in order to allow collapsing of the reinforcement element simultaneously with the stent structure.

Moreover, in another realisation, the reinforcement elements may be essentially of the same size and form as the retaining arches of the stent, hence forming an inner attachment rail. The reinforcement elements, however, shall be of thinner material than the retaining arches. This is due to the fact that thick material may limit the ability of the endoprosthesis to be collapsed to a small size.

In particular, the inner attachment rail may have the same fastening holes and notches longitudinally distributed at given locations as the retaining arches of the stent. Again, the attachment rail may be placed on the inner surface of the bendable transition area of the prosthetic heart valve, opposite to the retaining arches of the stent. Thus, the material of the prosthetic heart valve may be clamped in between the stent and the reinforcement element, which are connected through sutures. The reinforcement element thus may act as an inner attachment rail for the leaflets of the prosthetic heart valve to bend over and evenly distribute stress loads affecting the valve material over a large attachment rail rather than individual suture points.

Although most embodiments of the disclosure use sutures to fix the reinforcement element or valve material to the stent, it is conceivable to use different attachment methods like welding, soldering, locking fixture and rivets. For instance, these methods could be used to attach the aforementioned inner attachment rail to the retaining arches of the stent. This would result in clamping the prosthetic heart valve material in between the inner surface of the stent and the outer surface of the reinforcement element without penetrating the valve material with needles of suture.

Another alternative attachment concept includes a reinforcing element attached to the back side of the prosthetic heart valve material. This concept may be suitable for attachment in a high stress area of a commissure attachment region on top of the retaining arches, which is described in more detail below. This concept involves creating a strengthened region by folding the prosthetic heart valve material and wrapping it with the reinforcing element. Thus, the reinforcement element forms an outer wrapping element which is mounted to the outer surface of the bendable transition area of the prosthetic heart valve, at the commissure attachment region of the stent. The reinforced bendable transition area of the prosthetic heart valve can then be securely attached to the retaining arches of the stent or the commissure attachment region of the stent.

The aforementioned outer wrapping element of the reinforcing element is preferably made of a polymer material such as PTFE or a PET fabric or sheet. However, it could also be a more rigid U-shaped clip or bendable material that can pinch the folded valve material. One advantage this concept has over the other reinforcing elements is that the reinforcing material is not placed on the inner surface of the prosthetic heart valve, hence does not disrupt the blood flow or potentially be a site for thrombus formation.

The outer wrapping element of the reinforcing element may also provide an opening buffer to keep the valve leaflet material from opening too wide and hitting the stent, which would cause wear of the valve material. Similar to the rounded edges of the other reinforcement elements, these buffers should be rounded, smooth or soft to avoid wear when the open valve material hits them. The buffer should be small enough to not significantly over restrict leaflet material opening.

An especially beneficial embodiment of the present invention includes an attachment concept with reinforcement elements attached to the inner surface and to the outer surface of the transition area of the prosthetic heart valve. This configuration optimally prevents stress concentration and resulting wear of the prosthetic heart valve.

In particular, a first reinforcement element is connected to the outer surface of the bendable area of the prosthetic heart valve, preferably lining the retaining arches and the commissure attachment region over their entire length. The said reinforcement element, which is connected to the outer surface of the prosthetic heart valve, can be made of animal pericardial tissue, such as the one used for the prosthetic heart valve itself. Of course, it is conceivable to use any other suitable material for the reinforcement element, such as synthetic materials or even homograft (human) tissue. The reinforcement element, connected to the outer surface of the prosthetic heart valve, has several advantages, such as preventing any rubbing and wear between the leaflet and the stent at the retaining arches or commissure attachment region respectively. Even if the attachment is tightly sutured, the tissue will have strain cycles at the surface during opening and closing motion of the leaflets, which can cause wear against the stent from micro movements. Furthermore, the reinforcement element allows for an additional spring-like compression to tighten the attachment of the leaflet to the stent, providing a more durable attachment than the one achieved by suturing the leaflets to a rigid surface. Also, the reinforcement element serves as a bumper during opening to limit full opening and reduce the accompanied shock affecting the prosthetic heart valve at opening.

In another embodiment, the reinforcement element, which is connected to the outer surface of the prosthetic heart valve, extends along the retaining arches and along the commissure attachment region, having a wider surface than the surface of the retaining arches or the surface of the commissure attachment region respectively. For this reason, the reinforcement element provides a surface, sufficient to cover the retaining arches and the commissure attachment region completely. Thus, abrasion or wear of the tissue at the retaining arches or commissure attachment region respectively is avoided reliably.

Concerning the attachment of the aforementioned reinforcement element another advantageous embodiment includes wrapping the reinforcement element around the retaining arches and the commissure attachment region and securing this connection by means of wrapping and stitching. That is to say that the reinforcement element is secured firmly to the retaining arches or commissure attachment region respectively, providing a stable surface for attachment of the prosthetic heart valve.

With regard to the reinforcement element, which is connected to the inner surface of the transition area of the prosthetic heart valve, in another realisation, the reinforcement element consists of a folded strip of porcine pericardium and is attached to the transition area and stent by means of sutures. This folded strip of porcine pericardium allows the sutures to spread out the compressive forces that secure the leaflet tissue. A tight suture attachment is required to avoid any movement or slipping under physiological loads. If attached tightly, the loads from the leaflet will be at least partially transferred to the stent through friction and not directly to the sutures at the needle holes. This minimizes the stress concentration by spreading out the stresses, especially at the commissure attachment region. Also, the strip of porcine pericardium serves as a bumper to absorb the impact of the tissue during closing and reduces the dynamic stresses transferred to the sutures. Of course, it is conceivable to use different materials to implement the reinforcement element, which is connected to the inner surface of the prosthetic heart valve, such as wires, brackets, synthetic materials or even homograft (human) tissue. In order to reduce or prevent leakage during closed state of the prosthetic heart valve, however, the aforementioned reinforcement element has to be constructed with a minimal size, so as to avoid the formation of a gap in between the closed leaflets.

According to another embodiment of the present invention, the reinforcement elements are wrapped in tissue to avoid wear of the prosthetic heart valve tissue during operation. This is especially advantageous in the case of the implementation of rigid reinforcement elements, such as wires or brackets. The tissue, wrapped around the reinforcement elements, provides a soft contact surface for the prosthetic heart valve tissue and hence prevents it from rubbing and reduces wear.

In addition to the reinforcement elements, other stent structures may also be wrapped in tissue or any other suitable synthetic cover. That is, in order to avoid abrasion of the prosthetic heart valve against the stent structure (e.g. retaining arches), the stent may be wrapped in tissue or any other suitable material. In accordance with this particular embodiment of the present disclosure, the heart valve tissue may not be sutured directly to the metallic stent structure but to the tissue or synthetic material covering it. This could provide a closer contact between the prosthetic heart valve and the stent so as to reliably prevent paravalvular leakage.

Yet another modification of the present disclosure includes exposing the prosthetic heart valve material surface and structure to polymeric material in order to reinforce it. Materials according to this embodiment could be cyanoacrylates or polyepoxides which imply excellent bonding of body tissue and could even be used for suture-less surgery.

In a similar realisation the bendable transition portion of the prosthetic heart valve material includes a layering of various materials with differing mechanical properties used to improve the durability of the prosthetic heart valve. To this end, layer materials with very high suture retention strength overlapping the valve material in regions of very high stress load may be applied. As to that, material layers with high suture retention in lower parts of the transition area of the prosthetic heart valve may be provided, whereas the upper parts of the transition area shall be designed to be flexible for improving the durability of the valve. Examples for such layer materials will be explained in more detail, with reference to the "reinforcement elements" below.

With regard to another embodiment of the present disclosure, an attachment for the prosthetic heart valve material that reduces the concentration of stresses at the bendable transition portion is disclosed. In this embodiment, the bendable transition portion of the prosthetic heart valve is attached to the retaining arches of the stent by folding the valve material from the outside of the stent through slotts provided along the retaining arches. As mentioned previously, the edges of the slotted retaining arches may be rounded and smooth to avoid abrading or wearing of the valve material. In this design, there is some material thickness on the outside of the stent, which could impinge on the anchoring of the stent at the position of the diseased natural prosthetic heart valve.

To accommodate this issue, a thinning of the retaining arches relative to the rest of the stent structure could be conducted. This would also allow for a recess when the stent is compressed so that the collapsed prosthesis does not require a larger delivery catheter.

According to an alternative embodiment of the present disclosure, the prosthetic heart valve is assembled with three separate pieces of pericardial tissue. According to this, the three separate pieces of pericardial tissue are advantageous regarding the thickness of the prosthetic heart valve tissue. When using a one piece flat tissue in order to form the prosthetic heart valve, the thickness of the leaflets can vary and result in less desirable valve performance, unsymmetrical valve opening and closure or less desirable hemodynamics, such as a short durability or insufficient leaflet closure. Therefore, three smaller pieces of pericardial tissue provide the possibility to form prosthetic heart valve with more uniform thicknesses and mechanical properties.

To this end, another embodiment of the present disclosure includes that each of the three separate pieces has a flat tissue pattern in an essentially T-shirt like shape, exhibiting sleeves for connection between the adjacent pieces. As mentioned previously, the adjacent pieces can be constructed, as to reinforce the contiguous edges of the adjacent pieces. To accomplish this, the sleeves of adjacent pieces can be folded to the outside and sutured together to reinforce the joining connection. Attaching this reinforced area to the stent commissure attachment region helps to more uniformly distribute leaflet stresses supported by the commissure attachment.

In order to further improve the reinforcement of the contiguous edges of the separate pieces, in another embodiment of the present invention, the reinforcement elements consist of outer wrapping elements, wrapped around the sleeves of the three separate pieces, in order to reinforce the prosthetic heart valve and attach it to the commissure attachment region of the stent. That is, an outer wrapping element can be used in order to further improve the durability of the prosthetic heart valve. In this regard, the outer wrapping element can consist of a piece of pericardial tissue or a synthetic material respectively. Also, the outer wrapping element is used to attach the reinforced prosthetic heart valve to the commissure attachment region of the stent by means of sutures. Therefore, the stresses due to the suturing between the stent and the prosthetic heart valve is mainly introduced into the material of the reinforcement element, avoiding high stress concentrations in the prosthetic heart valve.

The following will make reference to the attached drawings in describing preferred embodiments of the prosthetic heart valve, a corresponding stent and a transcatheter delivered endoprosthesis according to the present disclosure in greater detail.

Figure 2A:
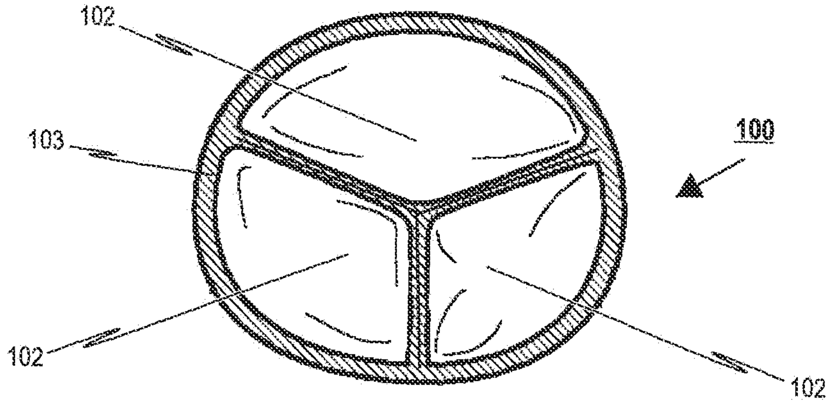
Figure 2B:
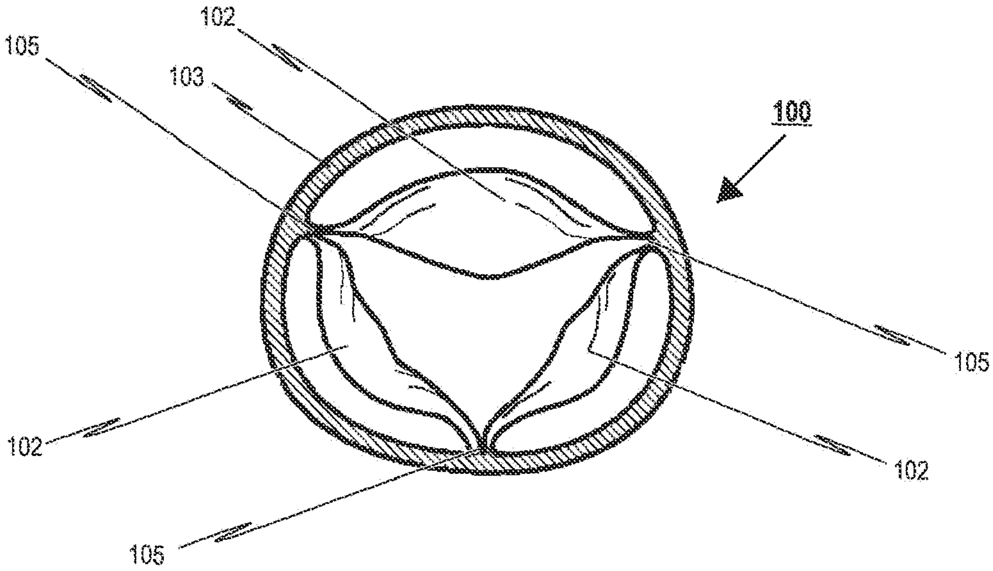
Figure 3:
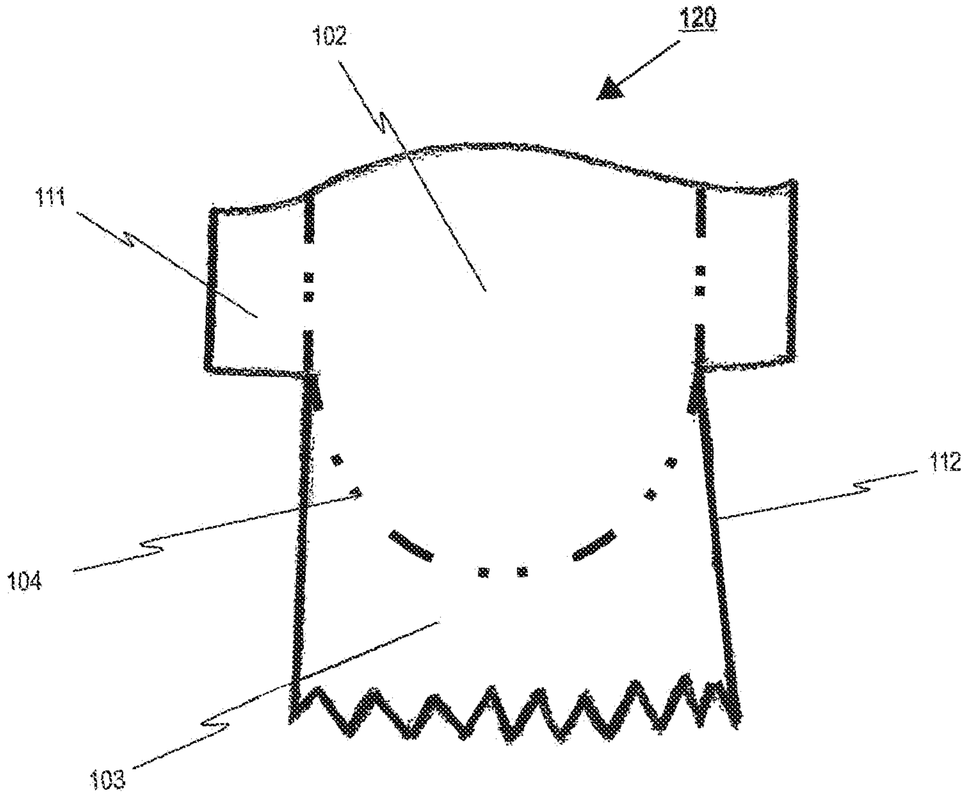
Figure 4:
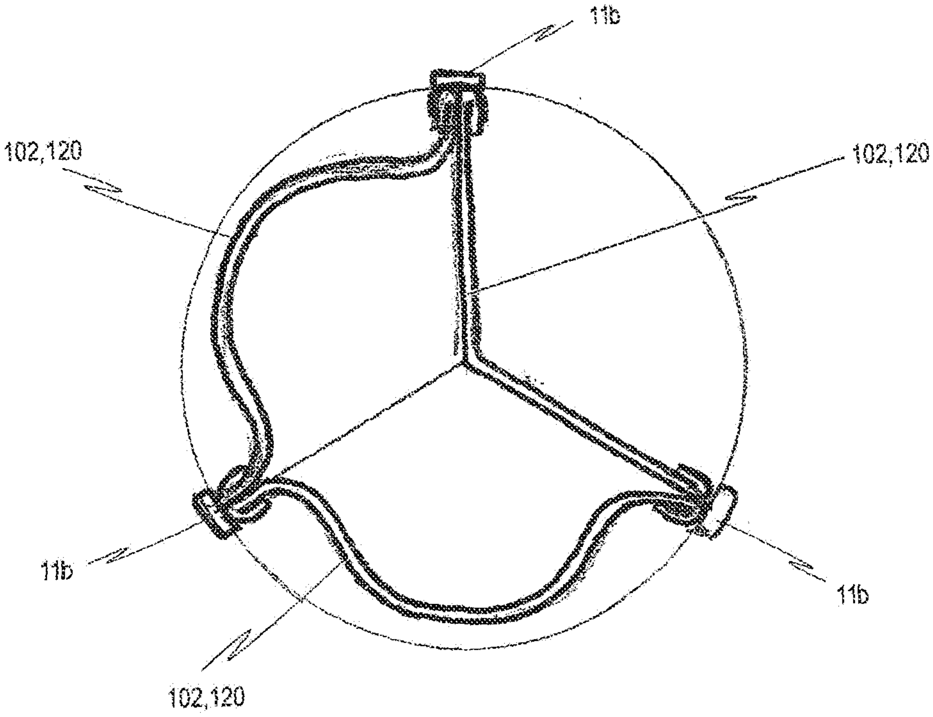
Figure 5A:
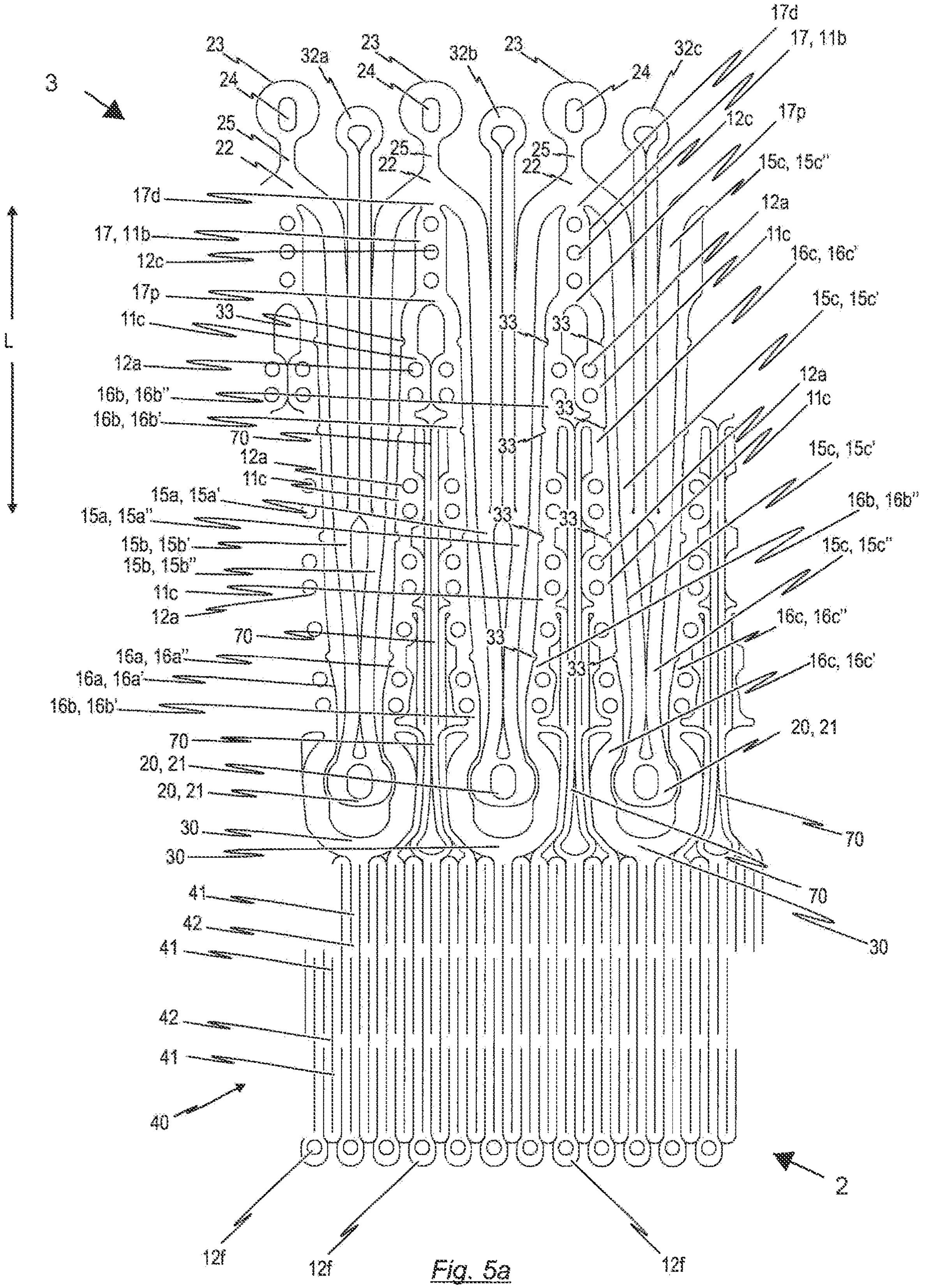
Figure 5B:
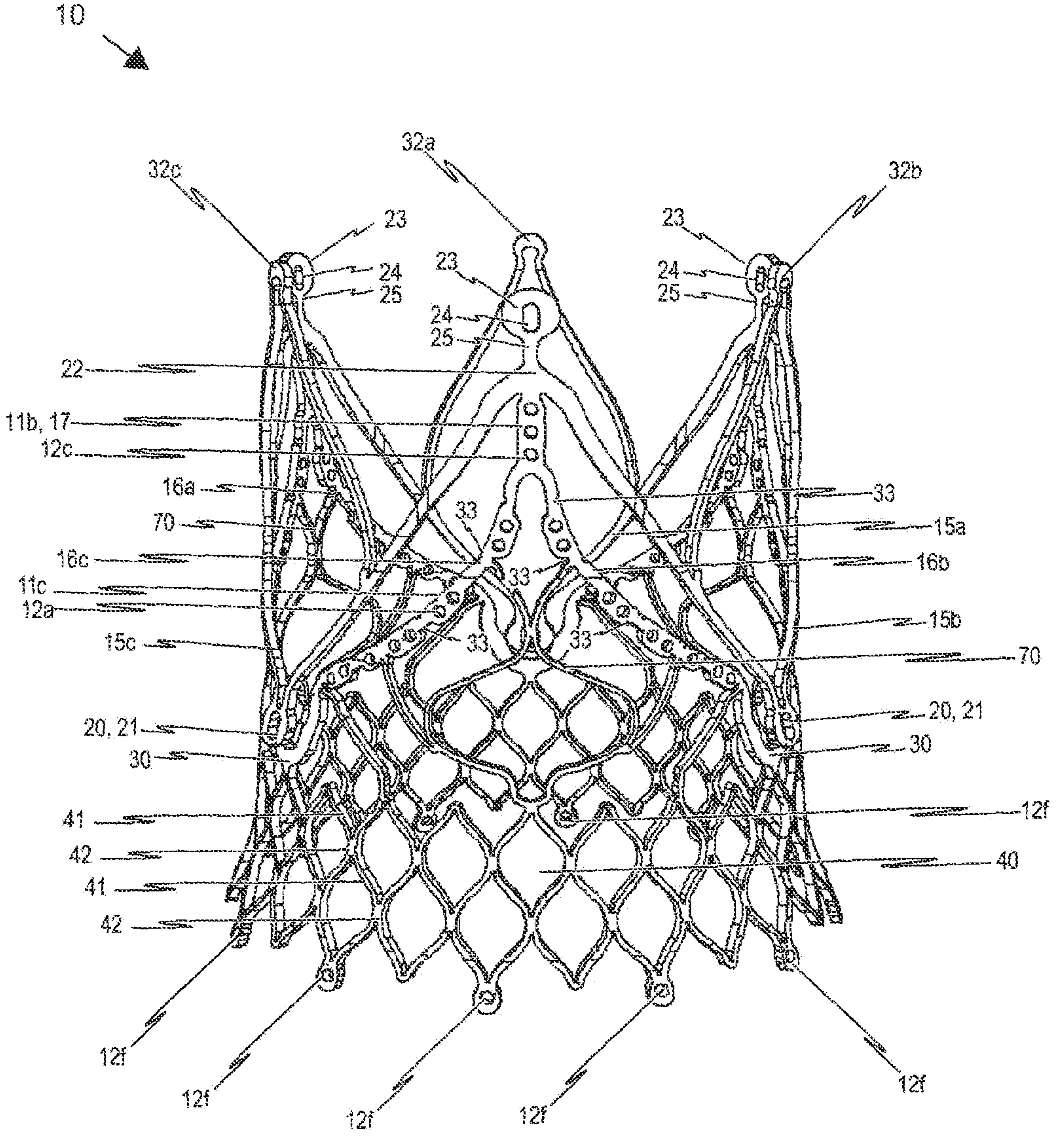
Figure 5C:
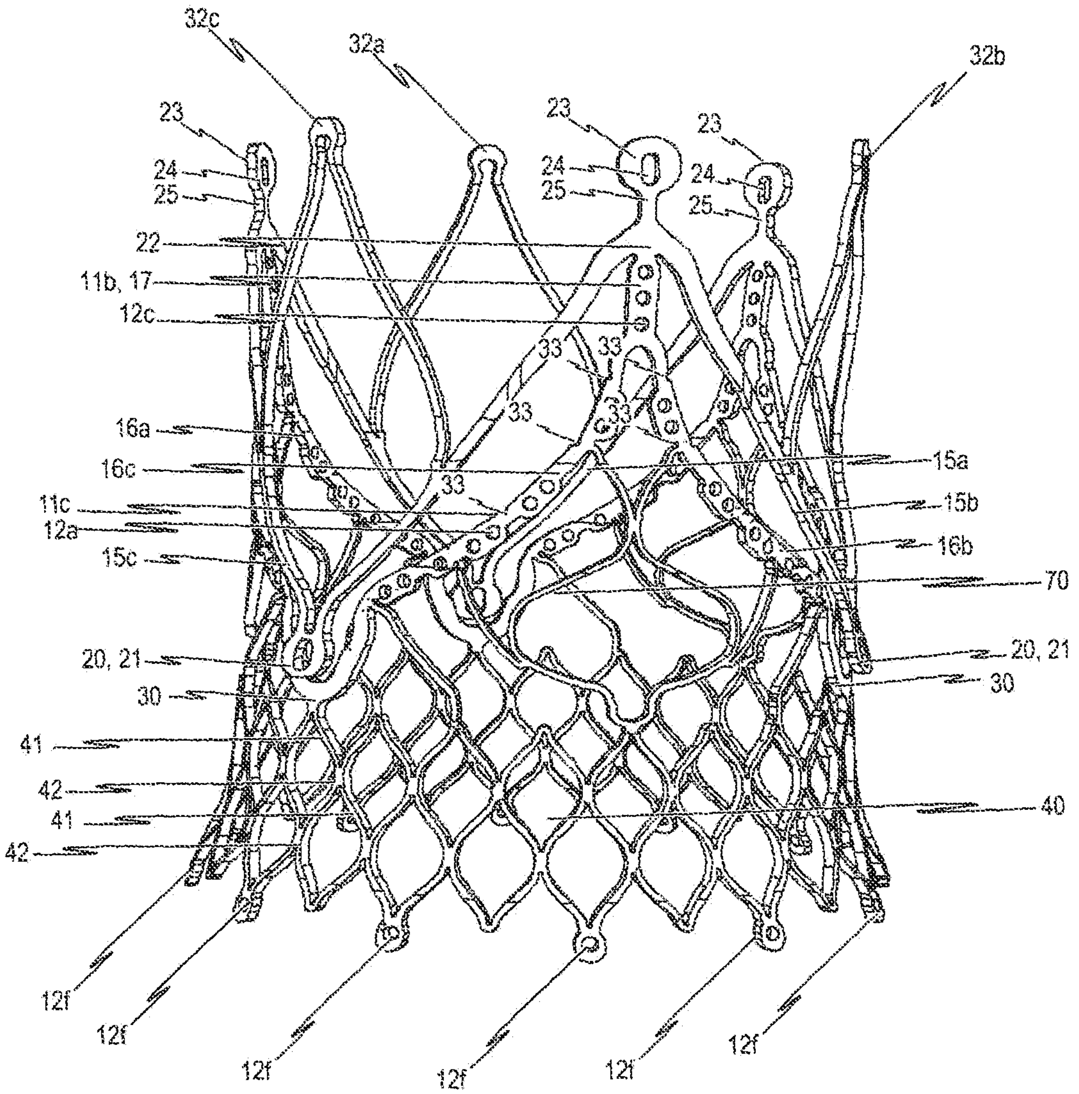
Figure 5D:
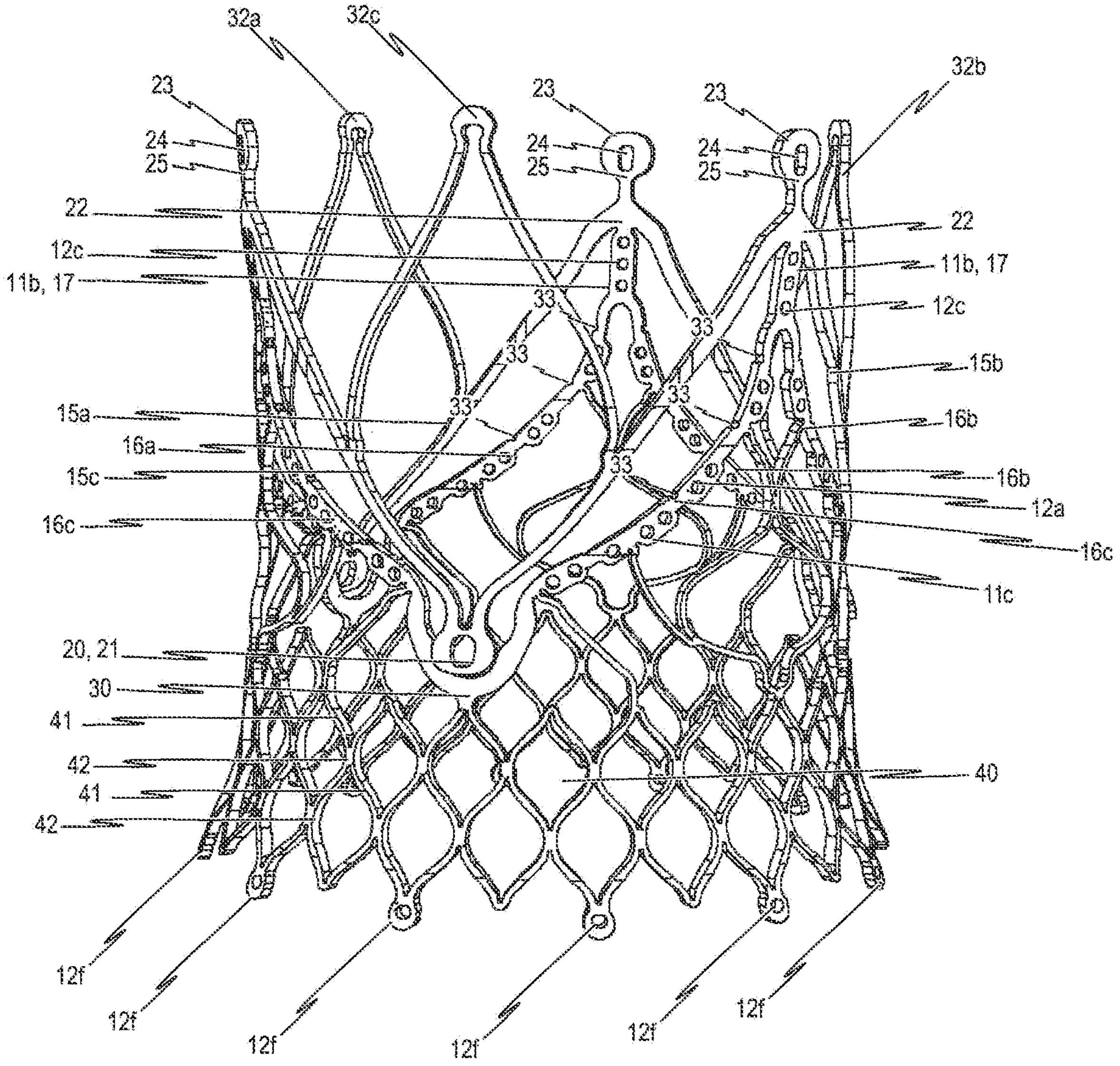
Figure 5E:
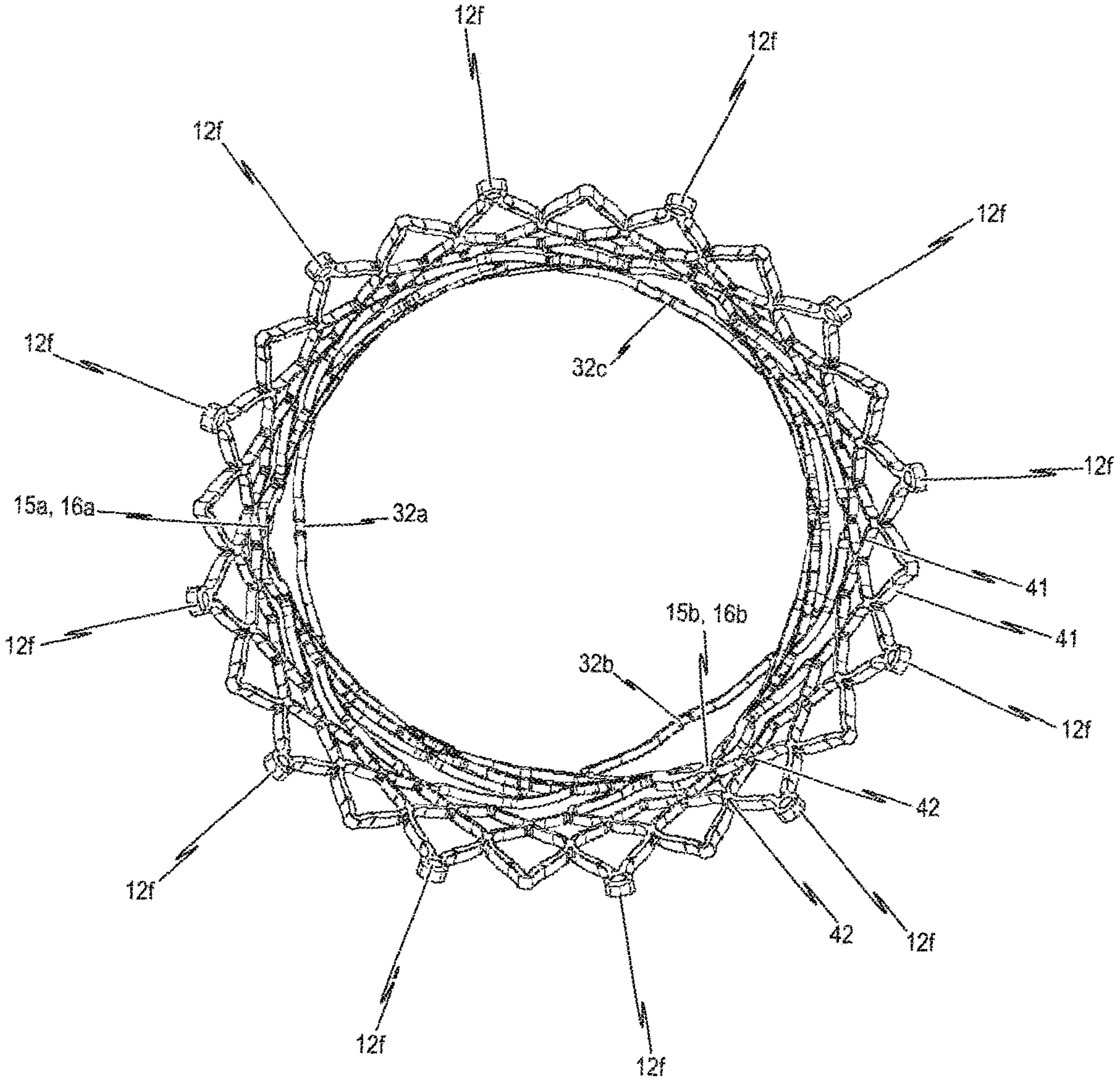
Figure 6A:
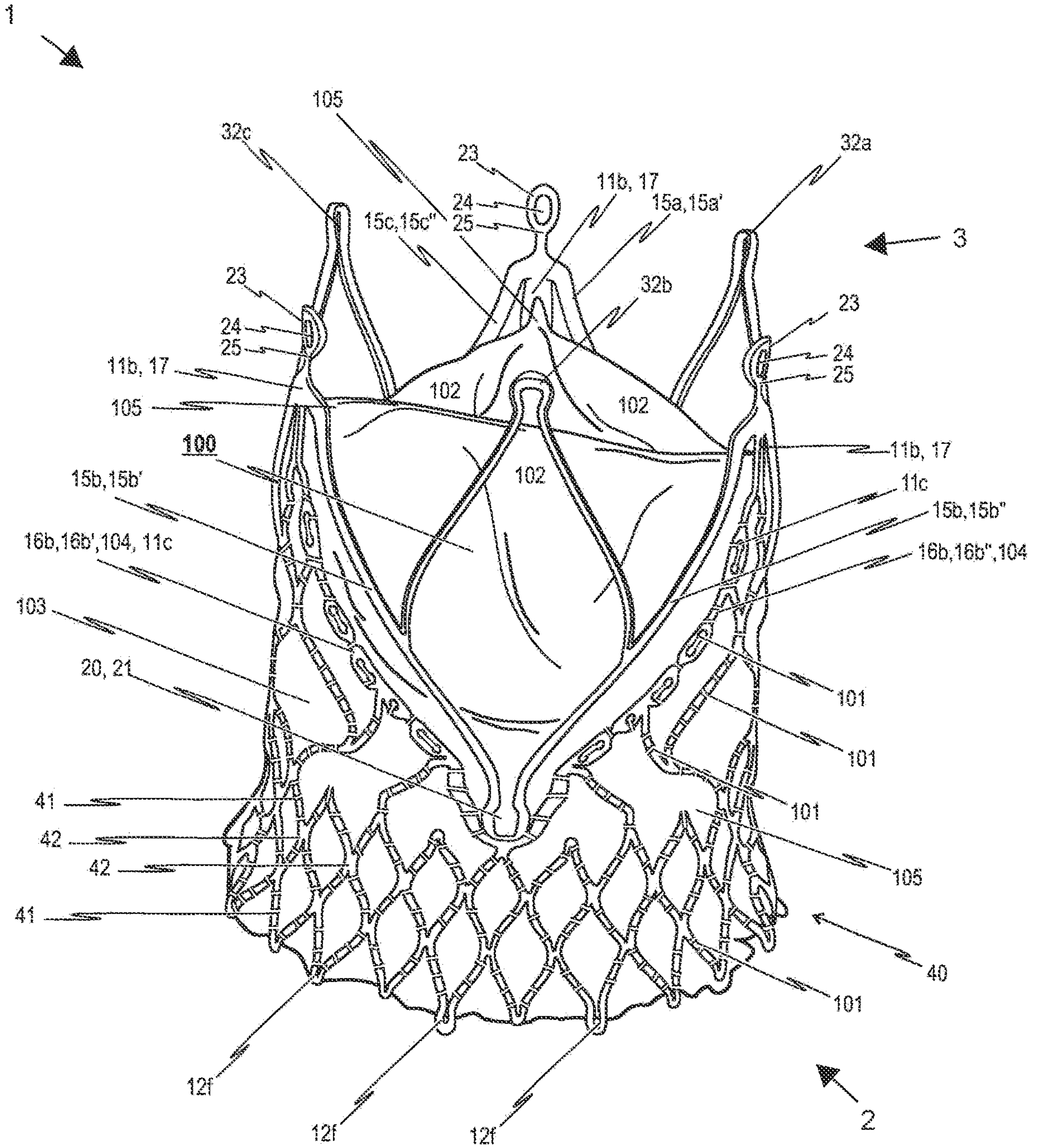
Figure 6B:
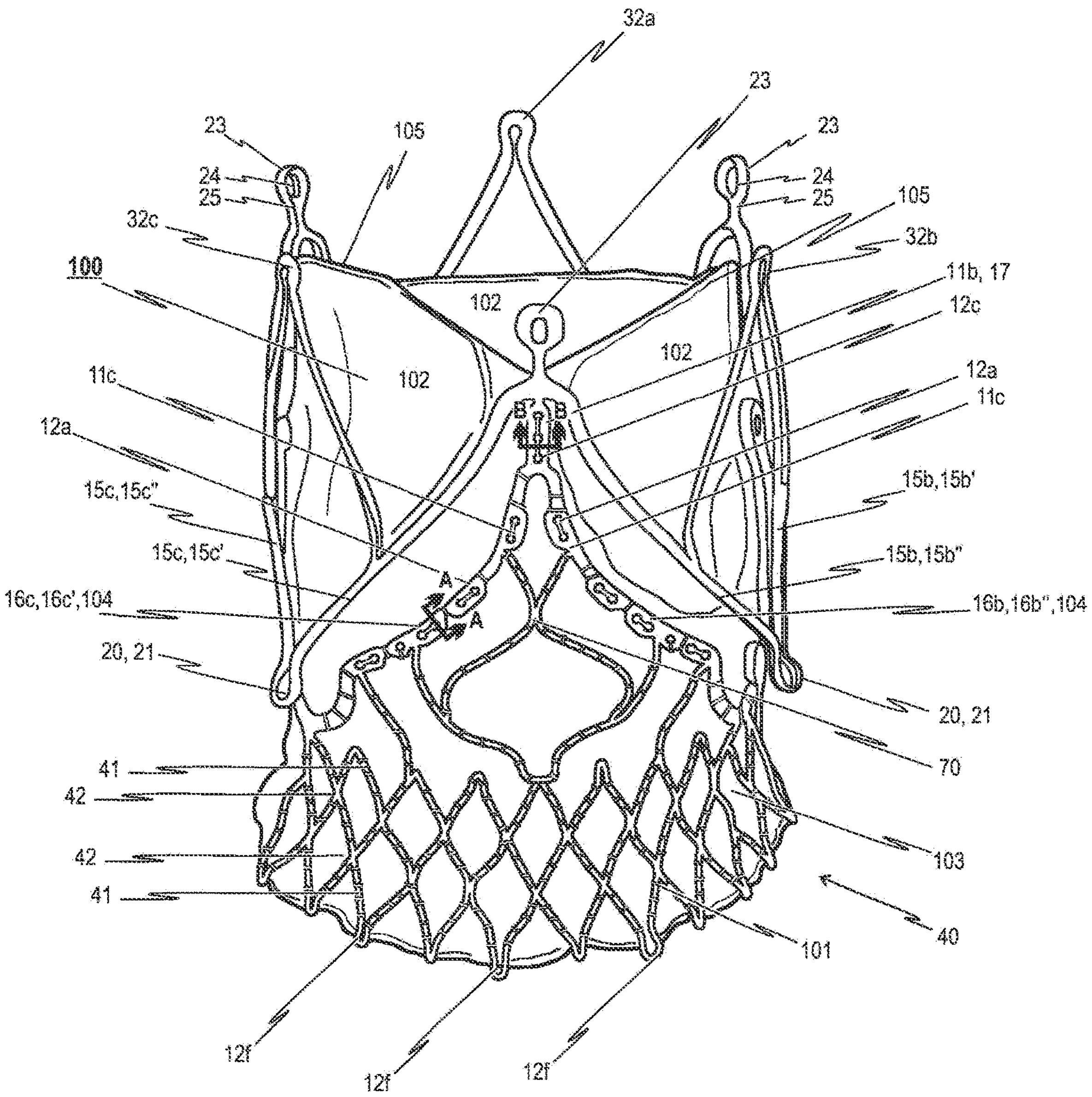
Figure 7A:
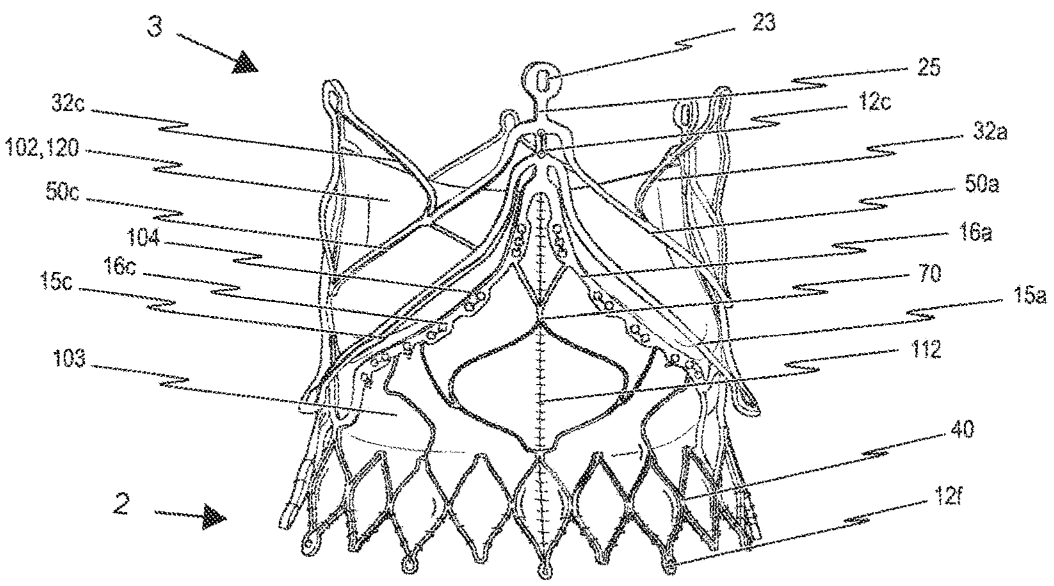
Figure 7B:
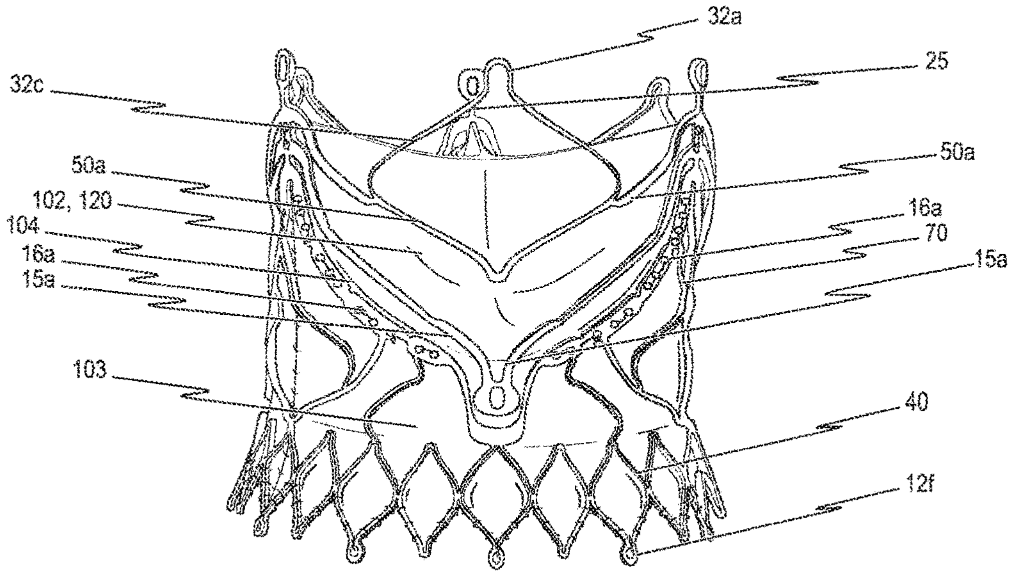
Figure 8A:
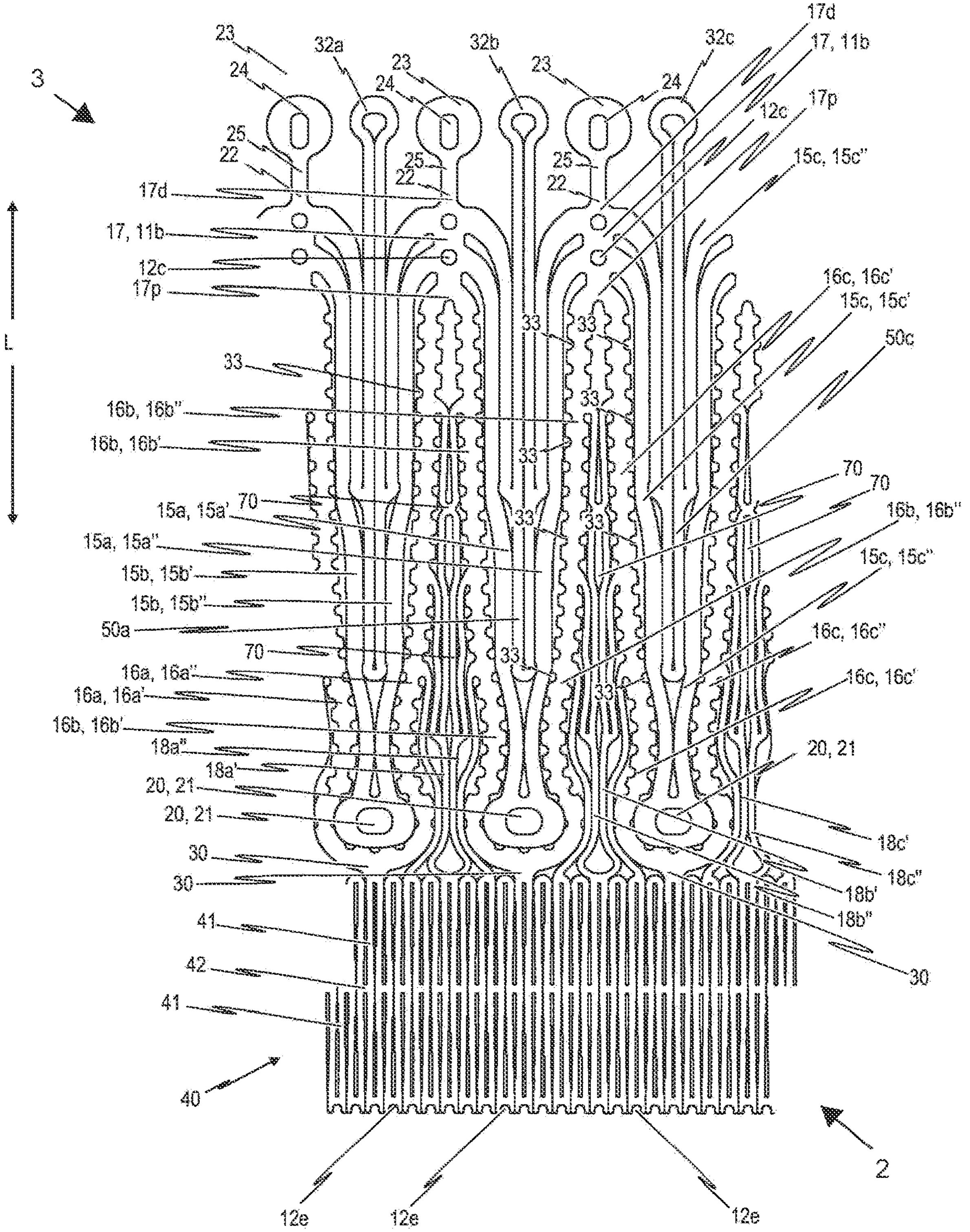
Figure 8B:
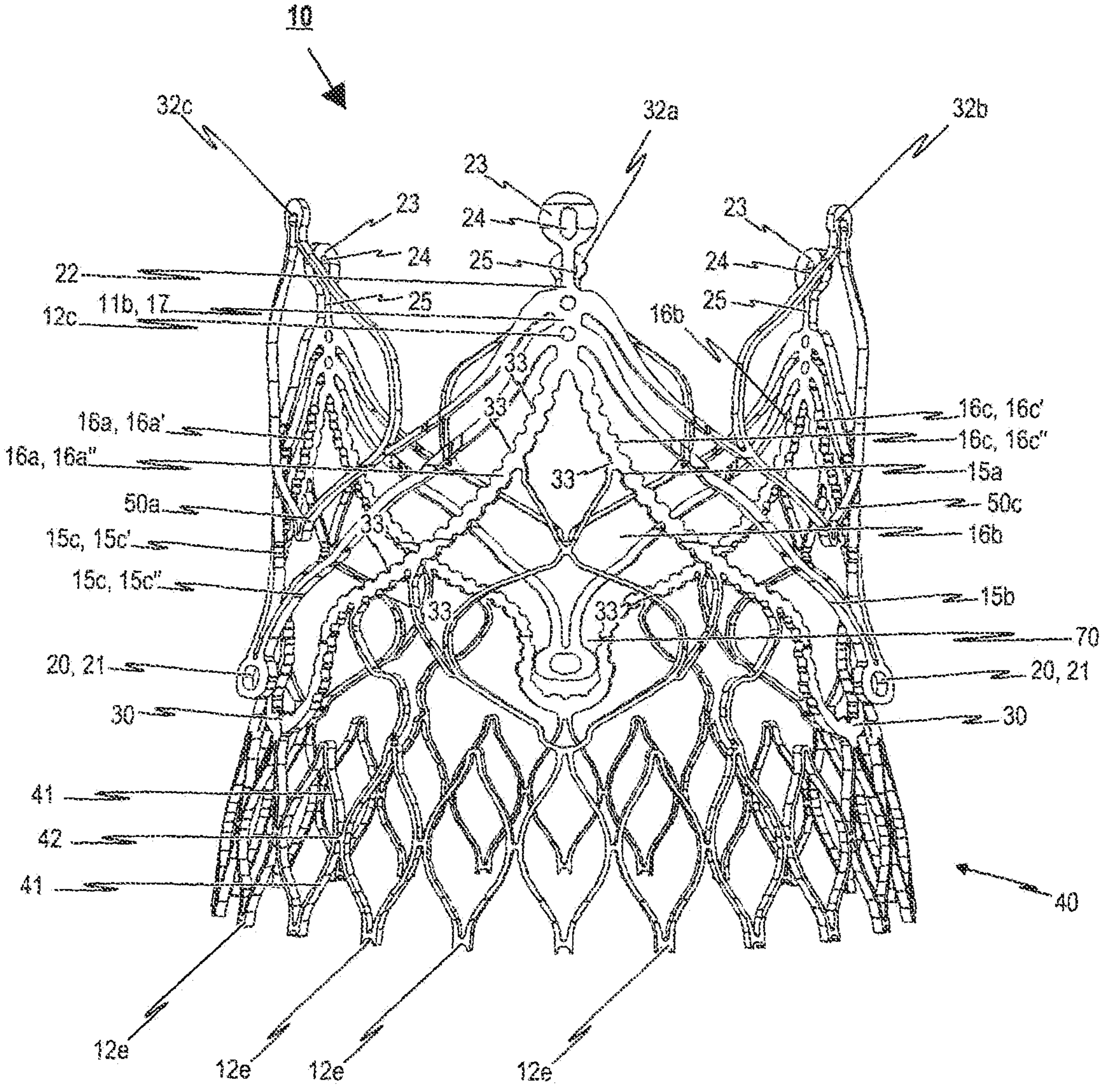
Figure 8C:
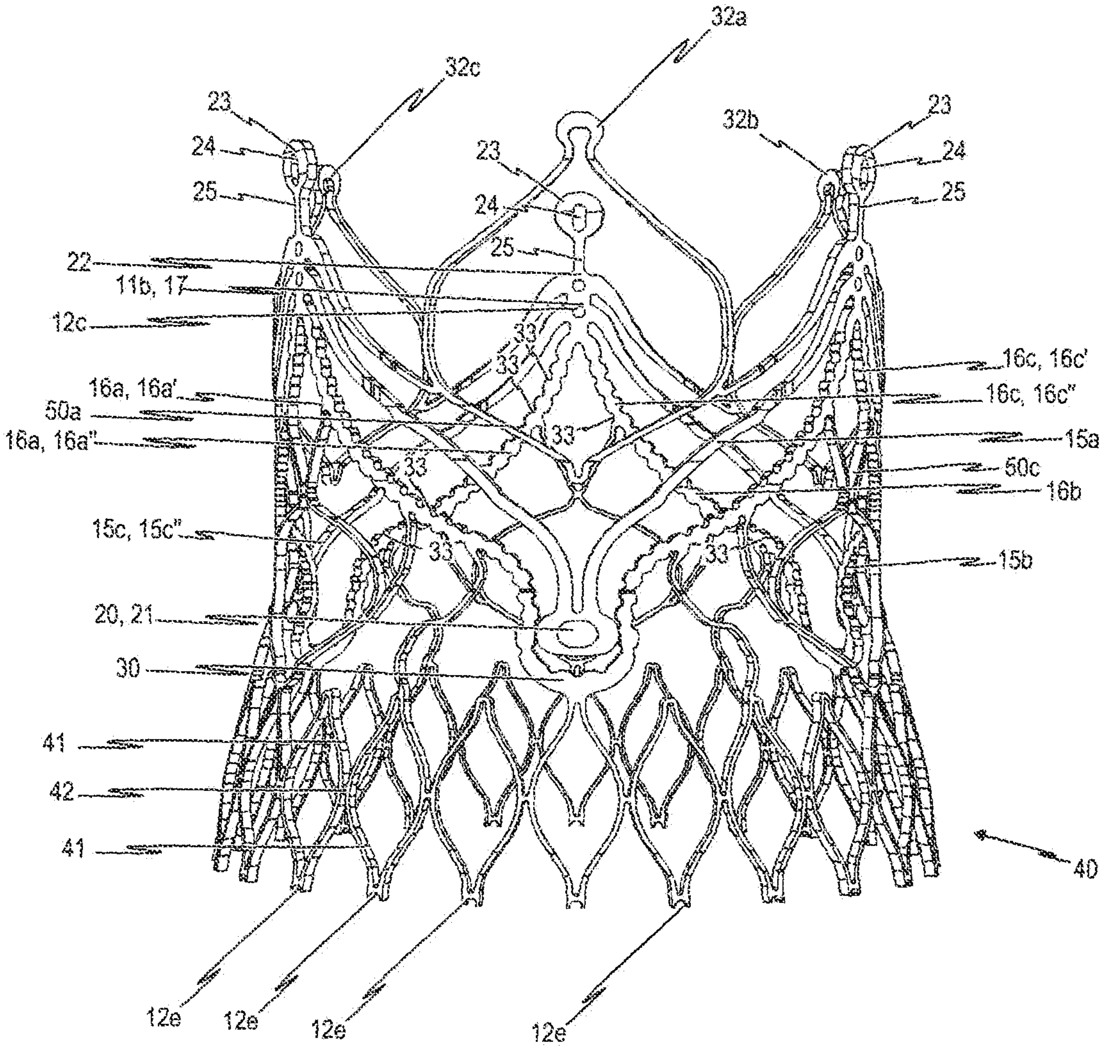
Figure 8D:
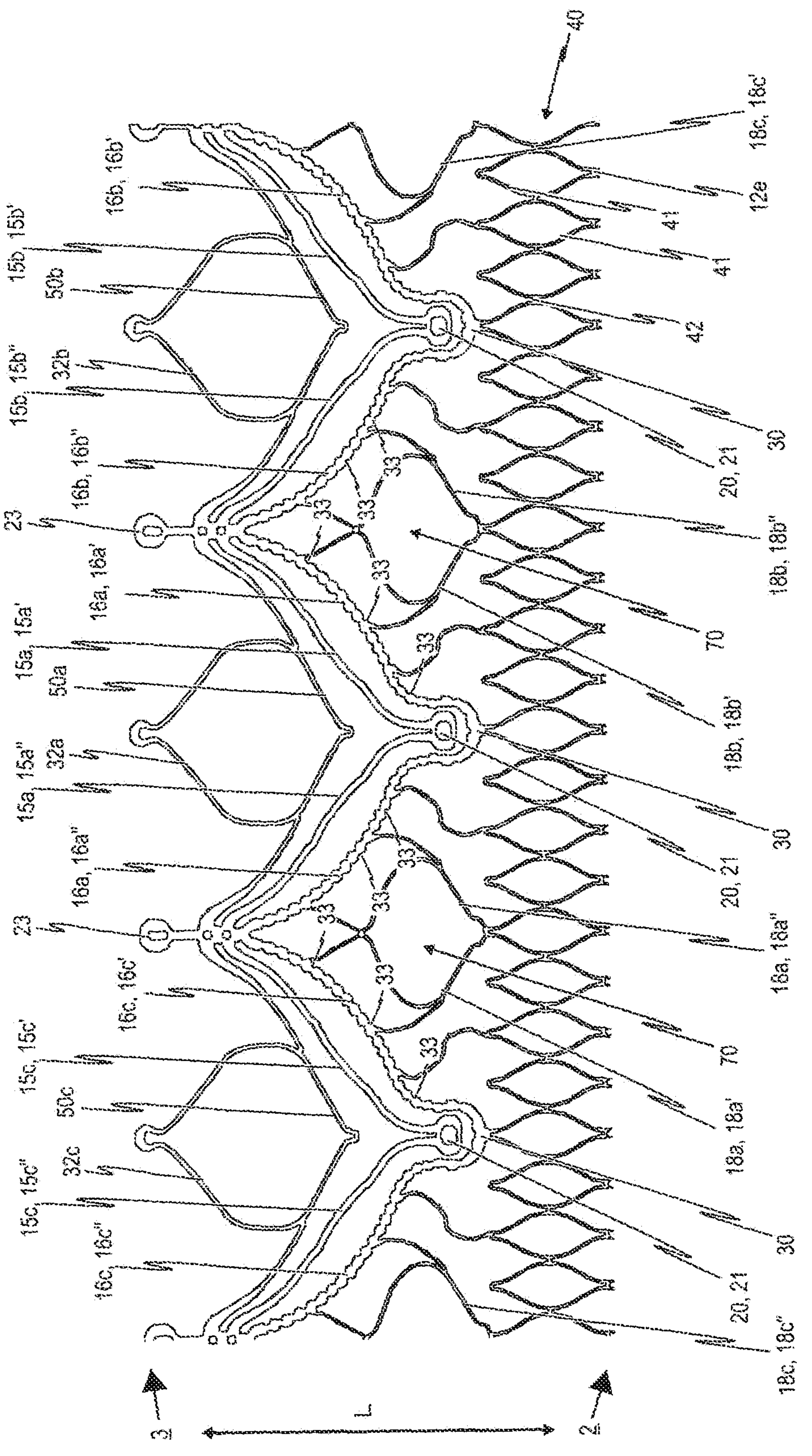
Figure 9:
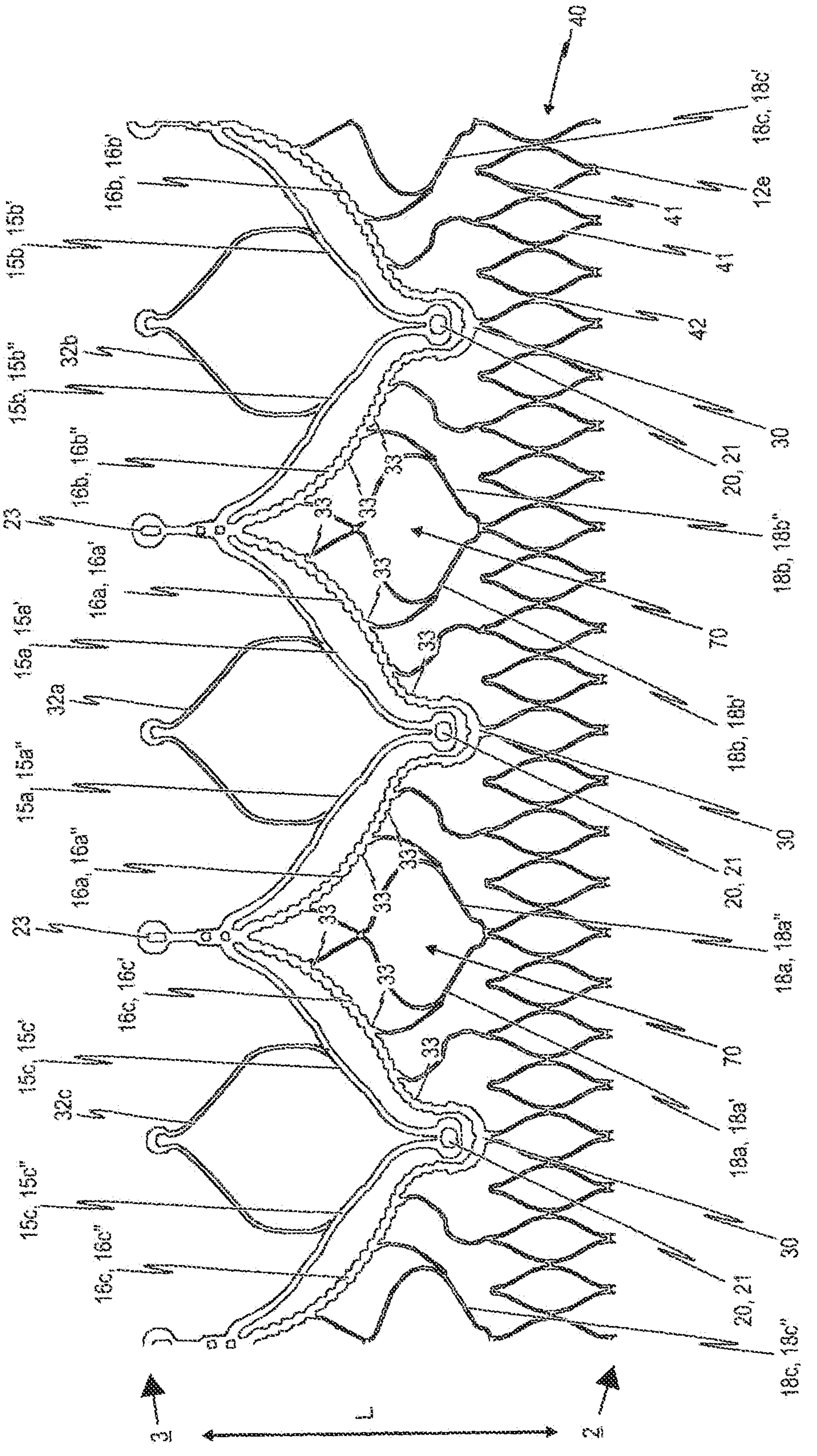
Figure 10:
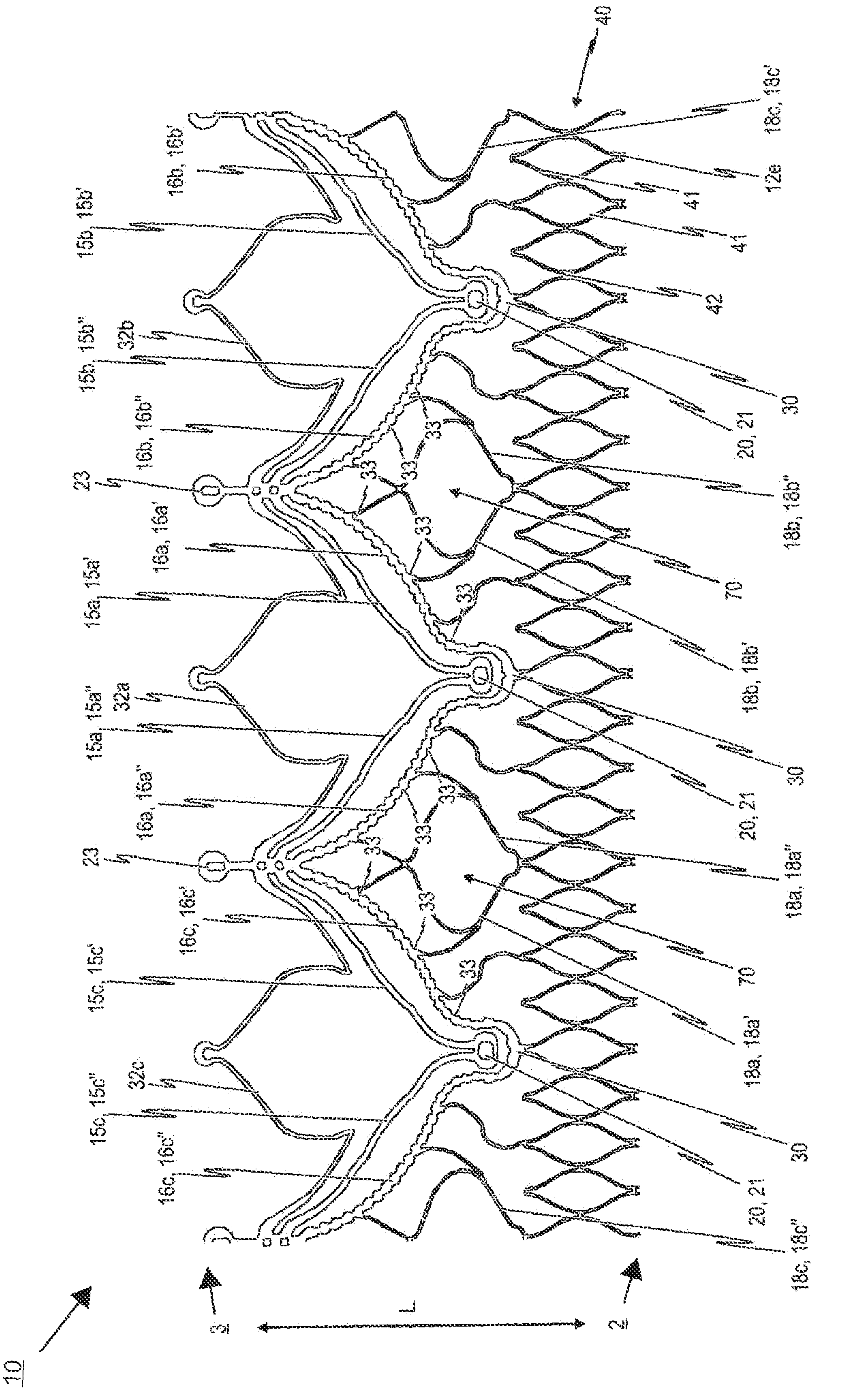
Figure 11A:
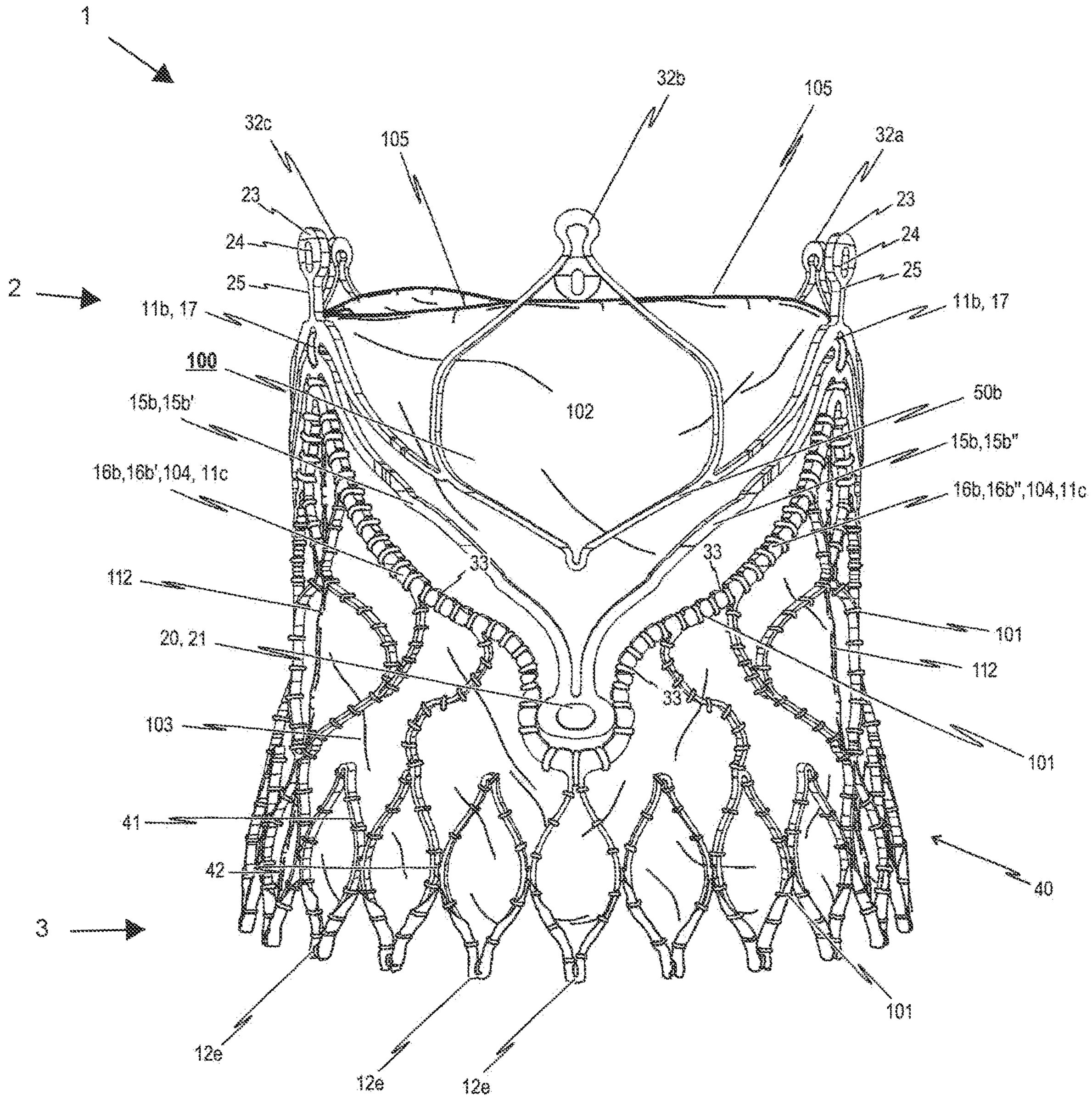
Figure 11B:
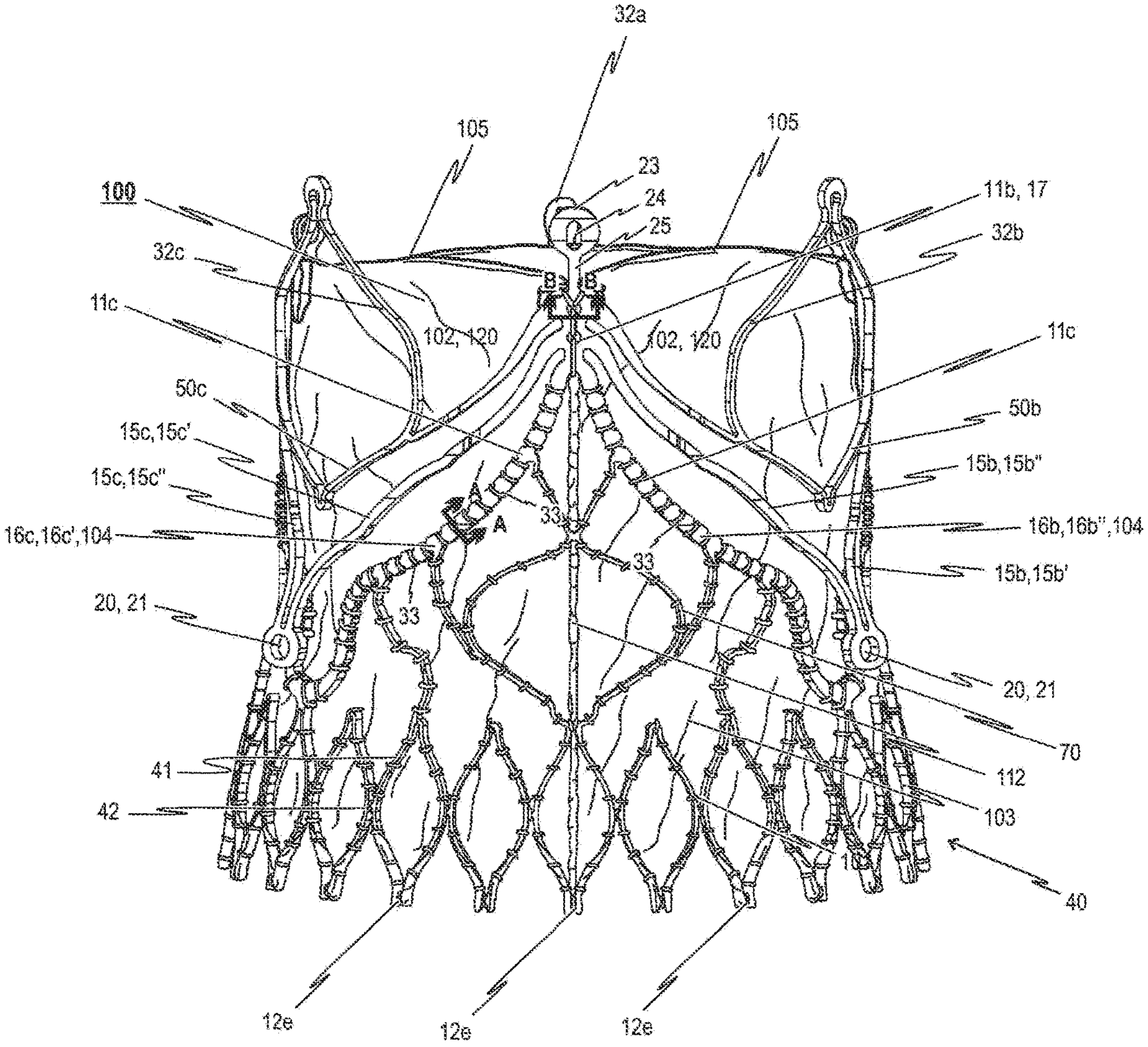
Figure 11C:
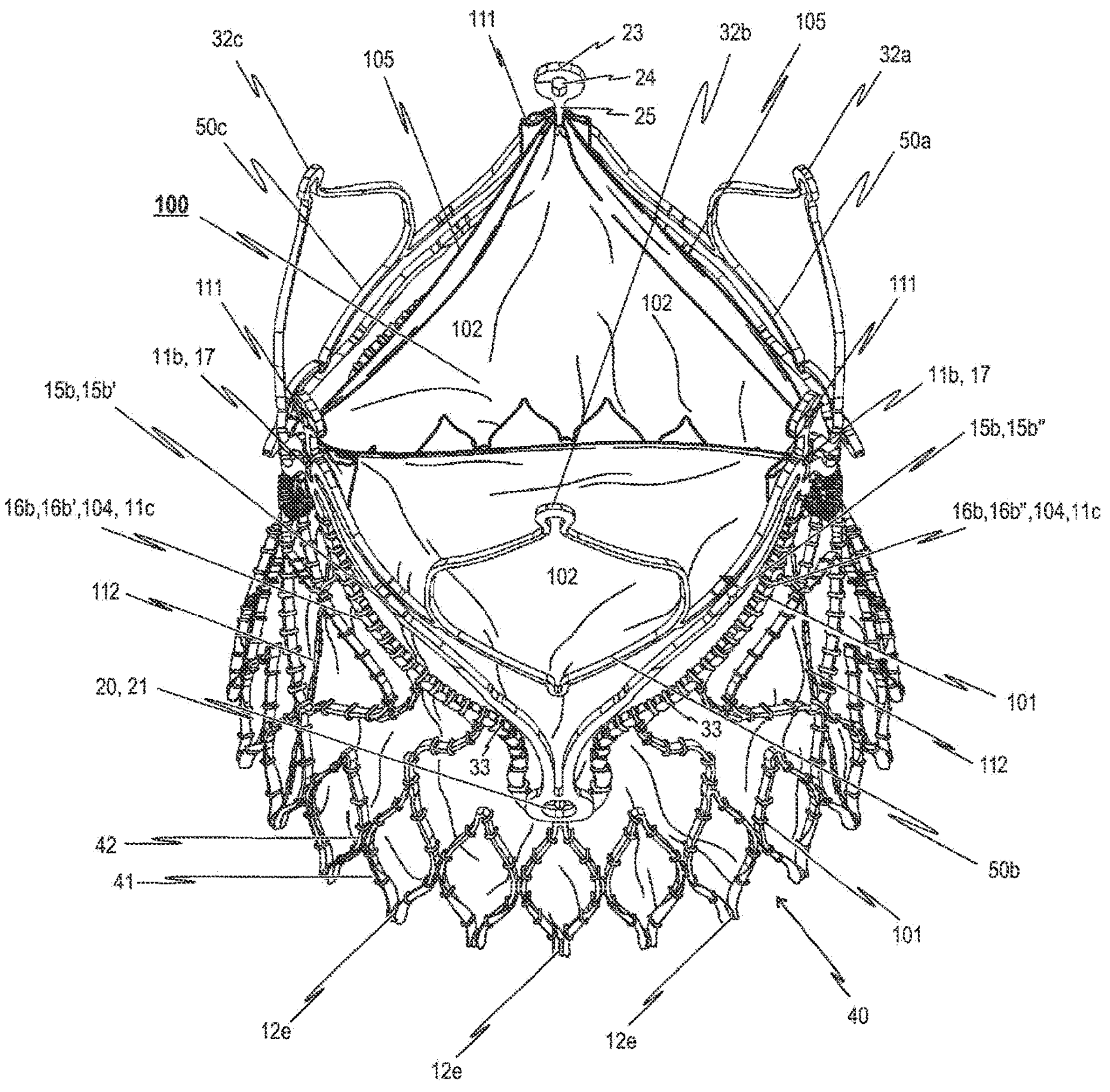
Figure 12:
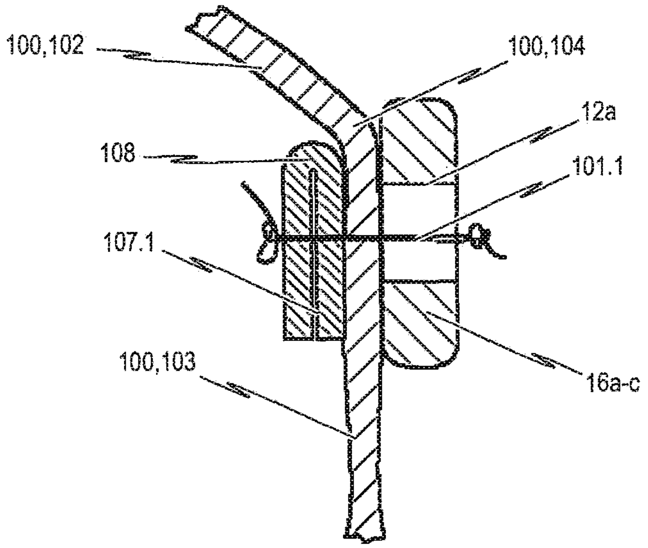
Figure 13:
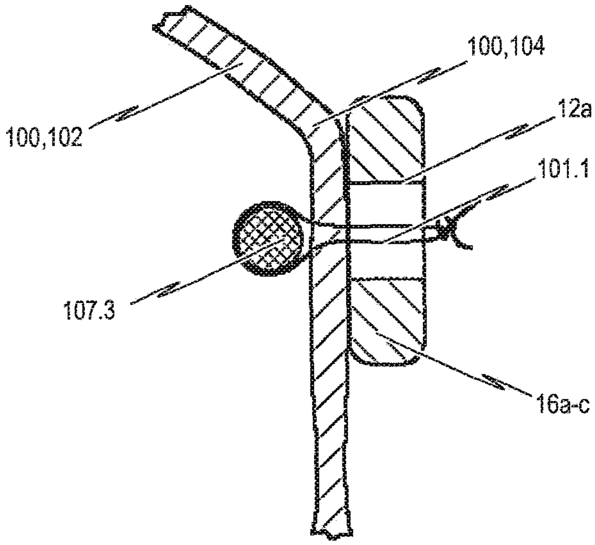
Figure 14:
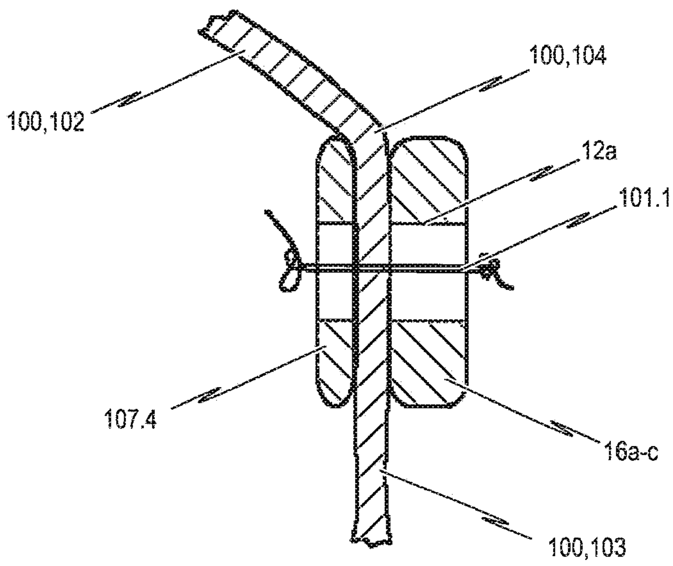
Figure 15:
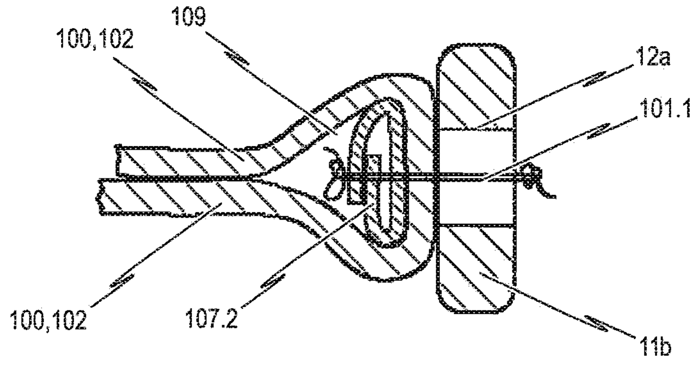
Figure 16:
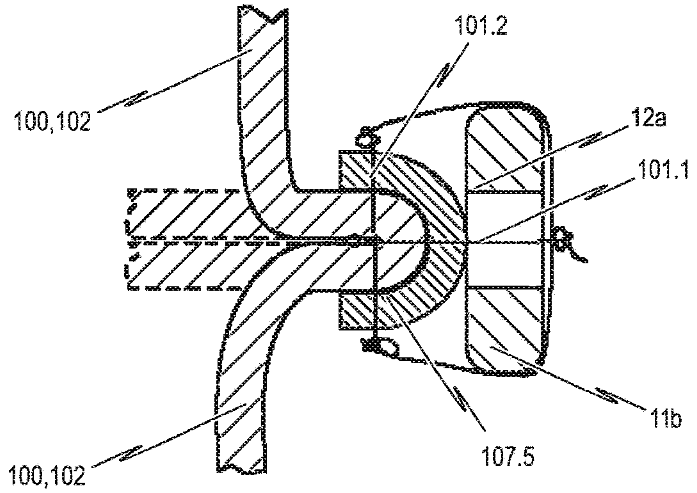
Figure 17:
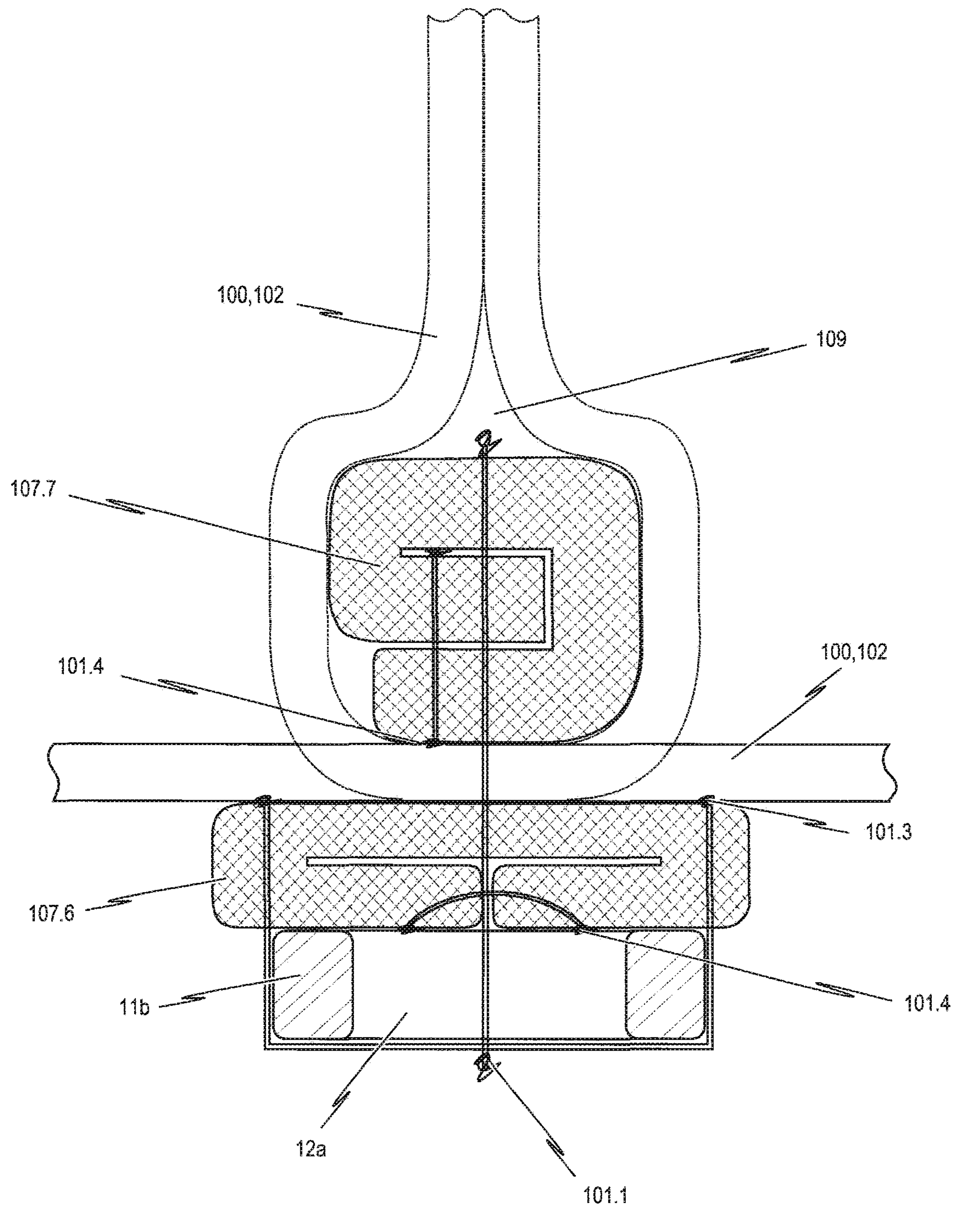
Figure 18:
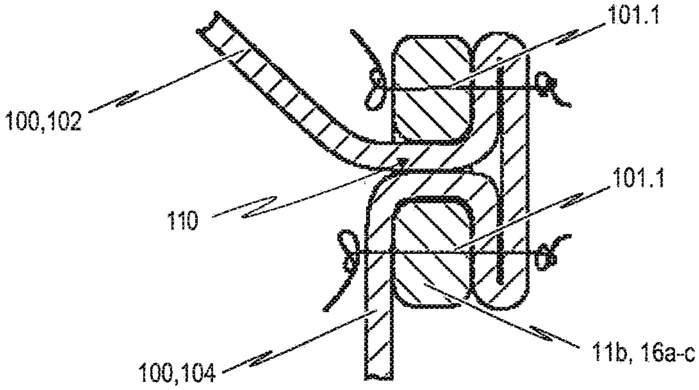
Figure 19A:
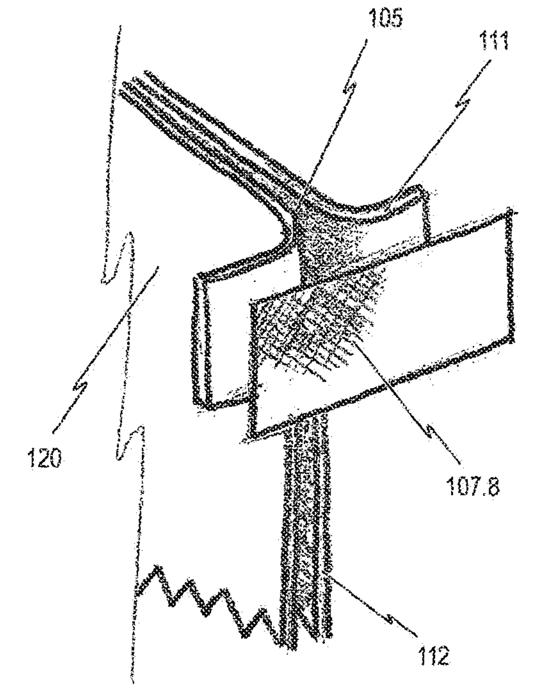
Figure 19B:
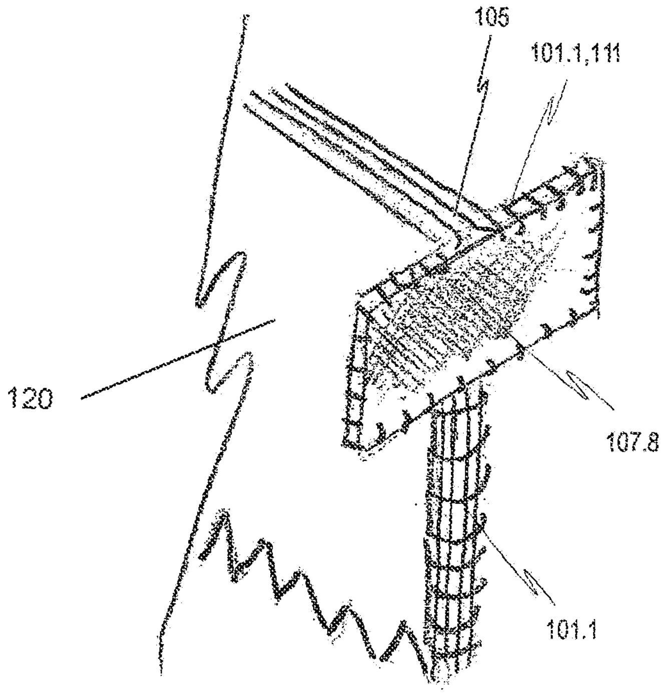
Figure 19C:
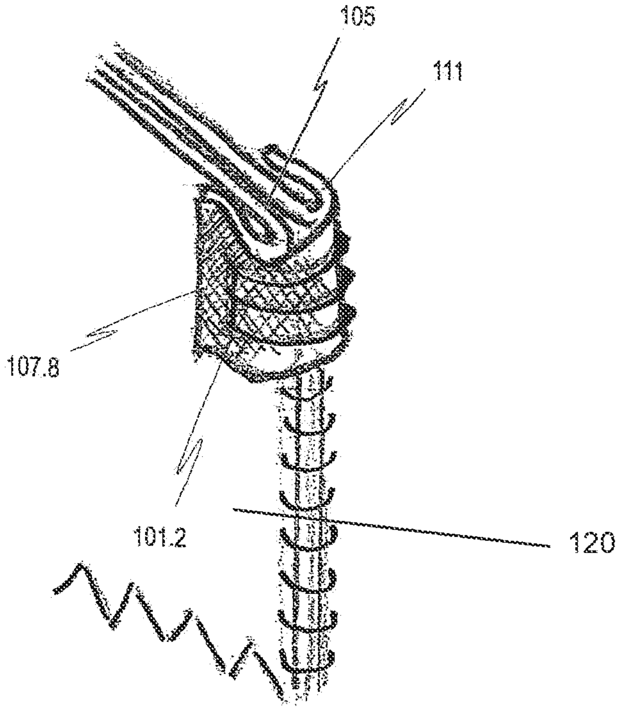
Figure 20:
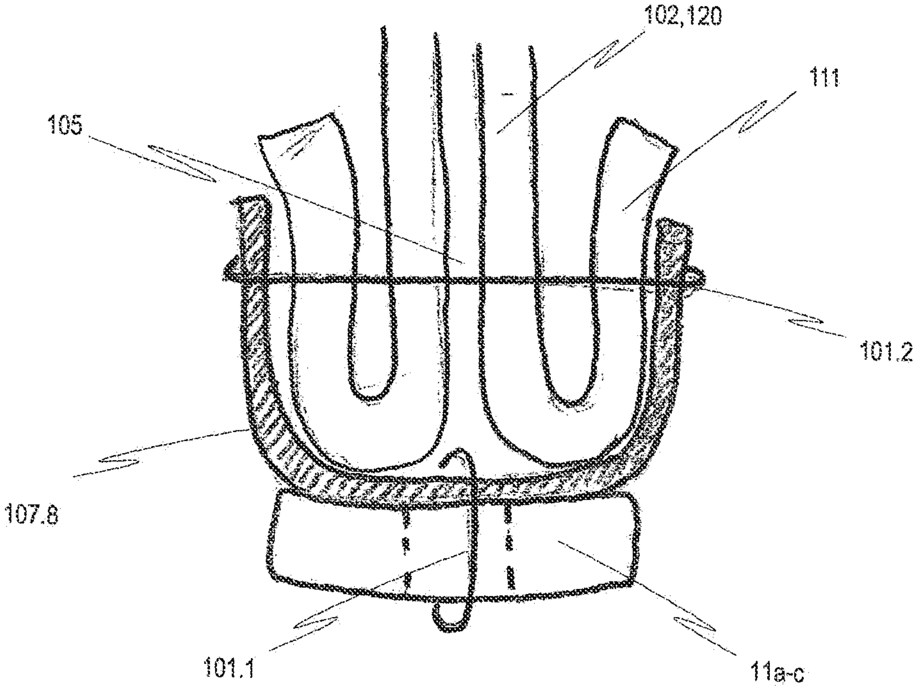
Figure 21:
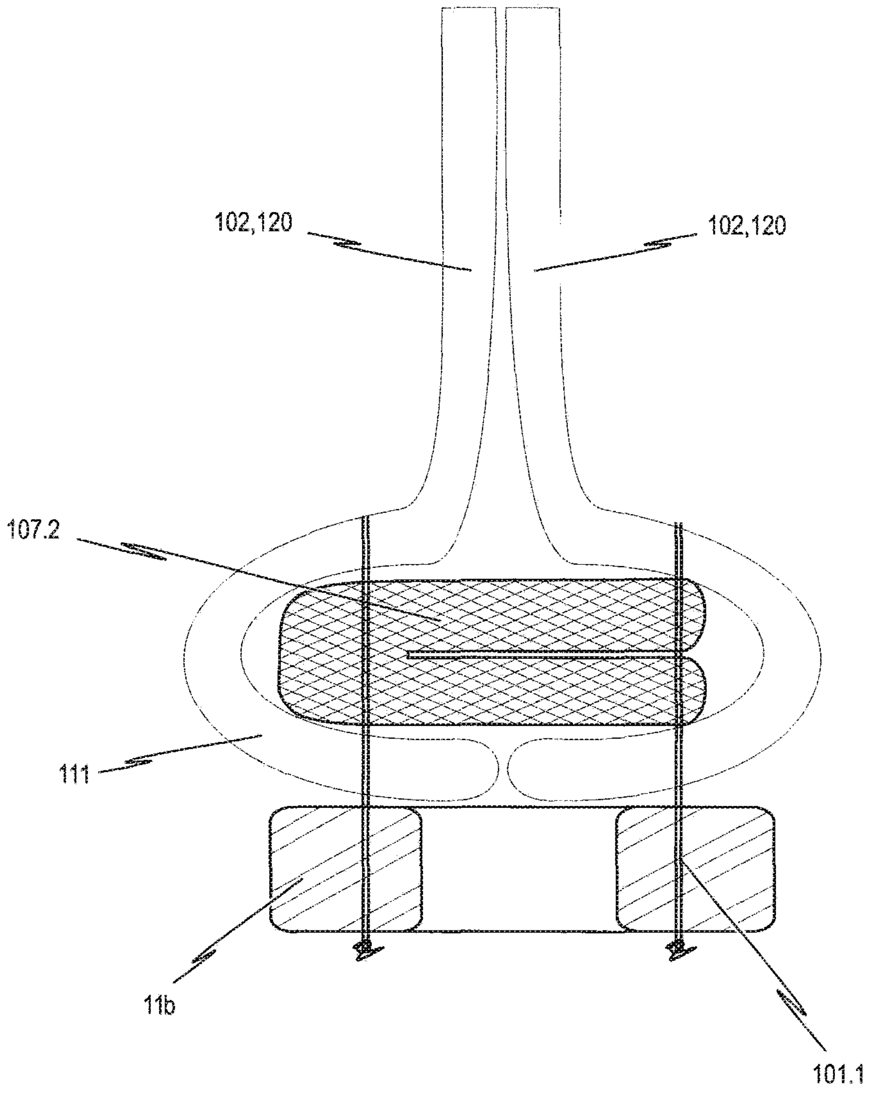

Shown are:

FIG. 1 a roll-out view of a prosthetic heart valve according to an exemplary embodiment of the disclosure;

FIG. 2*a* a plan view of the upper end of the prosthetic heart valve in its closed state;

FIG. 2*b* a plan view of the upper end of the prosthetic heart valve in its opened state;

FIG. 3 a flat pattern of a prosthetic heart valve material piece having an essentially t-shirt like shape for a prosthetic heart valve according to a further exemplary embodiment of the disclosure;

FIG. 4 a top view of the three prosthetic heart valve material pieces sewn together and attached to commissure attachment regions of a stent according to the further exemplary embodiment of the disclosure; and FIG. 5*a* a flat roll-out view of an exemplary embodiment of a first cardiac valve stent which may be used in the endoprosthesis according to FIG. 6*a*, 6*b*, 7*a* or 7*b* for fixing a prosthetic heart valve according to an exemplary embodiment of the disclosure;

FIG. 5*b* a first perspective side view of a first cardiac valve stent capable of supporting and anchoring a prosthetic heart valve according to an exemplary embodiment of the disclosure, whereby the cardiac valve stent is shown in its expanded state;

FIG. 5*c* a second perspective side view of a first cardiac valve stent capable of supporting and anchoring a prosthetic heart valve according to an exemplary embodiment of the disclosure, whereby the cardiac valve stent is shown in its expanded state;

FIG. 5*d* a third perspective side view of a first cardiac valve stent capable of supporting and anchoring a prosthetic heart valve according to an exemplary embodiment of the disclosure, whereby the cardiac valve stent is shown in its expanded state;

FIG. 5*e* a plan view of the lower end of a first cardiac valve stent capable of supporting and anchoring a prosthetic heart valve according to an exemplary embodiment of the disclosure, whereby the cardiac valve stent is shown in its expanded state;

FIG. 6*a* a first perspective side view of an endoprosthesis for treating a narrowed cardiac valve or a cardiac valve insufficiency, where the endoprosthesis is shown in an expanded state and where the endoprosthesis comprises a cardiac valve stent and a prosthetic heart valve according to an exemplary embodiment of the disclosure, said cardiac valve stent is used for holding the prosthetic heart valve;

FIG. 6*b* a second perspective side view of an endoprosthesis for treating a narrowed cardiac valve or a cardiac valve insufficiency, where the endoprosthesis is shown in an expanded state and where the endoprosthesis comprises a cardiac valve stent and a prosthetic heart valve according to an exemplary embodiment of the disclosure, said cardiac valve stent is used for holding the prosthetic heart valve;

FIG. 7*a* a first perspective side view of an endoprosthesis for treating a narrowed cardiac valve or a cardiac valve insufficiency, where the endoprosthesis is shown in an expanded state and where the endoprosthesis comprises a cardiac valve stent and a prosthetic heart valve according to an exemplary embodiment of the disclosure, said cardiac valve stent is used for holding the prosthetic heart valve;

FIG. 7*b* a second perspective side view of the endoprosthesis depicted in FIG. 7*a*, where the endoprosthesis is shown in an expanded state and where the endoprosthesis comprises a cardiac valve stent and a prosthetic heart valve according to an exemplary embodiment of the disclosure, said cardiac valve stent is used for holding the prosthetic heart valve;

FIG. 8*a* a flat roll-out view of an exemplary embodiment of a second cardiac valve stent, in its compressed state, which may be used in the endoprosthesis according to FIG. 11*a* or FIG. 11*b* for fixing a prosthetic heart valve according to an exemplary embodiment of the disclosure;

FIG. 8*b* a first perspective side view of the second cardiac valve stent capable of supporting and anchoring a prosthetic heart valve according to an exemplary embodiment of the disclosure, whereby the cardiac valve stent is shown in its expanded state;

FIG. 8*c* a second perspective side view of the second cardiac valve stent capable of supporting and anchoring a prosthetic heart valve according to an exemplary embodiment of the disclosure, whereby the cardiac valve stent is shown in its expanded state;

FIG. 8*d* a second flat roll-out view of an exemplary embodiment of a second cardiac valve stent, in its expanded state, which may be used in the endoprosthesis according to FIG. 11*a* or FIG. 11*b* for fixing a prosthetic heart valve according to an exemplary embodiment of the disclosure;

FIG. 9 a flat roll-out view of an exemplary embodiment of a third cardiac valve stent, in its expanded state, which may be used in an endoprosthesis for fixing a prosthetic heart valve according to an exemplary embodiment of the disclosure;

FIG. 10 a flat roll-out view of an exemplary embodiment of a fourth cardiac valve stent, in its expanded state, which may be used an endoprosthesis for fixing a prosthetic heart valve according to an exemplary embodiment of the disclosure;

FIG. 11*a* a first perspective side view of an endoprosthesis for treating a narrowed cardiac valve or a cardiac valve insufficiency, where the endoprosthesis is shown in an expanded state and where the endoprosthesis comprises a cardiac valve stent and a prosthetic heart valve according to an exemplary embodiment of the disclosure, said cardiac valve stent is used for holding the prosthetic heart valve;

FIG. 11*b* a second perspective side view of the endoprosthesis depicted in FIG. 11*a*, where the endoprosthesis is shown in an expanded state and where the endoprosthesis comprises a cardiac valve stent and a prosthetic heart valve according to an exemplary embodiment of the disclosure, said cardiac valve stent is used for holding the prosthetic heart valve;

FIG. 11*c* a perspective top view of the endoprosthesis depicted in FIG. 11*a*, where the endoprosthesis is shown in an expanded state and where the endoprosthesis comprises a cardiac valve stent and a prosthetic heart valve according to an exemplary embodiment of the disclosure, said cardiac valve stent is used for holding the prosthetic heart valve;

FIG. 12 a cross sectional view along the line A-A shown in FIG. 6*b* or 11*b* showing a first exemplary embodiment of reinforcement elements which may be utilized in the endoprosthesis according to the present disclosure for fixing a prosthetic heart valve to a cardiac valve stent;

FIG. 13 a cross sectional view along the line A-A shown in FIG. 6*b* or 111) showing a second exemplary embodiment of reinforcement elements which may be utilized in the endoprosthesis according to the present disclosure for fixing a prosthetic heart valve to a cardiac valve stent;

FIG. 14 a cross sectional view along the line A-A shown in FIG. 6*b* or 11*b* showing a third exemplary embodiment of reinforcement elements which may be utilized in the endoprosthesis according to the present disclosure for fixing a prosthetic heart valve to a cardiac valve stent;

FIG. 15 a cross sectional view along the line B-B shown in FIG. 6*b* or 11*b* for explaining a fourth exemplary embodiment of reinforcement elements which may be utilized in the endoprosthesis according to the present disclosure for fixing a prosthetic heart valve to a cardiac valve stent;

FIG. 16 a cross sectional view along the line B-B shown in FIG. 6*b* or 11*b* showing a fifth exemplary embodiment of reinforcement elements which may be utilized in the endoprosthesis according to the present disclosure for fixing a prosthetic heart valve to a cardiac valve stent;

FIG. 17 a cross sectional view along the line B-B shown in FIG. 6*b* or 11*b* showing a sixth exemplary embodiment of reinforcement elements which may be utilized in the endoprosthesis according to the present disclosure for fixing a prosthetic heart valve to a cardiac valve stent;

FIG. 18 a cross sectional view along the line B-B shown in FIG. 6*b* or 11*b* showing an alternative attachment solution for fixing a prosthetic heart valve to a cardiac valve stent;

FIG. 19*a-c* the steps for connecting two separate prosthetic heart valve material pieces along their contiguous edges according to the second exemplary embodiment of the prosthetic heart valve;

FIG. 20 a top view of the attachment of the prosthetic heart valve to the commissure attachment regions of a stent according to the second exemplary embodiment of the prosthetic heart valve;

FIG. 21 a detailed perspective view of an alternative attachment of the prosthetic heart valve to the commissure attachment regions of a stent according to the second exemplary embodiment of the prosthetic heart valve.

FIG. 1 shows a view of a flat tissue pattern for a prosthetic heart valve 100 according to an exemplary disclosed embodiment. The prosthetic heart valve 100 may comprise at least two leaflets, and as shown in the exemplary embodiment of the flat tissue pattern for a prosthetic heart valve 100 depicted in FIG. 1 three leaflets 102. Each of the leaflets 102 comprises a natural tissue and/or synthetic material. The leaflets 102 are attached to a skirt portion 103. As will be discussed later on in detail, the skirt portion 103 is used for mounting the prosthetic heart valve 100 to a stent 10.

The leaflets 102 of the prosthetic heart valve 100 are adapted to be moveable from a first opened position for opening the heart chamber and a second closed position for closing the heart chamber. In particular, in the implanted state of the prosthetic heart valve 100, the leaflets 102 may switch between their first and second position in response to the blood flow through the patient's heart. During ventricular systole, pressure rises in the left ventricle of the patient's heart. When the pressure in the left ventricle of the patient's heart rises above the pressure in the aorta the leaflets 102 of prosthetic heart valve 100 opens, allowing blood to exit the left ventricle into the aorta. When ventricular systole ends, pressure in the left ventricle rapidly drops. When the pressure in the left ventricle decreases, the aortic pressure forces the leaflets 102 of the prosthetic heart valve 100 to close.

FIGS. 2*a* and 2*b* respectively show a plan view of the upper end of a prosthetic heart valve 100 in the closed and opened state. In the closed position of the prosthetic heart valve 100 (see FIG. 2*a*), the three leaflets 102 come together in the centre of the prosthetic heart valve 100 thereby creating a region of sealing.

During the opening phase the leaflets pivot about a bendable transition area 104, as depicted in FIG. 1. The bendable transition area 104 forms a junction between the leaflets 102 and the skirt portion 103 and progresses in a substantial U-shaped manner, similar to the cusp shape of a natural aortic or pulmonary heart valve. Still within the opening phase, the commissure region 105 and the leaflets 102 move radially outwards opening the valve in response to increased differential pressure allowing blood to flow through the prosthesis.

In the exemplary embodiment depicted in FIG. 1, the prosthetic heart valve 100 is made of one piece of flat pericardial tissue. This pericardial tissue can either be extracted from an animal's heart (xenograft) or a human's heart (homograft). The extracted tissue may be cut by a laser or knife or might be pressed in order to form a flat tissue pattern representing each of the leaflets 102 and the skirt portion 103. After said forming of the flat tissue pattern, the so made heart valve tissue may be sewn into a cylindrical or conical shape, ready to be attached to a corresponding stent structure 10. As will be discussed in detail with respect to FIGS. 6*a*, 6*b*, the skirt portion 103 represents an area of the prosthetic heart valve 100 that is used for connecting the prosthetic heart valve 100 to a stent 10, for example, by means of sutures 101.

As can be seen from FIGS. 1 and 2, the pattern of the prosthetic heart valve 100 represents each of the leaflets 102, commissure region 105 and the skirt portion 103 of the intended prosthetic heart valve 100. Hence, the flat tissue pattern is designed so as to form the leaflets 102 in a manner, having three half-moon shaped leaflets like the aortic or pulmonary heart valve. The leaflets 102 can be designed in various shapes such as the geometry of an ellipse, U-shape or substantially oval. Preferably the three leaflets 102 are formed in such a manner that all of them have the same general shape.

Another aspect shown by FIG. 1 is a flared lower end section of prosthetic heart valve 100. As will be explained in more detail below, such a flared lower end section may be advantageous in order to fit the prosthetic heart valve 100 to an annular collar 40 of a respective cardiac heart valve 10. Alternatively, it is further conceivable to produce a prosthetic heart valve 100 comprising a tapered lower end section. A flare or taper at the lower end section of the prosthetic heart valve 100 may be adapted to the geometry of the blood vessel at the implantation site of the prosthesis, so as to obtain the most reliable fit of said prosthesis to said blood vessel.

Between the leaflets 102 and the skirt portion 103, the valve pattern shows the bendable transition area 104 progressing in a substantial U-shaped manner, similar to the cusp-shape of a natural aortic or pulmonary heart valve.

As can be derived from FIG. 2*a*, the leaflet portion of the prosthetic heart valve 100 is designed to provide redundant coaptation for potential annular distortion. Accordingly, the redundant coaptation may reduce stress on the leaflets 102 and assures a reliable closure of the heart chamber in the second closed position of the leaflets 102. This redundant coaptation provides for more surface contact between the leaflets, allowing for the prosthetic heart valve of the present disclosure to be implanted in a distorted valve annulus, still maintaining sufficient coaptation.

Although not depicted in FIG. 1, the prosthetic heart valve 100 can comprise a plurality of fastening holes 106 provided along the progression of the transition area 104. These fastening holes 106 are introduced into the tissue material of the prosthetic heart valve 100 by means of laser cutting for strengthening the tissue area around the fastening holes 106. Alternatively, however, it is conceivable that fastening holes 106 are introduced by the needle during the sewing process.

The bendable transition area 104 shown in FIG. 1 may include a layering of various materials with differing mechanical properties. Accordingly, the lower parts, particularly associated with retaining arches of a cardiac valve stent, may be more rigid to provide high suture retention, whereas the upper parts, particularly associated with a commissure attachment region 11*b* of the stent, may be designed to be more flexible in order to support the movement of the leaflets 102. On the same note, the leaflets 102 and the leaflet support portion 103 may exhibit different stability characteristics. This might be achieved by the use of different cross-linking processes for the leaflets 102 or the leaflet support portion 103 respectively. Alternatively, the leaflets 102 or the leaflet support portion 103 could be reinforced by attaching small sheets of tissue or synthetic material in order to increase the mechanical stability.

As the size and diameter of different blood vessels of different patients varies to a certain extent, it may be advantageous to provide prosthetic heart valves 100 of different designs. In particular, tissue material with a thickness of 160 μm to 300 μm, more preferably 220 μm to 260 μm may be used, depending on the particular tissue material used to manufacture the prosthetic heart valve. Furthermore, the prosthetic heart valve 100, according to the present disclosure, may have a diameter ranging form 19 mm to 28 mm.

Reference is made in the following to FIGS. 6*a, b* which respectively show a first and second perspective side view of an endoprosthesis 1 for treating a narrowed cardiac valve or a cardiac valve insufficiency, where the endoprosthesis 1 comprises an exemplary embodiment of a cardiac valve stent 10 for holding a prosthetic heart valve 100. In the illustrations according to FIGS. 6*a, b*, the endoprosthesis 1 is shown in an expanded state.

As can be seen from the illustrations according to FIGS. 6*a, b*, in the affixed state of the prosthetic heart valve 100, the transition area 104 of the prosthetic heart valve 100 extends along the retaining arches 16*a*, 16*b*, 16*c* and, in particular, along the lower leaflet attachment region 11*c* and the commissure attachment region 11*b* of the retaining arches 16*a*, 16*b*, 16*c* of the stent 10. The bendable transition area 104 of the prosthetic heart valve 100 is attached to retaining arches 16*a*, 16*b*, 16*c* of the stent 10 such as to enable the leaflets 102 of the prosthetic heart valve 100 to bend inwards in a controlled manner to the centre of the stent 10 forming the valvular leaflets 102.

For adapting the prosthetic heart valve 100 to a corresponding stent 10 so that the valvular leaflets 102 are properly formed and prosthetic heart valve is properly fitted to the stent structure, the pattern of the flat-tissue material of the prosthetic heart valve 100 shall be cut so as to incorporate the leaflet structures, the annular skirt portion 103 and the transition area 104 in between them. In other words, after the prosthetic heart valve material is sewn into its cylindrical or conical shape, the valve exhibits a flared portion at the lower end. This flared geometry fits the structure of the stent 10 and is constructed to optimally fit the vascular wall at the implantation site of the diseased heart valve.

In the exemplary embodiment of the transcatheter delivered endoprosthesis 1 depicted in FIGS. 6*a, b*, the prosthetic heart valve 100, which is affixed to the stent 10, consists of a one piece flat pericardial tissue material extracted from an animal or human pericardial sack and cut into a pattern representing each of the three leaflets 102 and the skirt portion 103, wherein the pattern is sewn into a cylindrical shape before attachment to the stent 10. In addition, the prosthetic heart valve 100 includes a transition area 104 which is connected to the retaining arches 16*a*, 16*b*, 16*c* and commissure attachment regions 11*b* of the stent. The transition area 104 connects the leaflets 102 with the skirt portion 103. In particular, the transition area 104 is essentially U-shaped, similar to the cusp shape of a natural aortic or pulmonary heart valve. For this reason, the transition area 104 allows for an opening and closing motion of the leaflets 102, causing minimal stresses within the biological prosthetic heart valve tissue.

Upon assembly of this tissue pattern (see FIG. 1) to a stent 10, the regions of tissue between the retaining arches become the valve leaflets 102. These leaflets can be folded inwards so as to form three essentially closed leaflets. In case of a pressure gradient in a downstream direction (in response to a rising blood pressure in the heart chamber), the leaflets 102 are forced apart, in the direction of the stent 10, enabling blood to exit the heart chambers. On the other hand, if there is a pressure gradient in the opposite, upstream direction (retrograde gradient, in response to an intake pressure in the heart chamber), the blood rushes into the leaflets 102, thereby pressing the leaflets 102 together in the centre of stent 10 and closing the transcatheter delivered endoprosthesis 1.

As has been described in more detail with reference to FIGS. 5*a-e* and FIGS. 8 to 10, a suitable stent 10, to which the prosthetic heart valve 100 may be attached for forming an endoprosthesis 1, may include an annular collar 40 arranged to a lower section of stent 10. The annular collar 40 of the stent 10 serves as an additional anchoring measure to hold the transcatheter delivered endoprosthesis 1 in a desired location at the site of the diseased heart valve. In the exemplary embodiment of the transcatheter delivered endoprosthesis 1 depicted in FIGS. 6*a, b*, FIGS. 7*a, b* and FIGS. 11*a* to 11*c*, the annular collar 40 of the stent 100 has a flared shape.

Accordingly, the lower part of leaflet support portion 103 of the prosthetic heart valve 100 affixed to the stent 10 also exhibits an extended diameter in order to accommodate the flared shape of the annular collar 40.

The prosthetic heart valve 100 is fixed to the stent 10 by means of sutures, threads or wires 101 which are attached to the skirt portion 103 and/or the transition area 104 of the prosthetic heart valve 100. The skirt portion 103 serves for keeping the prosthetic heart valve 100 in a predefined position relative to the stent 10.

As will be described in more detail below, a suitable stent 10, to which the prosthetic heart valve 100 may be attached for forming an endoprosthesis 1, may include an annular collar 40 arranged to a lower section of stent 10. The annular collar 40 of the stent 10 serves as an additional anchoring measure to hold the transcatheter delivered endoprosthesis 1 in a desired location at the site of the diseased heart valve.

As can be seen from the illustrations in FIGS. 6*a, b*, the skirt portion 103 of the prosthetic heart valve 100 may also be attached to the annular collar 40 of the stent 10 by means of sutures, threads or wires 101. For this purpose, multi-filament sutures 101 of a diameter up to 0.2 mm, preferably between 0.1 mm and 0.2 mm may be used.

Moreover, a common running stitch pattern may be used to obtain said bonding. According to the disclosure, the stitch pattern is preferably a locking stitch or a blanket stitch respectively. Of course, any other suitable stitch pattern (i.e. overlocking stitch, slipstitch or topstitch) is also possible.

As indicated by FIGS. 6*a* and 6*b*, the bendable transition area 104 of the prosthetic heart valve may be attached to retaining arches 16*a*, 16*b*, 16*c* of the stent 10 by means of sutures 101, having a diameter larger than the diameter of the sutures 101 used for attachment of the prosthetic heart valve to an annular collar 40 of the stent 10. Due to this, the prosthetic heart valve 100 can be reliably attached to the stent without adding too much bulk to the stent 10, in order to collapse the endoprosthesis to a small diameter.

In the exemplary embodiment of the transcatheter delivered endoprosthesis 1 depicted in FIGS. 6*a, b*, the annular collar 40 of the stent 100 has a flared shape. Accordingly, the lower part of skirt portion 103 of the prosthetic heart valve 100 affixed to the stent 10 also exhibits an extended diameter in order to accommodate the flared shape of the annular collar 40.

The scope of the present disclosure will become more clear by considering some of the possible embodiments of a stent 10 with the prosthetic heart valve 100 attached thereto thereby forming an endoprosthesis. Hence, reference is made in the following to FIGS. 5*a-e* for describing an exemplary embodiment of a stent 10 to which a prosthetic heart valve 100 may be affixed in order to form the transcatheter delivered endoprosthesis 1 depicted in FIGS. 6*a, b*.

In particular, FIG. 5*b* is a first perspective side view of a cardiac valve stent 10, whereby the cardiac valve stent 10 is shown in its expanded state. Second and third side views of the cardiac valve stent 10 in its expanded state are shown in FIGS. 5*c* and 5*d*.

On the other hand, FIG. 5*e* shows a plan view of the lower end of the cardiac valve stent 10 according to the exemplary embodiment of the disclosure in its expanded state, whereas a flat roll-out view of a stent 10 according to the exemplary embodiment is shown in FIG. 5*a*.

The stent 10 depicted in FIGS. 5*a-e* is also provided with an annular collar 40 which is arranged at the lower end section of the stent body. The at least one collar 40 may serve as an additional anchoring measure for the stent 10.

In addition, the stent 10 according to the exemplary embodiment has a total of three positioning arches 15*a*, 15*b*, 15*c*, which undertake the function of automatic positioning of the stent 10. Each of the positioning arches 15*a*, 15*b*, 15*c* has a radiused head portion 20, which engages in the pockets of the native heart valve being treated during positioning of the stent 10 at the implantation site in the heart.

The exemplary embodiment of the stent 10 also includes radial arches 32*a*, 32*b*, 32*c*. In particular, the stent 10 has three radial arches 32*a*, 32*b*, 32*c*, with each arch 32*a*, 32*b*, 32*c* located between the two arms 15*a*, 15*a*', 15*b*, 15*b*', 15*c*, 15*c*' of each positioning arch 15*a*, 15*b*, 15*c*. Each radial arch 32*a*, 32*b*, 32*c* has a shape that is roughly inverse to each positioning arch 15*a*, 15*b*, 15*c* and extends in the opposite direction to each one of the positioning arches 15*a*, 15*b*, 15*c*.

In addition, the stent 10 according to the exemplary embodiment depicted in FIGS. 5*a-e* is provided with corresponding retaining arches 16*a*, 16*b*, 16*c*. Each one of the retaining arches 16*a*, 16*b*, 16*c* is allocated to one of the positioning arches 15*a*, 15*b*, 15*c*. Also, according to this exemplary embodiment of the stent 10, a number of commissure attachment regions 11*b* with a number of additional fastening holes 12*c* is configured at one end of each arm 16*a*', 16*a*", 16*b*', 16*b*", 16*c*', 16*c*" of the retaining arches 16*a*, 16*b*, 16*c*.

In addition to the commissure attachment regions 11*b*, the stent 10 also comprises second lower leaflet attachment regions 11*c* for additional fastening of the tissue component (s) of a prosthetic heart valve 100 (see FIGS. 6*a, b*). In this regard, the stent 10 according to the exemplary embodiment depicted in FIGS. 5*a-e* has a configuration with a number of attachment regions 11*b*, 11*c* to attach the material of a prosthetic heart valve 100.

The stent 10 may also be provided with leaflet guard arches, wherein one leaflet guard arch may be provided in between each positioning arch 15*a*, 15*b*, 15*c*. The structure and function of the leaflet guard arches will be described later with reference to FIGS. 7*a* and 7*b*. Hence, although for reasons of clarity not explicitly shown, in the stent design according to the exemplary embodiment depicted in FIGS. 5*a-e*, one leaflet guard arch may be allocated to each positioning arch 15*a*, 15*b*, 15*c*.

The exemplary embodiment of the sent 10 is characterized by a specific structure of the respective arms 16*a*', 16*a*", 16*b*', 16*b*", 16*c*', 16*c*" of the retaining arches 16*a*, 16*b*, 16*c*. In detail, in the expanded state of the stent 10, the respective arms 16*a*', 16*a*", 16*b*', 16*b*", 16*c*', 16*c*" of the retaining arches 16*a*, 16*b*, 16*c* have a shape similar to a prosthetic heart valve 100. Furthermore, the respective arms 16*a*', 16*a*", 16*b*', 16*b*", 16*c*', 16*c*" of the retaining arches 16*a*, 16*b*, 16*c* are provided with a number of lower leaflet attachment regions 11*c*, each having a number of additional fastening holes 12*a* or eyelets provided for fastening the tissue component(s) of a prosthetic heart valve 100. These additional fastening holes 12*a* or eyelets provide attachment points for the bendable transition area 104 of a prosthetic heart valve 100 attached to the stent 10.

As will be described in more detailed below, in an alternative embodiment, the respective arms 16*a*', 16*a*", 16*b*', 16*b*", 16*c*', 16*c*" of the retaining arches 16*a*, 16*b*, 16*c* may be provided with a number of fastening notches which can be used to fix the bendable transition area 104 to stent 10. Thus, in this alternative embodiment, there are no additional fastening holes 12*a* needed along the respective arms 16*a*', 16*a*", 16*b*', 16*b*", 16*c*', 16*c*" of the retaining arches 16*a*, 16*b*, 16*c*.

According to the stent designs of the embodiments depicted in FIGS. 5*a-e* and FIGS. 8 to 10, in the expanded state of the stent 10, the respective arms 16*a*', 16*a*", 16*b*', 16*b*", 16*c*', 16*c*" of the retaining arches 16*a*, 16*b*, 16*c* have a shape that substantially matches the transition area 104 of a prosthetic heart valve 100 attached to the stent 10 (see FIG. 6*a, b* or 11*a, b*).

This specific design of the respective arms 16*a*', 16*a*", 16*b*', 16*b*", 16C, 16*c*" of the retaining arches 16*a*, 16*b*, 16*c* has valve durability advantages. The so formed arms 16*a*', 16*a*", 16*b*', 16*b*", 16*c*', 16*c*" of the retaining arches 16*a*, 16*b*, 16*c* serve for supporting the skirt portion 103 and edge of the leaflets 102 of a prosthetic heart valve 100 attached to the stent 10.

As depicted, for example, in FIGS. 6*a, b* and 11*a, b*, the respective arms 16*a*', 16*a*", 16*b*', 16*b*", 16*c*', 16*c*" of the retaining arches 16*a*, 16*b*, 16*c* follow the shape of the bendable transition area 104 of a prosthetic heart valve 100 affixed to the stent 10 in its expanded state. Furthermore, the respective arms 16*a*', 16*a*", 16*b*', 16*b*", 16*c*', 16*c*" of the retaining arches 16*a*, 16*b*, 16*c* are designed to have a minimized unsupported gap from one arm to the other arm of a retaining arch 16*a*, 16*b*, 16*c* at the location behind the positioning arches 15*a-c*.

In detail and as depicted in the cutting pattern shown in FIG. 5*a*, the respective arms 16*a*', 16*a*", 16*b*', 16*b*", 16*c*', 16*c*" of the retaining arches 16*a*, 16*b*, 16*c* are provided with a plurality of bending edges 33. These bending edges 33 divide each arm 16*a*', 16*a*", 16*b*', 16*b*", 16*c*', 16*c*" into a plurality of arm segments. The arm segments of a single arm 16*a*', 16*a*", 16*b*', 16*b*", 16*c*', 16*c*" of the retaining arches 16*a*, 16*b*, 16*c* are interconnected thereby constituting a retaining arch arm which describes an essentially straight line in the not-expanded state of the stent 10. In this regard, reference is also made to the cutting pattern depicted in FIG. 5*a* which shows the uncurved configuration of the respective arms 16*a*', 16*a*", 16*b*', 16*b*", 16*c*', 16*c*" of the retaining arches 16*a*, 16*b*, 16*c*.

When manufacturing the stent 10, the stent structure and in particular the structure of the retaining arches 16*a*, 16*b*, 16*c* is programmed such that the respective arms 16*a*', 16*a*", 16*b*', 16*b*", 16*c*', 16*c*" of the retaining arches 16*a*, 16*b*, 16*c* have a curved shape in the expanded state of the stent 10. The shape of the respective arms 16*a*', 16*a*", 16*b*', 16*b*", 16*c*', 16*c*" of the retaining arches 16*a*, 16*b*, 16*c* is such defined that the arms follow the shape of the transition area 104 of a prosthetic heart valve 100 to be affixed to the stent 10 (see FIGS. 6*a* and 6*b*).

Hence, the respective arms 16*a*', 16*a*", 16*b*', 16*b*", 16*c*', 16*c*" of the retaining arches 16*a*, 16*b*, 16*c* of the stent 10, onto which the transition area 104 of a prosthetic heart valve 100 is sewn or sewable, will change their shape when the stent 10 expands, wherein the retaining arches 16*a*, 16*b*, 16*c* are curved in the expanded state of the stent 10, but relatively straight when the stent 10 is collapsed.

As can be seen, for example, in FIGS. 5*b-d*, the curvature of the respective arms 16*a*', 16*a*", 16*b*', 16*b*", 16*c*', 16*c*" of the retaining arches 16*a*, 16*b*, 16*c* is achieved by segmenting the arms 16*a*', 16*a*", 16*b*', 16*b*", 16*c*', 16*c*". In detail, the arms 16*a*', 16*a*", 16*b*', 16*b*", 16*c*', 16*c*" are segmented by providing a plurality of bending edges 33. In the expanded state of the stent 10, two neighboring arm segments are angled relative to each other, wherein the bending point of these two neighboring arm segments is defined by the bending edge 33 which is provided in between the both neighboring arm segments. Hence, the greater the number of bending edges 33 provided in an arm 16*a*', 16*a*", 16*b*', 16*b*", 16*c*', 16*c*" of a retaining arch 16*a*, 16*b*, 16*c*, the greater the number of arm segments which may extend in different directions in the expanded state of the stent 10. In this respect, the shape of the respective arms 16*a*', 16*a*", 16*b*', 16*b*", 16*c*', 16*c*" of the retaining arches 16*a*, 16*b*, 16*c* can be precisely adapted to the shape of transition area 104 of a prosthetic heart valve 100 to be affixed to the stent 10. Also, it should be noted that the embodiments depicted in FIGS. 8 to 10 show an even higher number of bending edges 33 providing a plurality of arm segments. Further to this, the bending edges 33 depicted in FIGS. 8 to 10 are formed so as to provide a plurality of fastening notches along the retaining arches 16*a*, 16*b*, 16*c*, as will be described in more detail below.

The stent 10 depicted in FIGS. 5*a-e* is also provided with an annular collar 40 which is arranged at the lower end section of the stent body. The at least one annular collar 40 may serve as an additional anchoring measure for the stent.

In the embodiment depicted in FIGS. 6*a* and 6*b*, the stent 10 corresponds to a stent pursuant the exemplary embodiment previously described with reference to FIGS. 5*a-e*. On the other hand, the prosthetic heart valve 100 affixed to the stent 10 corresponds to the exemplary embodiment of the prosthetic heart valve 100 previously described with reference to FIG. 1 and FIGS. 2*a, b*.

Hence, as shown in the exemplary embodiment of the transcatheter delivered endoprosthesis 1 depicted in FIGS. 6*a, b*, the prosthetic heart valve 100 affixed to the stent 10 comprises three leaflets 102 made from a biological or synthetic material.

To reduce longitudinal displacement of the prosthetic heart valve 100 relative to the stent 10, the stent 10 comprises a plurality of fastening portions in the form of lower leaflet attachment regions 11*c*, essentially extending in the longitudinal direction L of stent 10. In addition, the stent 100 is provided with commissure attachment regions 11*b*. By means of the lower leaflet attachment regions 11*c* and the commissure attachment regions 11*b* (both acting as fastening portion), the tissue components of the prosthetic heart valve 100 are affixed to the stent 10.

In detail, the prosthetic heart valve 100 is fastened to the stent 10 by means of sutures 101, threads or a thin wire which is guided through fastening holes 12*a*, 12*c* of the lower leaflet attachment regions 11*c* and the commissure attachment regions 11*b* respectively. This allows fixing of the tissue components of the prosthetic heart valve 100 to the stent 10 at a predefined position relative to the stent 10.

Alternatively, as will be described with reference to FIGS. 8 to 10, the sutures 101, threads or wires may be guided by fastening notches provided along the retaining arches 16*a*, 16*b*, 16*c*, instead of the aforementioned fastening holes 12*a*. Hence, in the alternative embodiments according to FIGS. 8 to 10, the fastening holes 12*a* of the lower leaflet attachment region 11*c* are replaced by notches (provided by bending edges 33), whereas the commissure attachment region 11*b* may still be provided with fastening holes 12*c*.

It can further be seen from the FIG. 6*a* or FIG. 6*b* illustration how the prosthetic heart valve 100 can be affixed to the stent 10 by means of sutures 101. In the depicted embodiment, a pericardial prosthetic heart valve 100 is used which is sewn to fastening holes 12*a*, 12*c* provided in the fastening portions of the retaining arches 16*a*, 16*b*, 16*c*, i.e. the lower leaflet attachment regions 11*c* on the one hand and in the commissure attachment regions 11*b* on the other hand. In order to improve the attachment of the prosthetic heart valve 100 to the stent 10, the skirt portion 103 may be sewn to the annular collar 40 as well as other parts of the stent structure. The prosthetic heart valve 100 may be tubular with a substantially circular cross-section.

On the other hand, it is conceivable to mount the prosthetic heart valve 100 to the outer surface of a support stent 1. That is, the skirt portion 102 could be in direct contact with the diseased native heart valve and could be attached to the stent 10 by means of sutures, Mounting the prosthetic heart valve 100 to the outer surface of the stent 10 supports the load transfer from the leaflet 102 to the stent 1. This greatly reduces stresses on the leaflets 102 during closing and consequently improves the durability thereof. Also, it is possible to design the valve to obtain improved hemodynamics in the case of mounting the skirt portion and commissures to the outer surface of the stent. Additionally, the heart valve material which is in direct contact with the diseased native heart valve provides a good interface for sealing against leakage (i.e., paravalvular leakage), tissue ingrowth and attachment.

The material for the prosthetic heart valve 100 and, in particular the material for the leaflets 102 of the prosthetic heart valve 100 can be made from synthetics, animal valves or other animal tissues such as pericardium. The animal tissues can be from a number of types of animals. Preferably, the leaflet material of the prosthetic heart valve 100 is from either bovine or porcine pericardium, but other animals can also be considered, for example equine, kangaroo, etc.

Reference is made in the following to FIGS. 12 to 17 for describing exemplary embodiments of reinforcement elements 107.1 to 107.8 which may be utilized in the endoprosthesis 1 according to the present disclosure. The reinforcement elements 107.1 to 107.8 may reduce the stress concentration in the tissue material of the prosthetic heart valve 100 at the connection between the bendable transition area 104 and the lower leaflet attachment region 11*c* (FIGS. 12 to 14) and/or the commissure attachment regions 11*b* (FIGS. 15 to 17) of the stent 10.

The reinforcement elements 107.1 to 107.8 can be at discrete locations or continuously along the path of the stitching. For example, they can be placed opposite to the retaining arches of the stent on the other side of the prosthetic heart valve material. The depicted reinforcement elements 107.1 to 107.8 are applied in order to strengthen the attachment to the stent and reduce stress concentrations in the leaflet material that would occur by suturing directly to the bendable transition portion 104 or leaflet support portion 103 respectively. Further to this, the reinforcement elements 107.1 to 107.8 may avoid direct contact between knots of the sutures and the tissue of the prosthetic heart valve. Also, direct contact between the heart valve tissue and the stent structure or any other metallic component of the endoprosthesis can be avoided by the reinforcement elements.

The reinforcement elements 107.1 to 107.8 are preferably designed with rounded edges to avoid abrasion of the valve tissue during opening and closing of the prosthetic heart valve 100.

In more detail, FIG. 12 shows a cross sectional view along the line A-A in FIG. 6*b* or FIG. 11*b* respectively, i.e. a cross sectional view of one retaining arch 16*a*, 16*b*, 16*c* of the stent 10 utilized in an endoprosthesis 1 of the present disclosure. As depicted in FIG. 12, a first exemplary embodiment of reinforcement elements 107.1 may be utilized for fixing the prosthetic heart valve 100 to the stent 10.

According to this exemplary embodiment, the connection of the prosthetic heart valve tissue to the stent 10 is reinforced by means of at least one reinforcement element in the form of a inner cushion 107.1 which is intended to reduce stress concentrations in the tissue material of the prosthetic heart valve 100, said that stress concentrations may occur from direct stitching in the tissue material of the prosthetic heart valve 100. The at least one reinforcement element in the form of the inner cushion 107.1 is placed between a suture 101.1 and the tissue material of the prosthetic heart valve 100. In this respect, any stress caused by the suture 101.1 is distributed over a larger area of the tissue material of the prosthetic heart valve 100. The at least one reinforcement element in the form of the inner cushion 107.1 is placed opposite to the corresponding retaining arch 16*a*, 16*b*, 16*c* of the stent 10 on the other side of the tissue material of the prosthetic heart valve 100. That is, the at least one reinforcement element in the form of the inner cushion 107.1 is mounted to the inner surface of the bendable transition area 104 of the prosthetic heart valve 100. The at least one inner cushion 107.1 representing a first embodiment of the reinforcement elements may be folded in such a way that at least one round edge 108 is formed. This at least one round edge 108 is designed to avoid abrasion of tissue material of the leaflets 102 during opening and closing of the prosthetic heart valve 100.

The reinforcement element in the form of the inner cushion 107.1 may be made of one or multiple layer materials, consisting of materials like polyester velour, PTFE, pericardial tissue, or any other material suitable for forming round edges, distributing or buffering stresses in the tissue material of the prosthetic heart valve 100. The reinforcement element in the form of the inner cushion 107.1 can be applied to span across the gap formed between the lower end of two neighbouring arms 16*a*', 16*a*"; 16*b*', 16*b*"; 16*c*', 16*c*" of one retaining arches 16*a*, 16*b*, 16*c* (see FIG. 6*a*) for supporting the tissue material of the prosthetic heart valve 100 across the gap.

Reference is further made to FIG. 15, which is a cross sectional view along the line B-B (commissure attachment region 11*b*) shown in FIG. 6*b* or 11*b* for explaining a second exemplary embodiment of the reinforcement elements which may be utilized in the transcatheter delivered endoprosthesis 1 of the present disclosure, for fixing a prosthetic heart valve 100 to a cardiac valve stent 10.

Again, the reinforcement element may be made of one or multiple layer materials and consisting of materials like polyester velour, PTFE, pericardial tissue or any other material suitable for forming round edges. As shown in FIG. 15, at the upper end section of the prosthetic heart valve 100, the tissue material of the prosthetic heart valve 100 may be attached to the commissure attachment region 11*b* in such a manner that when the leaflets 102 are folded together, during closure of the heart valve, a small cavity 109 is created. Inside this cavity 109, a reinforcement element in the form of an inner cushion 107.2 is inserted. It has to be noted that the cavity 109 is formed, so as to be as small as possible in order to avoid leakage during the closing phase of the heart valve prosthesis 1.

FIG. 13 is a cross sectional view along the line A-A shown in FIG. 6*b* or 11*b* for explaining a third exemplary embodiment of reinforcement elements which may be utilized in the endoprosthesis 1 according the present disclosure. According to this exemplary embodiment, the reinforcement element may consist of a wire rail 107.3 which is substantially at the same place as the reinforcement elements consisting of an inner cushion 107.1 illustrated in FIG. 12. In this case, the sutures 101.1 are coiled around the wire rail 107.3 on the inner surface of the prosthetic heart valve 100, whilst on the outer surface of the biological prosthetic heart valve, the sutures 101.1 are attached to a retaining arch 16*a*, 16*b*, 16*c* by means of a suitable stitch pattern. That is, the wire rail 107.3 is mounted to the inner surface of the bendable transition area 104 of the prosthetic heart valve. The wire rail 107.3 is preferably made of Nitinol, thus allowing for the wire rail 107.3 to collapse together with the stent 10. Again, the reinforcement element of the third embodiment is designed with rounded edges to avoid abrasion of the leaflet tissue during opening and closing of the prosthetic heart valve 100.

FIG. 14 is a cross sectional view along the line A-A shown in FIG. 6*b* or 11*b* for explaining a fourth exemplary embodiment of reinforcement elements which may be utilized in the endoprosthesis 1 according to the present disclosure. Hence, instead of using inner cushions 107.1, 107.2 which consist of materials like polyester velour or PTFE, the reinforcement element, according to the fourth exemplary embodiment, can be arranged as essential copies of the retaining arches 16*a*, 16*b*, 16*c*. In this embodiment, however, the reinforcement element is an inner attachment rail 107.4 which is thinner than a corresponding retaining arch 16*a*, 16*b*, 16*c* since a thick material would inhibit the endoprosthesis 1 from being collapsed to a small size. In particular, the inner attachment rail 107.4 has the same fastening holes 12*a* and notches longitudinally distributed at given locations as the corresponding retaining arch 16*a*, 16*b*, 16*c*.

Moreover, the inner attachment rail 107.4 is placed on the inner surface of the tissue material of the prosthetic heart valve 100, opposite to the retaining arches 16*a*, 16*b*, 16*c*. Thus the prosthetic heart valve 100 is clamped in between the retaining arches 16*a*, 16*b*, 16*c* and the inner attachment rail 107.4, wherein the retaining arches 16*a*, 16*b*, 16*c* and the inner attachment rail 107.4 are connected by means of sutures 101.1.

In an alternative embodiment, however, the connection between retaining arches 16 and the inner attachment rail 107.4 may utilize rivets, welding or soldering, so as to clamp the biological prosthetic heart valve tissue without penetrating it with needles or suture. In turn, it is preferable, that the inner attachment rail 107.4 may be made of Nitinol, in order to allow simultaneously collapsing with the stent 10.

Of course, the edges of the inner attachment rail 107.4 may be rounded in order to prevent abrasion of the leaflets 102. In addition, the inner attachment rail 107.4 could be wrapped in tissue or synthetic material to further reduce the potential wear during the contact with the leaflet material upon the heart valve operation.

FIG. 16 shows a cross sectional view along the line B-B shown in FIG. 6*b* or 11*b* for explaining a fifth exemplary embodiment of reinforcement elements which may be utilized in the endoprosthesis 1 of the present disclosure.

As depicted in FIG. 16, the reinforcement element according to this exemplary embodiment is an outer wrapping element 107.5 attached to the back side of the prosthetic heart valve tissue, at the commissure attachment region 11*b* of the stent 10. The leaflets 102 are folded without forming a cavity. Rather, the outer wrapping element 107.5 is clamped on the outer surface of the biological prosthetic heart valve 100, more particularly to the outer surface of the bendable transition area 104, pressing the leaflets 102 together. Thereby, a strengthened region is created by folding the prosthetic heart valve tissue and wrapping it with the outer wrapping element 107.5.

The outer wrapping element 107.5 is attached the commissure attachment region 11*b* by means of sutures 101.1. Additional lateral sutures 101.2 are provided to press the outer wrapping element 107.5 onto the outer surface of the bendable transition area 104 of the prosthetic heart valve 100.

The outer wrapping element 107.5 is preferably made of a polymer material such as PTFE, PET fabric or sheet or a piece of pericardial tissue. However, it could also be a more rigid u-shaped clip or bendable material that can pinch the folded tissue material of the prosthetic heart valve 100 without the use of additional lateral sutures 101.2. In addition, this outer wrapping element 107.5 acts as a bumper to limit the opening of the leaflets 102 in order to prevent them from hitting stent 10.

The dashed lines in FIG. 16 represent the closed position of the leaflets 102.

FIG. 18 shows an alternative attachment solution where the prosthetic heart valve 100 is mounted to the stent 10 from the outside. For this purpose, the tissue material of the prosthetic heart valve 100 is folded and passes through slots 110 provided in the retaining arches 16*a*, 16*b*, 16*c*. The edges of the slots 110 are preferably rounded and smooth to avoid abrading or wearing the tissue material of the prosthetic heart valve 100. Furthermore, to further reduce wear of the tissue, the slots 110 could be wrapped in thin pericardial tissue. In this design, there is some material thickness on the outside of the stent 10, which could impinge on the anchoring of the stent 10 at the position of the diseased natural prosthetic heart valve.

One embodiment might include thinning the retaining arches 16*a*, 16*b*, 16*c* on the outer surface relative to the rest of the stent structure, to accommodate the tissue material on the outside surface. This would also allow for a recess when the stent 10 is compressed so that the collapsed prosthesis does not require a larger delivery catheter.

FIG. 17 is a cross sectional view along the line B-B depicted in FIG. 6*b* or 11*b* showing a sixth exemplary embodiment of reinforcement elements 107.6, 107.7 which may be utilized in the endoprosthesis according present disclosure.

In detail, FIG. 17 shows an embodiment where reinforcement elements 107.6 and 107.7 are attached to the inner surface and the outer surface of the transition area 104 of the prosthetic heart valve 100. Although FIG. 17 only shows a cross sectional view along the line B-B, it should be noted that the depicted sixth embodiment of the reinforcement elements may also be applied along the retaining arches 16*a*, 16*b*, 16*c* (line A-A) of the stent. In this regard, the outer reinforcement element 107.6 may consist of a wide strip of 200 μm thick porcine pericardium that is long enough to cover the entire length of the retaining arches 16*a*, 16*b*, 16*c* (lower leaflet attachment region 11*c*) and the commissure attachment region 11*b*. This strip of pericardium which forms the outer reinforcement element 107.6 can be cut into three short segments of about 5 mm each to match the length of the commissure attachment region 11*b* and three long segments of about 45 mm each to match the length along the retaining arches 16*a*, 16*b*, 16*c* (lower leaflet attachment region 11*c*) from one commissure attachment region 11*b* to the adjacent.

The 4 mm wide porcine pericardium outer reinforcement element 107.6 may be folded in half and sutured using a fine clinging suture 101.4 (e.g. a 8-0 suture) with a running stitch very close to the free edges. The sutured outer reinforcement element 107.6 is then placed along the inner surface of the retaining arches 16*a*, 16*b*, 16*c* and/or the commissure attachment region 11*b* with a 8-0 running stitch placed along the stent surface. The outer reinforcement element 107.6 is sutured to the stent to line the inner surface using 6-0 surrounding sutures 101.3 and zig-zag crossing stitches that wrap around the commissure attachment region 11*b* and/or the retaining arches 16*a*, 16*b*, 16*c* (not through the eyelets).

With regards to the inner reinforcement element 107.7, the material is preferably a strip of 200 μm porcine pericardium, which is about 3.5 mm wide and cut and overlapped or rolled to three layers. The length of the piece of tissue depends on whether only the commissure attachment region 11*b* or the retaining arches 16*a*, 16*b*, 16*c* are reinforced. For only the commissure attachment region 11*b*, three short segments of about 5 mm are needed. The strip is held in the overlapped or rolled shape by clinging sutures 101.4 with an 8-0 running stitch. The inner reinforcement element 107.7 may be constructed such as to exhibit minimal size to avoid causing too big of a cavity 109 in between the leaflets 102 during closure of the prosthetic heart valve 100. The inner reinforcement element 107.7 is secured on the inner surface of the bendable transition area 104 of the prosthetic heart valve 100 and to the stent 10 through the eyelets 12*a*. Preferably, 4-0 sutures 101.1 with a locking stitch on the outer diameter are used for this purpose. These sutures 101.1 are the most critical in the assembly and need to be very tight with no slack and locking. Instead of a single 4-0 suture 101.1, it is contemplated that two 6-0 sutures for redundancy and similar overall total strength are used. Furthermore, the 4-0 sutures 101.1 hold the outer reinforcement element 107.6 in place.

When opening and closing the leaflets 102 of the prosthetic heart valve 100, the outer reinforcement element 107.6 acts as a bumper to absorb shocks which affect the leaflets 102 during opening. In turn, the inner reinforcement element 107.7 spreads out the compressive forces induced by the sutures 101.1, thus avoiding stress concentration at the transition area 104 of the prosthetic heart valve 100.

In the following, reference is made to FIGS. 7*a, b* for describing a further exemplary embodiment of a cardiac valve stent capable of supporting and anchoring a prosthetic heart valve. In detail, FIG. 7*a* shows a first perspective side view of a transcatheter delivered endoprosthesis 1 for treating a narrowed cardiac valve or a cardiac valve insufficiency, where the endoprosthesis 1 comprises a cardiac valve stent 10 according to the first exemplary embodiment of the stent (FIGS. 5*a-e*) for holding a prosthetic heart valve. FIG. 7*b* shows a second perspective side view of the endoprosthesis 1 depicted in FIG. 7*a*.

In contrast to the exemplary embodiment shown in FIGS. 6*a* and 6*b*, the endoprosthesis depicted in FIGS. 7*a, b* shows the prosthetic heart valve 100 according to the second valve embodiment. That is, the prosthetic heart valve 100 attached to the stent 10 of FIGS. 7*a, b* consists of three separate pieces 120 being sewn together along their contiguous edges 112. These three separate pieces 120 may either be cut from a single pericardial sack (xenograft or homograft) or from a plurality of pericardial sacks.

The endoprosthesis 1 according to the exemplary embodiment illustrated by FIGS. 7*a* and 7*b* comprises a stent 10 according to the first stent embodiment depicted by FIGS. 5*a* to 5*e*. This stent 10 comprises a plurality of positioning arches 15*a*, 15*b*, 15*c* configured to be positioned within a plurality of pockets of the patient's native heart valve and positioned on a first side of a plurality of native heart valve leaflets, and a plurality of retaining arches 16*a*, 16*b*, 16*c* configured to be positioned on a second side of the plurality of native heart valve leaflets opposite the first side, wherein furthermore a plurality of leaflet guard arches 50*a*, 50*b*, 50*c* are provided, each interspaced between the two arms 15*a*', 15*a*", 15*b*', 15*b*", 15*c*', 15*c*" of one of the plurality of positioning arches 15*a*, 15*b*, 15*c*. In addition, the respective arms 16*a*', 16*a*", 16*b*', 16*b*", 16*c*', 16*c*" of the retaining arches 16*a*, 16*b*, 16*c* are preferably provided with a plurality of bending edges 33 in order to divide each arm 16*a*', 16*a*", 16*b*', 16*b*", 16*c*', 16*c*" into a plurality of arm segments, wherein the structure of the stent 10 is programmed such that the respective arms 16*a*', 16*a*", 16*b*', 16*b*", 16*c*', 16*c*" of the retaining arches 16*a*, 16*b*, 16*c* have a curved shape at least in the expanded state of the stent 10. In particular, the shape of the respective arms 16*a*', 16*a*", 16*b*', 16*b*", 16*c*', 16*c*" of the retaining arches 16*a*, 16*b*, 16*c* shall be such defined that the arms follow the shape of the leaflets 102 of a prosthetic heart valve 100 to be affixed to the stent 10.

In the structure of the stent 10 according to the embodiment depicted in FIGS. 7*a* and 7*b*, one leaflet guard arch 50*a*, 50*b*, 50*c* is provided in between each positioning arch 15*a*, 15*b*, 15*c*. Hence, one leaflet guard arch 50*a*, 50*b*, 50*c* is allocated to each positioning arch 15*a*, 15*b*, 15*c*.

Each leaflet guard arch 50*a*, 50*b*, 50*c* has a substantially U-shaped or V-shaped structure which is closed to the lower end 2 of the stent 10. In particular, each leaflet guard arch 50*a*, 50*b*, 50*c* has a shape that is roughly similar to the shape of the positioning arch 15*a*, 15*b*, 15*c* and each leaflet guard arch 50*a*, 50*b*, 50*c* is arranged within the arms of the corresponding positioning arch 15*a*, 15*b*, 15*c*. Furthermore, each of the leaflet guard arches 50*a*, 50*b*, 50*c* extends in the same direction as the positioning arch 15*a*, 15*b*, 15*c*.

The leaflet guard arches 50*a*, 50*b*, 50*c* are preferably programmed so that they extend in a radial direction outside the circumference of the stent 10 when the stent 10 is in its expanded state. In this way, an increased contact force can be applied to the leaflets of the native (diseased) cardiac valve when the stent 10 is in its expanded and implanted state. This, in turn, allows an increased security in the fixing of the stent 10 in situ.

When the stent 10 is in its expanded and implanted state, the leaflet guard arches 50*a*, 50*b*, 50*c* actively keep the diseased leaflets, i.e. the leaflets of the native cardiac valve, from impinging the leaflets 102 of a prosthetic heart valve 100 attached to the stent 10, when the positioning arches 15*a*, 15*b*, 15*c* are placed outside the native leaflets. In addition, the leaflet guard arches 50*a*, 50*b*, 50*c* may also provide additional anchoring and securing against migration.

An alternative embodiment of a stent 10 is shown in FIGS. 8*a-d* (hereinafter also named "second stent embodiment"). The stent 10 according to the embodiment depicted in FIGS. 8*a-d* essentially comprises the same features as the stent described with reference to FIGS. 5*a-e*, In particular, the stent 10 also comprises positioning arches 15*a*, 15*b*, 15*c* as well as retaining arches 16*a*, 16*b*, 16*c* and an annular collar 40.

In contrast to the first embodiment of a stent 10 depicted in FIGS. 5*a-e*, the stent 10 of the second stent embodiment comprises retaining arches 16*a*, 16*b*, 16*c* which are not provided with a number of lower leaflet attachment regions 11*c*, each having a number of additional fastening holes 12*a* or eyelets provided for fastening the tissue components of a prosthetic heart valve 100. Rather, the stent of the second stent embodiment is provided with retaining arches 16*a*, 16*b*, 16*c* whose arms 16*a*', 16*a*", 16*b*', 16*b*", 16*c*', 16*c*" are segmented by a plurality of bending edges 33 which are not only used for defining a bending point of two neighboring arm segments, but also as fastening notches which can be used for fixing the prosthetic heart valve prosthesis 100 to the stent 10. It is conceivable, of course, that the fastening notches are adapted to the thickness of the suture, thread or wire. In particular, the additional notches may be radiused to minimize damage to the suture, thread or wire. Due to the increased number of bending edges 33 providing fastening notches along the retaining arches 16*a*, 16*b*, 16*c*, the retaining arches 16*a*, 16*b*, 16*c* allow for more continuous bending along the entire length of their respective arms 16*a*', 16*a*", 16*b*', 16*b*", 16*c*', 16*c*", simplifying the attachment of said retaining arches 16*a*, 16*b*, 16*c* to the bendable transition area 104 of the prosthetic heart valve 100.

In more detail, FIG. 8*a* shows a flat roll-out view of a cardiac valve stent 10 pursuant the second embodiment of the stent 10, whereby the stent 10 is in its non-expanded state. This flat roll-out view corresponds to a two-dimensional projection of a cutting pattern which can be used in the manufacture of the stent 10 pursuant the second embodiment. This enables a one-piece stent 10 to be cut from a portion of tube, in particular a metal tube.

FIG. 8*b* shows a first perspective side view of a cardiac valve stent 10 according to the second stent embodiment, whereby the cardiac valve stent 10 is shown in its expanded state, and FIG. 8*c* shows a second perspective side view the stent 10 according to the second stent embodiment, whereby the cardiac valve stent is also shown in its expanded state.

FIG. 8*d* shows a flat roll-out view of a cardiac valve stent 10 according to the second embodiment of the stent. Contrary to the flat roll-out view depicted in FIG. 8*a*, however, the flat roll-out view according to FIG. 8*d* shows the cardiac valve stent 10 is in its expanded state.

Thus, the stent 10 according to the second stent embodiment comprises a plurality of positioning arches 15*a*, 15*b*, 15*c* and a plurality of retaining arches 16*a*, 16*b*, 16*c*. Each of the plurality of positioning arches 15*a*, 15*b*, 15*c* is configured to be positioned within a plurality of pockets of the patient's native heart valve and positioned on a first side of a plurality of native heart valve leaflets. On the other hand, each of the plurality of retaining arches 16*a*, 16*b*, 16*c* is configured to be positioned on a second side of the plurality of native heart valve leaflets opposite the first side.

Furthermore, a plurality of leaflet guard arches 50*a*, 50*b*, 50*c* are provided, each interspaced between the two arms 15*a*', 15*a*", 15*b*', 15*b*", 15*c*', 15*c*" of one of the plurality of positioning arches 15*a*, 15*b*, 15*c*. In addition, the respective arms 16*a*', 16*a*", 16*b*', 16*b*", 16*c*', 16*c*" of the retaining arches 16*a*, 16*b*, 16*c* are preferably provided with a plurality of bending edges 33 in order to divide each arm 16*a*', 16*a*", 16*b*', 16*b*", 16*c*', 16*c*" into a plurality of arm segments, wherein the structure of the stent 10 is programmed such that the respective arms 16*a*', 16*a*", 16*b*', 16*b*", 16*c*', 16*c*" of the retaining arches 16*a*, 16*b*, 16*c* have a curved shape at least in the expanded state of the stent 10. In particular, the shape of the respective arms 16*a*', 16*a*", 16*b*', 16*b*", 16*c*', 16*c*" of the retaining arches 16*a*, 16*b*, 16*c* shall be such defined that the arms follow the shape of the bendable transition area 104 of the prosthetic heart valve 100 to be affixed to the stent 10.

In detail and as depicted in the flat roll-out view shown in FIG. 8*a*, the respective arms 16*a*', 16*a*", 16*b*', 16*b*", 16*c*', 16*c*" of the retaining arches 16*a*, 16*b*, 16*c* are provided with a plurality of bending edges 33. These bending edges 33 may be uniformly distributed along the length of each retaining arch arm 16*a*', 16*a*", 16*b*', 16*b*", 16*c*', 16*c*" thereby dividing each arm 16*a*', 16*a*", 16*b*', 16*b*", 16*c*', 16*c*" into a plurality of arm segments. The arm segments of a corresponding retaining arch arm 16*a*', 16*a*", 16*b*', 16*b*", 16*c*', 16*c*" are interconnected thereby constituting a retaining arch arm which describes an essentially straight line in the not-expanded state of the stent 10. In this regard, reference is made to the flat roll-out view depicted in FIG. 8*a* which shows the uncurved configuration of the respective arms 16*a*', 16*a*", 161D', 16*b*", 16*c*', 16*c*" of the retaining arches 16*a*, 16*b*, 16*c*.

When manufacturing the stent 10, the stent structure and in particular the structure of the retaining arches 16*a*, 16*b*, 16*c* is programmed such that the respective retaining arch arms 16*a*', 16*a*", 16*b*', 16*b*", 16*c*', 16*c*" have a curved shape in the expanded state of the stent 10. The shape of the respective retaining arch arms 16*a*', 16*a*", 16*b*', 16*b*", 16*c*', 16*c*" is such defined that the arms follow the shape of the leaflets of a prosthetic heart valve 100 to be affixed to the stent 10 (cf. FIG. 8*d*).

Hence, the respective retaining arch arms 16*a*', 16*a*", 16*b*', 16*b*", 16*c*', 16*c*", onto which the prosthetic heart valve 100 is sewn or sewable, will change their shape when the stent 10 expands, wherein the retaining arches 16*a*, 16*b*, 16*c* are curved in the expanded state of the stent 10, but relatively straight when the stent 10 is collapsed. Thus, when in the expanded state, the retaining arches 16*a*, 16*b*, 16*c* of the stent 10 are adapted to fit to the shape of the bendable transition area 104 of the prosthetic heart valve 100. In detail, in their expanded state, the retaining arches 16*a*, 16*b*, 16*c* are adapted to progress in an essentially u-shaped manner, similar to the shape of a natural aortic or pulmonary heart valve, for reducing tissue stresses during the opening and closing motion of the leaflets 102.

As can be seen, for example, in FIG. 8*d*, the essentially u-shaped curvature of the respective retaining arch arms 16*a*', 16*a*", 16*b*', 16*b*", 16*c*', 16*c*" is achieved by segmenting the arms 16*a*', 16*a*", 16*b*', 16*b*", 16*c*', 16*c*". In detail, the arms 16*a*', 16*a*", 16*b*', 16*b*", 16*c*', 16*c*" are segmented by providing a plurality of bending edges 33. In the expanded state of the stent 10, two neighboring arm segments are angled relative to each other, wherein the bending point of these two neighboring arm segments is defined by the bending edge 33 which is provided in between neighboring arm segments. Hence, the greater the number of bending edges 33 provided in an arm 16*a*', 16*a*", 16*b*', 16*b*", 16*c*', 16*c*" of a retaining arch 16*a*, 16*b*, 16*c*, the greater the number of arm segments which may extend in different directions in the expanded state of the stent 10. In this respect, the shape of the respective retaining arch arms 16*a*', 16*a*", 16*b*', 16*b*", 16*c*', 16*c*" can be adapted to the shape of the leaflets 102 of the prosthetic heart valve 100 to be affixed to the stent 10.

According to the design of the second stent embodiment, the respective arms 16*a*', 16*a*", 16*b*', 16*b*", 16*c*', 16*c*" of the retaining arches 16*a*, 16*b*, 16*c* are not provided with fastening holes 12*a*, as it is the case, for example, in the first embodiment of the stent (FIGS. 5*a* to 5*e*). Rather, in the second stent embodiment, the bending edges 33 provided in the retaining arch arms 16*a*', 16*a*", 16*b*', 16*b*", 16*c*', 16*c*" are not only used for defining a bending point of two neighboring arm segments, but also as fastening notches which can be used for fixing a prosthetic heart valve 100 to the stent 10.

A comparison with, for example, the flat roll-out view pursuant to FIG. 5*a* (first stent embodiment) illustrates directly that the respective retaining arch arms 16*a*', 16*a*", 16*b*', 16*b*", 16*c*', 16*c*" of the stent design according to the second stent embodiment is at least partly much more thinner compared with the respective retaining arch arms of the first stent embodiment which are provided with lower leaflet attachment regions having fastening holes 12*a*. By reducing the width of the retaining arch arms 16*a*', 16*a*", 16*b*', 16*b*", 16*c*', 16*c*", the bendability of the arms is increased which allows a more precise adaptation of the shape of the respective retaining arch arms 16*a*', 16*a*", 16*b*', 16*b*", 16*c*', 16*c*" to the shape of the bendable transition area 104 of the prosthetic heart valve 100 to be affixed to the stent 10.

Moreover, by using the bending edges 33 provided in the retaining arch arms 16*a*', 16*a*", 16*b*', 16*b*", 16*c*', 16*c*" as fastening notches for fixing a heart valve prosthesis to the stent 10, a greater number of attachment points compared with the number of fastening holes 12*a* can be generated. In this regard, high stress concentrations at each single attachment point can be effectively avoided. Furthermore, the fastening notches provide space and allow for the sutures 101 to be protected during collapsing of the valve 100 into the catheter. Therefore, adjacent members of the stent 10 do not impinge on and damage the sutures 101 used to attach the prosthetic heart valve 100 to the retaining arches 16*a*, 16*b*, 16*c*, during collapsing and deployment of the prosthetic heart valve 100.

In addition, in the second embodiment of the stent, the attachment points (bending edges 33) to be used for fixing a heart valve prosthesis to the retaining arch arms 16*a*', 16*a*", 16*b*', 16*b*", 16*c*', 16*c*" of the stent 10 are more uniformly distributed along the respective retaining arch arms 16*a*', 16*a*", 16*b*', 16*b*", 16*c*', 16*c*", thereby providing a more uniform fixation of a heart valve prosthesis to the stent. Hence, the risk of an axial displacement of the heart valve prosthesis relative to the stent may be further reduced. Each individual bending edge 30 provided in the respective retaining arch arms 16*a*', 16*a*", 16*b*', 16*b*", 16*c*', 16*c*" thereby serves to guide a thread or thin wire with which the tissue component(s) of the prosthetic heart valve is affixed or sewn to the corresponding retaining arch arm 16*a*', 16*a*", 16*b*', 16*b*", 16*c*', 16*c*" of the stent 10. In detail, the means (thread or thin wire) provided for fastening the tissue component(s) of the prosthetic heart valve to the respective retaining arch arms 16*a*', 16*a*", 16*b*', 16*b*", 16*c*', 16*c*" is guided by way of the bending edge 33 acting as fastening notch so that a longitudinal displacement of the prosthetic heart valve relative to the stent 10 is substantially minimized. This also allows exact positioning of the prosthetic heart valve relative the stent 10.

In addition, the stent 10 according to the second stent embodiment may further include at least one auxiliary arch 18*a*, 18*b*, 18*c* interspaced between two adjacent retaining arches 16*a*, 16*b*, 16*c*, wherein the at least one auxiliary arch 18*a*, 18*b*, 18*c* includes a first arm 18*a*', 18*b*', 18*c*' connected at a first end thereof to a first retaining arch 16*a*, 16*b*, 16*c* and a second arm 18*a*", 18*b*", 18*c*" connected at a first end thereof to a second retaining arch 16*a*, 16*b*, 16*c*, and wherein the first and second arms 18*a*', 18*a*", 18*b*', 18*b*", 18*c*', 18*c*" of the at least one auxiliary arch 18*a*, 18*b*, 18*c* each include respective second ends connected to an annular collar 40 which is arranged at the lower end section of the stent body. As in the previously described stent design (first stent embodiment), this at least one collar 40 serves as an additional anchoring measure for a stent cut from a portion of a tube by using the cutting pattern depicted in FIG. 8*a*.

In detail, the respective first and second arms 18*a*', 18*a*", 18*b*', 18*b*", 18*c*', 18*c*" of the at least one auxiliary arch 18*a*, 18*b*, 18*c* are part of a strut or web structure which is provided between the first and second arms 18*a*', 18*a*", 18*b*', 18*b*", 18*c*', 18*c*" of two adjacent auxiliary arches 18*a*, 18*b*, 18*c* in order to support the prosthetic heart valve 100 to be affixed to the stent 10 (see, for example, FIGS. 11*a* and 11*b*). As can be seen, for example, from FIG. 8*d* the strut or web structure may be composed by a plurality of struts or strut-like members which are inter-connected such as to form a reinforcement structure. Each strut or strut-like element of the reinforcement structure serves as reinforcement member in order to increase the strength or resistance to deformation of the area between the first and second arms 18*a*', 18*a*", 18*b*', 18*b*", 18*c*', 18*c*" of two adjacent auxiliary arches 18*a*, 18*b*, 18*c*. The reinforcement structure thereby provides mechanical reinforcement to the stent 10. Moreover, the reinforcement members of the reinforcement structure between the first and second arms 18*a*', 18*a*", 18*b*', 18*b*", 18*c*', 18*c*" of two adjacent auxiliary arches 18*a*, 18*b*, 18*c* provides for an additional support for the skirt portion 103 of a prosthetic heart valve 100 to be attached to the stent 10. In fact, it is conceivable to attach the skirt portion 103 of a prosthetic heart valve 100 directly to the auxiliary arches 18*a*, 18*b*, 18*c* by means of sutures, threads or thin wires, as will be explained in more detail with reference to FIGS. 11*a* and 11*b* below.

The terms "strength" or "resistance to deformation" as used herein may be used to denote any of a number of different properties associated with the reinforcement members. For example, the terms may be used to refer to properties of the material from which the reinforcement members are made, such as the yield strength, the modulus of elasticity, the modulus of rigidity, or the elongation percentage. Similarly, the terms may be used to refer to the hardness of the reinforcement members. Hardness may be characterized as the "durometer" of the material, in reference to the apparatus used to measure the hardness of the material. The terms may also be used to denote geometric characteristics of the reinforcement members, such as the thickness of the reinforcement members. The terms "strength" or "resistance to deformation" may also be used to characterize any combination of the above properties as well as additional properties and/or characteristics.

The strength or resistance to deformation of the area between the first and second arms 18*a*', 18*a*", 18*b*', 18*b*", 18*c*', 18*c*" of two adjacent auxiliary arches 18*a*, 18*b*, 18*c* can be increased in any number of ways. As can be seen from FIG. 8*d*, the strength or resistance to deformation of the area between the first and second arms 18*a*', 18*a*", 18*b*', 18*b*", 18*c*', 18*c*" of two adjacent auxiliary arches 18*a*, 18*b*, 18*c* can be increased, for example, by providing a reinforcement structure formed by at least one, and preferably by a plurality of reinforcement elements (e.g. struts or strut-like members) which are interconnected to each other.

It is also conceivable that a reinforcement web is provided in order to increase the strength or resistance to deformation of the area between the first and second arms 18*a*', 18*a*", 18*b*', 18*b*", 18*c*', 18*c*" of two adjacent auxiliary arches 18*a*, 18*b*, 18*c*. This reinforcement web may also be composed by a plurality of reinforcement elements (e.g. struts or strut-like members) which are interconnected to each other thereby forming a rhomboidal pattern.

The strength or resistance to deformation of the area between the first and second arms 18*a*', 18*a*", 18*b*', 18*b*", 18*c*', 18*c*" of two adjacent auxiliary arches 18*a*, 18*b*, 18*c* can be increased, for example, by increasing the thickness of the reinforcement members, by eliminating stress concentration risers in the design of the stent 10, or by changing other aspects of the geometry of the reinforcement members. The strength can also be increased by changing the material properties of the stent 10 and/or the reinforcement members. For example, the reinforcement members can be made from a number of different materials, preferably shape memory materials, each having a different level of hardness. In this regard, it is conceivable to vary the stoichiometric composition of the material used for forming the stent and the reinforcement members such as to adapt the material properties of the stent 10 and/or the reinforcement members to the specific needs of each stent application. It is also conceivable to use different materials, for example nitinol and a shape-memory polymer, for forming the stent and the reinforcement members. In this manner, the selection of the reinforcement members can be tailored to the specific needs of each stent application. For example, in regions where a high external force is expected, reinforcement members having a high hardness may be preferred. The strength may also be increased by combining material properties with geometric changes.

As can be seen from FIG. 8*d*, the stent 10 according to the second stent embodiment is provided with a reinforcement structure which is constituted by a plurality of lattice cells 70 formed by a plurality of struts in the area between the arms 16*a*', 16*a*", 16*b*', 16*b*", 16*c*', 16*c*" of two neighbouring (adjacent) retaining arches 16*a*, 16*b*, 16*c*, thereby providing for an additional support for the bendable transition area 104 of a prosthetic heart valve 100 to be attached to the stent 10.

In addition, this structure of the lattice cells 70 formed by a plurality of struts in the area between the adjacent arms of two neighbouring retaining arches 16*a*, 16*b*, 16*c* may provide uniform stent structure which may minimize blood leakage in the implanted stage of the stent 10 having a heart valve prosthesis attached thereto.

The upper end sections of the respective struts which are forming the structure of the lattice cells 70 are connected to the respective arms of the retaining arches 16*a*, 16*b*, 16*c*. Preferably, the upper end sections of the struts comprise a widened diameter in order to strengthen the connection between the upper end sections of the struts and the arms of the retaining arches 16*a*, 16*b*, 16*c*.

The already mentioned annular collar 40, which is provided at the lower end section of the stent body, is connected with the stent body via the retaining arches 16*a*, 16*b*, 16*c* on the one hand and the second ends of the respective arms 18*a*', 18*a*", 18*b*', 18*b*", 18*c*', 18*c*" of the at least one auxiliary arch 18*a*, 18*b*, 18*c* on the other hand, wherein these arms 18*a*', 18*a*", 18*b*', 18*b*", 18*c*', 18*c*" of the at least one auxiliary arch 18*a*, 18*b*, 18*c* are part of the structure of the lattice cells 70. In particular, the stent 10 according to the second embodiment is provided with an annular collar 40 which is shortened in its length by having only a single row of cells.

As can be seen from the flat roll-out view pursuant to FIG. 8*a*, the annular collar 40 at the lower end section of the stent body exhibits a plurality of supporting webs 41 which run parallel to the longitudinal axis L of the stent 10 in the non-expanded state of the stent 10 and are inter-connected by transversal webs 42. As can be seen from the two-dimensional roll-out view pursuant to FIG. 8*c*, however, in the expanded state of the stent 10, the supporting webs 41 and the transversal webs 42 forms a rhomboidal or serpentine-like annular collar 40 which abuts against the vascular wall in the implanted state of the stent 10.

In order to further improve securing of the position of an implanted and expanded endoprosthesis 1 and preventing antegrade migration, the stent 10 according to the second stent embodiment is provided with a flared or tapered section with a radius shape at its lower end section 2. In detail and as depicted in FIGS. 8*b* and 8*c*, in the expanded state of the stent 10, the lower end section of the annular collar 40 constitutes the flared or tapered section of the stent 10. As has been described before, the prosthetic heart valve 100 according to the present disclosure, may comprise a flared or tapered lower end section so as to fit to the described stent shapes.

The stent 10 depicted in FIGS. 8*b* and 8*c* has at its lower end section 2 a flared or tapered section with a radius shape; however, it is also conceivable that the flared or tapered section is not uniformly around the circumference of the stent 10. For example, the stent 10 may have a flare only near the locations of the positioning arches 15*a*, 15*b*, 15*c*, wherein no flare is provided near the commissure regions, i.e. the regions in between the two arms 15*a*', 15*a*", 15*b*', 15*b*", 15*c*', 15*c*" of two neighboring positioning arches 15*a*, 15*b*, 15*c*.

As depicted in FIGS. 8*b* and 8*c*, the stent 10 according to the second stent embodiment comprises a continuous design of its lower end section 2. Due to this continuous design, in the implanted and expanded state of the stent 10, via the lower end section 2 of the stent 10 an uniform radial force is applied to the wall of the blood vessel into which the stent 10 is deployed.

If the implanted and expanded stent together with a prosthetic heart valve affixed thereto extend too far below the annulus of the heart, there may be the risk that the implanted endoprosthesis consisting of the stent 10 on the one hand and the prosthetic heart valve 100 on the other hand contacts the nerve bundles and heart block. The nerve bundles may enter at a location approximately 6 to 10 mm below the annulus of the heart.

In order to avoid the lower end section 2 of the implanted stent 10 touching the atrioventricular node, the stent 10 pursuant to the second stent embodiment is provided with an annular collar 40 which is shortened in its length by having only a single row of cells. In this regard, the total height of the stent 10 and thus the total height of the endoprosthesis 1 to be implanted into the body of the patient are reduced.

Moreover, in the programming process during which the shape of the desired (expanded) stent structure is fixed, the supporting webs 41 of the annular collar 40 may be programmed so that—when the stent 10 of the second embodiment is in its expanded state—only the upper section of the annular collar 40 extends in a radial direction outside the circumference of the stent 10, whereas the lower end section of the annular collar 40 bended relative to the upper section of the annular collar 40 in the radial direction inside the circumference of the stent 10. The lower end section of the annular collar 40 may be bent such that it extends, for example, approximately parallel to the longitudinal direction L of the stent 10. In this way, an increased contact force (radial force) is applied by the upper section of the annular collar 40 to the wall of the blood vessel into which the stent 10 is deployed, whereas the risk is reduced that the lower end section of the annular collar 40 can touch the atrioventricular node.

It is important to note, that the stent 10 according to the second stent embodiment comprises a number of notches 12*e* uniformly distributed around the lower end section of the annular collar 40. These notches 12*e* can be used for fixing a heart valve prosthesis (not shown in FIGS. 8*b* and 8*c*) to the stent 10, which may reduce the risk of an axial displacement of the heart valve prosthesis 100 relative to the stent 10. Since a plurality of notches 12*e* are used as additional fastening means it is possible to utilize the lower end sections of every supporting web 41 of the annular collar 40 for additionally fastening a heart valve prosthesis to the stent 10. This appears directly from the flat roll-out view pursuant to FIG. 8*a*.

A comparison with, for example, the flat roll-out view pursuant to FIG. 5*a* (first stent embodiment) illustrates directly that the provision of eyelets 12*f* at the lower end sections of every supporting web 41 of the annular collar 40 requires much more material for each eyelet 12*f* compared with the amount of material which is necessary for forming respective notches 12*e*. Since it is conceivable for the stent 10 to exhibit a structure integrally cut from a portion of tube, in particular from a metal tube, which incorporates all structural components of the stent 10, in particular the positioning arches 15*a*, 15*b*, 15*c*, the retaining arches 16*a*, 16*b*, 16*c* and the annular collar 40 with defined additional fastening means at the lower end thereof, an elaborate cutting pattern for forming the design of the stent 10 from the original tube portion is important. In particular, it must be taken into account that the structure of the stent 10 with all structural stent components must be cut from the limited lateral area of the original tube portion.

Hence, by providing notches 12*e* instead of eyelets 12*f* as additional fastening means at the lower end section of the annular collar 40, a greater number of notches 12*e* compared with the number of eyelets 12*f* can be generated. In detail, according to the second stent embodiment, the lower end sections of every supporting web 41 of the annular collar 40 is provided with a corresponding notch 12*e* acting as additional fastening means. In contrast, in the first embodiment of the stent (FIGS. 5*a* to 5*e*) only the lower end sections of every second supporting web 41 of the annular collar 40 can be provided with a corresponding eyelet 12*f* acting as additional fastening means.

In this regard, the stent design according to the second stent embodiment differs from the first stent design in that at the lower end section of every supporting web 41 of the annular collar 40 an additional fastening means is provided. This is due to the fact that, in the second embodiment of the stent 10, notches 12*e* are used as additional fastening means.

Hence, in the second stent embodiment, the additional fastening means to be used for fixing a heart valve prosthesis to the stent 10 are more uniformly distributed around the lower end section of the annular collar 40, thereby providing a more uniform fixation of a prosthetic heart valve to the stent. Hence, the risk of an axial displacement of the heart valve prosthesis relative to the stent may be further reduced. Each individual notch 12*e* provided at the lower end section of the annular collar 40 thereby serves to guide a thread or thin wire with which the tissue component(s) of the prosthetic heart valve is affixed or sewn to the lower end section of the annular collar 40 of the stent 10. In detail, the means (thread or thin wire) provided for fastening the tissue component(s) of the prosthetic heart valve 100 to the lower end section of the annular collar 40 is guided by way of the notches 12*e* so that a longitudinal displacement of the prosthetic heart valve relative to the stent 10 is substantially minimized. This also allows positioning of the prosthetic heart valve relative the stent 10. To this end, as can be seen in FIG. 1, the prosthetic heart valve 100 may further comprise an essentially zig-zag shaped pattern at a lower end section.

Moreover, by using corresponding notches 12*e* for the secure and defined fixing of the tissue component(s) of the prosthetic heart valve to the lower end section of the annular collar 40 of the stent 10, the means (threads or thin wires) used to fasten the tissue component(s) to the stent 10 are effectively prevented from being squeezed and thus degraded when the stent 10 with the prosthetic heart valve affixed thereto, i.e. the endoprosthesis 1, is compressed and brought into its collapsed shape such as to be ready for being inserted into a catheter system which is used for implanting the endoprosthesis 1. In this regard, the risk of structural deterioration in the threads or thin wires used to fasten the tissue component(s) of the prosthetic heart valve 100 to the stent 10 is reduced.

The cross-sectional shape of the notches 12*e* may be adapted to the cross-sectional shape of the thread or thin wire used to fasten the tissue component(s) of the prosthetic heart valve 100. This allows fixing of the tissue component (s) of the prosthetic heart valve 100 to the stent 10 at a precise predefined position relative to the stent 10. Because the fastening holes 12 are adapted to the thickness and/or the cross-sectional shape of the thread or thin wire used to affix the prosthetic heart valve 100 to the stent 10, relative movement between the stent 10 and the tissue component(s) of the prosthetic heart valve 100 due to the peristaltic motion of the heart can be effectively prevented when the endoprosthesis 1 is implanted. In the fully expanded and implanted state of the endoprosthesis 1, the tissue component(s) of the prosthetic heart valve 100 is/are thus fastened to the stent 10 with minimal play, based on which friction-induced wear of the thread or thin wire used to affix the prosthetic heart valve is minimized. As shown in, for example, in FIG. 8*a*, the notches 12*e* have a semi-circular cross-sectional shape.

As can be seen, in particular from FIGS. 8*b* to 8*d*, the stent 10 according to the second stent embodiment of the invention may further comprise at least one radial arch 32*a*, 32*b*, 32*c* which enables a particularly secure anchoring of the stent 10 in the site of implantation in the heart and which is substantially circumferentially aligned with at least one of the plurality of positioning arches 15*a*, 15*b*, 15*c*. In addition to its radial arches 32*a*, 32*b*, 32*c*, the stent 10 is further provided with a total of three leaflet guard arches 50*a*, 50*b*, 50*c*, each comprising two leaflet guard arms. It can be seen from the flat roll-out view shown in FIG. 8*a* that, in the structure of the stent according to the second stent embodiment, a leaflet guard arch 50*a*, 50*b*, 50*c* is provided in between each positioning arch 15*a*, 15*b*, 15*c*. Hence, in the stent according to the second stent embodiment, a leaflet guard arch 50*a*, 50*b*, 50*c* is allocated to each positioning arch 15*a*, 15*b*, 15*c*.

Referring to the flat roll-out view shown in FIG. 8*a*, the radial arches 32*a*, 32*b*, 32*c* of the stent 10 according to the second stent embodiment extend from the leaflet guard arches 50*a*, 50*b*, 50*c* towards the upper end 3 of the stent 10. As is shown most clearly in FIG. 8*a*, the stent 10 has three radial arches 32*a*, 32*b*, 32*c*, with each arch 32*a*, 32*b*, 32*c* located between the two arms of each leaflet guard arch 50*a*, 50*b*, 50*c*. Each radial arch 32*a*, 32*b*, 32*c* has a shape that is roughly inverse to each positioning arch 15*a*, 15*b*, 15*c* and extends in the opposite direction to each one of the positioning arches 15*a*, 15*b*, 15*c*.

On the other hand, each leaflet guard arch 50*a*, 50*b*, 50*c* has a substantially U-shaped or V-shaped structure which is closed to the lower end 2 of stent. Again, each leaflet guard arch 50*a*, 50*b*, 50*c* has a shape that is roughly similar to the shape of the positioning arch 15*a*, 15*b*, 15*c* in between the corresponding leaflet guard arch 50*a*, 50*b*, 50*c* is arranged. Furthermore, each leaflet guard arch 50*a*, 50*b*, 50*c* extends in the same direction as the positioning arch 15*a*, 15*b*, 15*c*.

In the stent design of the second stent embodiment, each arm of a leaflet guard arch 50*a*, 50*b*, 50*c* merges at about the mid-point of the length of an arm of a radial arch 32*a*, 32*b*, 32*c* into the arm of an opposing radial arch 32*a*, 32*b*, 32*c*. According to the stent design of the second stent embodiment, the leaflet guard arches 50*a*, 50*b*, 50*c* project in the longitudinal direction L of the stent and have a reduced length such that the positioning arches 15*a*, 15*b*, 15*c* can deploy during the expansion of the stent 10 and the leaflet guard arches 50*a*, 50*b*, 50*c* do not interfere during deployment.

The positioning arches 15*a*, 15*b*, 15*c* disposed on the stent 10 and also the retaining arches 16*a*, 16*b*, 16*c* may be curved in convex and arched fashion in the direction to the lower end section of the stent; i.e. toward the lower end 2 of the stent, whereby such a rounded form may reduce injuries to the artery as well as facilitate the unfolding during the self-expansion. Such a design may enable an easier insertion of the positioning arches 15*a*, 15*b*, 15*c* into the pockets of the native cardiac valve without correspondingly injuring the neighbouring tissue or blood vessels.

Although not explicitly illustrated in the flat roll-out view according to FIG. 8*a*, in the programming process during which the shape of the desired (expanded) stent structure is fixed, the leaflet guard arches 50*a*, 50*b*, 50*c* are preferably programmed so that they extend in a radial direction outside the circumference of the stent 10 when the stent 10 of the second stent embodiment is in its expanded state. In this way, an increased contact force can be applied to the leaflets of the native (diseased) cardiac valve when the stent of the second stent embodiment is in its expanded and implanted state. This, in turn, allows an increased security in the fixing of the stent in situ.

When the stent is in its expanded and implanted state, the leaflet guard arches 50*a*, 50*b*, 50*c* actively keep the diseased leaflets, i.e. the leaflets of the native cardiac valve, from impinging the leaflet tissue of the prosthetic heart valve 100 attached to the stent 10, when the positioning arches 15*a*, 15*b*, 15*c* are placed outside the native leaflets. In addition, the leaflet guard arches 50*a*, 50*b*, 50*c* may also provide additional anchoring and securing against migration. This feature may be unique compared to the cage known from the prior art stent designs which are not provided with positioning arches to push the diseased leaflets out of the way.

As can be seen from the roll-out view depicted in FIG. 8*a*, according to the stent design of the second stent embodiment, the two arms 32', 32" of each radial arch 32*a*, 32*b*, 32*c* are connected together at the upper end 3 of the stent 10 by means of a radiused connecting portion or head. This head is not only radiused but also widens at the tip so that the head abuts against the interior wall of the vessel over as large a contact area as possible when the stent 10 is in its expanded and implanted state. The heads of each radial arch 32*a*, 32*b*, 32*c* may also serve as additional means by which the stent 10 may be retained in a catheter before and during implantation and/or to recapture the stent after implantation.

In the programming process during which the shape of the desired (expanded) stent structure is fixed, the radial arches 32*a*, 32*b*, 32*c* are programmed so that they extend in a radial direction outside the circumference of the stent 10 when the stent 10 is in its expanded state. In this way an increased contact force can be applied to the vessel wall by the upper end region of the stent 10, This, in turn, allows an increased security in the fixing of the stent 10 in situ, thereby reducing the likelihood of migration of the stent 10. Therefore, in its expanded state, in addition to the clamping effect of the positioning arches 15*a*, 15*b*, 15*c* and in addition to the additional anchoring obtainable by the leaflet guard arches 50*a*, 50*b*, 50*c*, the stent 10 of the second stent embodiment is secured in place on implantation via radial forces exerted by the retaining arches 16*a*, 16*b*, 16*c*, the auxiliary arches 18*a*, 18*b*, 18*c*, the radial arches 32*a*, 32*b*, 32*c*, and the annular collar 40, all of which project outwards in a radial direction from the circumference of the stent 10.

It can be seen from the flat roll-out view shown in FIG. 8*a* that the radial arches 32*a*, 32*b*, 32*c* do not project in the longitudinal direction L of the stent 10 beyond the plane in which the catheter retaining means 23 or the fastening means with fastening eyelets 24 are situated. This may ensure that the catheter retaining means 23 can co-operate with corresponding means within a suitable implantation catheter without interference from the heads of the radial arches 32*a*, 32*b*, 32*c*. Indeed, as explained above, the heads themselves can be used as additional catheter retaining means or additional means to effect explanation of the stent 10.

In principle, the stent 10 may have more than three radial arches 32 in order to increase the radial contact force further. It is also possible to provide barb elements on all or some of the radial arches 32*a*, 32*b*, 32*c*, for example, to allow a still better anchoring of the stent 10 at the implantation site.

Moreover, with respect to fixing the upper area 3 of stent 10 to the wall of the blood vessel into which the stent 10 is deployed, it would be conceivable for the stent 10 to comprise barb members arranged, for example, on the eyelets 24, the tips of the barbs pointing toward the lower end 2 of stent 10.

In addition, a liner or sheath, typically a fabric, polymeric or pericardial sheet, membrane, or the like, may be provided over at least a portion of the exterior of the stent 10 to cover all or most of the surface of the outside of the stent 10, extending from a location near the lower end section of the stent to a location near the upper end section of the stent. The liner may be attached to the stent 10 at at least one end, as well as at a plurality of locations between said ends thereby forming an exterior coverage. Such exterior coverage provides a circumferential seal against the inner wall of the blood vessel lumen in order to inhibit leakage of blood flow between the stent 10 and the luminal wall thereby and to prevent a blood flow bypassing the endoprosthesis 1.

For example, the liner may be stitched or otherwise secured to the stent 10 along a plurality of circumferentially spaced-apart axial lines. Such attachment permits the liner to fold along a plurality of axial fold lines when the stent 10 is radially compressed. The liner will further be able to open and conform to the luminal wall of the tubular frame as the frame expands. Alternatively, the liner may heat welded, or ultrasonically welded to the stent 10. The liner may be secured to the plurality of independent arches (positioning arches 15*a*, 15*b*, 15*c*, retaining arches 16*a*, 16*b*, 16*c*, auxiliary arches 18*a*, 18*b*, 18*c*, leaflet guard arches 50*a*, 50*b*, 50*c*) preferably along axial lines. In addition, the liner may be secured to the annular collar 40 provided at the lower end section 2 of the stent 10. The liner will preferably be circumferentially sealed against the stent 10 at at least one end.

By covering at least a part of the outside surface of the stent 10 with the liner or sheath, thrombogenicity of the endoprosthesis 1 resulting from exposed stent elements is greatly reduced or eliminated. Such reduction of thrombogenicity is achieved while maintaining the benefits of having a stent structure which is used for spreading up a prosthetic heart valve 100 and for anchoring the prosthetic heart valve 100 in place.

As already mentioned, the stent 10 can be compressed from a relaxed, large diameter configuration to a small diameter configuration to facilitate introduction. It is necessary, of course, that the outer liner remain attached to the stent 10 both in its radially compressed configuration and in its expanded, relaxed configuration.

The liner is composed of pericardial material or conventional biological graft materials, such as polyesters, polytetrafluoroethylenes (PTFE's), polyurethanes, and the like, usually being in the form of woven fabrics, non-woven fabrics, polymeric sheets, membranes, and the like. A presently preferred fabric liner material is a plain woven polyester, such as Dacron® yarn (Dupont, Wilmington, Delaware).

A third embodiment of the stent 10 according to the present invention is described in the following with reference to FIG. 9 which is a flat roll-out view of this embodiment, whereby the cardiac valve stent 10 is shown in its expanded state.

The third embodiment of the stent 10 is similar in structure and function with respect to the second embodiment. To avoid repetition, reference is therefore made to the above description of the second embodiment. In particular, the lower end section of the stent 10 is constituted by an annular collar 40 which is likewise provided with notches 12*e* acting as additional fastening means.

In addition, the stent 10 according to the third stent embodiment is provided with retaining arches 16*a*, 16*b*, 16*c* whose arms 16*a*', 16*a*", 16*b*', 16*b*", 16*c*', 16*c*" are segmented by a plurality of bending edges 33 which are not only used for defining a bending point of two neighboring arm segments, but also as fastening notches which can be used for fixing a heart valve prosthesis 100 to the stent 10. In turn, the retaining arches 16*a*, 16*b*, 16*c* of the third stent embodiment are adapted to extend along the bendable transition area 104 of the prosthetic heart valve, when the endoprosthesis is assembled.

The third embodiment of the stent 10 also includes radial arches 32*a*, 32*b*, 32*c* extending from the positioning arches 15*a*, 15*b*, 15*c* towards the upper end 3 of the stent 10. As is shown in the FIG. 9, the stent 10 has three radial arches 32*a*, 32*b*, 32*c*, with each arch 32*a*, 32*b*, 32*c* located between the two arms 15*a*, 15*a*', 15*b*, 15*b*', 15*c*, 15*c*' of each positioning arch 15*a*, 15*b*, 15*c*. Each radial arch 32*a*, 32*b*, 32*c* has a shape that is roughly inverse to each positioning arch 15*a*, 15*b*, 15*c* and extends in the opposite direction to each one of the positioning arches 15*a*, 15*b*, 15*c*.

Contrary to the stent design of the second stent embodiment, however, the stent design of the third embodiment is not provided with leaflet guard arches 50*a*, 50*b*, 50*c*. Furthermore, each arm of a radial arch 32*a*, 32*b*, 32*c* merges at about the mid-point of the length of the stent 10 into an arm 15*a*', 15*a*", 15*b*", 15*c*', 15*c*" of an opposing positioning arch 15*a*, 15*b*, 15*c*.

A fourth embodiment of the stent 10 according to the present invention is described in the following with reference to FIG. 10. In detail, FIG. 10 is a flat roll-out view of the fourth stent embodiment, whereby the cardiac valve stent 10 is shown in its expanded state.

From a comparison of FIG. 10 with FIG. 8*d* it is derivable that the fourth embodiment of the stent 10 is similar in structure and function with respect to the second embodiment. To avoid repetition, reference is therefore made to the above description of the second embodiment.

The fourth embodiment of the stent 10 only differs from the second stent embodiment in that the respective lower end sections of the leaflet guard arches 50*a*, 50*b*, 50*c* are removed. In particular, the lower end sections of the leaflet guard arches 50*a*, 50*b*, 50*c* between the points where each arm of a radial arch 32*a*, 32*b*, 32*c* merges is removed.

Another embodiment of an endoprosthesis 1 according to the present disclosure is shown by FIGS. 11*a* to 11*c*. In detail, this third embodiment of an endoprosthesis 1 includes a stent 10 according to the second stent embodiment (FIGS. 8*a* to 8*d*) and a prosthetic heart valve 100, in accordance with the second heart valve embodiment (FIGS. 3 and 4), affixed thereto.

In particular, FIG. 11*a* shows a first side view of the third embodiment of the endoprosthesis 1. From this first side view, the characteristic U-shape of the retaining arches 16*a*, 16*b*, 16*c* becomes readily apparent.

As indicated hereinbefore, this U-shape of the respective arms 16*a*', 16*a*", 16*b*', 16*b*", 16*c*', 16*c*" of the retaining arches 16*a*, 16*b*, 16*c* is achieved by segmenting the arms 16*a*', 16*a*", 16*b*', 16*b*", 16*c*', 16*c*". In detail, the arms 16*a*', 16*a*", 16*b*', 16*b*", 16*c*', 16*c*" are segmented by providing a plurality of bending edges 33. In the depicted expanded state of the stent 10, two neighboring arm segments are angled relative to each other, wherein the bending point of these two neighboring arm segments is defined by the bending edge 33 which is provided in between the both neighboring arm segments. Hence, the greater the number of bending edges 33 provided in an arm 16*a*', 16*a*", 16*b*', 16*b*", 16*c*', 16*c*" of a retaining arch 16*a*, 16*b*, 16*c*, the greater the number of arm segments which may extend in different directions in the expanded state of the stent 10. In this respect, the shape of the respective arms 16*a*', 16*a*", 16*b*', 16*b*", 16*c*', 16*c*" of the retaining arches 16*a*, 16*b*, 16*c* can be adapted to the shape of transition area 104 of a prosthetic heart valve 100 to be affixed to the stent 10 adapted so as to fit the retaining arches 16*a*, 16*b*, 16*c* to the progression of the bendable transition area 104 of the prosthetic heart valve 100.

Further to this, FIG. 11*a* shows the bending edges providing a number of fastening notches which are used to fix the bendable transition area 104 to stent 10. Thus, in this third endoprosthesis embodiment, there are no additional fastening holes 12*a* needed along the respective arms 16*a*', 16*a*", 16*b*', 16*b*", 16*c*', 16*c*" of the retaining arches 16*a*, 16*b*, 16*c*. Rather, the sutures 101 are wrapped around the retaining arches 16*a*, 16*b*, 16*c* and sewn to the bendable transition area 104, whilst being held in place by the fastening notches which extend essentially in the same direction as the bendable transition area 104 of the prosthetic heart valve. That is, the prosthetic heart valve 100 of the present third embodiment of the endoprosthesis 1 is more securely attached to the stent 10 as the fastening notches provide a greater number of attachment points compared with the number of fastening holes 12*a*, used in the embodiment according to FIGS. 6*a* and 6*b* of the present disclosure. In this regard, high stress concentrations at each single attachment point can be effectively avoided.

Another feature which has already been described with reference to the second embodiment of the endoprosthesis 1 depicted by FIGS. 7*a* and 7*b*, is the provision of leaflet guard arches 50*a*, 50*b*, 50*c*. To avoid repetition, reference is therefore made to the above description of the second endoprosthesis embodiment depicted by FIGS. 7*a* and 7*b*.

FIG. 11*b* shows the connection between the skirt portion 103 and the aforementioned plurality of lattice cells 70. This plurality of lattice cells 70 formed by a plurality of struts in the area between the arms 16*a*', 16*a*", 16*b*', 16*b*", 16*c*', 16*c*" of two neighbouring (adjacent) retaining arches 16*a*, 16*b*, 16*c*, provides for an additional support for the bendable transition area 104 of a prosthetic heart valve 100 to be attached to the stent 10. As depicted by FIG. 11*b*, the prosthetic heart valve 100 may be directly sewn to the lattice cells 70 by means of sutures 101, threads or thin wires.

As can further be derived from FIG. 11*b*, the prosthetic heart valve 100 according to the third embodiment of the endoprosthesis 1, comprises three separate pieces 120 being sewn together at their contiguous edges 112. FIG. 11*c* shows a perspective top view of the third embodiment of the endoprosthesis. In detail, FIG. 11*c* illustrates the attachment of the three separate pieces 120 being sewn together in a cylindrical manner along their contiguous edges 112. After the contiguous edges 112 of the separate pieces 120 are aligned and sewn together, the sleeves 111 of the separate pieces 120 are turned to the outside and attached to the commissural attachment region 11*b* of the stent 10. A more detailed description of this particular attachment method will be described with reference to FIGS. 19*a-c* and 20.

It should be noted that this third endoprosthesis embodiment is not meant to be restrictive. Of course, it is also conceivable to attach a one piece prosthetic heart valve, in accordance with the first valve embodiment (FIG. 1) of the present disclosure, to the stent 10 shown in FIGS. 8*a* to 8*d*.

In the figures of this specification, the prosthetic heart valve 100 is generally mounted to the inner surface of the stent 10. Of course, it is also conceivable to mount the prosthetic heart valve 100 to the outer surface of a support stent 10. That is, the skirt portion 102 could be in direct contact with the diseased native heart valve and could be attached to the stent 10 by means of sutures. Mounting the prosthetic heart valve 100 to the outer surface of the stent 10 supports the load transfer from the leaflet 102 to the stent 10 and reduces the stress concentration near the attachment regions 11*b*, 11*c*. This greatly reduces stresses on the leaflets 102 during closing and consequently improves the durability thereof. Also, it is possible to design the valve to obtain improved hemodynamics in the case of mounting the skirt portion to the outer surface of the stent. Additionally, the heart valve material which is in direct contact with the diseased native heart valve provides a good interface for sealing against leakage (i.e., paravalvular leakage), tissue in-growth and attachment.

An alternative second embodiment of a prosthetic heart valve 100 is shown in FIGS. 3 and 4 as well as FIGS. 19*a-c* and 20.

In particular, FIGS. 3 and 4 illustrate a flat pattern of the prosthetic heart valve material, which has an essentially t-shirt like shape. According to this realisation, the prosthetic heart valve 100 is made of three separate pieces 120 exhibiting the depicted t-shirt like shape. The three separate pieces 120 are connected to each other at their contiguous edges 112 by suturing, in order to form the cylindrical or conical shape of the prosthetic heart valve 100. The three separate pieces 120 may be cut from more than one pericardial sack, so as to obtain three pieces 120 having matching characteristics, e.g., tissue thickness and properties. In addition, the bendable transition area 104 is implied in the drawing of FIG. 3. That is, that each of the separate pieces 120 is intended to represent one of the three leaflets 102 of the prosthetic heart valve 100, in addition to the transition area 104 and skirt portion 103, FIG. 4 shows a top view of the three separate pieces 120 sewn together and attached to a commissure attachment regions 11*b* of a stent according to the further exemplary embodiment of the disclosure.

The steps for the connection of two of the three separate pieces 120 on their contiguous edges 112 are depicted in FIGS. 19*a-c*.

In a first step, the contiguous edges 112 are brought together and sleeves 111 of the separate pieces 120 are turned to the outside, as shown in FIG. 19*a*.

A reinforcement element 107.8 may then be attached to the front surface of the sleeves 111 by means of sutures 101.1, preferably applying a blanket stitch. At the same time, the continuous edges 112 are sewn together by means of the same sutures 101.1, again preferably applying a blanket stitch.

In a third step, the reinforced sleeves 111 are turned even further to the outside, so that they end up being folded rearwards onto the surface of the leaflets 102. This rearward folded position is then secured by means of lateral sutures 101.2 stitched on the outer surface of the reinforcement element 107.8.

A top view of the three separate pieces 120 sewn together and attached to the commissure attachment regions 11*b* of a stent 10 is illustrated in FIG. 4. As mentioned before, each of the three separated pieces 120 represents one of the three leaflets 102 of the prosthetic heart valve 100.

A detailed perspective view of the attachment of the prosthetic heart valve 100 to the commissure attachment regions 11*b* of the present embodiment is shown in FIG. 20. The reinforcement element 107.8 is wrapped around the rearward folded sleeves 111. This rearward folded position is held by the lateral suture 101.2 connecting the opposite ends of the reinforcement element 107.8. The material of the reinforcement element 107.8 preferably has much higher suturing retention strength than the heart valve material of the three separate pieces 120.

For this reason, the reinforcement element 107.8 is used to attach the prosthetic heart valve 100 to the commissure attachment regions 11*b* of the stent 10, by means of suturing 101.1. Thus, stresses due to the suturing 101.1 between the stent 10 and the prosthetic heart valve 100 are mainly introduced into the material of the reinforcement element 107.8, avoiding high stress concentrations in the prosthetic heart valve 100. Additionally, the intent of this design is to limit the leaflet travel during the opening phase by pinching the commissure area to prevent the leaflets 102 from hitting the stent 10. Also, this assembly method displaces the valve commissures inward radially from the stent post to further limit the leaflets from hitting the stent.

FIG. 21 illustrates an alternative way of attachment of the prosthetic heart valve 100 according to FIGS. 3 and 4 of the present disclosure. In detail, the sleeves 111 of adjacent separate pieces 120 are formed to enclose an inner cushion 107.2. Therefore, in turn, the leaflets 102 are displaced from the commissure attachment region 11*b* to limit the leaflets 102 form hitting the stent. Furthermore, the sutures 101.1 extending through the sleeves 111 and the inner cushion 107.2 are more hidden and the edges of the sleeves 111 are tucked under the inner cushion 107.2. Therefore, in this embodiment, the wear of the prosthetic heart valve 100, is significantly reduced as the leaflets 102 of the prosthetic heart valve are not in direct contact with knots of the sutures 101.1 or the edges of the sleeves 111 respectively. Of course, it is generally advantageous for any of the described embodiments, to avoid direct contact between the knots of the sutures 101 and the prosthetic heart valve material by means of reinforcement elements 107.1-107.8, in order to reduce wear.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the disclosure such that the disclosure should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

LIST OF REFERENCE NUMERALS

1 endoprosthesis
2 lower end of the stent/endoprosthesis
3 upper end of the stent/endoprosthesis
10 cardiac valve stent/stent
11*b* commissure attachment region of the stent
11*c* lower leaflet attachment region of the stent
12*a*, 12*c* additional fastening holes
12*b* auxiliary fastening holes
15*a*-15*c* positioning arches
15*a*'-15*a*" arms of the first positioning arch
15*b*'-15*b*" arms of the second positioning arch
15*c*'-15*c*" arms of the third positioning arch
16*a*-16*c* retaining arches
16*a*'-16*a*" arms of the first retaining arch
16*b*'-16*b*" arms of the second retaining arch
16*c*'-16*c*" arms of the third retaining arch
17 first connecting web
17*d* upper end of the first connecting web
17*p* lower end of the first connecting web
20 head portion of the positioning arch
21 reference marker
22 connecting portion between the arms of neighbouring positioning arches
23 catheter retaining means
24 eyelet
25 second connecting web
30 head portion/connecting portion of the retaining arch
32*a*-32*c* radial arches
33 bending edges in the arms of the retaining arches
40 annular collar
41 supporting web
42 transversal web
50*a*-50*c* leaflet guard arches
70 structure of lattice cells
100 prosthetic heart valve
101 thread
101.1 suture
101.2 lateral suture

101.3 surrounding suture
101.4 clinging suture
102 leaflet of the prosthetic heart valve
103 skirt portion
104 transition area
105 commissures
106 fastening holes
107.1-107.8 reinforcement element
108 round edge
109 cavity
110 slot
111 sleeves
112 contiguous edges
120 separate piece of prosthetic heart valve
L longitudinal direction of the stent

The invention claimed is:

1. A prosthetic heart valve comprising:

a stent comprising a plurality of cells, a plurality of retaining arches comprising a plurality of bending edges and defining an outflow edge of the plurality of cells, and a plurality of commissure attachment regions;

at least two leaflets comprising natural tissue and/or synthetic material and having a first opened position for opening the heart chamber and a second closed position for closing the heart chamber, the leaflets configured to switch between the first opened position and the second closed position in response to a blood flow through the heart, the at least two leaflets each coupled to one or more commissure attachment regions of the plurality of commissure attachment regions at one end of each leaflet of the at least two leaflets and each leaflet coupled to a respective retaining arch of the plurality of retaining arches by one or more sutures secured to the plurality of retaining arches by the bending edges;

a skirt portion comprising natural tissue and/or synthetic material, the skirt portion coupled to the plurality of cells and the plurality of retaining arches; and a bendable transition area formed at the plurality of retaining arches and defining a junction between at least one of the at least two leaflets and the skirt portion, the bendable transition area progressing essentially in a U-shaped manner and configured to reduce tissue stresses during opening and closing motion of the at least two leaflets.

2. The prosthetic heart valve of claim 1, wherein the skirt portion is integral with the at least one of the at least two leaflets.

3. The prosthetic heart valve of claim 1, wherein the stent further comprises a plurality of positioning arches configured to be inserted into cusps of native leaflets of a native valve.

4. The prosthetic heart valve of claim 3, wherein a native leaflet is positioned between each positioning arch of the plurality of positioning arches and each retaining arch of the plurality of retaining arches when plurality of positioning arches are inserted into the cusps of the native valve.

5. The prosthetic heart valve of claim 3, wherein each positioning arch of the plurality of positioning arches is circumferentially aligned with each retaining arch of the plurality of retaining arches.

6. The prosthetic heart valve of claim 1, wherein the bending edges of the plurality of retaining arches form fastening notches configured to receive the one or more sutures.

7. The prosthetic heart valve of claim 1, wherein the bending edges divide each retaining arch of the plurality of retaining arches into a plurality of arm segments.

8. The prosthetic heart valve of claim 1, wherein the commissure attachment region is positioned at an outflow region of the stent.

9. The prosthetic heart valve of claim 1, wherein the skirt portion and at least a portion of the plurality of cells are configured to form a seal against an inner wall of a blood vessel.

10. The prosthetic heart valve of claim 1, wherein each leaflet of the plurality of leaflets comprise a tab extending only a portion of a length of each leaflet and configured to be secured to a respective commissure attachment region of the plurality of commissure attachment regions.

11. A prosthetic heart valve comprising:

a stent comprising a plurality of cells, a plurality of retaining arches comprising a plurality of bending edges and defining an outflow edge of the plurality of cells, and a plurality of commissure attachment regions; and a prosthetic valve comprising a plurality of pieces, each piece of the prosthetic valve configured to be secured to at least one commissure attachment region of the plurality of commissure attachment regions and the plurality of cells via one or more sutures and further configured to be secured to a retaining arch of the plurality of retaining arches by one or more second sutures positioned around the bending edges of the retaining arches, wherein the one or more second sutures secure each piece of the plurality of pieces of the prosthetic valve to a respective retaining arch of the plurality of retaining arches to define a transition area in each piece of the plurality of pieces, resulting in a skirt portion on an inflow side of the respective retaining arch and a prosthetic valve portion on an outflow side of the respective retaining arch, the prosthetic valve portion configured to transition between an open position and a closed position.

12. The prosthetic heart valve of claim 11, wherein the prosthetic valve comprises natural tissue and/or synthetic material.

13. The prosthetic heart valve of claim 11, wherein the stent further comprises a plurality of positioning arches configured to be inserted into cusps of native leaflets a native valve.

14. The prosthetic heart valve of claim 13, wherein a native leaflet is positioned between each positioning arch of the plurality of positioning arches and each retaining arch of the plurality of retaining arches when plurality of positioning arches are inserted into the cusps of the native valve.

15. The prosthetic heart valve of claim 13, wherein each positioning arch of the plurality of positioning arches is circumferentially aligned with each retaining arch of the plurality of retaining arches.

16. The prosthetic heart valve of claim 11, wherein the bending edges of the plurality of retaining arches form fastening notches configured to receive the one or more sutures.

17. The prosthetic heart valve of claim 11, wherein the bending edges divide each retaining arch of the plurality of retaining arches into a plurality of arm segments.

18. The prosthetic heart valve of claim 11, wherein the plurality of commissure attachment regions is positioned at an outflow region of the stent.

19. The prosthetic heart valve of claim 11, wherein the skirt portion and at least a portion of the plurality of cells are configured to form a seal against an inner wall of a blood vessel.

20. The prosthetic heart valve of claim 11, wherein each pieces of the plurality of pieces of the prosthetic valve comprise a tab extending only a portion of a length of each leaflet and configured to be secured to a respective commissure attachment region of the plurality of commissure attachment regions.

* * * * *